US009150890B2

(12) United States Patent
Poetter et al.

(10) Patent No.: US 9,150,890 B2
(45) Date of Patent: Oct. 6, 2015

(54) ***CANDIDA TROPICALIS* CELLS AND USE THEREOF**

(71) Applicants: Markus Poetter, Muenster (DE); Hans-Georg Hennemann, Bedburg (DE); Steffen Schaffer, Herten (DE); Thomas Haas, Muenster (DE)

(72) Inventors: Markus Poetter, Muenster (DE); Hans-Georg Hennemann, Bedburg (DE); Steffen Schaffer, Herten (DE); Thomas Haas, Muenster (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/609,714

(22) Filed: Jan. 30, 2015

(65) Prior Publication Data

US 2015/0140617 A1 May 21, 2015

Related U.S. Application Data

(62) Division of application No. 13/764,996, filed on Feb. 12, 2013, now Pat. No. 8,999,684, which is a division of application No. 12/943,145, filed on Nov. 10, 2010, now abandoned.

(30) Foreign Application Priority Data

Nov. 11, 2009 (DE) .......................... 10 2009 046 626

(51) Int. Cl.
| C12P 7/62 | (2006.01) |
| C12N 1/16 | (2006.01) |
| C12N 9/02 | (2006.01) |
| C12P 7/42 | (2006.01) |
| C12P 13/04 | (2006.01) |
| C07C 51/347 | (2006.01) |
| C07C 67/42 | (2006.01) |
| C07C 227/06 | (2006.01) |
| C07C 227/08 | (2006.01) |

(52) U.S. Cl.
CPC .............. *C12P 7/62* (2013.01); *C07C 51/347* (2013.01); *C07C 67/42* (2013.01); *C07C 227/06* (2013.01); *C07C 227/08* (2013.01); *C12N 1/16* (2013.01); *C12N 9/004* (2013.01); *C12N 9/0042* (2013.01); *C12P 7/42* (2013.01); *C12P 7/625* (2013.01); *C12P 13/04* (2013.01); *C12Y 101/01001* (2013.01)

(58) Field of Classification Search
CPC ..................................... C12P 7/62; C12P 7/42
USPC .................................................. 435/128, 136
See application file for complete search history.

(56) References Cited

U.S. PATENT DOCUMENTS

| 5,254,466 A | 10/1993 | Picataggio et al. |
| 7,157,610 B2 | 1/2007 | Hofen et al. |
| 8,158,391 B2 | 4/2012 | Gross et al. |
| 8,216,813 B2 | 7/2012 | Thum et al. |
| 8,372,595 B2 | 2/2013 | Schaffer et al. |
| 8,404,470 B2 | 3/2013 | Thum et al. |
| 8,486,677 B2 | 7/2013 | Thum et al. |
| 8,604,227 B2 | 12/2013 | Petrat et al. |
| 8,796,000 B2 | 8/2014 | Thum et al. |
| 2003/0212298 A1 | 11/2003 | Brasse et al. |
| 2004/0014198 A1 | 1/2004 | Craft |
| 2010/0068773 A1 | 3/2010 | Marx et al. |
| 2010/0167360 A1 | 7/2010 | Thum et al. |
| 2010/0167361 A1 | 7/2010 | Craft |
| 2010/0190224 A1 | 7/2010 | Poetter et al. |
| 2010/0261237 A1 | 10/2010 | Verseck et al. |
| 2010/0285545 A1 | 11/2010 | Gross et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Poetter et al. |
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0257429 A1 | 10/2011 | Schraven et al. |
| 2012/0034665 A1 | 2/2012 | Haas et al. |
| 2012/0041216 A1 | 2/2012 | Sieber et al. |
| 2012/0245375 A1 | 9/2012 | Hannen et al. |
| 2012/0264182 A1 | 10/2012 | Reinecke et al. |
| 2013/0035403 A1 | 2/2013 | Schaffer et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0245276 A1 | 9/2013 | Klasovsky et al. |
| 2013/0331580 A1 | 12/2013 | Klasovsky et al. |
| 2014/0199736 A1 | 7/2014 | Köhler et al. |

FOREIGN PATENT DOCUMENTS

| DE | 10 2007 060 705 A1 | 6/2009 |
| WO | WO 91/06660 A1 | 5/1991 |

(Continued)

OTHER PUBLICATIONS

European Search Report issued Feb. 24, 2011, in European Patent Application No. 10188993.9.

(Continued)

*Primary Examiner* — Tekchand Saidha

(74) *Attorney, Agent, or Firm* — Oblon, McClelland, Maier & Neustadt, L.L.P.

(57) ABSTRACT

The invention relates to genetically engineered *Candida tropicalis* cells, use thereof and a method of production of ω-hydroxycarboxylic acids and ω-hydroxycarboxylic acid esters.

10 Claims, No Drawings

(56) References Cited

FOREIGN PATENT DOCUMENTS

| WO | WO 03/100013 A2 | 12/2003 |
| WO | WO 03/100013 A3 | 12/2003 |
| WO | WO 2009/077461 | 6/2009 |
| WO | WO 2011/008232 A2 | 1/2011 |

OTHER PUBLICATIONS

European Search Report issued Sep. 21, 2011 in Patent Application No. 11173560.1 with English Translation of Category of Cited Documents.

Search Report issued Apr. 17, 2013 in European Application No. 13158305.6 (With English Translation of Category of Cited Documents).

Search Report issued Apr. 17, 2013 in European Application No. 13158308.0 (With English Translation of Category of Cited Documents).

Search Report issued Apr. 17, 2013 in European Application No. 13158312.2 (With English Translation of Category of Cited Documents).

J.E. Ness., et al., "candida tropicalis strain H5343 clone B11 alcohol dehydrogenase (ADH) gene, partial cds.", Database Accession No. GU056287, XP-002694311, Oct. 22, 2009, 1 page.

D. Fabritius, et al., "Identification and production of 3-hydroxy-$\Delta^9$-cis-1,18-octadecenedioic acid by mutants of *Candida tropicalis*", Appl. Microbiol. Biotechnol., vol. 45, No. 3, 1996, pp. 342-348.

Qi Cheng, et al., "*Candida* yeast long chain fatty alcohol oxidase is c-type haemoprotein and plays an important role in long chain fatty acid metabolism", Biochimica et Biophysica Acta, vol. 1735, No. 3, Aug. 15, 2005, pp. 192-203.

SEQUENCE LISTING

```
<160> NUMBER OF SEQ ID NOS: 68

<210> SEQ ID NO 1
<211> LENGTH: 1575
<212> TYPE: DNA
<213> ORGANISM: Candida tropicalis
<220> FEATURE:
<221> NAME/KEY: CDS
<222> LOCATION: (1)..(1572)

<400> SEQUENCE: 1 atg gcc aca caa gaa att att gat tct gca ctt ccg tac ttg aca aag      48
Met Ala Thr Gln Glu Ile Ile Asp Ser Ala Leu Pro Tyr Leu Thr Lys
1               5                   10                  15 tgg tat act gtt atc act tta gca gct ttg gtt ttc tta att tca tct      96
Trp Tyr Thr Val Ile Thr Leu Ala Ala Leu Val Phe Leu Ile Ser Ser
                20                  25                  30 aat att aaa aat tac gtc aag gct aag aag ttg aaa tgc aga gat cct     144
Asn Ile Lys Asn Tyr Val Lys Ala Lys Lys Leu Lys Cys Arg Asp Pro
            35                  40                  45 cca tat ttc aaa gga gcc ggt tgg aca ggt att agt cca tta att gaa     192
Pro Tyr Phe Lys Gly Ala Gly Trp Thr Gly Ile Ser Pro Leu Ile Glu
        50                  55                  60 att att aaa gtt aaa ggt aat ggt aga ttg gca aga ttt tgg ccg ata     240
Ile Ile Lys Val Lys Gly Asn Gly Arg Leu Ala Arg Phe Trp Pro Ile
65                  70                  75                  80 aaa aca ttc gac gac tat cca aac cat act ttt tac atg tct att att     288
Lys Thr Phe Asp Asp Tyr Pro Asn His Thr Phe Tyr Met Ser Ile Ile
                85                  90                  95 ggt gct ttg aaa atc gtc ttg act gtg atc caa gaa aat att aaa gct     336
Gly Ala Leu Lys Ile Val Leu Thr Val Ile Gln Glu Asn Ile Lys Ala
                100                 105                 110 gtt ttg gct act caa ttt act gat ttc tcc tta ggt act aga cat gcc     384
Val Leu Ala Thr Gln Phe Thr Asp Phe Ser Leu Gly Thr Arg His Ala
            115                 120                 125 cat ttc tat cca tta tta ggt gat ggt att ttt act ttg gat ggt gaa     432
His Phe Tyr Pro Leu Leu Gly Asp Gly Ile Phe Thr Leu Asp Gly Glu
        130                 135                 140 ggt tgg aaa cat agt aga gct atg ttg aga cca caa ttt gct aga gat     480
Gly Trp Lys His Ser Arg Ala Met Leu Arg Pro Gln Phe Ala Arg Asp
145                 150                 155                 160 caa att ggt cat gtt aaa gct ttg gaa cca cat att caa atc ttg gct     528
Gln Ile Gly His Val Lys Ala Leu Glu Pro His Ile Gln Ile Leu Ala
                165                 170                 175 aaa caa atc aaa ttg aat aaa ggt aaa act ttt gat att caa gaa ttg     576
Lys Gln Ile Lys Leu Asn Lys Gly Lys Thr Phe Asp Ile Gln Glu Leu
            180                 185                 190 ttt ttc aga ttt act gtt gat act gct act gaa ttc ttg ttt ggt gaa     624
Phe Phe Arg Phe Thr Val Asp Thr Ala Thr Glu Phe Leu Phe Gly Glu
        195                 200                 205 tct gtt cac tct ttg tat gat gaa aaa tta ggt att cct act cca aat     672
Ser Val His Ser Leu Tyr Asp Glu Lys Leu Gly Ile Pro Thr Pro Asn
```

-continued

```
            210                 215                 220
gaa att cca ggt aga gat aat ttt gca act gct ttt aac act tct caa         720
Glu Ile Pro Gly Arg Asp Asn Phe Ala Thr Ala Phe Asn Thr Ser Gln
225                 230                 235                 240 cat tat ttg gct acc aga aca tac tcc caa act ttc tac ttt tta act         768
His Tyr Leu Ala Thr Arg Thr Tyr Ser Gln Thr Phe Tyr Phe Leu Thr
                    245                 250                 255 aac cct aag gaa ttt aga gac tgt aat gct aaa gtt cat tac ttg gct         816
Asn Pro Lys Glu Phe Arg Asp Cys Asn Ala Lys Val His Tyr Leu Ala
                260                 265                 270 aaa tat ttt gtc aat aaa gct ttg aat ttc act ccg gaa gaa att gaa         864
Lys Tyr Phe Val Asn Lys Ala Leu Asn Phe Thr Pro Glu Glu Ile Glu
            275                 280                 285 gaa aag tcc aaa tct ggt tat gtt ttc ttg tat gaa ttg gtt aaa caa         912
Glu Lys Ser Lys Ser Gly Tyr Val Phe Leu Tyr Glu Leu Val Lys Gln
        290                 295                 300 acc aga gat cca aaa gtt tta caa gat caa tta ttg aac att atg gtt         960
Thr Arg Asp Pro Lys Val Leu Gln Asp Gln Leu Leu Asn Ile Met Val
305                 310                 315                 320 gcc ggt aga gat acc act gct ggt tta tta tca ttt gca atg ttt gaa        1008
Ala Gly Arg Asp Thr Thr Ala Gly Leu Leu Ser Phe Ala Met Phe Glu
                    325                 330                 335 tta gct aga cat cca gaa att tgg tct aaa tta aga gaa gaa att gaa        1056
Leu Ala Arg His Pro Glu Ile Trp Ser Lys Leu Arg Glu Glu Ile Glu
                340                 345                 350 gtt aac ttt ggt gtt ggt gaa gaa tct cgt gtt gaa gaa att act ttt        1104
Val Asn Phe Gly Val Gly Glu Glu Ser Arg Val Glu Glu Ile Thr Phe
            355                 360                 365 gaa tct ttg aag aga tgt gaa tac ttg aaa gct att ctt aat gaa act        1152
Glu Ser Leu Lys Arg Cys Glu Tyr Leu Lys Ala Ile Leu Asn Glu Thr
370                 375                 380 ttg cgt atg tat cct tct gtt cca gtt aat tcc aga aca gcc act aga        1200
Leu Arg Met Tyr Pro Ser Val Pro Val Asn Ser Arg Thr Ala Thr Arg
385                 390                 395                 400 gat acc aca tta cca aga ggt ggt gga cca aat ggt act gat cca att        1248
Asp Thr Thr Leu Pro Arg Gly Gly Gly Pro Asn Gly Thr Asp Pro Ile
                    405                 410                 415 ttt att cca aag ggt tcc act gtt gct tat att gtt tac aaa act cat        1296
Phe Ile Pro Lys Gly Ser Thr Val Ala Tyr Ile Val Tyr Lys Thr His
                420                 425                 430 cgt tta gaa gaa tat tat ggt aaa gat gct gat gat ttc aga cca gaa        1344
Arg Leu Glu Glu Tyr Tyr Gly Lys Asp Ala Asp Asp Phe Arg Pro Glu
            435                 440                 445 aga tgg ttt gaa cca tca act aaa aag tta ggt tgg gct tat gtt cca        1392
Arg Trp Phe Glu Pro Ser Thr Lys Lys Leu Gly Trp Ala Tyr Val Pro
450                 455                 460 ttt aat ggt ggt cca aga att tgt tta ggc caa caa ttt gct tta act        1440
Phe Asn Gly Gly Pro Arg Ile Cys Leu Gly Gln Gln Phe Ala Leu Thr
465                 470                 475                 480 gaa gct tct tat gtt att acc aga ttg gta caa atg ttt gaa act gtt        1488
Glu Ala Ser Tyr Val Ile Thr Arg Leu Val Gln Met Phe Glu Thr Val
                    485                 490                 495 tct tct ccc cca gat gtt gaa tac cct cca cca aaa tgt att cat ttg        1536
Ser Ser Pro Pro Asp Val Glu Tyr Pro Pro Pro Lys Cys Ile His Leu
                500                 505                 510 act atg agt cat gat gat ggt gtt ttc gtt aaa atg taa                    1575
Thr Met Ser His Asp Asp Gly Val Phe Val Lys Met
            515                 520
```

-continued

```
<210> SEQ ID NO 2
<211> LENGTH: 524
<212> TYPE: PRT
<213> ORGANISM: Candida tropicalis

<400> SEQUENCE: 2

Met Ala Thr Gln Glu Ile Ile Asp Ser Ala Leu Pro Tyr Leu Thr Lys
1               5                   10                  15

Trp Tyr Thr Val Ile Thr Leu Ala Ala Leu Val Phe Leu Ile Ser Ser
                20                  25                  30

Asn Ile Lys Asn Tyr Val Lys Ala Lys Lys Leu Lys Cys Arg Asp Pro
            35                  40                  45

Pro Tyr Phe Lys Gly Ala Gly Trp Thr Gly Ile Ser Pro Leu Ile Glu
    50                  55                  60

Ile Ile Lys Val Lys Gly Asn Gly Arg Leu Ala Arg Phe Trp Pro Ile
65                  70                  75                  80

Lys Thr Phe Asp Asp Tyr Pro Asn His Thr Phe Tyr Met Ser Ile Ile
                85                  90                  95

Gly Ala Leu Lys Ile Val Leu Thr Val Ile Gln Glu Asn Ile Lys Ala
            100                 105                 110

Val Leu Ala Thr Gln Phe Thr Asp Phe Ser Leu Gly Thr Arg His Ala
        115                 120                 125

His Phe Tyr Pro Leu Leu Gly Asp Gly Ile Phe Thr Leu Asp Gly Glu
    130                 135                 140

Gly Trp Lys His Ser Arg Ala Met Leu Arg Pro Gln Phe Ala Arg Asp
145                 150                 155                 160

Gln Ile Gly His Val Lys Ala Leu Glu Pro His Ile Gln Ile Leu Ala
                165                 170                 175

Lys Gln Ile Lys Leu Asn Lys Gly Lys Thr Phe Asp Ile Gln Glu Leu
            180                 185                 190

Phe Phe Arg Phe Thr Val Asp Thr Ala Thr Glu Phe Leu Phe Gly Glu
        195                 200                 205

Ser Val His Ser Leu Tyr Asp Glu Lys Leu Gly Ile Pro Thr Pro Asn
    210                 215                 220

Glu Ile Pro Gly Arg Asp Asn Phe Ala Thr Ala Phe Asn Thr Ser Gln
225                 230                 235                 240

His Tyr Leu Ala Thr Arg Thr Tyr Ser Gln Thr Phe Tyr Phe Leu Thr
                245                 250                 255

Asn Pro Lys Glu Phe Arg Asp Cys Asn Ala Lys Val His Tyr Leu Ala
            260                 265                 270

Lys Tyr Phe Val Asn Lys Ala Leu Asn Phe Thr Pro Glu Glu Ile Glu
        275                 280                 285

Glu Lys Ser Lys Ser Gly Tyr Val Phe Leu Tyr Glu Leu Val Lys Gln
    290                 295                 300

Thr Arg Asp Pro Lys Val Leu Gln Asp Gln Leu Leu Asn Ile Met Val
305                 310                 315                 320

Ala Gly Arg Asp Thr Thr Ala Gly Leu Leu Ser Phe Ala Met Phe Glu
                325                 330                 335

Leu Ala Arg His Pro Glu Ile Trp Ser Lys Leu Arg Glu Glu Ile Glu
            340                 345                 350

Val Asn Phe Gly Val Gly Glu Glu Ser Arg Val Glu Glu Ile Thr Phe
        355                 360                 365

Glu Ser Leu Lys Arg Cys Glu Tyr Leu Lys Ala Ile Leu Asn Glu Thr
    370                 375                 380
```

```
Leu Arg Met Tyr Pro Ser Val Pro Val Asn Ser Arg Thr Ala Thr Arg
385                 390                 395                 400

Asp Thr Thr Leu Pro Arg Gly Gly Pro Asn Gly Thr Asp Pro Ile
            405                 410                 415

Phe Ile Pro Lys Gly Ser Thr Val Ala Tyr Ile Val Tyr Lys Thr His
                420                 425                 430

Arg Leu Glu Glu Tyr Tyr Gly Lys Asp Ala Asp Phe Arg Pro Glu
            435                 440                 445

Arg Trp Phe Glu Pro Ser Thr Lys Lys Leu Gly Trp Ala Tyr Val Pro
        450                 455                 460

Phe Asn Gly Gly Pro Arg Ile Cys Leu Gly Gln Gln Phe Ala Leu Thr
465                 470                 475                 480

Glu Ala Ser Tyr Val Ile Thr Arg Leu Val Gln Met Phe Glu Thr Val
                485                 490                 495

Ser Ser Pro Pro Asp Val Glu Tyr Pro Pro Lys Cys Ile His Leu
            500                 505                 510

Thr Met Ser His Asp Asp Gly Val Phe Val Lys Met
            515                 520

<210> SEQ ID NO 3
<211> LENGTH: 1572
<212> TYPE: DNA
<213> ORGANISM: Candida tropicalis
<220> FEATURE:
<221> NAME/KEY: CDS
<222> LOCATION: (1)..(1569)

<400> SEQUENCE: 3 atg gcc aca caa gaa atc atc gat tct gta ctt ccg tac ttg acc aaa    48
Met Ala Thr Gln Glu Ile Ile Asp Ser Val Leu Pro Tyr Leu Thr Lys
1               5                   10                  15 tgg tac act gtg att act gca gca gta tta gtc ttc ctt atc tcc aca    96
Trp Tyr Thr Val Ile Thr Ala Ala Val Leu Val Phe Leu Ile Ser Thr
                20                  25                  30 aac atc aag aac tac gtc aag gca aag aaa ttg aaa tgt gtc gat cca   144
Asn Ile Lys Asn Tyr Val Lys Ala Lys Lys Leu Lys Cys Val Asp Pro
            35                  40                  45 cca tac ttg aag gat gcc ggt ctc act ggt att ctg tct ttg atc gcc   192
Pro Tyr Leu Lys Asp Ala Gly Leu Thr Gly Ile Leu Ser Leu Ile Ala
        50                  55                  60 gcc atc aag gcc aag aac gac ggt aga ttg gct aac ttt gcc gat gaa   240
Ala Ile Lys Ala Lys Asn Asp Gly Arg Leu Ala Asn Phe Ala Asp Glu
65                  70                  75                  80 gtt ttc gac gag tac cca aac cac acc ttc tac ttg tct gtt gcc ggt   288
Val Phe Asp Glu Tyr Pro Asn His Thr Phe Tyr Leu Ser Val Ala Gly
                85                  90                  95 gct ttg aag att gtc atg act gtt gac cca gaa aac atc aag gct gtc   336
Ala Leu Lys Ile Val Met Thr Val Asp Pro Glu Asn Ile Lys Ala Val
            100                 105                 110 ttg gcc acc caa ttc act gac ttc tcc ttg ggt acc aga cac gcc cac   384
Leu Ala Thr Gln Phe Thr Asp Phe Ser Leu Gly Thr Arg His Ala His
        115                 120                 125 ttt gct cct ttg ttg ggt gac ggt atc ttc acc ttg gac gga gaa ggt   432
Phe Ala Pro Leu Leu Gly Asp Gly Ile Phe Thr Leu Asp Gly Glu Gly
130                 135                 140 tgg aag cac tcc aga gct atg ttg aga cca cag ttt gct aga gac cag   480
Trp Lys His Ser Arg Ala Met Leu Arg Pro Gln Phe Ala Arg Asp Gln
145                 150                 155                 160 att gga cac gtt aaa gcc ttg gaa cca cac atc caa atc atg gct aag   528
```

```
                Ile Gly His Val Lys Ala Leu Glu Pro His Ile Gln Ile Met Ala Lys
                                165                 170                 175 cag atc aag ttg aac cag gga aag act ttc gat atc caa gaa ttg ttc         576
Gln Ile Lys Leu Asn Gln Gly Lys Thr Phe Asp Ile Gln Glu Leu Phe
            180                 185                 190 ttt aga ttt acc gtc gac acc gct act gag ttc ttg ttt ggt gaa tcc         624
Phe Arg Phe Thr Val Asp Thr Ala Thr Glu Phe Leu Phe Gly Glu Ser
        195                 200                 205 gtt cac tcc ttg tac gat gaa aaa ttg ggc atc cca act cca aac gaa         672
Val His Ser Leu Tyr Asp Glu Lys Leu Gly Ile Pro Thr Pro Asn Glu
    210                 215                 220 atc cca gga aga gaa aac ttt gcc gct gct ttc aac gtt tcc caa cac         720
Ile Pro Gly Arg Glu Asn Phe Ala Ala Ala Phe Asn Val Ser Gln His
225                 230                 235                 240 tac ttg gcc acc aga agt tac tcc cag act ttt tac ttt ttg acc aac         768
Tyr Leu Ala Thr Arg Ser Tyr Ser Gln Thr Phe Tyr Phe Leu Thr Asn
                245                 250                 255 cct aag gaa ttc aga gac tgt aac gcc aag gtc cac cac ttg gcc aag         816
Pro Lys Glu Phe Arg Asp Cys Asn Ala Lys Val His His Leu Ala Lys
            260                 265                 270 tac ttt gtc aac aag gcc ttg aac ttt act cct gaa gaa ctc gaa gag         864
Tyr Phe Val Asn Lys Ala Leu Asn Phe Thr Pro Glu Glu Leu Glu Glu
        275                 280                 285 aaa tcc aag tcc ggt tac gtt ttc ttg tac gaa ttg gtt aag caa acc         912
Lys Ser Lys Ser Gly Tyr Val Phe Leu Tyr Glu Leu Val Lys Gln Thr
    290                 295                 300 aga gat cca aag gtc ttg caa gat caa ttg ttg aac att atg gtt gcc         960
Arg Asp Pro Lys Val Leu Gln Asp Gln Leu Leu Asn Ile Met Val Ala
305                 310                 315                 320 gga aga gac acc act gcc ggt ttg ttg tcc ttt gct ttg ttt gaa ttg         1008
Gly Arg Asp Thr Thr Ala Gly Leu Leu Ser Phe Ala Leu Phe Glu Leu
                325                 330                 335 gct aga cac cca gag atg tgg tcc aag ttg aga gaa gaa atc gaa gtt         1056
Ala Arg His Pro Glu Met Trp Ser Lys Leu Arg Glu Glu Ile Glu Val
            340                 345                 350 aac ttt ggt gtt ggt gaa gac tcc cgc gtt gaa gaa att acc ttc gaa         1104
Asn Phe Gly Val Gly Glu Asp Ser Arg Val Glu Glu Ile Thr Phe Glu
        355                 360                 365 gcc ttg aag aga tgt gaa tac ttg aag gct atc ctt aac gaa acc ttg         1152
Ala Leu Lys Arg Cys Glu Tyr Leu Lys Ala Ile Leu Asn Glu Thr Leu
    370                 375                 380 cgt atg tac cca tct gtt cct gtc aac ttt aga acc gcc acc aga gac         1200
Arg Met Tyr Pro Ser Val Pro Val Asn Phe Arg Thr Ala Thr Arg Asp
385                 390                 395                 400 acc act ttg cca aga ggt ggt ggt gct aac ggt acc gac cca atc tac         1248
Thr Thr Leu Pro Arg Gly Gly Gly Ala Asn Gly Thr Asp Pro Ile Tyr
                405                 410                 415 att cct aaa ggc tcc act gtt gct tac gtt gtc tac aag acc cac cgt         1296
Ile Pro Lys Gly Ser Thr Val Ala Tyr Val Val Tyr Lys Thr His Arg
            420                 425                 430 ttg gaa gaa tac tac ggt aag gac gct aac gac ttc aga cca gaa aga         1344
Leu Glu Glu Tyr Tyr Gly Lys Asp Ala Asn Asp Phe Arg Pro Glu Arg
        435                 440                 445 tgg ttt gaa cca tct act aag aag ttg ggc tgg gct tat gtt cca ttc         1392
Trp Phe Glu Pro Ser Thr Lys Lys Leu Gly Trp Ala Tyr Val Pro Phe
    450                 455                 460 aac ggt ggt cca aga gtc tgc ttg ggt caa caa ttc gcc ttg act gaa         1440
Asn Gly Gly Pro Arg Val Cys Leu Gly Gln Gln Phe Ala Leu Thr Glu
465                 470                 475                 480
```

```
gct tct tat gtg atc act aga ttg gcc cag atg ttt gaa act gtc tca    1488
Ala Ser Tyr Val Ile Thr Arg Leu Ala Gln Met Phe Glu Thr Val Ser
            485                 490                 495 tct gat cca ggt ctc gaa tac cct cca cca aag tgt att cac ttg acc    1536
Ser Asp Pro Gly Leu Glu Tyr Pro Pro Pro Lys Cys Ile His Leu Thr
        500                 505                 510 atg agt cac aac gat ggt gtc ttt gtc aag atg taa                    1572
Met Ser His Asn Asp Gly Val Phe Val Lys Met
        515                 520
```

<210> SEQ ID NO 4
<211> LENGTH: 523
<212> TYPE: PRT
<213> ORGANISM: Candida tropicalis

<400> SEQUENCE: 4

```
Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
            20                  25                  30

Asn Ile Lys Asn Tyr Val Lys Ala Lys Lys Leu Lys Cys Val Asp Pro
        35                  40                  45

Pro Tyr Leu Lys Asp Ala Gly Leu Thr Gly Ile Leu Ser Leu Ile Ala
    50                  55                  60

Ala Ile Lys Ala Lys Asn Asp Gly Arg Leu Ala Asn Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125

Phe Ala Pro Leu Leu Gly Asp Gly Ile Phe Thr Leu Asp Gly Glu Gly
    130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320
```

```
Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Ile Glu Val
            340                 345                 350

Asn Phe Gly Val Gly Glu Asp Ser Arg Val Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415

Ile Pro Lys Gly Ser Thr Val Ala Tyr Val Val Tyr Lys Thr His Arg
                420                 425                 430

Leu Glu Glu Tyr Tyr Gly Lys Asp Ala Asn Asp Phe Arg Pro Glu Arg
            435                 440                 445

Trp Phe Glu Pro Ser Thr Lys Lys Leu Gly Trp Ala Tyr Val Pro Phe
        450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Lys Cys Ile His Leu Thr
                500                 505                 510

Met Ser His Asn Asp Gly Val Phe Val Lys Met
            515                 520

<210> SEQ ID NO 5
<211> LENGTH: 1569
<212> TYPE: DNA
<213> ORGANISM: Candida tropicalis
<220> FEATURE:
<221> NAME/KEY: CDS
<222> LOCATION: (1)..(1566)

<400> SEQUENCE: 5 atg act gta cac gat att atc gcc aca tac ttc acc aaa tgg tac gtg      48
Met Thr Val His Asp Ile Ile Ala Thr Tyr Phe Thr Lys Trp Tyr Val
1               5                   10                  15 ata gta cca ctc gct ttg att gct tat aga gtc ctc gac tac ttc tat      96
Ile Val Pro Leu Ala Leu Ile Ala Tyr Arg Val Leu Asp Tyr Phe Tyr
            20                  25                  30 ggc aga tac ttg atg tac aag ctt ggt gct aaa cca ttt ttc cag aaa     144
Gly Arg Tyr Leu Met Tyr Lys Leu Gly Ala Lys Pro Phe Phe Gln Lys
        35                  40                  45 cag aca gac ggc tgt ttc gga ttc aaa gct ccg ctt gaa ttg ttg aag     192
Gln Thr Asp Gly Cys Phe Gly Phe Lys Ala Pro Leu Glu Leu Leu Lys
    50                  55                  60 aag aag agc gac ggt acc ctc ata gac ttc aca ctc cag cgt atc cac     240
Lys Lys Ser Asp Gly Thr Leu Ile Asp Phe Thr Leu Gln Arg Ile His
65                  70                  75                  80 gat ctc gat cgt ccc gat atc cca act ttc aca ttc ccg gtc ttt tcc     288
Asp Leu Asp Arg Pro Asp Ile Pro Thr Phe Thr Phe Pro Val Phe Ser
                85                  90                  95 atc aac ctt gtc aat acc ctt gag ccg gag aac atc aag gcc atc ttg     336
Ile Asn Leu Val Asn Thr Leu Glu Pro Glu Asn Ile Lys Ala Ile Leu
            100                 105                 110
```

| | | |
|---|---|---|
| gcc act cag ttc aac gat ttc tcc ttg ggt acc aga cac tcg cac ttt<br>Ala Thr Gln Phe Asn Asp Phe Ser Leu Gly Thr Arg His Ser His Phe<br>115 120 125 | | 384 |
| gct cct ttg ttg ggt gat ggt atc ttt acg ttg gat ggc gcc ggc tgg<br>Ala Pro Leu Leu Gly Asp Gly Ile Phe Thr Leu Asp Gly Ala Gly Trp<br>130 135 140 | | 432 |
| aag cac agc aga tct atg ttg aga cca cag ttt gcc aga gaa cag att<br>Lys His Ser Arg Ser Met Leu Arg Pro Gln Phe Ala Arg Glu Gln Ile<br>145 150 155 160 | | 480 |
| tcc cac gtc aag ttg ttg gag cca cac gtt cag gtg ttc ttc aaa cac<br>Ser His Val Lys Leu Leu Glu Pro His Val Gln Val Phe Phe Lys His<br>165 170 175 | | 528 |
| gtc aga aag gca cag ggc aag act ttt gac atc cag gaa ttg ttt ttc<br>Val Arg Lys Ala Gln Gly Lys Thr Phe Asp Ile Gln Glu Leu Phe Phe<br>180 185 190 | | 576 |
| aga ttg acc gtc gac tcc gcc acc gag ttt ttg ttt ggt gaa tcc gtt<br>Arg Leu Thr Val Asp Ser Ala Thr Glu Phe Leu Phe Gly Glu Ser Val<br>195 200 205 | | 624 |
| gag tcc ttg aga gat gaa tct atc ggc atg tcc atc aat gcg ctt gac<br>Glu Ser Leu Arg Asp Glu Ser Ile Gly Met Ser Ile Asn Ala Leu Asp<br>210 215 220 | | 672 |
| ttt gac ggc aag gct ggc ttt gct gat gct ttt aac tat tcg cag aat<br>Phe Asp Gly Lys Ala Gly Phe Ala Asp Ala Phe Asn Tyr Ser Gln Asn<br>225 230 235 240 | | 720 |
| tat ttg gct tcg aga gcg gtt atg caa caa ttg tac tgg gtg ttg aac<br>Tyr Leu Ala Ser Arg Ala Val Met Gln Gln Leu Tyr Trp Val Leu Asn<br>245 250 255 | | 768 |
| ggg aaa aag ttt aag gag tgc aac gct aaa gtg cac aag ttt gct gac<br>Gly Lys Lys Phe Lys Glu Cys Asn Ala Lys Val His Lys Phe Ala Asp<br>260 265 270 | | 816 |
| tac tac gtc aac aag gct ttg gac ttg acg cct gaa caa ttg gaa aag<br>Tyr Tyr Val Asn Lys Ala Leu Asp Leu Thr Pro Glu Gln Leu Glu Lys<br>275 280 285 | | 864 |
| cag gat ggt tat gtg ttt ttg tac gaa ttg gtc aag caa acc aga gac<br>Gln Asp Gly Tyr Val Phe Leu Tyr Glu Leu Val Lys Gln Thr Arg Asp<br>290 295 300 | | 912 |
| aag caa gtg ttg aga gac caa ttg ttg aac atc atg gtt gct ggt aga<br>Lys Gln Val Leu Arg Asp Gln Leu Leu Asn Ile Met Val Ala Gly Arg<br>305 310 315 320 | | 960 |
| gac acc acc gcc ggt ttg ttg tcg ttt gtt ttc ttt gaa ttg gcc aga<br>Asp Thr Thr Ala Gly Leu Leu Ser Phe Val Phe Phe Glu Leu Ala Arg<br>325 330 335 | | 1008 |
| aac cca gaa gtt acc aac aag ttg aga gaa gaa att gag gac aag ttt<br>Asn Pro Glu Val Thr Asn Lys Leu Arg Glu Glu Ile Glu Asp Lys Phe<br>340 345 350 | | 1056 |
| gga ctc ggt gag aat gct agt gtt gaa gac att tcc ttt gag tcg ttg<br>Gly Leu Gly Glu Asn Ala Ser Val Glu Asp Ile Ser Phe Glu Ser Leu<br>355 360 365 | | 1104 |
| aag tcc tgt gaa tac ttg aag gct gtt ctc aac gaa acc ttg aga ttg<br>Lys Ser Cys Glu Tyr Leu Lys Ala Val Leu Asn Glu Thr Leu Arg Leu<br>370 375 380 | | 1152 |
| tac cca tcc gtg cca cag aat ttc aga gtt gcc acc aag aac act acc<br>Tyr Pro Ser Val Pro Gln Asn Phe Arg Val Ala Thr Lys Asn Thr Thr<br>385 390 395 400 | | 1200 |
| ctc cca aga ggt ggt ggt aag gac ggg ttg tct cct gtt ttg gtg aga<br>Leu Pro Arg Gly Gly Gly Lys Asp Gly Leu Ser Pro Val Leu Val Arg<br>405 410 415 | | 1248 |
| aag ggt cag acc gtt att tac ggt gtc tac gca gcc cac aga aac cca<br>Lys Gly Gln Thr Val Ile Tyr Gly Val Tyr Ala Ala His Arg Asn Pro<br>420 425 430 | | 1296 |

```
gct gtt tac ggt aag gac gct ctt gag ttt aga cca gag aga tgg ttt    1344
Ala Val Tyr Gly Lys Asp Ala Leu Glu Phe Arg Pro Glu Arg Trp Phe
            435                 440                 445 gag cca gag aca aag aag ctt ggc tgg gcc ttc ctc cca ttc aac ggt    1392
Glu Pro Glu Thr Lys Lys Leu Gly Trp Ala Phe Leu Pro Phe Asn Gly
    450                 455                 460 ggt cca aga atc tgt ttg gga cag cag ttt gcc ttg aca gaa gct tcg    1440
Gly Pro Arg Ile Cys Leu Gly Gln Gln Phe Ala Leu Thr Glu Ala Ser
465                 470                 475                 480 tat gtc act gtc agg ttg ctc cag gag ttt gca cac ttg tct atg gac    1488
Tyr Val Thr Val Arg Leu Leu Gln Glu Phe Ala His Leu Ser Met Asp
                485                 490                 495 cca gac acc gaa tat cca cct aag aaa atg tcg cat ttg acc atg tcg    1536
Pro Asp Thr Glu Tyr Pro Pro Lys Lys Met Ser His Leu Thr Met Ser
        500                 505                 510 ctt ttc gac ggt gcc aat att gag atg tat tag                        1569
Leu Phe Asp Gly Ala Asn Ile Glu Met Tyr
        515                 520
```

<210> SEQ ID NO 6
<211> LENGTH: 522
<212> TYPE: PRT
<213> ORGANISM: Candida tropicalis

<400> SEQUENCE: 6

```
Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
            20                  25                  30

Gly Arg Tyr Leu Met Tyr Lys Leu Gly Ala Lys Pro Phe Phe Gln Lys
        35                  40                  45

Gln Thr Asp Gly Cys Phe Gly Phe Lys Ala Pro Leu Glu Leu Leu Lys
    50                  55                  60

Lys Lys Ser Asp Gly Thr Leu Ile Asp Phe Thr Leu Gln Arg Ile His
65                  70                  75                  80

Asp Leu Asp Arg Pro Asp Ile Pro Thr Phe Thr Phe Pro Val Phe Ser
                85                  90                  95

Ile Asn Leu Val Asn Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Val Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
```

```
                    245                 250                 255
Gly Lys Lys Phe Lys Glu Cys Asn Ala Lys Val His Lys Phe Ala Asp
                260                 265                 270

Tyr Tyr Val Asn Lys Ala Leu Asp Leu Thr Pro Glu Gln Leu Glu Lys
            275                 280                 285

Gln Asp Gly Tyr Val Phe Leu Tyr Glu Leu Val Lys Gln Thr Arg Asp
        290                 295                 300

Lys Gln Val Leu Arg Asp Gln Leu Leu Asn Ile Met Val Ala Gly Arg
305                 310                 315                 320

Asp Thr Thr Ala Gly Leu Leu Ser Phe Val Phe Glu Leu Ala Arg
                325                 330                 335

Asn Pro Glu Val Thr Asn Lys Leu Arg Glu Glu Ile Glu Asp Lys Phe
                340                 345                 350

Gly Leu Gly Glu Asn Ala Ser Val Glu Asp Ile Ser Phe Glu Ser Leu
            355                 360                 365

Lys Ser Cys Glu Tyr Leu Lys Ala Val Leu Asn Glu Thr Leu Arg Leu
        370                 375                 380

Tyr Pro Ser Val Pro Gln Asn Phe Arg Val Ala Thr Lys Asn Thr Thr
385                 390                 395                 400

Leu Pro Arg Gly Gly Lys Asp Gly Leu Ser Pro Val Leu Val Arg
                405                 410                 415

Lys Gly Gln Thr Val Ile Tyr Gly Val Tyr Ala Ala His Arg Asn Pro
                420                 425                 430

Ala Val Tyr Gly Lys Asp Ala Leu Glu Phe Arg Pro Glu Arg Trp Phe
            435                 440                 445

Glu Pro Glu Thr Lys Lys Leu Gly Trp Ala Phe Leu Pro Phe Asn Gly
        450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ala His Leu Ser Met Asp
                485                 490                 495

Pro Asp Thr Glu Tyr Pro Pro Lys Lys Met Ser His Leu Thr Met Ser
            500                 505                 510

Leu Phe Asp Gly Ala Asn Ile Glu Met Tyr
        515                 520

<210> SEQ ID NO 7
<211> LENGTH: 1569
<212> TYPE: DNA
<213> ORGANISM: Candida tropicalis
<220> FEATURE:
<221> NAME/KEY: CDS
<222> LOCATION: (1)..(1566)

<400> SEQUENCE: 7 atg act gca cag gat att atc gcc aca tac atc acc aaa tgg tac gtg      48
Met Thr Ala Gln Asp Ile Ile Ala Thr Tyr Ile Thr Lys Trp Tyr Val
1               5                   10                  15 ata gta cca ctc gct ttg att gct tat agg gtc ctc gac tac ttt tac      96
Ile Val Pro Leu Ala Leu Ile Ala Tyr Arg Val Leu Asp Tyr Phe Tyr
            20                  25                  30 ggc aga tac ttg atg tac aag ctt ggt gct aaa ccg ttt ttc cag aaa      144
Gly Arg Tyr Leu Met Tyr Lys Leu Gly Ala Lys Pro Phe Phe Gln Lys
        35                  40                  45 caa aca gac ggt tat ttc gga ttc aaa gct cca ctt gaa ttg tta aaa      192
Gln Thr Asp Gly Tyr Phe Gly Phe Lys Ala Pro Leu Glu Leu Leu Lys
    50                  55                  60
```

-continued

```
aag aag agt gac ggt acc ctc ata gac ttc act ctc gag cgt atc caa       240
Lys Lys Ser Asp Gly Thr Leu Ile Asp Phe Thr Leu Glu Arg Ile Gln
65                  70                  75                  80 gcg ctc aat cgt cca gat atc cca act ttt aca ttc cca atc ttt tcc       288
Ala Leu Asn Arg Pro Asp Ile Pro Thr Phe Thr Phe Pro Ile Phe Ser
                85                  90                  95 atc aac ctt atc agc acc ctt gag ccg gag aac atc aag gct atc ttg       336
Ile Asn Leu Ile Ser Thr Leu Glu Pro Glu Asn Ile Lys Ala Ile Leu
            100                 105                 110 gcc acc cag ttc aac gat ttc tcc ttg ggc acc aga cac tcg cac ttt       384
Ala Thr Gln Phe Asn Asp Phe Ser Leu Gly Thr Arg His Ser His Phe
        115                 120                 125 gct cct ttg ttg ggc gat ggt atc ttt acc ttg gac ggt gcc ggc tgg       432
Ala Pro Leu Leu Gly Asp Gly Ile Phe Thr Leu Asp Gly Ala Gly Trp
    130                 135                 140 aag cac agc aga tct atg ttg aga cca cag ttt gcc aga gaa cag att       480
Lys His Ser Arg Ser Met Leu Arg Pro Gln Phe Ala Arg Glu Gln Ile
145                 150                 155                 160 tcc cac gtc aag ttg ttg gag cca cac atg cag gtg ttc ttc aag cac       528
Ser His Val Lys Leu Leu Glu Pro His Met Gln Val Phe Phe Lys His
                165                 170                 175 gtc aga aag gca cag ggc aag act ttt gac atc caa gaa ttg ttt ttc       576
Val Arg Lys Ala Gln Gly Lys Thr Phe Asp Ile Gln Glu Leu Phe Phe
            180                 185                 190 aga ttg acc gtc gac tcc gcc act gag ttt ttg ttt ggt gaa tcc gtt       624
Arg Leu Thr Val Asp Ser Ala Thr Glu Phe Leu Phe Gly Glu Ser Val
        195                 200                 205 gag tcc ttg aga gat gaa tct att ggg atg tcc atc aat gca ctt gac       672
Glu Ser Leu Arg Asp Glu Ser Ile Gly Met Ser Ile Asn Ala Leu Asp
    210                 215                 220 ttt gac ggc aag gct ggc ttt gct gat gct ttt aac tac tcg cag aac       720
Phe Asp Gly Lys Ala Gly Phe Ala Asp Ala Phe Asn Tyr Ser Gln Asn
225                 230                 235                 240 tat ttg gct tcg aga gcg gtt atg caa caa ttg tac tgg gtg ttg aac       768
Tyr Leu Ala Ser Arg Ala Val Met Gln Gln Leu Tyr Trp Val Leu Asn
                245                 250                 255 ggg aaa aag ttt aag gag tgc aac gct aaa gtg cac aag ttt gct gac       816
Gly Lys Lys Phe Lys Glu Cys Asn Ala Lys Val His Lys Phe Ala Asp
            260                 265                 270 tat tac gtc agc aag gct ttg gac ttg aca cct gaa caa ttg gaa aag       864
Tyr Tyr Val Ser Lys Ala Leu Asp Leu Thr Pro Glu Gln Leu Glu Lys
        275                 280                 285 cag gat ggt tat gtg ttc ttg tac gag ttg gtc aag caa acc aga gac       912
Gln Asp Gly Tyr Val Phe Leu Tyr Glu Leu Val Lys Gln Thr Arg Asp
    290                 295                 300 agg caa gtg ttg aga gac cag ttg ttg aac atc atg gtt gcc ggt aga       960
Arg Gln Val Leu Arg Asp Gln Leu Leu Asn Ile Met Val Ala Gly Arg
305                 310                 315                 320 gac acc acc gcc ggt ttg ttg tcg ttt gtt ttc ttt gaa ttg gcc aga      1008
Asp Thr Thr Ala Gly Leu Leu Ser Phe Val Phe Phe Glu Leu Ala Arg
                325                 330                 335 aac cca gag gtg acc aac aag ttg aga gaa gaa atc gag gac aag ttt      1056
Asn Pro Glu Val Thr Asn Lys Leu Arg Glu Glu Ile Glu Asp Lys Phe
            340                 345                 350 ggt ctt ggt gag aat gct cgt gtt gaa gac att tcc ttt gag tcg ttg      1104
Gly Leu Gly Glu Asn Ala Arg Val Glu Asp Ile Ser Phe Glu Ser Leu
        355                 360                 365 aag tca tgt gaa tac ttg aag gct gtt ctc aac gaa act ttg aga ttg      1152
Lys Ser Cys Glu Tyr Leu Lys Ala Val Leu Asn Glu Thr Leu Arg Leu
```

```
                 370                 375                 380
tac cca tcc gtg cca cag aat ttc aga gtt gcc acc aaa aac act acc      1200
Tyr Pro Ser Val Pro Gln Asn Phe Arg Val Ala Thr Lys Asn Thr Thr
385                 390                 395                 400 ctt cca agg gga ggt ggt aag gac ggg tta tct cct gtt ttg gtc aga      1248
Leu Pro Arg Gly Gly Gly Lys Asp Gly Leu Ser Pro Val Leu Val Arg
                405                 410                 415 aag ggt caa acc gtt atg tac ggt gtc tac gct gcc cac aga aac cca      1296
Lys Gly Gln Thr Val Met Tyr Gly Val Tyr Ala Ala His Arg Asn Pro
            420                 425                 430 gct gtc tac ggt aag gac gcc ctt gag ttt aga cca gag agg tgg ttt      1344
Ala Val Tyr Gly Lys Asp Ala Leu Glu Phe Arg Pro Glu Arg Trp Phe
        435                 440                 445 gag cca gag aca aag aag ctt ggc tgg gcc ttc ctt cca ttc aac ggt      1392
Glu Pro Glu Thr Lys Lys Leu Gly Trp Ala Phe Leu Pro Phe Asn Gly
    450                 455                 460 ggt cca aga att tgc ttg gga cag cag ttt gcc ttg aca gaa gct tcg      1440
Gly Pro Arg Ile Cys Leu Gly Gln Gln Phe Ala Leu Thr Glu Ala Ser
465                 470                 475                 480 tat gtc act gtc aga ttg ctc caa gag ttt gga cac ttg tct atg gac      1488
Tyr Val Thr Val Arg Leu Leu Gln Glu Phe Gly His Leu Ser Met Asp
                485                 490                 495 ccc aac acc gaa tat cca cct agg aaa atg tcg cat ttg acc atg tcc      1536
Pro Asn Thr Glu Tyr Pro Pro Arg Lys Met Ser His Leu Thr Met Ser
            500                 505                 510 ctt ttc gac ggt gcc aac att gag atg tat tag                          1569
Leu Phe Asp Gly Ala Asn Ile Glu Met Tyr
        515                 520

<210> SEQ ID NO 8
<211> LENGTH: 522
<212> TYPE: PRT
<213> ORGANISM: Candida tropicalis

<400> SEQUENCE: 8

Met Thr Ala Gln Asp Ile Ile Ala Thr Tyr Ile Thr Lys Trp Tyr Val
1               5                   10                  15

Ile Val Pro Leu Ala Leu Ile Ala Tyr Arg Val Leu Asp Tyr Phe Tyr
            20                  25                  30

Gly Arg Tyr Leu Met Tyr Lys Leu Gly Ala Lys Pro Phe Phe Gln Lys
        35                  40                  45

Gln Thr Asp Gly Tyr Phe Gly Phe Lys Ala Pro Leu Glu Leu Leu Lys
    50                  55                  60

Lys Lys Ser Asp Gly Thr Leu Ile Asp Phe Thr Leu Glu Arg Ile Gln
65                  70                  75                  80

Ala Leu Asn Arg Pro Asp Ile Pro Thr Phe Thr Phe Pro Ile Phe Ser
                85                  90                  95

Ile Asn Leu Ile Ser Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Met Gln Val Phe Phe Lys His
                165                 170                 175
```

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
            260                 265                 270

Tyr Tyr Val Ser Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
290                 295                 300

Arg Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Arg Val Glu Asp Ile Ser Phe Glu Ser Leu
        355                 360                 365

Lys Ser Cys Glu Tyr Leu Lys Ala Val Leu Asn Glu Thr Leu Arg Leu
370                 375                 380

Tyr Pro Ser Val Pro Gln Asn Phe Arg Val Ala Thr Lys Asn Thr Thr
385                 390                 395                 400

Leu Pro Arg Gly Gly Lys Asp Gly Leu Ser Pro Val Leu Val Arg
                405                 410                 415

Lys Gly Gln Thr Val Met Tyr Gly Val Tyr Ala Ala His Arg Asn Pro
            420                 425                 430

Ala Val Tyr Gly Lys Asp Ala Leu Glu Phe Arg Pro Glu Arg Trp Phe
        435                 440                 445

Glu Pro Glu Thr Lys Lys Leu Gly Trp Ala Phe Leu Pro Phe Asn Gly
450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Gly His Leu Ser Met Asp
                485                 490                 495

Pro Asn Thr Glu Tyr Pro Pro Arg Lys Met Ser His Leu Thr Met Ser
            500                 505                 510

Leu Phe Asp Gly Ala Asn Ile Glu Met Tyr
        515                 520

<210> SEQ ID NO 9
<211> LENGTH: 1623
<212> TYPE: DNA
<213> ORGANISM: Candida tropicalis
<220> FEATURE:
<221> NAME/KEY: CDS
<222> LOCATION: (1)..(1620)

<400> SEQUENCE: 9 atg tcg tct tct cca tcg ttt gcc caa gag gtt ctc gct acc act agt        48
Met Ser Ser Ser Pro Ser Phe Ala Gln Glu Val Leu Ala Thr Thr Ser

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
cct tac atc gag tac ttt ctt gac aac tac acc aga tgg tac tac ttc      96
Pro Tyr Ile Glu Tyr Phe Leu Asp Asn Tyr Thr Arg Trp Tyr Tyr Phe
             20                  25                  30 ata cct ttg gtg ctt ctt tcg ttg aac ttt ata agt ttg ctc cac aca     144
Ile Pro Leu Val Leu Leu Ser Leu Asn Phe Ile Ser Leu Leu His Thr
         35                  40                  45 agg tac ttg gaa cgc agg ttc cac gcc aag cca ctc ggt aac ttt gtc     192
Arg Tyr Leu Glu Arg Arg Phe His Ala Lys Pro Leu Gly Asn Phe Val
 50                  55                  60 agg gac cct acg ttt ggt atc gct act ccg ttg ctt ttg atc tac ttg     240
Arg Asp Pro Thr Phe Gly Ile Ala Thr Pro Leu Leu Leu Ile Tyr Leu
 65                  70                  75                  80 aag tcg aaa ggt acg gtc atg aag ttt gct tgg ggc ctc tgg aac aac     288
Lys Ser Lys Gly Thr Val Met Lys Phe Ala Trp Gly Leu Trp Asn Asn
                 85                  90                  95 aag tac atc gtc aga gac cca aag tac aag aca act ggg ctc agg att     336
Lys Tyr Ile Val Arg Asp Pro Lys Tyr Lys Thr Thr Gly Leu Arg Ile
            100                 105                 110 gtt ggc ctc cca ttg att gaa acc atg gac cca gag aac atc aag gct     384
Val Gly Leu Pro Leu Ile Glu Thr Met Asp Pro Glu Asn Ile Lys Ala
        115                 120                 125 gtt ttg gct act cag ttc aat gat ttc tct ttg gga acc aga cac gat     432
Val Leu Ala Thr Gln Phe Asn Asp Phe Ser Leu Gly Thr Arg His Asp
    130                 135                 140 ttc ttg tac tcc ttg ttg ggt gac ggt att ttc acc ttg gac ggt gct     480
Phe Leu Tyr Ser Leu Leu Gly Asp Gly Ile Phe Thr Leu Asp Gly Ala
145                 150                 155                 160 ggc tgg aaa cat agt aga act atg ttg aga cca cag ttt gct aga gaa     528
Gly Trp Lys His Ser Arg Thr Met Leu Arg Pro Gln Phe Ala Arg Glu
                165                 170                 175 cag gtt tct cac gtc aag ttg ttg gag cca cac gtt cag gtg ttc ttc     576
Gln Val Ser His Val Lys Leu Leu Glu Pro His Val Gln Val Phe Phe
            180                 185                 190 aag cac gtt aga aag cac cgc ggt caa acg ttc gac atc caa gaa ttg     624
Lys His Val Arg Lys His Arg Gly Gln Thr Phe Asp Ile Gln Glu Leu
        195                 200                 205 ttc ttc agg ttg acc gtc gac tcc gcc acc gag ttc ttg ttt ggt gag     672
Phe Phe Arg Leu Thr Val Asp Ser Ala Thr Glu Phe Leu Phe Gly Glu
    210                 215                 220 tct gct gaa tcc ttg agg gac gaa tct att gga ttg acc cca acc acc     720
Ser Ala Glu Ser Leu Arg Asp Glu Ser Ile Gly Leu Thr Pro Thr Thr
225                 230                 235                 240 aag gat ttc gat ggc aga aga gat ttc gct gac gct ttc aac tat tcg     768
Lys Asp Phe Asp Gly Arg Arg Asp Phe Ala Asp Ala Phe Asn Tyr Ser
                245                 250                 255 cag act tac cag gcc tac aga ttt ttg ttg caa caa atg tac tgg atc     816
Gln Thr Tyr Gln Ala Tyr Arg Phe Leu Leu Gln Gln Met Tyr Trp Ile
            260                 265                 270 ttg aat ggc tcg gaa ttc aga aag tcg att gct gtc gtg cac aag ttt     864
Leu Asn Gly Ser Glu Phe Arg Lys Ser Ile Ala Val Val His Lys Phe
        275                 280                 285 gct gac cac tat gtg caa aag gct ttg gag ttg acc gac gat gac ttg     912
Ala Asp His Tyr Val Gln Lys Ala Leu Glu Leu Thr Asp Asp Asp Leu
    290                 295                 300 cag aaa caa gac ggc tat gtg ttc ttg tac gag ttg gct aag caa acc     960
Gln Lys Gln Asp Gly Tyr Val Phe Leu Tyr Glu Leu Ala Lys Gln Thr
305                 310                 315                 320 aga gac cca aag gtc ttg aga gac cag tta ttg aac att ttg gtt gcc    1008
```

```
Arg Asp Pro Lys Val Leu Arg Asp Gln Leu Leu Asn Ile Leu Val Ala
            325                 330                 335 ggt aga gac acg acc gcc ggt ttg ttg tca ttt gtt ttc tac gag ttg   1056
Gly Arg Asp Thr Thr Ala Gly Leu Leu Ser Phe Val Phe Tyr Glu Leu
            340                 345                 350 tca aga aac cct gag gtg ttt gct aag ttg aga gag gag gtg gaa aac   1104
Ser Arg Asn Pro Glu Val Phe Ala Lys Leu Arg Glu Glu Val Glu Asn
            355                 360                 365 aga ttt gga ctc ggt gaa gaa gct cgt gtt gaa gag atc tcg ttt gag   1152
Arg Phe Gly Leu Gly Glu Glu Ala Arg Val Glu Glu Ile Ser Phe Glu
        370                 375                 380 tcc ttg aag tct tgt gag tac ttg aag gct gtc atc aat gaa acc ttg   1200
Ser Leu Lys Ser Cys Glu Tyr Leu Lys Ala Val Ile Asn Glu Thr Leu
385                 390                 395                 400 aga ttg tac cca tcg gtt cca cac aac ttt aga gtt gct acc aga aac   1248
Arg Leu Tyr Pro Ser Val Pro His Asn Phe Arg Val Ala Thr Arg Asn
                405                 410                 415 act acc ctc cca aga ggt ggt ggt gaa gat gga tac tcg cca att gtc   1296
Thr Thr Leu Pro Arg Gly Gly Gly Glu Asp Gly Tyr Ser Pro Ile Val
            420                 425                 430 gtc aag aag ggt caa gtt gtc atg tac act gtt att gct acc cac aga   1344
Val Lys Lys Gly Gln Val Val Met Tyr Thr Val Ile Ala Thr His Arg
            435                 440                 445 gac cca agt atc tac ggt gcc gac gct gac gtc ttc aga cca gaa aga   1392
Asp Pro Ser Ile Tyr Gly Ala Asp Ala Asp Val Phe Arg Pro Glu Arg
        450                 455                 460 tgg ttt gaa cca gaa act aga aag ttg ggc tgg gca tac gtt cca ttc   1440
Trp Phe Glu Pro Glu Thr Arg Lys Leu Gly Trp Ala Tyr Val Pro Phe
465                 470                 475                 480 aat ggt ggt cca aga atc tgt ttg ggt caa cag ttt gcc ttg acc gaa   1488
Asn Gly Gly Pro Arg Ile Cys Leu Gly Gln Gln Phe Ala Leu Thr Glu
                485                 490                 495 gct tca tac gtc act gtc aga ttg ctc cag gag ttt gca cac ttg tct   1536
Ala Ser Tyr Val Thr Val Arg Leu Leu Gln Glu Phe Ala His Leu Ser
            500                 505                 510 atg gac cca gac acc gaa tat cca cca aaa ttg cag aac acc ttg acc   1584
Met Asp Pro Asp Thr Glu Tyr Pro Pro Lys Leu Gln Asn Thr Leu Thr
            515                 520                 525 ttg tcg ctc ttt gat ggt gct gat gtt aga atg tac taa                1623
Leu Ser Leu Phe Asp Gly Ala Asp Val Arg Met Tyr
            530                 535                 540

<210> SEQ ID NO 10
<211> LENGTH: 540
<212> TYPE: PRT
<213> ORGANISM: Candida tropicalis

<400> SEQUENCE: 10

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Arg Tyr Leu Glu Arg Arg Phe His Ala Lys Pro Leu Gly Asn Phe Val
    50                  55                  60

Arg Asp Pro Thr Phe Gly Ile Ala Thr Pro Leu Leu Leu Ile Tyr Leu
65                  70                  75                  80

Lys Ser Lys Gly Thr Val Met Lys Phe Ala Trp Gly Leu Trp Asn Asn
```

```
            85                  90                  95
Lys Tyr Ile Val Arg Asp Pro Lys Tyr Lys Thr Thr Gly Leu Arg Ile
            100                 105                 110

Val Gly Leu Pro Leu Ile Glu Thr Met Asp Pro Glu Asn Ile Lys Ala
            115                 120                 125

Val Leu Ala Thr Gln Phe Asn Asp Phe Ser Leu Gly Thr Arg His Asp
        130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Glu Ser Ile Gly Leu Thr Pro Thr Thr
225                 230                 235                 240

Lys Asp Phe Asp Gly Arg Arg Asp Phe Ala Asp Ala Phe Asn Tyr Ser
                245                 250                 255

Gln Thr Tyr Gln Ala Tyr Arg Phe Leu Leu Gln Met Tyr Trp Ile
            260                 265                 270

Leu Asn Gly Ser Glu Phe Arg Lys Ser Ile Ala Val Val His Lys Phe
        275                 280                 285

Ala Asp His Tyr Val Gln Lys Ala Leu Glu Leu Thr Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
    370                 375                 380

Ser Leu Lys Ser Cys Glu Tyr Leu Lys Ala Val Ile Asn Glu Thr Leu
385                 390                 395                 400

Arg Leu Tyr Pro Ser Val Pro His Asn Phe Arg Val Ala Thr Arg Asn
                405                 410                 415

Thr Thr Leu Pro Arg Gly Gly Glu Asp Gly Tyr Ser Pro Ile Val
            420                 425                 430

Val Lys Lys Gly Gln Val Val Met Tyr Thr Val Ile Ala Thr His Arg
        435                 440                 445

Asp Pro Ser Ile Tyr Gly Ala Asp Ala Asp Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Ala His Leu Ser
            500                 505                 510
```

```
Met Asp Pro Asp Thr Glu Tyr Pro Lys Leu Gln Asn Thr Leu Thr
        515                 520                 525
Leu Ser Leu Phe Asp Gly Ala Asp Val Arg Met Tyr
    530                 535                 540

<210> SEQ ID NO 11
<211> LENGTH: 1623
<212> TYPE: DNA
<213> ORGANISM: Candida tropicalis
<220> FEATURE:
<221> NAME/KEY: CDS
<222> LOCATION: (1)..(1620)

<400> SEQUENCE: 11 atg tcg tct tct cca tcg ttt gct cag gag gtt ctc gct acc act agt      48
Met Ser Ser Ser Pro Ser Phe Ala Gln Glu Val Leu Ala Thr Thr Ser
 1               5                  10                  15 cct tac atc gag tac ttt ctt gac aac tac acc aga tgg tac tac ttc      96
Pro Tyr Ile Glu Tyr Phe Leu Asp Asn Tyr Thr Arg Trp Tyr Tyr Phe
                20                  25                  30 atc cct ttg gtg ctt ctt tcg ttg aac ttc atc agc ttg ctc cac aca     144
Ile Pro Leu Val Leu Leu Ser Leu Asn Phe Ile Ser Leu Leu His Thr
            35                  40                  45 aag tac ttg gaa cgc agg ttc cac gcc aag ccg ctc ggt aac gtc gtg     192
Lys Tyr Leu Glu Arg Arg Phe His Ala Lys Pro Leu Gly Asn Val Val
        50                  55                  60 ttg gat cct acg ttt ggt atc gct act ccg ttg atc ttg atc tac tta     240
Leu Asp Pro Thr Phe Gly Ile Ala Thr Pro Leu Ile Leu Ile Tyr Leu
65                  70                  75                  80 aag tcg aaa ggt aca gtc atg aag ttt gcc tgg agc ttc tgg aac aac     288
Lys Ser Lys Gly Thr Val Met Lys Phe Ala Trp Ser Phe Trp Asn Asn
                85                  90                  95 aag tac att gtc aaa gac cca aag tac aag acc act ggc ctt aga att     336
Lys Tyr Ile Val Lys Asp Pro Lys Tyr Lys Thr Thr Gly Leu Arg Ile
            100                 105                 110 gtc ggc ctc cca ttg att gaa acc ata gac cca gag aac atc aaa gct     384
Val Gly Leu Pro Leu Ile Glu Thr Ile Asp Pro Glu Asn Ile Lys Ala
        115                 120                 125 gtg ttg gct act cag ttc aac gat ttc tcc ttg gga act aga cac gat     432
Val Leu Ala Thr Gln Phe Asn Asp Phe Ser Leu Gly Thr Arg His Asp
    130                 135                 140 ttc ttg tac tcc ttg ttg ggc gat ggt att ttt acc ttg gac ggt gct     480
Phe Leu Tyr Ser Leu Leu Gly Asp Gly Ile Phe Thr Leu Asp Gly Ala
145                 150                 155                 160 ggc tgg aaa cac agt aga act atg ttg aga cca cag ttt gct aga gaa     528
Gly Trp Lys His Ser Arg Thr Met Leu Arg Pro Gln Phe Ala Arg Glu
                165                 170                 175 cag gtt tcc cac gtc aag ttg ttg gaa cca cac gtt cag gtg ttc ttc     576
Gln Val Ser His Val Lys Leu Leu Glu Pro His Val Gln Val Phe Phe
            180                 185                 190 aag cac gtt aga aaa cac cgc ggt cag act ttt gac atc caa gaa ttg     624
Lys His Val Arg Lys His Arg Gly Gln Thr Phe Asp Ile Gln Glu Leu
        195                 200                 205 ttc ttc aga ttg acc gtc gac tcc gcc acc gag ttc ttg ttt ggt gag     672
Phe Phe Arg Leu Thr Val Asp Ser Ala Thr Glu Phe Leu Phe Gly Glu
    210                 215                 220 tct gct gaa tcc ttg aga gac gac tct gtt ggt ttg acc cca acc acc     720
Ser Ala Glu Ser Leu Arg Asp Asp Ser Val Gly Leu Thr Pro Thr Thr
225                 230                 235                 240 aag gat ttc gaa ggc aga gga gat ttc gct gac gct ttc aac tac tcg     768
```

```
                    Lys Asp Phe Glu Gly Arg Gly Asp Phe Ala Asp Ala Phe Asn Tyr Ser
                                    245                 250                 255 cag act tac cag gcc tac aga ttt ttg ttg caa caa atg tac tgg att              816
Gln Thr Tyr Gln Ala Tyr Arg Phe Leu Leu Gln Gln Met Tyr Trp Ile
                260                 265                 270 ttg aat ggc gcg gaa ttc aga aag tcg att gcc atc gtg cac aag ttt              864
Leu Asn Gly Ala Glu Phe Arg Lys Ser Ile Ala Ile Val His Lys Phe
            275                 280                 285 gct gac cac tat gtg caa aag gct ttg gag ttg acc gac gat gac ttg              912
Ala Asp His Tyr Val Gln Lys Ala Leu Glu Leu Thr Asp Asp Asp Leu
        290                 295                 300 cag aaa caa gac ggc tat gtg ttc ttg tac gag ttg gct aag caa act              960
Gln Lys Gln Asp Gly Tyr Val Phe Leu Tyr Glu Leu Ala Lys Gln Thr
305                 310                 315                 320 aga gac cca aag gtc ttg aga gac cag ttg ttg aac att ttg gtt gcc             1008
Arg Asp Pro Lys Val Leu Arg Asp Gln Leu Leu Asn Ile Leu Val Ala
                325                 330                 335 ggt aga gac acg acc gcc ggt ttg ttg tcg ttt gtg ttc tac gag ttg             1056
Gly Arg Asp Thr Thr Ala Gly Leu Leu Ser Phe Val Phe Tyr Glu Leu
            340                 345                 350 tcg aga aac cct gaa gtg ttt gcc aag ttg aga gag gag gtg gaa aac             1104
Ser Arg Asn Pro Glu Val Phe Ala Lys Leu Arg Glu Glu Val Glu Asn
        355                 360                 365 aga ttt gga ctc ggc gaa gag gct cgt gtt gaa gag atc tct ttt gag             1152
Arg Phe Gly Leu Gly Glu Glu Ala Arg Val Glu Glu Ile Ser Phe Glu
370                 375                 380 tcc ttg aag tcc tgt gag tac ttg aag gct gtc atc aat gaa gcc ttg             1200
Ser Leu Lys Ser Cys Glu Tyr Leu Lys Ala Val Ile Asn Glu Ala Leu
385                 390                 395                 400 aga ttg tac cca tct gtt cca cac aac ttc aga gtt gcc acc aga aac             1248
Arg Leu Tyr Pro Ser Val Pro His Asn Phe Arg Val Ala Thr Arg Asn
                405                 410                 415 act acc ctt cca aga ggc ggt ggt aaa gac gga tgc tcg cca att gtt             1296
Thr Thr Leu Pro Arg Gly Gly Gly Lys Asp Gly Cys Ser Pro Ile Val
            420                 425                 430 gtc aag aag ggt caa gtt gtc atg tac act gtc att ggt acc cac aga             1344
Val Lys Lys Gly Gln Val Val Met Tyr Thr Val Ile Gly Thr His Arg
        435                 440                 445 gac cca agt atc tac ggt gcc gac gcc gac gtc ttc aga cca gaa aga             1392
Asp Pro Ser Ile Tyr Gly Ala Asp Ala Asp Val Phe Arg Pro Glu Arg
450                 455                 460 tgg ttc gag cca gaa act aga aag ttg ggc tgg gca tat gtt cca ttc             1440
Trp Phe Glu Pro Glu Thr Arg Lys Leu Gly Trp Ala Tyr Val Pro Phe
465                 470                 475                 480 aat ggt ggt cca aga atc tgt ttg ggt cag cag ttt gcc ttg act gaa             1488
Asn Gly Gly Pro Arg Ile Cys Leu Gly Gln Gln Phe Ala Leu Thr Glu
                485                 490                 495 gct tca tac gtc act gtc aga ttg ctc caa gag ttt gga aac ttg tcc             1536
Ala Ser Tyr Val Thr Val Arg Leu Leu Gln Glu Phe Gly Asn Leu Ser
            500                 505                 510 ctg gat cca aac gct gag tac cca cca aaa ttg cag aac acc ttg acc             1584
Leu Asp Pro Asn Ala Glu Tyr Pro Pro Lys Leu Gln Asn Thr Leu Thr
        515                 520                 525 ttg tca ctc ttt gat ggt gct gac gtt aga atg ttc taa                         1623
Leu Ser Leu Phe Asp Gly Ala Asp Val Arg Met Phe
530                 535                 540

<210> SEQ ID NO 12
<211> LENGTH: 540
<212> TYPE: PRT
```

<213> ORGANISM: Candida tropicalis

<400> SEQUENCE: 12

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Lys Tyr Leu Glu Arg Arg Phe His Ala Lys Pro Leu Gly Asn Val Val
    50                  55                  60

Leu Asp Pro Thr Phe Gly Ile Ala Thr Pro Leu Ile Leu Ile Tyr Leu
65                  70                  75                  80

Lys Ser Lys Gly Thr Val Met Lys Phe Ala Trp Ser Phe Trp Asn Asn
                85                  90                  95

Lys Tyr Ile Val Lys Asp Pro Lys Tyr Lys Thr Thr Gly Leu Arg Ile
            100                 105                 110

Val Gly Leu Pro Leu Ile Glu Thr Ile Asp Pro Glu Asn Ile Lys Ala
        115                 120                 125

Val Leu Ala Thr Gln Phe Asn Asp Phe Ser Leu Gly Thr Arg His Asp
130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
210                 215                 220

Ser Ala Glu Ser Leu Arg Asp Asp Ser Val Gly Leu Thr Pro Thr Thr
225                 230                 235                 240

Lys Asp Phe Glu Gly Arg Gly Asp Phe Ala Asp Ala Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ala Glu Phe Arg Lys Ser Ile Ala Ile Val His Lys Phe
        275                 280                 285

Ala Asp His Tyr Val Gln Lys Ala Leu Glu Leu Thr Asp Asp Asp Leu
290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
370                 375                 380

Ser Leu Lys Ser Cys Glu Tyr Leu Lys Ala Val Ile Asn Glu Ala Leu
385                 390                 395                 400

```
Arg Leu Tyr Pro Ser Val Pro His Asn Phe Arg Val Ala Thr Arg Asn
            405                 410                 415

Thr Thr Leu Pro Arg Gly Gly Lys Asp Gly Cys Ser Pro Ile Val
        420                 425                 430

Val Lys Lys Gly Gln Val Val Met Tyr Thr Val Ile Gly Thr His Arg
        435                 440                 445

Asp Pro Ser Ile Tyr Gly Ala Asp Ala Asp Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Gly Asn Leu Ser
            500                 505                 510

Leu Asp Pro Asn Ala Glu Tyr Pro Pro Lys Leu Gln Asn Thr Leu Thr
        515                 520                 525

Leu Ser Leu Phe Asp Gly Ala Asp Val Arg Met Phe
        530                 535                 540

<210> SEQ ID NO 13
<211> LENGTH: 1554
<212> TYPE: DNA
<213> ORGANISM: Candida tropicalis
<220> FEATURE:
<221> NAME/KEY: CDS
<222> LOCATION: (1)..(1551)

<400> SEQUENCE: 13 atg att gaa caa ctc cta gaa tat tgg tat gtc gtt gtg cca gtg ttg        48
Met Ile Glu Gln Leu Leu Glu Tyr Trp Tyr Val Val Val Pro Val Leu
1               5                   10                  15 tac atc atc aaa caa ctc ctt gca tac aca aag act cgc gtc ttg atg        96
Tyr Ile Ile Lys Gln Leu Leu Ala Tyr Thr Lys Thr Arg Val Leu Met
            20                  25                  30 aaa aag ttg ggt gct gct cca gtc aca aac aag ttg tac gac aac gct       144
Lys Lys Leu Gly Ala Ala Pro Val Thr Asn Lys Leu Tyr Asp Asn Ala
        35                  40                  45 ttc ggt atc gtc aat gga tgg aag gct ctc cag ttc aag aaa gag ggc       192
Phe Gly Ile Val Asn Gly Trp Lys Ala Leu Gln Phe Lys Lys Glu Gly
    50                  55                  60 agg gct caa gag tac aac gat tac aag ttt gac cac tcc aag aac cca       240
Arg Ala Gln Glu Tyr Asn Asp Tyr Lys Phe Asp His Ser Lys Asn Pro
65                  70                  75                  80 agc gtg ggc acc tac gtc agt att ctt ttc ggc acc agg atc gtc gtg       288
Ser Val Gly Thr Tyr Val Ser Ile Leu Phe Gly Thr Arg Ile Val Val
                85                  90                  95 acc aaa gat cca gag aat atc aaa gct att ttg gca acc cag ttt ggt       336
Thr Lys Asp Pro Glu Asn Ile Lys Ala Ile Leu Ala Thr Gln Phe Gly
            100                 105                 110 gat ttt tct ttg ggc aag agg cac act ctt ttt aag cct ttg tta ggt       384
Asp Phe Ser Leu Gly Lys Arg His Thr Leu Phe Lys Pro Leu Leu Gly
        115                 120                 125 gat ggg atc ttc aca ttg gac ggc gaa ggc tgg aag cac agc aga gcc       432
Asp Gly Ile Phe Thr Leu Asp Gly Glu Gly Trp Lys His Ser Arg Ala
    130                 135                 140 atg ttg aga cca cag ttt gcc aga gaa caa gtt gct cat gtg acg tcg       480
Met Leu Arg Pro Gln Phe Ala Arg Glu Gln Val Ala His Val Thr Ser
145                 150                 155                 160 ttg gaa cca cac ttc cag ttg ttg aag aag cat att ctt aag cac aag       528
```

```
Leu Glu Pro His Phe Gln Leu Leu Lys Lys His Ile Leu Lys His Lys
            165                 170                 175 ggt gaa tac ttt gat atc cag gaa ttg ttc ttt aga ttt acc gtt gat    576
Gly Glu Tyr Phe Asp Ile Gln Glu Leu Phe Phe Arg Phe Thr Val Asp
            180                 185                 190 tcg gcc acg gag ttc tta ttt ggt gag tcc gtg cac tcc tta aag gac    624
Ser Ala Thr Glu Phe Leu Phe Gly Glu Ser Val His Ser Leu Lys Asp
            195                 200                 205 gaa tct att ggt atc aac caa gac gat ata gat ttt gct ggt aga aag    672
Glu Ser Ile Gly Ile Asn Gln Asp Asp Ile Asp Phe Ala Gly Arg Lys
210                 215                 220 gac ttt gct gag tcg ttc aac aaa gcc cag gaa tac ttg gct att aga    720
Asp Phe Ala Glu Ser Phe Asn Lys Ala Gln Glu Tyr Leu Ala Ile Arg
225                 230                 235                 240 acc ttg gtg cag acg ttc tac tgg ttg gtc aac aac aag gag ttt aga    768
Thr Leu Val Gln Thr Phe Tyr Trp Leu Val Asn Asn Lys Glu Phe Arg
            245                 250                 255 gac tgt acc aag ctg gtg cac aag ttc acc aac tac tat gtt cag aaa    816
Asp Cys Thr Lys Leu Val His Lys Phe Thr Asn Tyr Tyr Val Gln Lys
            260                 265                 270 gct ttg gat gct agc cca gaa gag ctt gaa aag caa agt ggg tat gtg    864
Ala Leu Asp Ala Ser Pro Glu Glu Leu Glu Lys Gln Ser Gly Tyr Val
            275                 280                 285 ttc ttg tac gag ctt gtc aag cag aca aga gac ccc aat gtg ttg cgt    912
Phe Leu Tyr Glu Leu Val Lys Gln Thr Arg Asp Pro Asn Val Leu Arg
290                 295                 300 gac cag tct ttg aac atc ttg ttg gcc gga aga gac acc act gct ggg    960
Asp Gln Ser Leu Asn Ile Leu Leu Ala Gly Arg Asp Thr Thr Ala Gly
305                 310                 315                 320 ttg ttg tcg ttt gct gtc ttt gag ttg gcc aga cac cca gag atc tgg   1008
Leu Leu Ser Phe Ala Val Phe Glu Leu Ala Arg His Pro Glu Ile Trp
            325                 330                 335 gcc aag ttg aga gag gaa att gaa caa cag ttt ggt ctt gga gaa gac   1056
Ala Lys Leu Arg Glu Glu Ile Glu Gln Gln Phe Gly Leu Gly Glu Asp
            340                 345                 350 tct cgt gtt gaa gag att acc ttt gag agc ttg aag aga tgt gag tac   1104
Ser Arg Val Glu Glu Ile Thr Phe Glu Ser Leu Lys Arg Cys Glu Tyr
            355                 360                 365 ttg aaa gcg ttc ctt aat gaa acc ttg cgt att tac cca agt gtc cca   1152
Leu Lys Ala Phe Leu Asn Glu Thr Leu Arg Ile Tyr Pro Ser Val Pro
370                 375                 380 aga aac ttc aga atc gcc acc aag aac acg aca ttg cca agg ggc ggt   1200
Arg Asn Phe Arg Ile Ala Thr Lys Asn Thr Thr Leu Pro Arg Gly Gly
385                 390                 395                 400 ggt tca gac ggt acc tcg cca atc ttg atc caa aag gga gaa gct gtg   1248
Gly Ser Asp Gly Thr Ser Pro Ile Leu Ile Gln Lys Gly Glu Ala Val
            405                 410                 415 tcg tat ggt atc aac tct act cat ttg gac cct gtc tat tac ggc cct   1296
Ser Tyr Gly Ile Asn Ser Thr His Leu Asp Pro Val Tyr Tyr Gly Pro
            420                 425                 430 gat gct gct gag ttc aga cca gag aga tgg ttt gag cca tca acc aaa   1344
Asp Ala Ala Glu Phe Arg Pro Glu Arg Trp Phe Glu Pro Ser Thr Lys
            435                 440                 445 aag ctc ggc tgg gct tac ttg cca ttc aac ggt ggt cca aga atc tgt   1392
Lys Leu Gly Trp Ala Tyr Leu Pro Phe Asn Gly Gly Pro Arg Ile Cys
450                 455                 460 ttg ggt cag cag ttt gcc ttg acg gaa gct ggc tat gtg ttg gtt aga   1440
Leu Gly Gln Gln Phe Ala Leu Thr Glu Ala Gly Tyr Val Leu Val Arg
465                 470                 475                 480
```

```
ttg gtg caa gag ttc tcc cac gtt agg ctg gac cca gac gag gtg tac    1488
Leu Val Gln Glu Phe Ser His Val Arg Leu Asp Pro Asp Glu Val Tyr
                485                 490                 495 ccg cca aag agg ttg acc aac ttg acc atg tgt ttg cag gat ggt gct    1536
Pro Pro Lys Arg Leu Thr Asn Leu Thr Met Cys Leu Gln Asp Gly Ala
        500                 505                 510 att gtc aag ttt gac tag                                            1554
Ile Val Lys Phe Asp
        515

<210> SEQ ID NO 14
<211> LENGTH: 517
<212> TYPE: PRT
<213> ORGANISM: Candida tropicalis

<400> SEQUENCE: 14

Met Ile Glu Gln Leu Leu Glu Tyr Trp Tyr Val Val Pro Val Leu
1               5                   10                  15

Tyr Ile Ile Lys Gln Leu Leu Ala Tyr Thr Lys Thr Arg Val Leu Met
                20                  25                  30

Lys Lys Leu Gly Ala Ala Pro Val Thr Asn Lys Leu Tyr Asp Asn Ala
            35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
                100                 105                 110

Asp Phe Ser Leu Gly Lys Arg His Thr Leu Phe Lys Pro Leu Leu Gly
            115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
                180                 185                 190

Ser Ala Thr Glu Phe Leu Phe Gly Glu Ser Val His Ser Leu Lys Asp
            195                 200                 205

Glu Ser Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Leu Val His Lys Phe Thr Asn Tyr Tyr Val Gln Lys
                260                 265                 270

Ala Leu Asp Ala Ser Pro Glu Glu Leu Glu Lys Gln Ser Gly Tyr Val
            275                 280                 285

Phe Leu Tyr Glu Leu Val Lys Gln Thr Arg Asp Pro Asn Val Leu Arg
    290                 295                 300

Asp Gln Ser Leu Asn Ile Leu Leu Ala Gly Arg Asp Thr Thr Ala Gly
305                 310                 315                 320
```

```
Leu Leu Ser Phe Ala Val Phe Glu Leu Ala Arg His Pro Glu Ile Trp
            325                 330                 335

Ala Lys Leu Arg Glu Glu Ile Glu Gln Gln Phe Gly Leu Gly Glu Asp
        340                 345                 350

Ser Arg Val Glu Glu Ile Thr Phe Glu Ser Leu Lys Arg Cys Glu Tyr
            355                 360                 365

Leu Lys Ala Phe Leu Asn Glu Thr Leu Arg Ile Tyr Pro Ser Val Pro
        370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
            405                 410                 415

Ser Tyr Gly Ile Asn Ser Thr His Leu Asp Pro Val Tyr Tyr Gly Pro
        420                 425                 430

Asp Ala Ala Glu Phe Arg Pro Glu Arg Trp Phe Glu Pro Ser Thr Lys
        435                 440                 445

Lys Leu Gly Trp Ala Tyr Leu Pro Phe Asn Gly Gly Pro Arg Ile Cys
        450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Leu Asp Pro Asp Glu Val Tyr
            485                 490                 495

Pro Pro Lys Arg Leu Thr Asn Leu Thr Met Cys Leu Gln Asp Gly Ala
        500                 505                 510

Ile Val Lys Phe Asp
        515

<210> SEQ ID NO 15
<211> LENGTH: 1554
<212> TYPE: DNA
<213> ORGANISM: Candida tropicalis
<220> FEATURE:
<221> NAME/KEY: CDS
<222> LOCATION: (1)..(1551)

<400> SEQUENCE: 15 atg att gaa caa atc cta gaa tat tgg tat att gtt gtg cct gtg ttg      48
Met Ile Glu Gln Ile Leu Glu Tyr Trp Tyr Ile Val Val Pro Val Leu
1               5                   10                  15 tac atc atc aaa caa ctc att gcc tac agc aag act cgc gtc ttg atg      96
Tyr Ile Ile Lys Gln Leu Ile Ala Tyr Ser Lys Thr Arg Val Leu Met
            20                  25                  30 aaa cag ttg ggt gct gct cca atc aca aac cag ttg tac gac aac gtt     144
Lys Gln Leu Gly Ala Ala Pro Ile Thr Asn Gln Leu Tyr Asp Asn Val
        35                  40                  45 ttc ggt atc gtc aac gga tgg aag gct ctc cag ttc aag aaa gag ggc     192
Phe Gly Ile Val Asn Gly Trp Lys Ala Leu Gln Phe Lys Lys Glu Gly
    50                  55                  60 aga gct caa gag tac aac gat cac aag ttt gac agc tcc aag aac cca     240
Arg Ala Gln Glu Tyr Asn Asp His Lys Phe Asp Ser Ser Lys Asn Pro
65                  70                  75                  80 agc gtc ggc acc tat gtc agt att ctt ttt ggc acc aag att gtc gtg     288
Ser Val Gly Thr Tyr Val Ser Ile Leu Phe Gly Thr Lys Ile Val Val
                85                  90                  95 acc aag gat cca gag aat atc aaa gct att ttg gca acc cag ttt ggc     336
Thr Lys Asp Pro Glu Asn Ile Lys Ala Ile Leu Ala Thr Gln Phe Gly
            100                 105                 110
```

```
gat ttt tct ttg ggc aag aga cac gct ctt ttt aaa cct ttg tta ggt    384
Asp Phe Ser Leu Gly Lys Arg His Ala Leu Phe Lys Pro Leu Leu Gly
        115                 120                 125 gat ggg atc ttc acc ttg gac ggc gaa ggc tgg aag cat agc aga tcc    432
Asp Gly Ile Phe Thr Leu Asp Gly Glu Gly Trp Lys His Ser Arg Ser
    130                 135                 140 atg tta aga cca cag ttt gcc aga gaa caa gtt gct cat gtg acg tcg    480
Met Leu Arg Pro Gln Phe Ala Arg Glu Gln Val Ala His Val Thr Ser
145                 150                 155                 160 ttg gaa cca cac ttc cag ttg ttg aag aag cat atc ctt aaa cac aag    528
Leu Glu Pro His Phe Gln Leu Leu Lys Lys His Ile Leu Lys His Lys
                165                 170                 175 ggt gag tac ttt gat atc cag gaa ttg ttc ttt aga ttt act gtc gac    576
Gly Glu Tyr Phe Asp Ile Gln Glu Leu Phe Phe Arg Phe Thr Val Asp
            180                 185                 190 tcg gcc acg gag ttc tta ttt ggt gag tcc gtg cac tcc tta aag gac    624
Ser Ala Thr Glu Phe Leu Phe Gly Glu Ser Val His Ser Leu Lys Asp
        195                 200                 205 gaa act atc ggt atc aac caa gac gat ata gat ttt gct ggt aga aag    672
Glu Thr Ile Gly Ile Asn Gln Asp Asp Ile Asp Phe Ala Gly Arg Lys
    210                 215                 220 gac ttt gct gag tcg ttc aac aaa gcc cag gag tat ttg tct att aga    720
Asp Phe Ala Glu Ser Phe Asn Lys Ala Gln Glu Tyr Leu Ser Ile Arg
225                 230                 235                 240 att ttg gtg cag acc ttc tac tgg ttg atc aac aac aag gag ttt aga    768
Ile Leu Val Gln Thr Phe Tyr Trp Leu Ile Asn Asn Lys Glu Phe Arg
                245                 250                 255 gac tgt acc aag ctg gtg cac aag ttt acc aac tac tat gtt cag aaa    816
Asp Cys Thr Lys Leu Val His Lys Phe Thr Asn Tyr Tyr Val Gln Lys
            260                 265                 270 gct ttg gat gct acc cca gag gaa ctt gaa aag caa ggc ggg tat gtg    864
Ala Leu Asp Ala Thr Pro Glu Glu Leu Glu Lys Gln Gly Gly Tyr Val
        275                 280                 285 ttc ttg tat gag ctt gtc aag cag acg aga gac ccc aag gtg ttg cgt    912
Phe Leu Tyr Glu Leu Val Lys Gln Thr Arg Asp Pro Lys Val Leu Arg
    290                 295                 300 gac cag tct ttg aac atc ttg ttg gca gga aga gac acc act gct ggg    960
Asp Gln Ser Leu Asn Ile Leu Leu Ala Gly Arg Asp Thr Thr Ala Gly
305                 310                 315                 320 ttg ttg tcc ttt gct gtg ttt gag ttg gcc aga aac cca cac atc tgg   1008
Leu Leu Ser Phe Ala Val Phe Glu Leu Ala Arg Asn Pro His Ile Trp
                325                 330                 335 gcc aag ttg aga gag gaa att gaa cag cag ttt ggt ctt gga gaa gac   1056
Ala Lys Leu Arg Glu Glu Ile Glu Gln Gln Phe Gly Leu Gly Glu Asp
            340                 345                 350 tct cgt gtt gaa gag att acc ttt gag agc ttg aag aga tgt gag tac   1104
Ser Arg Val Glu Glu Ile Thr Phe Glu Ser Leu Lys Arg Cys Glu Tyr
        355                 360                 365 ttg aaa gcg ttc ctt aac gaa acc ttg cgt gtt tac cca agt gtc cca   1152
Leu Lys Ala Phe Leu Asn Glu Thr Leu Arg Val Tyr Pro Ser Val Pro
    370                 375                 380 aga aac ttc aga atc gcc acc aag aat aca aca ttg cca agg ggt ggt   1200
Arg Asn Phe Arg Ile Ala Thr Lys Asn Thr Thr Leu Pro Arg Gly Gly
385                 390                 395                 400 ggt cca gac ggt acc cag cca atc ttg atc caa aag gga gaa ggt gtg   1248
Gly Pro Asp Gly Thr Gln Pro Ile Leu Ile Gln Lys Gly Glu Gly Val
                405                 410                 415 tcg tat ggt atc aac tct acc cac tta gat cct gtc tat tat ggc cct   1296
Ser Tyr Gly Ile Asn Ser Thr His Leu Asp Pro Val Tyr Tyr Gly Pro
            420                 425                 430
```

```
gat gct gct gag ttc aga cca gag aga tgg ttt gag cca tca acc aga    1344
Asp Ala Ala Glu Phe Arg Pro Glu Arg Trp Phe Glu Pro Ser Thr Arg
            435                 440                 445 aag ctc ggc tgg gct tac ttg cca ttc aac ggt ggg cca cga atc tgt    1392
Lys Leu Gly Trp Ala Tyr Leu Pro Phe Asn Gly Gly Pro Arg Ile Cys
        450                 455                 460 ttg ggt cag cag ttt gcc ttg acc gaa gct ggt tac gtt ttg gtc aga    1440
Leu Gly Gln Gln Phe Ala Leu Thr Glu Ala Gly Tyr Val Leu Val Arg
465                 470                 475                 480 ttg gtg caa gag ttc tcc cac att agg ctg gac cca gat gaa gtg tat    1488
Leu Val Gln Glu Phe Ser His Ile Arg Leu Asp Pro Asp Glu Val Tyr
                485                 490                 495 cca cca aag agg ttg acc aac ttg acc atg tgt ttg cag gat ggt gct    1536
Pro Pro Lys Arg Leu Thr Asn Leu Thr Met Cys Leu Gln Asp Gly Ala
            500                 505                 510 att gtc aag ttt gac tag                                            1554
Ile Val Lys Phe Asp
        515

<210> SEQ ID NO 16
<211> LENGTH: 517
<212> TYPE: PRT
<213> ORGANISM: Candida tropicalis

<400> SEQUENCE: 16

Met Ile Glu Gln Ile Leu Glu Tyr Trp Tyr Ile Val Val Pro Val Leu
1               5                   10                  15

Tyr Ile Ile Lys Gln Leu Ile Ala Tyr Ser Lys Thr Arg Val Leu Met
            20                  25                  30

Lys Gln Leu Gly Ala Ala Pro Ile Thr Asn Gln Leu Tyr Asp Asn Val
        35                  40                  45

Phe Gly Ile Val Asn Gly Trp Lys Ala Leu Gln Phe Lys Lys Glu Gly
    50                  55                  60

Arg Ala Gln Glu Tyr Asn Asp His Lys Phe Asp Ser Ser Lys Asn Pro
65                  70                  75                  80

Ser Val Gly Thr Tyr Val Ser Ile Leu Phe Gly Thr Lys Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Ala Leu Phe Lys Pro Leu Leu Gly
        115                 120                 125

Asp Gly Ile Phe Thr Leu Asp Gly Glu Gly Trp Lys His Ser Arg Ser
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Thr Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ser Ile Arg
225                 230                 235                 240

Ile Leu Val Gln Thr Phe Tyr Trp Leu Ile Asn Asn Lys Glu Phe Arg
```

-continued

```
                    245                 250                 255
Asp Cys Thr Lys Leu Val His Lys Phe Thr Asn Tyr Tyr Val Gln Lys
                260                 265                 270
Ala Leu Asp Ala Thr Pro Glu Glu Leu Glu Lys Gln Gly Gly Tyr Val
            275                 280                 285
Phe Leu Tyr Glu Leu Val Lys Gln Thr Arg Asp Pro Lys Val Leu Arg
        290                 295                 300
Asp Gln Ser Leu Asn Ile Leu Leu Ala Gly Arg Asp Thr Thr Ala Gly
305                 310                 315                 320
Leu Leu Ser Phe Ala Val Phe Glu Leu Ala Arg Asn Pro His Ile Trp
                325                 330                 335
Ala Lys Leu Arg Glu Glu Ile Glu Gln Gln Phe Gly Leu Gly Glu Asp
                340                 345                 350
Ser Arg Val Glu Glu Ile Thr Phe Glu Ser Leu Lys Arg Cys Glu Tyr
            355                 360                 365
Leu Lys Ala Phe Leu Asn Glu Thr Leu Arg Val Tyr Pro Ser Val Pro
        370                 375                 380
Arg Asn Phe Arg Ile Ala Thr Lys Asn Thr Thr Leu Pro Arg Gly Gly
385                 390                 395                 400
Gly Pro Asp Gly Thr Gln Pro Ile Leu Ile Gln Lys Gly Glu Gly Val
                405                 410                 415
Ser Tyr Gly Ile Asn Ser Thr His Leu Asp Pro Val Tyr Tyr Gly Pro
            420                 425                 430
Asp Ala Ala Glu Phe Arg Pro Glu Arg Trp Phe Glu Pro Ser Thr Arg
        435                 440                 445
Lys Leu Gly Trp Ala Tyr Leu Pro Phe Asn Gly Gly Pro Arg Ile Cys
    450                 455                 460
Leu Gly Gln Gln Phe Ala Leu Thr Glu Ala Gly Tyr Val Leu Val Arg
465                 470                 475                 480
Leu Val Gln Glu Phe Ser His Ile Arg Leu Asp Pro Asp Glu Val Tyr
                485                 490                 495
Pro Pro Lys Arg Leu Thr Asn Leu Thr Met Cys Leu Gln Asp Gly Ala
            500                 505                 510
Ile Val Lys Phe Asp
        515

<210> SEQ ID NO 17
<211> LENGTH: 1539
<212> TYPE: DNA
<213> ORGANISM: Candida tropicalis
<220> FEATURE:
<221> NAME/KEY: CDS
<222> LOCATION: (1)..(1536)

<400> SEQUENCE: 17 atg ctc gat cag atc tta cat tac tgg tac att gtc ttg cca ttg ttg      48
Met Leu Asp Gln Ile Leu His Tyr Trp Tyr Ile Val Leu Pro Leu Leu
1               5                   10                  15 gcc att atc aac cag atc gtg gct cat gtc agg acc aat tat ttg atg      96
Ala Ile Ile Asn Gln Ile Val Ala His Val Arg Thr Asn Tyr Leu Met
            20                  25                  30 aag aaa ttg ggt gct aag cca ttc aca cac gtc caa cgt gac ggg tgg     144
Lys Lys Leu Gly Ala Lys Pro Phe Thr His Val Gln Arg Asp Gly Trp
        35                  40                  45 ttg ggc ttc aaa ttc ggc cgt gaa ttc ctc aaa gca aaa agt gct ggg     192
Leu Gly Phe Lys Phe Gly Arg Glu Phe Leu Lys Ala Lys Ser Ala Gly
    50                  55                  60
```

-continued

```
aga ctg gtt gat tta atc atc tcc cgt ttc cac gat aat gag gac act    240
Arg Leu Val Asp Leu Ile Ile Ser Arg Phe His Asp Asn Glu Asp Thr
 65                  70                  75                  80 ttc tcc agc tat gct ttt ggc aac cat gtg gtg ttc acc agg gac ccc    288
Phe Ser Ser Tyr Ala Phe Gly Asn His Val Val Phe Thr Arg Asp Pro
                 85                  90                  95 gag aat atc aag gcg ctt ttg gca acc cag ttt ggt gat ttt tca ttg    336
Glu Asn Ile Lys Ala Leu Leu Ala Thr Gln Phe Gly Asp Phe Ser Leu
            100                 105                 110 ggc agc agg gtc aag ttc ttc aaa cca tta ttg ggg tac ggt atc ttc    384
Gly Ser Arg Val Lys Phe Phe Lys Pro Leu Leu Gly Tyr Gly Ile Phe
        115                 120                 125 aca ttg gac gcc gaa ggc tgg aag cac agc aga gcc atg ttg aga cca    432
Thr Leu Asp Ala Glu Gly Trp Lys His Ser Arg Ala Met Leu Arg Pro
    130                 135                 140 cag ttt gcc aga gaa caa gtt gct cat gtg acg tcg ttg gaa cca cac    480
Gln Phe Ala Arg Glu Gln Val Ala His Val Thr Ser Leu Glu Pro His
145                 150                 155                 160 ttc cag ttg ttg aag aag cat atc ctt aaa cac aag ggt gag tac ttt    528
Phe Gln Leu Leu Lys Lys His Ile Leu Lys His Lys Gly Glu Tyr Phe
                165                 170                 175 gat atc cag gaa ttg ttc ttt aga ttt act gtc gac tcg gcc acg gag    576
Asp Ile Gln Glu Leu Phe Phe Arg Phe Thr Val Asp Ser Ala Thr Glu
            180                 185                 190 ttc tta ttt ggt gag tcc gtg cac tcc tta aag gac gag gaa att ggc    624
Phe Leu Phe Gly Glu Ser Val His Ser Leu Lys Asp Glu Glu Ile Gly
        195                 200                 205 tac gac acg aaa gac atg tct gaa gaa aga cgc aga ttt gcc gac gcg    672
Tyr Asp Thr Lys Asp Met Ser Glu Glu Arg Arg Arg Phe Ala Asp Ala
    210                 215                 220 ttc aac aag tcg caa gtc tac gtg gcc acc aga gtt gct tta cag aac    720
Phe Asn Lys Ser Gln Val Tyr Val Ala Thr Arg Val Ala Leu Gln Asn
225                 230                 235                 240 ttg tac tgg ttg gtc aac aac aaa gag ttc aag gag tgc aat gac att    768
Leu Tyr Trp Leu Val Asn Asn Lys Glu Phe Lys Glu Cys Asn Asp Ile
                245                 250                 255 gtc cac aag ttt acc aac tac tat gtt cag aaa gcc ttg gat gct acc    816
Val His Lys Phe Thr Asn Tyr Tyr Val Gln Lys Ala Leu Asp Ala Thr
            260                 265                 270 cca gag gaa ctt gaa aag caa ggc ggg tat gtg ttc ttg tat gag ctt    864
Pro Glu Glu Leu Glu Lys Gln Gly Gly Tyr Val Phe Leu Tyr Glu Leu
        275                 280                 285 gtc aag cag acg aga gac ccc aag gtg ttg cgt gac cag tct ttg aac    912
Val Lys Gln Thr Arg Asp Pro Lys Val Leu Arg Asp Gln Ser Leu Asn
    290                 295                 300 atc ttg ttg gca gga aga gac acc act gct ggg ttg ttg tcc ttt gct    960
Ile Leu Leu Ala Gly Arg Asp Thr Thr Ala Gly Leu Leu Ser Phe Ala
305                 310                 315                 320 gtg ttt gag ttg gcc aga aac cca cac atc tgg gcc aag ttg aga gag   1008
Val Phe Glu Leu Ala Arg Asn Pro His Ile Trp Ala Lys Leu Arg Glu
                325                 330                 335 gaa att gaa cag cag ttt ggt ctt gga gaa gac tct cgt gtt gaa gag   1056
Glu Ile Glu Gln Gln Phe Gly Leu Gly Glu Asp Ser Arg Val Glu Glu
            340                 345                 350 att acc ttt gag agc ttg aag aga tgt gag tac ttg aag gcc gtg ttg   1104
Ile Thr Phe Glu Ser Leu Lys Arg Cys Glu Tyr Leu Lys Ala Val Leu
        355                 360                 365 aac gaa act ttg aga tta cac cca agt gtc cca aga aac gca aga ttt   1152
Asn Glu Thr Leu Arg Leu His Pro Ser Val Pro Arg Asn Ala Arg Phe
```

```
                 370                 375                 380
gcg att aaa gac acg act tta cca aga ggt ggt ggc ccc aac ggc aag      1200
Ala Ile Lys Asp Thr Thr Leu Pro Arg Gly Gly Gly Pro Asn Gly Lys
385                 390                 395                 400 gat cct atc ttg atc agg aag gat gag gtg gtg cag tac tcc atc tcg      1248
Asp Pro Ile Leu Ile Arg Lys Asp Glu Val Val Gln Tyr Ser Ile Ser
                405                 410                 415 gca act cag aca aat cct gct tat tat ggc gcc gat gct gct gat ttt      1296
Ala Thr Gln Thr Asn Pro Ala Tyr Tyr Gly Ala Asp Ala Ala Asp Phe
            420                 425                 430 aga ccg gaa aga tgg ttt gaa cca tca act aga aac ttg gga tgg gct      1344
Arg Pro Glu Arg Trp Phe Glu Pro Ser Thr Arg Asn Leu Gly Trp Ala
        435                 440                 445 ttc ttg cca ttc aac ggt ggt cca aga atc tgt ttg gga caa cag ttt      1392
Phe Leu Pro Phe Asn Gly Gly Pro Arg Ile Cys Leu Gly Gln Gln Phe
    450                 455                 460 gct ttg act gaa gcc ggt tac gtt ttg gtt aga ctt gtt cag gag ttt      1440
Ala Leu Thr Glu Ala Gly Tyr Val Leu Val Arg Leu Val Gln Glu Phe
465                 470                 475                 480 cca aac ttg tca caa gac ccc gaa acc aag tac cca cca cct aga ttg      1488
Pro Asn Leu Ser Gln Asp Pro Glu Thr Lys Tyr Pro Pro Pro Arg Leu
                485                 490                 495 gca cac ttg acg atg tgc ttg ttt gac ggt gca cac gtc aag atg tca      1536
Ala His Leu Thr Met Cys Leu Phe Asp Gly Ala His Val Lys Met Ser
            500                 505                 510 tag                                                                  1539

<210> SEQ ID NO 18
<211> LENGTH: 512
<212> TYPE: PRT
<213> ORGANISM: Candida tropicalis

<400> SEQUENCE: 18

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Lys Ala Lys Ser Ala Gly
    50                  55                  60

Arg Leu Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Ala Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190
```

Phe Leu Phe Gly Glu Ser Val His Ser Leu Lys Asp Glu Glu Ile Gly
    195                 200                 205

Tyr Asp Thr Lys Asp Met Ser Glu Glu Arg Arg Phe Ala Asp Ala
210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Val Gln Lys Ala Leu Asp Ala Thr
                260                 265                 270

Pro Glu Glu Leu Glu Lys Gln Gly Gly Tyr Val Phe Leu Tyr Glu Leu
                275                 280                 285

Val Lys Gln Thr Arg Asp Pro Lys Val Leu Arg Asp Gln Ser Leu Asn
290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335

Glu Ile Glu Gln Gln Phe Gly Leu Gly Glu Asp Ser Arg Val Glu Glu
                340                 345                 350

Ile Thr Phe Glu Ser Leu Lys Arg Cys Glu Tyr Leu Lys Ala Val Leu
                355                 360                 365

Asn Glu Thr Leu Arg Leu His Pro Ser Val Pro Arg Asn Ala Arg Phe
370                 375                 380

Ala Ile Lys Asp Thr Thr Leu Pro Arg Gly Gly Gly Pro Asn Gly Lys
385                 390                 395                 400

Asp Pro Ile Leu Ile Arg Lys Asp Glu Val Val Gln Tyr Ser Ile Ser
                405                 410                 415

Ala Thr Gln Thr Asn Pro Ala Tyr Tyr Gly Ala Asp Ala Ala Asp Phe
                420                 425                 430

Arg Pro Glu Arg Trp Phe Glu Pro Ser Thr Arg Asn Leu Gly Trp Ala
                435                 440                 445

Phe Leu Pro Phe Asn Gly Gly Pro Arg Ile Cys Leu Gly Gln Gln Phe
                450                 455                 460

Ala Leu Thr Glu Ala Gly Tyr Val Leu Val Arg Leu Val Gln Glu Phe
465                 470                 475                 480

Pro Asn Leu Ser Gln Asp Pro Glu Thr Lys Tyr Pro Pro Arg Leu
                485                 490                 495

Ala His Leu Thr Met Cys Leu Phe Asp Gly Ala His Val Lys Met Ser
                500                 505                 510

<210> SEQ ID NO 19
<211> LENGTH: 1539
<212> TYPE: DNA
<213> ORGANISM: Candida tropicalis
<220> FEATURE:
<221> NAME/KEY: CDS
<222> LOCATION: (1)..(1536)

<400> SEQUENCE: 19 atg ctc gac cag atc ttc cat tac tgg tac att gtc ttg cca ttg ttg      48
Met Leu Asp Gln Ile Phe His Tyr Trp Tyr Ile Val Leu Pro Leu Leu
1               5                   10                  15 gtc att atc aag cag atc gtg gct cat gcc agg acc aat tat ttg atg      96
Val Ile Ile Lys Gln Ile Val Ala His Ala Arg Thr Asn Tyr Leu Met
            20                  25                  30

| | | |
|---|---|---|
| aag aag ttg ggc gct aag cca ttc aca cat gtc caa cta gac ggg tgg<br>Lys Lys Leu Gly Ala Lys Pro Phe Thr His Val Gln Leu Asp Gly Trp<br>35　　　　　　　　40　　　　　　　　45 | | 144 |
| ttt ggc ttc aaa ttt ggc cgt gaa ttc ctc aaa gct aaa agt gct ggg<br>Phe Gly Phe Lys Phe Gly Arg Glu Phe Leu Lys Ala Lys Ser Ala Gly<br>　50　　　　　　　　55　　　　　　　　60 | | 192 |
| agg cag gtt gat tta atc atc tcc cgt ttc cac gat aat gag gac act<br>Arg Gln Val Asp Leu Ile Ile Ser Arg Phe His Asp Asn Glu Asp Thr<br>65　　　　　　　　70　　　　　　　　75　　　　　　　　80 | | 240 |
| ttc tcc agc tat gct ttt ggc aac cat gtg gtg ttc acc agg gac ccc<br>Phe Ser Ser Tyr Ala Phe Gly Asn His Val Val Phe Thr Arg Asp Pro<br>　　　　　　　85　　　　　　　　90　　　　　　　　95 | | 288 |
| gag aat atc aag gcg ctt ttg gca acc cag ttt ggt gat ttt tca ttg<br>Glu Asn Ile Lys Ala Leu Leu Ala Thr Gln Phe Gly Asp Phe Ser Leu<br>　　　　　　100　　　　　　　105　　　　　　　110 | | 336 |
| gga agc agg gtc aaa ttc ttc aaa cca ttg ttg ggg tac ggt atc ttc<br>Gly Ser Arg Val Lys Phe Phe Lys Pro Leu Leu Gly Tyr Gly Ile Phe<br>　　　　115　　　　　　　120　　　　　　　125 | | 384 |
| acc ttg gac ggc gaa ggc tgg aag cac agc aga gcc atg ttg aga cca<br>Thr Leu Asp Gly Glu Gly Trp Lys His Ser Arg Ala Met Leu Arg Pro<br>130　　　　　　　135　　　　　　　140 | | 432 |
| cag ttt gcc aga gag caa gtt gct cat gtg acg tcg ttg gaa cca cat<br>Gln Phe Ala Arg Glu Gln Val Ala His Val Thr Ser Leu Glu Pro His<br>145　　　　　　　150　　　　　　　155　　　　　　　160 | | 480 |
| ttc cag ttg ttg aag aag cat att ctt aag cac aag ggt gaa tac ttt<br>Phe Gln Leu Leu Lys Lys His Ile Leu Lys His Lys Gly Glu Tyr Phe<br>　　　　　　165　　　　　　　170　　　　　　　175 | | 528 |
| gat atc cag gaa ttg ttc ttt aga ttt acc gtt gat tca gcg acg gag<br>Asp Ile Gln Glu Leu Phe Phe Arg Phe Thr Val Asp Ser Ala Thr Glu<br>　　　　　　180　　　　　　　185　　　　　　　190 | | 576 |
| ttc tta ttt ggt gag tcc gtg cac tcc tta agg gac gag gaa att ggc<br>Phe Leu Phe Gly Glu Ser Val His Ser Leu Arg Asp Glu Glu Ile Gly<br>　　　　195　　　　　　　200　　　　　　　205 | | 624 |
| tac gat acg aag gac atg gct gaa gaa aga cgc aaa ttt gcc gac gcg<br>Tyr Asp Thr Lys Asp Met Ala Glu Glu Arg Arg Lys Phe Ala Asp Ala<br>210　　　　　　　215　　　　　　　220 | | 672 |
| ttc aac aag tcg caa gtc tat ttg tcc acc aga gtt gct tta cag aca<br>Phe Asn Lys Ser Gln Val Tyr Leu Ser Thr Arg Val Ala Leu Gln Thr<br>225　　　　　　　230　　　　　　　235　　　　　　　240 | | 720 |
| ttg tac tgg ttg gtc aac aac aaa gag ttc aag gag tgc aac gac att<br>Leu Tyr Trp Leu Val Asn Asn Lys Glu Phe Lys Glu Cys Asn Asp Ile<br>　　　　　　245　　　　　　　250　　　　　　　255 | | 768 |
| gtc cac aag ttc acc aac tac tat gtt cag aaa gcc ttg gat gct acc<br>Val His Lys Phe Thr Asn Tyr Tyr Val Gln Lys Ala Leu Asp Ala Thr<br>　　　　　　260　　　　　　　265　　　　　　　270 | | 816 |
| cca gag gaa ctt gaa aaa caa ggc ggg tat gtg ttc ttg tac gag ctt<br>Pro Glu Glu Leu Glu Lys Gln Gly Gly Tyr Val Phe Leu Tyr Glu Leu<br>　　　　275　　　　　　　280　　　　　　　285 | | 864 |
| gcc aag cag acg aaa gac ccc aat gtg ttg cgt gac cag tct ttg aac<br>Ala Lys Gln Thr Lys Asp Pro Asn Val Leu Arg Asp Gln Ser Leu Asn<br>290　　　　　　　295　　　　　　　300 | | 912 |
| atc ttg ttg gct gga agg gac acc act gct ggg ttg ttg tcc ttt gct<br>Ile Leu Leu Ala Gly Arg Asp Thr Thr Ala Gly Leu Leu Ser Phe Ala<br>305　　　　　　　310　　　　　　　315　　　　　　　320 | | 960 |
| gtg ttt gag ttg gcc agg aac cca cac atc tgg gcc aag ttg aga gag<br>Val Phe Glu Leu Ala Arg Asn Pro His Ile Trp Ala Lys Leu Arg Glu<br>　　　　　　325　　　　　　　330　　　　　　　335 | | 1008 |
| gaa att gaa tca cac ttt ggg ctg ggt gag gac tct cgt gtt gaa gag<br>Glu Ile Glu Ser His Phe Gly Leu Gly Glu Asp Ser Arg Val Glu Glu | | 1056 |

```
att acc ttt gag agc ttg aag aga tgt gag tac ttg aaa gcc gtg ttg      1104
Ile Thr Phe Glu Ser Leu Lys Arg Cys Glu Tyr Leu Lys Ala Val Leu
        355                 360                 365 aac gaa acg ttg aga tta cac cca agt gtc cca aga aac gca aga ttt      1152
Asn Glu Thr Leu Arg Leu His Pro Ser Val Pro Arg Asn Ala Arg Phe
370                 375                 380 gcg att aaa gac acg act tta cca aga ggt ggc ccc aac ggc aag          1200
Ala Ile Lys Asp Thr Thr Leu Pro Arg Gly Gly Pro Asn Gly Lys
385                 390                 395                 400 gat cct atc ttg atc aga aag aat gag gtg gtg caa tac tcc atc tcg      1248
Asp Pro Ile Leu Ile Arg Lys Asn Glu Val Val Gln Tyr Ser Ile Ser
                405                 410                 415 gca act cag aca aat cct gct tat tat ggc gcc gat gct gct gat ttt      1296
Ala Thr Gln Thr Asn Pro Ala Tyr Tyr Gly Ala Asp Ala Ala Asp Phe
            420                 425                 430 aga ccg gaa aga tgg ttt gag cca tca act aga aac ttg gga tgg gct      1344
Arg Pro Glu Arg Trp Phe Glu Pro Ser Thr Arg Asn Leu Gly Trp Ala
                435                 440                 445 tac ttg cca ttc aac ggt ggt cca aga atc tgc ttg gga caa cag ttt      1392
Tyr Leu Pro Phe Asn Gly Gly Pro Arg Ile Cys Leu Gly Gln Gln Phe
450                 455                 460 gct ttg acc gaa gcc ggt tac gtt ttg gtt aga ctt gtt cag gaa ttc      1440
Ala Leu Thr Glu Ala Gly Tyr Val Leu Val Arg Leu Val Gln Glu Phe
465                 470                 475                 480 cct agc ttg tca cag gac ccc gaa act gag tac cca cca cct aga ttg      1488
Pro Ser Leu Ser Gln Asp Pro Glu Thr Glu Tyr Pro Pro Pro Arg Leu
                485                 490                 495 gca cac ttg acg atg tgc ttg ttt gac ggg gca tac gtc aag atg caa      1536
Ala His Leu Thr Met Cys Leu Phe Asp Gly Ala Tyr Val Lys Met Gln
                500                 505                 510 tag                                                                  1539

<210> SEQ ID NO 20
<211> LENGTH: 512
<212> TYPE: PRT
<213> ORGANISM: Candida tropicalis

<400> SEQUENCE: 20

Met Leu Asp Gln Ile Phe His Tyr Trp Tyr Ile Val Leu Pro Leu Leu
1               5                   10                  15

Val Ile Ile Lys Gln Ile Val Ala His Ala Arg Thr Asn Tyr Leu Met
            20                  25                  30

Lys Lys Leu Gly Ala Lys Pro Phe Thr His Val Gln Leu Asp Gly Trp
        35                  40                  45

Phe Gly Phe Lys Phe Gly Arg Glu Phe Leu Lys Ala Lys Ser Ala Gly
    50                  55                  60

Arg Gln Val Asp Leu Ile Ile Ser Arg Phe His Asp Asn Glu Asp Thr
65                  70                  75                  80

Phe Ser Ser Tyr Ala Phe Gly Asn His Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Gly Glu Gly Trp Lys His Ser Arg Ala Met Leu Arg Pro
    130                 135                 140
```

```
Gln Phe Ala Arg Glu Gln Val Ala His Val Thr Ser Leu Glu Pro His
145                 150                 155                 160
Phe Gln Leu Leu Lys Lys His Ile Leu Lys His Lys Gly Glu Tyr Phe
            165                 170                 175
Asp Ile Gln Glu Leu Phe Phe Arg Phe Thr Val Asp Ser Ala Thr Glu
        180                 185                 190
Phe Leu Phe Gly Glu Ser Val His Ser Leu Arg Asp Glu Glu Ile Gly
    195                 200                 205
Tyr Asp Thr Lys Asp Met Ala Glu Glu Arg Arg Lys Phe Ala Asp Ala
210                 215                 220
Phe Asn Lys Ser Gln Val Tyr Leu Ser Thr Arg Val Ala Leu Gln Thr
225                 230                 235                 240
Leu Tyr Trp Leu Val Asn Asn Lys Glu Phe Lys Glu Cys Asn Asp Ile
            245                 250                 255
Val His Lys Phe Thr Asn Tyr Val Gln Lys Ala Leu Asp Ala Thr
        260                 265                 270
Pro Glu Glu Leu Glu Lys Gln Gly Gly Tyr Val Phe Leu Tyr Glu Leu
    275                 280                 285
Ala Lys Gln Thr Lys Asp Pro Asn Val Leu Arg Asp Gln Ser Leu Asn
290                 295                 300
Ile Leu Leu Ala Gly Arg Asp Thr Thr Ala Gly Leu Leu Ser Phe Ala
305                 310                 315                 320
Val Phe Glu Leu Ala Arg Asn Pro His Ile Trp Ala Lys Leu Arg Glu
            325                 330                 335
Glu Ile Glu Ser His Phe Gly Leu Gly Glu Asp Ser Arg Val Glu Glu
        340                 345                 350
Ile Thr Phe Glu Ser Leu Lys Arg Cys Glu Tyr Leu Lys Ala Val Leu
    355                 360                 365
Asn Glu Thr Leu Arg Leu His Pro Ser Val Pro Arg Asn Ala Arg Phe
370                 375                 380
Ala Ile Lys Asp Thr Thr Leu Pro Arg Gly Gly Gly Pro Asn Gly Lys
385                 390                 395                 400
Asp Pro Ile Leu Ile Arg Lys Asn Glu Val Val Gln Tyr Ser Ile Ser
            405                 410                 415
Ala Thr Gln Thr Asn Pro Ala Tyr Tyr Gly Ala Asp Ala Ala Asp Phe
        420                 425                 430
Arg Pro Glu Arg Trp Phe Glu Pro Ser Thr Arg Asn Leu Gly Trp Ala
    435                 440                 445
Tyr Leu Pro Phe Asn Gly Gly Pro Arg Ile Cys Leu Gly Gln Gln Phe
450                 455                 460
Ala Leu Thr Glu Ala Gly Tyr Val Leu Val Arg Leu Val Gln Glu Phe
465                 470                 475                 480
Pro Ser Leu Ser Gln Asp Pro Glu Thr Glu Tyr Pro Pro Arg Leu
            485                 490                 495
Ala His Leu Thr Met Cys Leu Phe Asp Gly Ala Tyr Val Lys Met Gln
        500                 505                 510

<210> SEQ ID NO 21
<211> LENGTH: 390
<212> TYPE: DNA
<213> ORGANISM: Candida tropicalis
<220> FEATURE:
<221> NAME/KEY: CDS
<222> LOCATION: (1)..(387)

<400> SEQUENCE: 21
```

```
atg acc gac aca gac acc acg acc acc atc tac acc cac gaa gag gtt        48
Met Thr Asp Thr Asp Thr Thr Thr Thr Ile Tyr Thr His Glu Glu Val
1               5                   10                  15 gcc cag cac acc acc cac gac gac ttg tgg gtt att ctc aat ggt aag        96
Ala Gln His Thr Thr His Asp Asp Leu Trp Val Ile Leu Asn Gly Lys
            20                  25                  30 gtc tac aac atc tcc aac tat ata gac gag cac cca ggt ggt gaa gaa       144
Val Tyr Asn Ile Ser Asn Tyr Ile Asp Glu His Pro Gly Gly Glu Glu
        35                  40                  45 gtc att ctt gat tgc gcc ggc aca gac gcc act gaa gcc ttt gac gac       192
Val Ile Leu Asp Cys Ala Gly Thr Asp Ala Thr Glu Ala Phe Asp Asp
50                  55                  60 att ggc cac tcc gac gag gcc cac gag atc ttg gaa aag ttg tac att       240
Ile Gly His Ser Asp Glu Ala His Glu Ile Leu Glu Lys Leu Tyr Ile
65                  70                  75                  80 ggt aac ttg aag ggc gct aag att gtt gag gcc aag cac gcg cag tcg       288
Gly Asn Leu Lys Gly Ala Lys Ile Val Glu Ala Lys His Ala Gln Ser
                85                  90                  95 ttc agc acg gaa gaa gac tcg ggt atc aac ttc cca ttg att gct gtt       336
Phe Ser Thr Glu Glu Asp Ser Gly Ile Asn Phe Pro Leu Ile Ala Val
            100                 105                 110 ggt gtg ttt ttg gct gct ttc ggt gtc tac tac tac aag acc aac ttt       384
Gly Val Phe Leu Ala Ala Phe Gly Val Tyr Tyr Tyr Lys Thr Asn Phe
        115                 120                 125 gcc taa                                                                390
Ala
```

<210> SEQ ID NO 22
<211> LENGTH: 129
<212> TYPE: PRT
<213> ORGANISM: Candida tropicalis

<400> SEQUENCE: 22

```
Met Thr Asp Thr Asp Thr Thr Thr Thr Ile Tyr Thr His Glu Glu Val
1               5                   10                  15

Ala Gln His Thr Thr His Asp Asp Leu Trp Val Ile Leu Asn Gly Lys
            20                  25                  30

Val Tyr Asn Ile Ser Asn Tyr Ile Asp Glu His Pro Gly Gly Glu Glu
        35                  40                  45

Val Ile Leu Asp Cys Ala Gly Thr Asp Ala Thr Glu Ala Phe Asp Asp
50                  55                  60

Ile Gly His Ser Asp Glu Ala His Glu Ile Leu Glu Lys Leu Tyr Ile
65                  70                  75                  80

Gly Asn Leu Lys Gly Ala Lys Ile Val Glu Ala Lys His Ala Gln Ser
                85                  90                  95

Phe Ser Thr Glu Glu Asp Ser Gly Ile Asn Phe Pro Leu Ile Ala Val
            100                 105                 110

Gly Val Phe Leu Ala Ala Phe Gly Val Tyr Tyr Tyr Lys Thr Asn Phe
        115                 120                 125

Ala
```

<210> SEQ ID NO 23
<211> LENGTH: 2115
<212> TYPE: DNA
<213> ORGANISM: Candida tropicalis
<220> FEATURE:
<221> NAME/KEY: CDS
<222> LOCATION: (1)..(2112)

-continued

<400> SEQUENCE: 23

```
atg gct cca ttt ttg ccc gac cag gtc gac tac aaa cac gtc gac acc      48
Met Ala Pro Phe Leu Pro Asp Gln Val Asp Tyr Lys His Val Asp Thr
1               5                  10                  15 ctt atg tta tta tgt gac ggg atc atc cac gaa acc acc gtg gac gaa      96
Leu Met Leu Leu Cys Asp Gly Ile Ile His Glu Thr Thr Val Asp Glu
            20                  25                  30 atc aaa gac gtc att gcc cct gac ttc ccc gcc gac aaa tac gag gag     144
Ile Lys Asp Val Ile Ala Pro Asp Phe Pro Ala Asp Lys Tyr Glu Glu
        35                  40                  45 tac gtc agg aca ttc acc aaa ccc tcc gaa acc cca ggg ttc agg gaa     192
Tyr Val Arg Thr Phe Thr Lys Pro Ser Glu Thr Pro Gly Phe Arg Glu
    50                  55                  60 acc gtc tac aac acc gtc aac gca aac acc atg gat gca atc cac cag     240
Thr Val Tyr Asn Thr Val Asn Ala Asn Thr Met Asp Ala Ile His Gln
65                  70                  75                  80 ttc att atc ttg acc aat gtt ttg gga tca agg gtc ttg gca cca gct     288
Phe Ile Ile Leu Thr Asn Val Leu Gly Ser Arg Val Leu Ala Pro Ala
                85                  90                  95 ttg acc aac tcg ttg act cct atc aag gac atg agc ttg gaa gac cgt     336
Leu Thr Asn Ser Leu Thr Pro Ile Lys Asp Met Ser Leu Glu Asp Arg
            100                 105                 110 gaa aag ttg tta gcc tcg tgg cgt gac tcc cct att gct gct aaa agg     384
Glu Lys Leu Leu Ala Ser Trp Arg Asp Ser Pro Ile Ala Ala Lys Arg
        115                 120                 125 aag ttg ttc agg ttg gtt tct acg ctt acc ttg gtc acg ttc acg aga     432
Lys Leu Phe Arg Leu Val Ser Thr Leu Thr Leu Val Thr Phe Thr Arg
    130                 135                 140 ttg gcc aat gag ttg cat ttg aaa gcc att cat tat cca gga aga gaa     480
Leu Ala Asn Glu Leu His Leu Lys Ala Ile His Tyr Pro Gly Arg Glu
145                 150                 155                 160 gac cgt gaa aag gct tat gaa acc cag gag att gac cct ttt aag tac     528
Asp Arg Glu Lys Ala Tyr Glu Thr Gln Glu Ile Asp Pro Phe Lys Tyr
                165                 170                 175 cag ttt ttg gaa aaa ccg aag ttt tac ggc gct gag ttg tac ttg cca     576
Gln Phe Leu Glu Lys Pro Lys Phe Tyr Gly Ala Glu Leu Tyr Leu Pro
            180                 185                 190 gat att gat gtg atc att att gga tct ggg gcc ggt gct ggt gtc gtg     624
Asp Ile Asp Val Ile Ile Ile Gly Ser Gly Ala Gly Ala Gly Val Val
        195                 200                 205 gcc cac act ttg acc aac gac ggc ttc aag agt ttg gtt ttg gaa aag     672
Ala His Thr Leu Thr Asn Asp Gly Phe Lys Ser Leu Val Leu Glu Lys
    210                 215                 220 ggc aga tac ttt agc aac tcc gag ttg aac ttt gat gac aag gac ggg     720
Gly Arg Tyr Phe Ser Asn Ser Glu Leu Asn Phe Asp Asp Lys Asp Gly
225                 230                 235                 240 gtt caa gaa tta tac caa agt gga ggt act ttg acc acc gtc aac cag     768
Val Gln Glu Leu Tyr Gln Ser Gly Gly Thr Leu Thr Thr Val Asn Gln
                245                 250                 255 cag ttg ttt gtt ctt gct ggt tcc act ttt ggt ggt ggt acc act gtc     816
Gln Leu Phe Val Leu Ala Gly Ser Thr Phe Gly Gly Gly Thr Thr Val
            260                 265                 270 aat tgg tcg gcc tgt ctt aaa acg cca ttc aag gtg cgt aag gaa tgg     864
Asn Trp Ser Ala Cys Leu Lys Thr Pro Phe Lys Val Arg Lys Glu Trp
        275                 280                 285 tat gat gag ttt ggc gtt gac ttt gct gcc gat gaa gcc tac gac aaa     912
Tyr Asp Glu Phe Gly Val Asp Phe Ala Ala Asp Glu Ala Tyr Asp Lys
    290                 295                 300 gca cag gat tat gtt tgg cag caa atg gga gct tct acc gaa ggc atc     960
Ala Gln Asp Tyr Val Trp Gln Gln Met Gly Ala Ser Thr Glu Gly Ile
```

|     |     |     |     |     |     |     |     |     |     |     |     |     |     |     |     |      |
|---|---|---|---|---|---|---|---|---|---|---|---|---|---|---|---|---|
| Ala | Gln | Asp | Tyr | Val | Trp | Gln | Gln | Met | Gly | Ala | Ser | Thr | Glu | Gly | Ile | |
| 305 | | | | 310 | | | | 315 | | | | | | 320 | | |

```
acc cac tct ttg gct aac gag att att att gaa ggt ggc aag aaa tta      1008
Thr His Ser Leu Ala Asn Glu Ile Ile Ile Glu Gly Gly Lys Lys Leu
                        325                 330                 335 ggt tac aag gcc aag gta tta gac caa aac agc ggt ggt cat cct cat      1056
Gly Tyr Lys Ala Lys Val Leu Asp Gln Asn Ser Gly Gly His Pro His
                        340                 345                 350 cac aga tgc ggt ttc tgt tat ttg ggt tgt aag cac ggt atc aag cag      1104
His Arg Cys Gly Phe Cys Tyr Leu Gly Cys Lys His Gly Ile Lys Gln
                        355                 360                 365 ggc tct gtt aat aac tgg ttt aga gac gca gct gcc cac ggt tct cag      1152
Gly Ser Val Asn Asn Trp Phe Arg Asp Ala Ala Ala His Gly Ser Gln
                370                 375                 380 ttc atg caa cag gtt aga gtt ttg caa atc ctt aac aag aag ggc atc      1200
Phe Met Gln Gln Val Arg Val Leu Gln Ile Leu Asn Lys Lys Gly Ile
385                 390                 395                 400 gct tat ggt atc ttg tgt gag gat gtt gta acc ggt gcc aag ttc acc      1248
Ala Tyr Gly Ile Leu Cys Glu Asp Val Val Thr Gly Ala Lys Phe Thr
                        405                 410                 415 att act ggc ccc aaa aag ttt gtt gtt gcc gcc ggc gcc tta aac act      1296
Ile Thr Gly Pro Lys Lys Phe Val Val Ala Ala Gly Ala Leu Asn Thr
                420                 425                 430 cca tct gtg ttg gtc aac tcc gga ttc aag aac aag aac atc ggt aag      1344
Pro Ser Val Leu Val Asn Ser Gly Phe Lys Asn Lys Asn Ile Gly Lys
                435                 440                 445 aac tta act ttg cat cca gtt tct gtc gtg ttt ggt gat ttt ggc aaa      1392
Asn Leu Thr Leu His Pro Val Ser Val Val Phe Gly Asp Phe Gly Lys
450                 455                 460 gac gtt caa gca gat cac ttc cac aac tcc atc atg act gct ctt tgt      1440
Asp Val Gln Ala Asp His Phe His Asn Ser Ile Met Thr Ala Leu Cys
465                 470                 475                 480 tca gaa gcc gct gat tta gac ggc aag ggt cat gga tgc aga att gaa      1488
Ser Glu Ala Ala Asp Leu Asp Gly Lys Gly His Gly Cys Arg Ile Glu
                        485                 490                 495 acc atc ttg aac gct cca ttc atc cag gct tca ttc tta cca tgg aga      1536
Thr Ile Leu Asn Ala Pro Phe Ile Gln Ala Ser Phe Leu Pro Trp Arg
                500                 505                 510 ggt agt aac gag gct aga cga gac ttg ttg cgt tac aac aac atg gtg      1584
Gly Ser Asn Glu Ala Arg Arg Asp Leu Leu Arg Tyr Asn Asn Met Val
                515                 520                 525 gcc atg tta ctt ctt agt cgt gat acc acc agt ggt tcc gtt tcg tcc      1632
Ala Met Leu Leu Leu Ser Arg Asp Thr Thr Ser Gly Ser Val Ser Ser
530                 535                 540 cat cca act aaa cct gaa gca tta gtt gtc gag tac gac gtg aac aag      1680
His Pro Thr Lys Pro Glu Ala Leu Val Val Glu Tyr Asp Val Asn Lys
545                 550                 555                 560 ttt gac aga aac tcc atc ttg cag gca ttg ttg gtc act gct gac ttg      1728
Phe Asp Arg Asn Ser Ile Leu Gln Ala Leu Leu Val Thr Ala Asp Leu
                        565                 570                 575 ttg tac att caa ggt gcc aag aga atc ctt agt ccc caa cca tgg gtg      1776
Leu Tyr Ile Gln Gly Ala Lys Arg Ile Leu Ser Pro Gln Pro Trp Val
                580                 585                 590 cca att ttt gaa tcc gac aag cca aag gat aag aga tca atc aag gac      1824
Pro Ile Phe Glu Ser Asp Lys Pro Lys Asp Lys Arg Ser Ile Lys Asp
                595                 600                 605 gag gac tat gtc gaa tgg aga gcc aag gtt gcc aag att cct ttt gac      1872
Glu Asp Tyr Val Glu Trp Arg Ala Lys Val Ala Lys Ile Pro Phe Asp
                610                 615                 620
```

-continued

| | | | | | | | | | | | | | | | |
|---|---|---|---|---|---|---|---|---|---|---|---|---|---|---|---|
| acc | tac | ggc | tcg | cct | tat | ggt | tcg | gcg | cat | caa | atg | tct | tct | tgt | cgt | 1920
| Thr | Tyr | Gly | Ser | Pro | Tyr | Gly | Ser | Ala | His | Gln | Met | Ser | Ser | Cys | Arg |
| 625 | | | | 630 | | | | | 635 | | | | | 640 | |

```
acc tac ggc tcg cct tat ggt tcg gcg cat caa atg tct tct tgt cgt    1920
Thr Tyr Gly Ser Pro Tyr Gly Ser Ala His Gln Met Ser Ser Cys Arg
625                 630                 635                 640 atg tca ggt aag ggt cct aaa tac ggt gct gtt gat acc gat ggt aga    1968
Met Ser Gly Lys Gly Pro Lys Tyr Gly Ala Val Asp Thr Asp Gly Arg
                645                 650                 655 ttg ttt gaa tgt tcg aat gtt tat gtt gct gac gct agt ctt ttg cca    2016
Leu Phe Glu Cys Ser Asn Val Tyr Val Ala Asp Ala Ser Leu Leu Pro
                660                 665                 670 act gct agc ggt gct aat cct atg gtc acc acc atg act ctt gca aga    2064
Thr Ala Ser Gly Ala Asn Pro Met Val Thr Thr Met Thr Leu Ala Arg
            675                 680                 685 cat gtt gcg tta ggt ttg gca gac tcc ttg aag acc aag gcc aag ttg    2112
His Val Ala Leu Gly Leu Ala Asp Ser Leu Lys Thr Lys Ala Lys Leu
690                 695                 700 tag                                                                2115
```

<210> SEQ ID NO 24
<211> LENGTH: 704
<212> TYPE: PRT
<213> ORGANISM: Candida tropicalis

<400> SEQUENCE: 24

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
                20                  25                  30

Ile Lys Asp Val Ile Ala Pro Asp Phe Pro Ala Asp Lys Tyr Glu Glu
            35                  40                  45

Tyr Val Arg Thr Phe Thr Lys Pro Ser Glu Thr Pro Gly Phe Arg Glu
        50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
        195                 200                 205

Ala His Thr Leu Thr Asn Asp Gly Phe Lys Ser Leu Val Leu Glu Lys
    210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
```

```
              260                 265                 270
Asn Trp Ser Ala Cys Leu Lys Thr Pro Phe Lys Val Arg Lys Glu Trp
            275                 280                 285
Tyr Asp Glu Phe Gly Val Asp Phe Ala Ala Asp Gly Ala Tyr Asp Lys
            290                 295                 300
Ala Gln Asp Tyr Val Trp Gln Gln Met Gly Ala Ser Thr Glu Gly Ile
305                 310                 315                 320
Thr His Ser Leu Ala Asn Glu Ile Ile Ile Glu Gly Lys Lys Leu
                325                 330                 335
Gly Tyr Lys Ala Lys Val Leu Asp Gln Asn Ser Gly His Pro His
                340                 345                 350
His Arg Cys Gly Phe Cys Tyr Leu Gly Cys Lys His Gly Ile Lys Gln
            355                 360                 365
Gly Ser Val Asn Asn Trp Phe Arg Asp Ala Ala His Gly Ser Gln
            370                 375                 380
Phe Met Gln Gln Val Arg Val Leu Gln Ile Leu Asn Lys Lys Gly Ile
385                 390                 395                 400
Ala Tyr Gly Ile Leu Cys Glu Asp Val Val Thr Gly Ala Lys Phe Thr
                405                 410                 415
Ile Thr Gly Pro Lys Lys Phe Val Val Ala Ala Gly Ala Leu Asn Thr
                420                 425                 430
Pro Ser Val Leu Val Asn Ser Gly Phe Lys Asn Lys Asn Ile Gly Lys
                435                 440                 445
Asn Leu Thr Leu His Pro Val Ser Val Phe Gly Asp Phe Gly Lys
        450                 455                 460
Asp Val Gln Ala Asp His Phe His Asn Ser Ile Met Thr Ala Leu Cys
465                 470                 475                 480
Ser Glu Ala Ala Asp Leu Asp Gly Lys Gly His Gly Cys Arg Ile Glu
                485                 490                 495
Thr Ile Leu Asn Ala Pro Phe Ile Gln Ala Ser Phe Leu Pro Trp Arg
            500                 505                 510
Gly Ser Asn Glu Ala Arg Arg Asp Leu Leu Arg Tyr Asn Asn Met Val
            515                 520                 525
Ala Met Leu Leu Leu Ser Arg Asp Thr Thr Ser Gly Ser Val Ser Ser
            530                 535                 540
His Pro Thr Lys Pro Glu Ala Leu Val Val Glu Tyr Asp Val Asn Lys
545                 550                 555                 560
Phe Asp Arg Asn Ser Ile Leu Gln Ala Leu Leu Val Thr Ala Asp Leu
                565                 570                 575
Leu Tyr Ile Gln Gly Ala Lys Arg Ile Leu Ser Pro Gln Pro Trp Val
            580                 585                 590
Pro Ile Phe Glu Ser Asp Lys Pro Lys Asp Lys Arg Ser Ile Lys Asp
            595                 600                 605
Glu Asp Tyr Val Glu Trp Arg Ala Lys Val Ala Lys Ile Pro Phe Asp
        610                 615                 620
Thr Tyr Gly Ser Pro Tyr Gly Ser Ala His Gln Met Ser Ser Cys Arg
625                 630                 635                 640
Met Ser Gly Lys Gly Pro Lys Tyr Gly Ala Val Asp Thr Asp Gly Arg
                645                 650                 655
Leu Phe Glu Cys Ser Asn Val Tyr Val Ala Asp Ala Ser Leu Leu Pro
                660                 665                 670
Thr Ala Ser Gly Ala Asn Pro Met Val Thr Thr Met Thr Leu Ala Arg
            675                 680                 685
```

His Val Ala Leu Gly Leu Ala Asp Ser Leu Lys Thr Lys Ala Lys Leu
    690             695             700

<210> SEQ ID NO 25
<211> LENGTH: 2115
<212> TYPE: DNA
<213> ORGANISM: Candida tropicalis
<220> FEATURE:
<221> NAME/KEY: CDS
<222> LOCATION: (1)..(2112)

<400> SEQUENCE: 25

```
atg aat acc ttc ttg cca gac gtg ctc gaa tac aaa cac gtc gac acc      48
Met Asn Thr Phe Leu Pro Asp Val Leu Glu Tyr Lys His Val Asp Thr
1               5                  10                  15 ctt ttg tta ttg tgt gac ggg atc atc cac gaa acc aca gtc gat cag      96
Leu Leu Leu Leu Cys Asp Gly Ile Ile His Glu Thr Thr Val Asp Gln
            20                  25                  30 atc aag gac gcc att gct ccc gac ttc cct gag gac cag tac gag gag     144
Ile Lys Asp Ala Ile Ala Pro Asp Phe Pro Glu Asp Gln Tyr Glu Glu
        35                  40                  45 tat ctc aag acc ttc acc aag cca tct gag acc cct ggg ttc aga gaa     192
Tyr Leu Lys Thr Phe Thr Lys Pro Ser Glu Thr Pro Gly Phe Arg Glu
    50                  55                  60 gcc gtc tac gac acg atc aac gcc acc cca acc gat gcc gtg cac atg     240
Ala Val Tyr Asp Thr Ile Asn Ala Thr Pro Thr Asp Ala Val His Met
65                  70                  75                  80 tgt att gtc ttg acc acc gca ttg gac tcc aga atc ttg gcc ccc acg     288
Cys Ile Val Leu Thr Thr Ala Leu Asp Ser Arg Ile Leu Ala Pro Thr
                85                  90                  95 ttg acc aac tcg ttg acg cct atc aag gat atg acc ttg aag gag cgt     336
Leu Thr Asn Ser Leu Thr Pro Ile Lys Asp Met Thr Leu Lys Glu Arg
            100                 105                 110 gaa caa ttg ttg gcc tct tgg cgt gat tcc ccg att gcg gca aag aga     384
Glu Gln Leu Leu Ala Ser Trp Arg Asp Ser Pro Ile Ala Ala Lys Arg
        115                 120                 125 aga ttg ttc aga ttg att tcc tcg ctt acc ttg acg acg ttt acg aga     432
Arg Leu Phe Arg Leu Ile Ser Ser Leu Thr Leu Thr Thr Phe Thr Arg
    130                 135                 140 ttg gcc agc gaa ttg cac ttg aaa gcc atc cac tac cct ggc aga gac     480
Leu Ala Ser Glu Leu His Leu Lys Ala Ile His Tyr Pro Gly Arg Asp
145                 150                 155                 160 ttg cgt gaa aag gcg tat gaa acc cag gtg gtt gac cct ttc agg tac     528
Leu Arg Glu Lys Ala Tyr Glu Thr Gln Val Val Asp Pro Phe Arg Tyr
                165                 170                 175 ctg ttt atg gag aaa cca aag ttt gac ggc gcc gaa ttg tac ttg cca     576
Leu Phe Met Glu Lys Pro Lys Phe Asp Gly Ala Glu Leu Tyr Leu Pro
            180                 185                 190 gat atc gac gtc atc atc att gga tca ggc gcc ggt gct ggt gtc atg     624
Asp Ile Asp Val Ile Ile Ile Gly Ser Gly Ala Gly Ala Gly Val Met
        195                 200                 205 gcc cac act ctc gcc aac gac ggg ttc aag acc ttg gtt ttg gaa aag     672
Ala His Thr Leu Ala Asn Asp Gly Phe Lys Thr Leu Val Leu Glu Lys
    210                 215                 220 gga aag tat ttc agc aac tcc gag ttg aac ttt aat gac gct gat ggc     720
Gly Lys Tyr Phe Ser Asn Ser Glu Leu Asn Phe Asn Asp Ala Asp Gly
225                 230                 235                 240 gtg aaa gag ttg tac caa ggt aaa ggt gct ttg gcc acc acc aat cag     768
Val Lys Glu Leu Tyr Gln Gly Lys Gly Ala Leu Ala Thr Thr Asn Gln
                245                 250                 255
```

```
                                                              -continued cag atg ttt att ctt gcc ggt tcc act ttg ggc ggt ggt acc act gtc    816
Gln Met Phe Ile Leu Ala Gly Ser Thr Leu Gly Gly Gly Thr Thr Val
        260                 265                 270 aac tgg tct gct tgc ctt aaa aca cca ttt aaa gtg cgt aag gag tgg    864
Asn Trp Ser Ala Cys Leu Lys Thr Pro Phe Lys Val Arg Lys Glu Trp
    275                 280                 285 tac gac gag ttt ggt ctt gaa ttt gct gcc gat gaa gcc tac gac aaa    912
Tyr Asp Glu Phe Gly Leu Glu Phe Ala Ala Asp Glu Ala Tyr Asp Lys
290                 295                 300 gcg cag gat tat gtt tgg aaa caa atg ggt gct tca aca gat gga atc    960
Ala Gln Asp Tyr Val Trp Lys Gln Met Gly Ala Ser Thr Asp Gly Ile
305                 310                 315                 320 act cac tcc ttg gcc aac gaa gtt gtt gtt gaa gga ggt aag aag ttg   1008
Thr His Ser Leu Ala Asn Glu Val Val Val Glu Gly Gly Lys Lys Leu
                325                 330                 335 ggc tac aag agc aag gaa att gag cag aac aac ggt ggc cac cct gac   1056
Gly Tyr Lys Ser Lys Glu Ile Glu Gln Asn Asn Gly Gly His Pro Asp
            340                 345                 350 cac cca tgt ggt ttc tgt tac ttg ggc tgt aag tac ggt att aaa cag   1104
His Pro Cys Gly Phe Cys Tyr Leu Gly Cys Lys Tyr Gly Ile Lys Gln
        355                 360                 365 ggt tct gtg aat aac tgg ttt aga gac gca gct gcc cac ggg tcc aag   1152
Gly Ser Val Asn Asn Trp Phe Arg Asp Ala Ala Ala His Gly Ser Lys
370                 375                 380 ttc atg caa caa gtc aga gtt gtg caa atc ctc aac aag aat ggc gtc   1200
Phe Met Gln Gln Val Arg Val Val Gln Ile Leu Asn Lys Asn Gly Val
385                 390                 395                 400 gct tat ggt atc ttg tgt gag gat gtc gaa acc gga gtc agg ttc act   1248
Ala Tyr Gly Ile Leu Cys Glu Asp Val Glu Thr Gly Val Arg Phe Thr
                405                 410                 415 att agt ggc ccc aaa aag ttt gtt gtt tct gct ggt tct ttg aac acg   1296
Ile Ser Gly Pro Lys Lys Phe Val Val Ser Ala Gly Ser Leu Asn Thr
            420                 425                 430 cca act gtg ttg acc aac tcc gga ttc aag aac aag cac att ggt aag   1344
Pro Thr Val Leu Thr Asn Ser Gly Phe Lys Asn Lys His Ile Gly Lys
        435                 440                 445 aac ttg acg ttg cac cca gtt tcc acc gtg ttt ggt gac ttt ggc aga   1392
Asn Leu Thr Leu His Pro Val Ser Thr Val Phe Gly Asp Phe Gly Arg
450                 455                 460 gac gtg caa gcc gac cat ttc cac aaa tct att atg act tcg ctt tgt   1440
Asp Val Gln Ala Asp His Phe His Lys Ser Ile Met Thr Ser Leu Cys
465                 470                 475                 480 tac gag gtt gct gac ttg gac ggc aag ggc cac gga tgc aga atc gaa   1488
Tyr Glu Val Ala Asp Leu Asp Gly Lys Gly His Gly Cys Arg Ile Glu
                485                 490                 495 acc atc ttg aac gct cca ttc atc caa gct tct ttg ttg cca tgg aga   1536
Thr Ile Leu Asn Ala Pro Phe Ile Gln Ala Ser Leu Leu Pro Trp Arg
            500                 505                 510 gga agt gac gag gtc aga aga gac ttg ttg cgt tac aac aac atg gtg   1584
Gly Ser Asp Glu Val Arg Arg Asp Leu Leu Arg Tyr Asn Asn Met Val
        515                 520                 525 gcc atg ttg ctt atc acg cgt gat acc acc agt ggt tca gtt tct gct   1632
Ala Met Leu Leu Ile Thr Arg Asp Thr Thr Ser Gly Ser Val Ser Ala
530                 535                 540 gac cca aag aag ccc gac gct ttg att gtc gac tat gag att aac aag   1680
Asp Pro Lys Lys Pro Asp Ala Leu Ile Val Asp Tyr Glu Ile Asn Lys
545                 550                 555                 560 ttt gac aag aat gcc atc ttg caa gct ttc ttg atc act tcc gac atg   1728
Phe Asp Lys Asn Ala Ile Leu Gln Ala Phe Leu Ile Thr Ser Asp Met
                565                 570                 575
```

| | | | | | | | | | | | | | | | |
|---|---|---|---|---|---|---|---|---|---|---|---|---|---|---|---|
| ttg | tac | att | gaa | ggt | gcc | aag | aga | atc | ctc | agt | cca | cag | cca | tgg | gtg | 1776 |
| Leu | Tyr | Ile | Glu | Gly | Ala | Lys | Arg | Ile | Leu | Ser | Pro | Gln | Pro | Trp | Val | |
| | | | 580 | | | | 585 | | | | | 590 | | | | |

```
ttg tac att gaa ggt gcc aag aga atc ctc agt cca cag cca tgg gtg      1776
Leu Tyr Ile Glu Gly Ala Lys Arg Ile Leu Ser Pro Gln Pro Trp Val
            580                 585                 590 cca atc ttt gag tcg aac aag cca aag gag caa aga acg atc aag gac      1824
Pro Ile Phe Glu Ser Asn Lys Pro Lys Glu Gln Arg Thr Ile Lys Asp
        595                 600                 605 aag gac tat gtt gag tgg aga gcc aag gct gct aag ata cct ttc gac      1872
Lys Asp Tyr Val Glu Trp Arg Ala Lys Ala Ala Lys Ile Pro Phe Asp
610                 615                 620 acc tac ggt tct gca tat ggg tcc gca cat caa atg tcc acc tgt cgt      1920
Thr Tyr Gly Ser Ala Tyr Gly Ser Ala His Gln Met Ser Thr Cys Arg
625                 630                 635                 640 atg tcc gga aag ggt cct aaa tac ggt gct gtt gat act gat ggt aga      1968
Met Ser Gly Lys Gly Pro Lys Tyr Gly Ala Val Asp Thr Asp Gly Arg
                645                 650                 655 ttg ttt gaa tgt tcg aat gtc tat gtt gct gat gct agt gtt ttg cct      2016
Leu Phe Glu Cys Ser Asn Val Tyr Val Ala Asp Ala Ser Val Leu Pro
            660                 665                 670 act gcc agc ggt gcc aac cca atg ata tcc acc atg acc ttt gct aga      2064
Thr Ala Ser Gly Ala Asn Pro Met Ile Ser Thr Met Thr Phe Ala Arg
        675                 680                 685 cag att gcg tta ggt ttg gct gac tcc ttg aag acc aaa ccc aag ttg      2112
Gln Ile Ala Leu Gly Leu Ala Asp Ser Leu Lys Thr Lys Pro Lys Leu
690                 695                 700 tag                                                                   2115
```

<210> SEQ ID NO 26
<211> LENGTH: 704
<212> TYPE: PRT
<213> ORGANISM: Candida tropicalis

<400> SEQUENCE: 26

```
Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Thr Val Asp Gln
            20                  25                  30

Ile Lys Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ala Thr Pro Thr Asp Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ser Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Glu Leu His Leu Lys Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Leu Phe Met Glu Lys Pro Lys Phe Asp Gly Ala Glu Leu Tyr Leu Pro
            180                 185                 190
```

```
Asp Ile Asp Val Ile Ile Ile Gly Ser Gly Ala Gly Val Met
            195                 200             205

Ala His Thr Leu Ala Asn Asp Gly Phe Lys Thr Leu Val Leu Glu Lys
210                 215                 220

Gly Lys Tyr Phe Ser Asn Ser Glu Leu Asn Phe Asn Asp Ala Asp Gly
225                 230                 235                 240

Val Lys Glu Leu Tyr Gln Gly Lys Gly Ala Leu Ala Thr Thr Asn Gln
                245                 250                 255

Gln Met Phe Ile Leu Ala Gly Ser Thr Leu Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
        290                 295                 300

Ala Gln Asp Tyr Val Trp Lys Gln Met Gly Ala Ser Thr Asp Gly Ile
305                 310                 315                 320

Thr His Ser Leu Ala Asn Glu Val Val Glu Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala His Gly Ser Lys
        370                 375                 380

Phe Met Gln Gln Val Arg Val Val Gln Ile Leu Asn Lys Asn Gly Val
385                 390                 395                 400

Ala Tyr Gly Ile Leu Cys Glu Asp Val Glu Thr Gly Val Arg Phe Thr
                405                 410                 415

Ile Ser Gly Pro Lys Lys Phe Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
530                 535                 540

Asp Pro Lys Lys Pro Asp Ala Leu Ile Val Asp Tyr Glu Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Pro Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
```

```
                610             615             620
Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
                660                 665                 670

Thr Ala Ser Gly Ala Asn Pro Met Ile Ser Thr Met Thr Phe Ala Arg
                675                 680                 685

Gln Ile Ala Leu Gly Leu Ala Asp Ser Leu Lys Thr Lys Pro Lys Leu
690                 695                 700

<210> SEQ ID NO 27
<211> LENGTH: 2115
<212> TYPE: DNA
<213> ORGANISM: Candida tropicalis
<220> FEATURE:
<221> NAME/KEY: CDS
<222> LOCATION: (1)..(2112)

<400> SEQUENCE: 27 atg aat acc ttc ttg cca gac gtg ctc gaa tac aaa cac gtc gat acc      48
Met Asn Thr Phe Leu Pro Asp Val Leu Glu Tyr Lys His Val Asp Thr
1               5                   10                  15 ctt ttg tta tta tgt gac ggg atc atc cac gaa acc aca gtc gac cag      96
Leu Leu Leu Leu Cys Asp Gly Ile Ile His Glu Thr Thr Val Asp Gln
            20                  25                  30 atc agg gac gcc att gct ccc gac ttc cct gaa gac cag tac gag gag     144
Ile Arg Asp Ala Ile Ala Pro Asp Phe Pro Glu Asp Gln Tyr Glu Glu
        35                  40                  45 tat ctc aag acc ttc acc aag cca tct gag acc cct ggg ttc aga gaa     192
Tyr Leu Lys Thr Phe Thr Lys Pro Ser Glu Thr Pro Gly Phe Arg Glu
    50                  55                  60 gcc gtc tac gac acg atc aac agc acc cca acc gag gct gtg cac atg     240
Ala Val Tyr Asp Thr Ile Asn Ser Thr Pro Thr Glu Ala Val His Met
65                  70                  75                  80 tgt att gta ttg acc acc gca ttg gac tcg aga atc ttg gcc ccc acg     288
Cys Ile Val Leu Thr Thr Ala Leu Asp Ser Arg Ile Leu Ala Pro Thr
                85                  90                  95 ttg acc aac tcg ttg acg cct atc aag gat atg acc ttg aaa gag cgt     336
Leu Thr Asn Ser Leu Thr Pro Ile Lys Asp Met Thr Leu Lys Glu Arg
            100                 105                 110 gaa caa ttg ttg gct gcc tgg cgt gat tcc ccg atc gcg gcc aag aga     384
Glu Gln Leu Leu Ala Ala Trp Arg Asp Ser Pro Ile Ala Ala Lys Arg
        115                 120                 125 aga ttg ttc aga ttg att tcc tca ctt acc ttg acg acc ttt acg aga     432
Arg Leu Phe Arg Leu Ile Ser Ser Leu Thr Leu Thr Thr Phe Thr Arg
    130                 135                 140 ttg gcc agc gac ttg cac ttg aga gcc atc cac tac cct ggc aga gac     480
Leu Ala Ser Asp Leu His Leu Arg Ala Ile His Tyr Pro Gly Arg Asp
145                 150                 155                 160 ttg cgt gaa aag gca tat gaa acc cag gtg gtt gac cct ttc agg tac     528
Leu Arg Glu Lys Ala Tyr Glu Thr Gln Val Val Asp Pro Phe Arg Tyr
                165                 170                 175 ctg ttt atg gaa aaa cca aag ttt gac ggc acc gag ttg tac ttg cca     576
Leu Phe Met Glu Lys Pro Lys Phe Asp Gly Thr Glu Leu Tyr Leu Pro
            180                 185                 190 gat atc gac gtc atc atc att gga tcc ggt gcc ggt gct ggt gtc atg     624
Asp Ile Asp Val Ile Ile Ile Gly Ser Gly Ala Gly Ala Gly Val Met
        195                 200                 205
```

| | |
|---|---|
| gcc cac act tta gcc aac gac ggg tac aag acc ttg gtt ttg gaa aag<br>Ala His Thr Leu Ala Asn Asp Gly Tyr Lys Thr Leu Val Leu Glu Lys<br>210 215 220 | 672 |
| gga aag tat ttc agc aac tcc gag ttg aac ttt aat gat gcc gat ggt<br>Gly Lys Tyr Phe Ser Asn Ser Glu Leu Asn Phe Asn Asp Ala Asp Gly<br>225 230 235 240 | 720 |
| atg aaa gag ttg tac caa ggt aaa tgt gcg ttg acc acc acg aac cag<br>Met Lys Glu Leu Tyr Gln Gly Lys Cys Ala Leu Thr Thr Thr Asn Gln<br>245 250 255 | 768 |
| cag atg ttt att ctt gcc ggt tcc act ttg ggc ggt ggt acc act gtt<br>Gln Met Phe Ile Leu Ala Gly Ser Thr Leu Gly Gly Gly Thr Thr Val<br>260 265 270 | 816 |
| aac tgg tct gct tgt ctt aaa aca cca ttt aaa gtg cgt aag gag tgg<br>Asn Trp Ser Ala Cys Leu Lys Thr Pro Phe Lys Val Arg Lys Glu Trp<br>275 280 285 | 864 |
| tac gac gag ttt ggt ctt gaa ttt gct gcc gac gaa gcc tac gac aaa<br>Tyr Asp Glu Phe Gly Leu Glu Phe Ala Ala Asp Glu Ala Tyr Asp Lys<br>290 295 300 | 912 |
| gca caa gac tat gtt tgg aaa caa atg ggc gct tct acc gaa gga atc<br>Ala Gln Asp Tyr Val Trp Lys Gln Met Gly Ala Ser Thr Glu Gly Ile<br>305 310 315 320 | 960 |
| act cac tct ttg gcg aac gcg gtt gtg gtt gaa gga ggt aag aag ttg<br>Thr His Ser Leu Ala Asn Ala Val Val Val Glu Gly Gly Lys Lys Leu<br>325 330 335 | 1008 |
| ggt tac aag agc aag gaa atc gag cag aac aat ggt ggc cat cct gac<br>Gly Tyr Lys Ser Lys Glu Ile Glu Gln Asn Asn Gly Gly His Pro Asp<br>340 345 350 | 1056 |
| cac ccc tgt ggt ttc tgt tac ttg ggc tgt aag tac ggt att aag cag<br>His Pro Cys Gly Phe Cys Tyr Leu Gly Cys Lys Tyr Gly Ile Lys Gln<br>355 360 365 | 1104 |
| ggt tct gtg aat aac tgg ttt aga gac gca gct gcc cac ggg tcc aag<br>Gly Ser Val Asn Asn Trp Phe Arg Asp Ala Ala Ala His Gly Ser Lys<br>370 375 380 | 1152 |
| ttc atg caa caa gtc aga gtt gtc caa atc ctc cac aat aaa ggc gtc<br>Phe Met Gln Gln Val Arg Val Val Gln Ile Leu His Asn Lys Gly Val<br>385 390 395 400 | 1200 |
| gct tat ggc atc ttg tgt gag gat gtc gag acc gga gtc aaa ttc act<br>Ala Tyr Gly Ile Leu Cys Glu Asp Val Glu Thr Gly Val Lys Phe Thr<br>405 410 415 | 1248 |
| atc agt ggc ccc aaa aag ttt gtt gtt tct gca ggt tct ttg aac acg<br>Ile Ser Gly Pro Lys Lys Phe Val Val Ser Ala Gly Ser Leu Asn Thr<br>420 425 430 | 1296 |
| cca acg gtg ttg acc aac tcc gga ttc aag aac aaa cac atc ggt aag<br>Pro Thr Val Leu Thr Asn Ser Gly Phe Lys Asn Lys His Ile Gly Lys<br>435 440 445 | 1344 |
| aac ttg acg ttg cac cca gtt tcg acc gtg ttt ggt gac ttt ggc aga<br>Asn Leu Thr Leu His Pro Val Ser Thr Val Phe Gly Asp Phe Gly Arg<br>450 455 460 | 1392 |
| gac gtg caa gcc gac cat ttc cac aaa tct att atg act tcg ctc tgt<br>Asp Val Gln Ala Asp His Phe His Lys Ser Ile Met Thr Ser Leu Cys<br>465 470 475 480 | 1440 |
| tac gaa gtc gct gac ttg gac ggc aag ggc cac gga tgc aga atc gag<br>Tyr Glu Val Ala Asp Leu Asp Gly Lys Gly His Gly Cys Arg Ile Glu<br>485 490 495 | 1488 |
| acc atc ttg aac gct cca ttc atc caa gct tct ttg ttg cca tgg aga<br>Thr Ile Leu Asn Ala Pro Phe Ile Gln Ala Ser Leu Leu Pro Trp Arg<br>500 505 510 | 1536 |
| gga agc gac gag gtc aga aga gac ttg ttg cgt tac aac aac atg gtg<br>Gly Ser Asp Glu Val Arg Arg Asp Leu Leu Arg Tyr Asn Asn Met Val | 1584 |

```
                515                 520                 525
gcc atg ttg ctt atc acc cgt gac acc acc agt ggt tca gtt tct gct    1632
Ala Met Leu Leu Ile Thr Arg Asp Thr Thr Ser Gly Ser Val Ser Ala
    530                 535                 540 gca cca aag aag ccc gac gct ttg att gtc gac tat gac atc aac aag    1680
Asp Pro Lys Lys Pro Asp Ala Leu Ile Val Asp Tyr Asp Ile Asn Lys
545                 550                 555                 560 ttt gac aag aat gcc atc ttg caa gct ttc ttg atc acc tcc gac atg    1728
Phe Asp Lys Asn Ala Ile Leu Gln Ala Phe Leu Ile Thr Ser Asp Met
                565                 570                 575 ttg tac atc gaa ggt gcc aag aga atc ctc agt cca cag gca tgg gtg    1776
Leu Tyr Ile Glu Gly Ala Lys Arg Ile Leu Ser Pro Gln Ala Trp Val
            580                 585                 590 cca atc ttt gag tcg aac aag cca aag gag caa aga aca atc aag gac    1824
Pro Ile Phe Glu Ser Asn Lys Pro Lys Glu Gln Arg Thr Ile Lys Asp
        595                 600                 605 aag gac tat gtc gaa tgg aga gcc aag gct gcc aag ata cct ttc gac    1872
Lys Asp Tyr Val Glu Trp Arg Ala Lys Ala Ala Lys Ile Pro Phe Asp
610                 615                 620 acc tac ggt tct gcc tat ggg tcc gca cat caa atg tcc acc tgt cgt    1920
Thr Tyr Gly Ser Ala Tyr Gly Ser Ala His Gln Met Ser Thr Cys Arg
625                 630                 635                 640 atg tcc gga aag ggt cct aaa tac ggc gcc gtt gat acc gat ggt aga    1968
Met Ser Gly Lys Gly Pro Lys Tyr Gly Ala Val Asp Thr Asp Gly Arg
                645                 650                 655 ttg ttt gaa tgt tcg aat gtc tat gtt gct gat gct agt gtt ttg cct    2016
Leu Phe Glu Cys Ser Asn Val Tyr Val Ala Asp Ala Ser Val Leu Pro
            660                 665                 670 act gcc agc ggt gcc aac cca atg atc tcc acc atg acg ttt gct aga    2064
Thr Ala Ser Gly Ala Asn Pro Met Ile Ser Thr Met Thr Phe Ala Arg
        675                 680                 685 cag att gcg tta ggt ttg gct gac tct ttg aag acc aaa ccc aag ttg    2112
Gln Ile Ala Leu Gly Leu Ala Asp Ser Leu Lys Thr Lys Pro Lys Leu
690                 695                 700 tag                                                                2115

<210> SEQ ID NO 28
<211> LENGTH: 704
<212> TYPE: PRT
<213> ORGANISM: Candida tropicalis

<400> SEQUENCE: 28

Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Val Thr Val Asp Gln
                20                  25                  30

Ile Arg Asp Ala Ile Ala Pro Asp Phe Pro Glu Asp Gln Tyr Glu Glu
            35                  40                  45

Tyr Leu Lys Thr Phe Thr Lys Pro Ser Glu Thr Pro Gly Phe Arg Glu
        50                  55                  60

Ala Val Tyr Asp Thr Ile Asn Ser Thr Pro Thr Glu Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ala Trp Arg Asp Ser Pro Ile Ala Ala Lys Arg
        115                 120                 125
```

```
Arg Leu Phe Arg Leu Ile Ser Ser Leu Thr Leu Thr Thr Phe Thr Arg
    130                 135                 140

Leu Ala Ser Asp Leu His Leu Arg Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Leu Phe Met Glu Lys Pro Lys Phe Asp Gly Thr Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Tyr Lys Thr Leu Val Leu Glu Lys
210                 215                 220

Gly Lys Tyr Phe Ser Asn Ser Glu Leu Asn Phe Asn Asp Ala Asp Gly
225                 230                 235                 240

Met Lys Glu Leu Tyr Gln Gly Lys Cys Ala Leu Thr Thr Thr Asn Gln
                245                 250                 255

Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
290                 295                 300

Ala Gln Asp Tyr Val Trp Lys Gln Met Gly Ala Ser Thr Glu Gly Ile
305                 310                 315                 320

Thr His Ser Leu Ala Asn Ala Val Val Val Glu Gly Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala His Gly Ser Lys
370                 375                 380

Phe Met Gln Gln Val Arg Val Val Gln Ile Leu His Asn Lys Gly Val
385                 390                 395                 400

Ala Tyr Gly Ile Leu Cys Glu Asp Val Glu Thr Gly Val Lys Phe Thr
                405                 410                 415

Ile Ser Gly Pro Lys Lys Phe Val Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
530                 535                 540
```

```
Asp Pro Lys Lys Pro Asp Ala Leu Ile Val Asp Tyr Asp Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Ala Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Lys Ile Pro Phe Asp
    610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700

<210> SEQ ID NO 29
<211> LENGTH: 1446
<212> TYPE: DNA
<213> ORGANISM: Candida tropicalis
<220> FEATURE:
<221> NAME/KEY: CDS
<222> LOCATION: (1)..(1443)

<400> SEQUENCE: 29 atg ata atg ttt gat atc gtc aaa tac acc tta att ggg tta ttt agc       48
Met Ile Met Phe Asp Ile Val Lys Tyr Thr Leu Ile Gly Leu Phe Ser
1               5                   10                  15 tat ttg cta tat gta att ctc gat ata gta cta cca cca ttc aat ttt       96
Tyr Leu Leu Tyr Val Ile Leu Asp Ile Val Leu Pro Pro Phe Asn Phe
            20                  25                  30 ccc aaa aat atc cca aca atc cca ttc tat gtt tcc ttc tta ggt gct      144
Pro Lys Asn Ile Pro Thr Ile Pro Phe Tyr Val Ser Phe Leu Gly Ala
        35                  40                  45 tac act aac ttg gat cag agg gat att tac aat ttg tat ttg aga gag      192
Tyr Thr Asn Leu Asp Gln Arg Asp Ile Tyr Asn Leu Tyr Leu Arg Glu
    50                  55                  60 aag ttg gaa aag tac ggg gca gta aag ata tat ttt gct tca aga tgg      240
Lys Leu Glu Lys Tyr Gly Ala Val Lys Ile Tyr Phe Ala Ser Arg Trp
65                  70                  75                  80 aac ata ctc att act agg cca gaa tat ctt ctt gaa atg ttt aga aat      288
Asn Ile Leu Ile Thr Arg Pro Glu Tyr Leu Leu Glu Met Phe Arg Asn
                85                  90                  95 gaa gat gtg tac tca aaa cgg gga aac cac cta aaa atc cct ggt tca      336
Glu Asp Val Tyr Ser Lys Arg Gly Asn His Leu Lys Ile Pro Gly Ser
            100                 105                 110 gtg atg gct aca tac act ggt gat aat atc att agt gct cat gga gaa      384
Val Met Ala Thr Tyr Thr Gly Asp Asn Ile Ile Ser Ala His Gly Glu
        115                 120                 125 tta tgg aaa tta tat cga gaa gtt att gcc aaa agt att caa ttt ccc      432
Leu Trp Lys Leu Tyr Arg Glu Val Ile Ala Lys Ser Ile Gln Phe Pro
    130                 135                 140 gat ttt gaa cca att acg aaa aat act aaa tca tta ctt gaa att att      480
Asp Phe Glu Pro Ile Thr Lys Asn Thr Lys Ser Leu Leu Glu Ile Ile
```

```
                145                 150                 155                 160
      gat ggt atg att gac agt gat aaa aat cat gca att att cca atc aca      528
      Asp Gly Met Ile Asp Ser Asp Lys Asn His Ala Ile Ile Pro Ile Thr
                      165                 170                 175 gat tta ttt caa aaa tat tca tta gca aac gtt aca gaa tct ata ctt      576
      Asp Leu Phe Gln Lys Tyr Ser Leu Ala Asn Val Thr Glu Ser Ile Leu
                      180                 185                 190 gga gta aat ttt aag gtt ctt gaa ggc gat caa tca atc atg cat caa      624
      Gly Val Asn Phe Lys Val Leu Glu Gly Asp Gln Ser Ile Met His Gln
                      195                 200                 205 aaa ata aag tac gtc aag ctg caa ata ttc aaa cct ttt ttc ttg aac      672
      Lys Ile Lys Tyr Val Lys Leu Gln Ile Phe Lys Pro Phe Phe Leu Asn
              210                 215                 220 ttt cct tat ttt gat agc ttt cct att cca agt agg tta caa gca aga      720
      Phe Pro Tyr Phe Asp Ser Phe Pro Ile Pro Ser Arg Leu Gln Ala Arg
      225                 230                 235                 240 aag gaa gtt att aat ttt agg aat tgg tat ggt caa agt att att gac      768
      Lys Glu Val Ile Asn Phe Arg Asn Trp Tyr Gly Gln Ser Ile Ile Asp
                      245                 250                 255 aag cat gat cca caa ctt cct aat agt gca gct aca aaa tta gtt gat      816
      Lys His Asp Pro Gln Leu Pro Asn Ser Ala Ala Thr Lys Leu Val Asp
                      260                 265                 270 ggc ttg atg caa gaa aaa ctc act gaa aaa caa ttt ttg gat aat gcc      864
      Gly Leu Met Gln Glu Lys Leu Thr Glu Lys Gln Phe Leu Asp Asn Ala
                      275                 280                 285 att att gtg atg att gct gga cat gaa aat cca ctt tta atg tta          912
      Ile Ile Val Met Ile Ala Gly His Glu Asn Pro Leu Leu Leu Met Leu
                      290                 295                 300 tcg ttg atg ttt gtt gct gca aaa tat cca aaa gtt cag gag gcc ata      960
      Ser Leu Met Phe Val Ala Ala Lys Tyr Pro Lys Val Gln Glu Ala Ile
      305                 310                 315                 320 cgt tca gaa ata gat cca aca aaa cct tat cta cac tct gtt att tat     1008
      Arg Ser Glu Ile Asp Pro Thr Lys Pro Tyr Leu His Ser Val Ile Tyr
                      325                 330                 335 gaa act tta aga atg tat cca cca ttg gga tta atc att aat cgt tat     1056
      Glu Thr Leu Arg Met Tyr Pro Pro Leu Gly Leu Ile Ile Asn Arg Tyr
                      340                 345                 350 acc acc aga cct act aaa cta ggc aac ata gta att ccc aaa ggt gtt     1104
      Thr Thr Arg Pro Thr Lys Leu Gly Asn Ile Val Ile Pro Lys Gly Val
                      355                 360                 365 tac tgt ggc tat aat aat ttt ggt acg ggt aga gac aga aat gtt tgg     1152
      Tyr Cys Gly Tyr Asn Asn Phe Gly Thr Gly Arg Asp Arg Asn Val Trp
              370                 375                 380 gga cca gac tcg gat gag ttt aaa cca gag aga tgg gga agg gat aat     1200
      Gly Pro Asp Ser Asp Glu Phe Lys Pro Glu Arg Trp Gly Arg Asp Asn
      385                 390                 395                 400 att gaa gaa ata aat cgc aat tat gct aat gcc aaa aga tca gct gaa     1248
      Ile Glu Glu Ile Asn Arg Asn Tyr Ala Asn Ala Lys Arg Ser Ala Glu
                      405                 410                 415 tta cct gcg ttt cat ggc aga aag aga gct tgt tta gga gaa aag tat     1296
      Leu Pro Ala Phe His Gly Arg Lys Arg Ala Cys Leu Gly Glu Lys Tyr
                      420                 425                 430 gcc tta tat gaa gtt aaa gaa ttg cta act agt att tta gga cat tac     1344
      Ala Leu Tyr Glu Val Lys Glu Leu Leu Thr Ser Ile Leu Gly His Tyr
                      435                 440                 445 aaa gtt act tta gat gca agt tgg aaa gag aaa ata acc cct gct gga     1392
      Lys Val Thr Leu Asp Ala Ser Trp Lys Glu Lys Ile Thr Pro Ala Gly
              450                 455                 460 cct att agt cca ttt ggt ttg aag gtg aaa ttt gaa aag ctt att gtt     1440
```

```
Pro Ile Ser Pro Phe Gly Leu Lys Val Lys Phe Glu Lys Leu Ile Val
465                 470                 475                 480 gca taa                                                              1446
Ala

<210> SEQ ID NO 30
<211> LENGTH: 481
<212> TYPE: PRT
<213> ORGANISM: Candida tropicalis

<400> SEQUENCE: 30

Met Ile Met Phe Asp Ile Val Lys Tyr Thr Leu Ile Gly Leu Phe Ser
1               5                   10                  15

Tyr Leu Leu Tyr Val Ile Leu Asp Ile Val Leu Pro Pro Phe Asn Phe
            20                  25                  30

Pro Lys Asn Ile Pro Thr Ile Pro Phe Tyr Val Ser Phe Leu Gly Ala
        35                  40                  45

Tyr Thr Asn Leu Asp Gln Arg Asp Ile Tyr Asn Leu Tyr Leu Arg Glu
    50                  55                  60

Lys Leu Glu Lys Tyr Gly Ala Val Lys Ile Tyr Phe Ala Ser Arg Trp
65                  70                  75                  80

Asn Ile Leu Ile Thr Arg Pro Glu Tyr Leu Glu Met Phe Arg Asn
                85                  90                  95

Glu Asp Val Tyr Ser Lys Arg Gly Asn His Leu Lys Ile Pro Gly Ser
            100                 105                 110

Val Met Ala Thr Tyr Thr Gly Asp Asn Ile Ile Ser Ala His Gly Glu
        115                 120                 125

Leu Trp Lys Leu Tyr Arg Glu Val Ile Ala Lys Ser Ile Gln Phe Pro
    130                 135                 140

Asp Phe Glu Pro Ile Thr Lys Asn Thr Lys Ser Leu Leu Glu Ile Ile
145                 150                 155                 160

Asp Gly Met Ile Asp Ser Asp Lys Asn His Ala Ile Ile Pro Ile Thr
                165                 170                 175

Asp Leu Phe Gln Lys Tyr Ser Leu Ala Asn Val Thr Glu Ser Ile Leu
            180                 185                 190

Gly Val Asn Phe Lys Val Leu Glu Gly Asp Gln Ser Ile Met His Gln
        195                 200                 205

Lys Ile Lys Tyr Val Lys Leu Gln Ile Phe Lys Pro Phe Phe Leu Asn
    210                 215                 220

Phe Pro Tyr Phe Asp Ser Phe Pro Ile Pro Ser Arg Leu Gln Ala Arg
225                 230                 235                 240

Lys Glu Val Ile Asn Phe Arg Asn Trp Tyr Gly Gln Ser Ile Ile Asp
                245                 250                 255

Lys His Asp Pro Gln Leu Pro Asn Ser Ala Ala Thr Lys Leu Val Asp
            260                 265                 270

Gly Leu Met Gln Glu Lys Leu Thr Glu Lys Gln Phe Leu Asp Asn Ala
        275                 280                 285

Ile Ile Val Met Ile Ala Gly His Glu Asn Pro Leu Leu Leu Met Leu
    290                 295                 300

Ser Leu Met Phe Val Ala Ala Lys Tyr Pro Lys Val Gln Glu Ala Ile
305                 310                 315                 320

Arg Ser Glu Ile Asp Pro Thr Lys Pro Tyr Leu His Ser Val Ile Tyr
                325                 330                 335

Glu Thr Leu Arg Met Tyr Pro Pro Leu Gly Leu Ile Ile Asn Arg Tyr
            340                 345                 350
```

```
Thr Thr Arg Pro Thr Lys Leu Gly Asn Ile Val Ile Pro Lys Gly Val
            355                 360                 365

Tyr Cys Gly Tyr Asn Asn Phe Gly Thr Gly Arg Asp Arg Asn Val Trp
    370                 375                 380

Gly Pro Asp Ser Asp Glu Phe Lys Pro Glu Arg Trp Gly Arg Asp Asn
385                 390                 395                 400

Ile Glu Glu Ile Asn Arg Asn Tyr Ala Asn Ala Lys Arg Ser Ala Glu
                405                 410                 415

Leu Pro Ala Phe His Gly Arg Lys Arg Ala Cys Leu Gly Glu Lys Tyr
                420                 425                 430

Ala Leu Tyr Glu Val Lys Glu Leu Leu Thr Ser Ile Leu Gly His Tyr
            435                 440                 445

Lys Val Thr Leu Asp Ala Ser Trp Lys Glu Lys Ile Thr Pro Ala Gly
            450                 455                 460

Pro Ile Ser Pro Phe Gly Leu Lys Val Lys Phe Glu Lys Leu Ile Val
465                 470                 475                 480

Ala

<210> SEQ ID NO 31
<211> LENGTH: 1623
<212> TYPE: DNA
<213> ORGANISM: Candida tropicalis
<220> FEATURE:
<221> NAME/KEY: CDS
<222> LOCATION: (1)..(1620)

<400> SEQUENCE: 31 atg tcg tcg tct cca tct att gct caa gaa ttt ctc gca acc att act      48
Met Ser Ser Ser Pro Ser Ile Ala Gln Glu Phe Leu Ala Thr Ile Thr
1               5                   10                  15 cca tat gtt gag tat tgt caa gag aat tat acc aaa tgg tac tac ttc      96
Pro Tyr Val Glu Tyr Cys Gln Glu Asn Tyr Thr Lys Trp Tyr Tyr Phe
                20                  25                  30 att cca ttg gtg att ctt tcg ttg aat ctt atc tcc atg ctt cat aca     144
Ile Pro Leu Val Ile Leu Ser Leu Asn Leu Ile Ser Met Leu His Thr
            35                  40                  45 aag tat ttg gaa cgt aaa ttt aag gct aaa ccg ctt gct gtc tat gtt     192
Lys Tyr Leu Glu Arg Lys Phe Lys Ala Lys Pro Leu Ala Val Tyr Val
        50                  55                  60 caa gat tat acc ttt ggt ctt att act cca ctt gtt ttg atc tac tac     240
Gln Asp Tyr Thr Phe Gly Leu Ile Thr Pro Leu Val Leu Ile Tyr Tyr
65                  70                  75                  80 aag tct aaa ggt acc gtg atg caa ttt gcc tgt gat tta tgg gac aag     288
Lys Ser Lys Gly Thr Val Met Gln Phe Ala Cys Asp Leu Trp Asp Lys
                85                  90                  95 aaa ctc att gtc agt gat cca aag gca aag act att ggt ctt aag att     336
Lys Leu Ile Val Ser Asp Pro Lys Ala Lys Thr Ile Gly Leu Lys Ile
            100                 105                 110 tta ggt att cca ttg att gaa act aaa gac cca gag aat gtc aag gct     384
Leu Gly Ile Pro Leu Ile Glu Thr Lys Asp Pro Glu Asn Val Lys Ala
        115                 120                 125 att tta gcc acc cag ttt aat gat ttt tct ttg gga act aga cat gat     432
Ile Leu Ala Thr Gln Phe Asn Asp Phe Ser Leu Gly Thr Arg His Asp
    130                 135                 140 ttc ttg tat tca ttg tta gga gat ggt att ttc act tta gat ggt gct     480
Phe Leu Tyr Ser Leu Leu Gly Asp Gly Ile Phe Thr Leu Asp Gly Ala
145                 150                 155                 160 ggc tgg aaa cac agc aga acc atg ttg aga cca caa ttc gct aga gag     528
```

-continued

| | | |
|---|---|---|
| Gly Trp Lys His Ser Arg Thr Met Leu Arg Pro Gln Phe Ala Arg Glu<br>165 170 175 | | |
| caa gtt tcg cat gta aag ttg ttg gaa ccc cat atg caa gtt tta ttt<br>Gln Val Ser His Val Lys Leu Leu Glu Pro His Met Gln Val Leu Phe<br>180 185 190 | 576 | |
| aaa cac att aga aaa cat cat ggc caa act ttt gat atc caa gaa ttg<br>Lys His Ile Arg Lys His His Gly Gln Thr Phe Asp Ile Gln Glu Leu<br>195 200 205 | 624 | |
| ttt ttc aga tta act gtt gat tcg gct act gag ttt ttg ttt ggt gaa<br>Phe Phe Arg Leu Thr Val Asp Ser Ala Thr Glu Phe Leu Phe Gly Glu<br>210 215 220 | 672 | |
| tct gct gaa tct tta aga gac gag tct gtc ggt tta act cca aca acc<br>Ser Ala Glu Ser Leu Arg Asp Glu Ser Val Gly Leu Thr Pro Thr Thr<br>225 230 235 240 | 720 | |
| aaa gat ttt gat ggt aga aat gag ttt gcc gat gcg ttc aac tat tct<br>Lys Asp Phe Asp Gly Arg Asn Glu Phe Ala Asp Ala Phe Asn Tyr Ser<br>245 250 255 | 768 | |
| caa act tac caa gcg tac aga ttc ttg ttg caa caa atg tat tgg att<br>Gln Thr Tyr Gln Ala Tyr Arg Phe Leu Leu Gln Gln Met Tyr Trp Ile<br>260 265 270 | 816 | |
| ttg aat ggt tct gaa ttt aga aaa tct att gct att gtc cac aag ttt<br>Leu Asn Gly Ser Glu Phe Arg Lys Ser Ile Ala Ile Val His Lys Phe<br>275 280 285 | 864 | |
| gct gac cac tat gtt caa aag gca ttg gaa tta act gat gaa gat ttg<br>Ala Asp His Tyr Val Gln Lys Ala Leu Glu Leu Thr Asp Glu Asp Leu<br>290 295 300 | 912 | |
| gaa aag aaa gaa ggc tat gta ttt tta ttc gag tta gcc aaa caa acc<br>Glu Lys Lys Glu Gly Tyr Val Phe Leu Phe Glu Leu Ala Lys Gln Thr<br>305 310 315 320 | 960 | |
| aga gat cca aag gtt ttg aga gat caa ttg tta aat atc ttg gtt gct<br>Arg Asp Pro Lys Val Leu Arg Asp Gln Leu Leu Asn Ile Leu Val Ala<br>325 330 335 | 1008 | |
| ggt aga gat acc aca gct ggc ttg ttg tcg ttt ctt ttc ttt gaa ttg<br>Gly Arg Asp Thr Thr Ala Gly Leu Leu Ser Phe Leu Phe Phe Glu Leu<br>340 345 350 | 1056 | |
| tct aga aac cca gaa ata ttt gca aaa ttg aga gaa gaa atc gaa aac<br>Ser Arg Asn Pro Glu Ile Phe Ala Lys Leu Arg Glu Glu Ile Glu Asn<br>355 360 365 | 1104 | |
| aag ttt ggt ctt gga caa gat gct cgt gtt gaa gag att tct ttt gaa<br>Lys Phe Gly Leu Gly Gln Asp Ala Arg Val Glu Glu Ile Ser Phe Glu<br>370 375 380 | 1152 | |
| aca ttg aaa tct tgt gaa tac ttg aag gct gtt atc aat gaa act ttg<br>Thr Leu Lys Ser Cys Glu Tyr Leu Lys Ala Val Ile Asn Glu Thr Leu<br>385 390 395 400 | 1200 | |
| aga att tat cct tcc gtc cca cat aat ttt aga gtt gct act aga aac<br>Arg Ile Tyr Pro Ser Val Pro His Asn Phe Arg Val Ala Thr Arg Asn<br>405 410 415 | 1248 | |
| aca act tta cca aga ggt ggt ggt gaa ggt ggt tta tcc cca att gct<br>Thr Thr Leu Pro Arg Gly Gly Gly Glu Gly Gly Leu Ser Pro Ile Ala<br>420 425 430 | 1296 | |
| att aag aag ggc caa gtt gtt atg tac acg att ctt gct act cac aga<br>Ile Lys Lys Gly Gln Val Val Met Tyr Thr Ile Leu Ala Thr His Arg<br>435 440 445 | 1344 | |
| gat aaa gac att tat ggt gaa gat gct tat gtt ttc agg cca gaa aga<br>Asp Lys Asp Ile Tyr Gly Glu Asp Ala Tyr Val Phe Arg Pro Glu Arg<br>450 455 460 | 1392 | |
| tgg ttt gaa cct gaa acc aga aaa ttg ggc tgg gca tat gtt cca ttc<br>Trp Phe Glu Pro Glu Thr Arg Lys Leu Gly Trp Ala Tyr Val Pro Phe<br>465 470 475 480 | 1440 | |

```
aat ggc ggt cca aga att tgt ttg ggt caa cag ttt gct tta act gaa    1488
Asn Gly Gly Pro Arg Ile Cys Leu Gly Gln Gln Phe Ala Leu Thr Glu
            485                 490                 495 gca tca tat gtc act gtt aga ttg ctt caa gaa ttt ggt aac ttg aaa    1536
Ala Ser Tyr Val Thr Val Arg Leu Leu Gln Glu Phe Gly Asn Leu Lys
                500                 505                 510 caa gat cca aat act gaa tat cca cca aaa tta caa aac aca ttg act    1584
Gln Asp Pro Asn Thr Glu Tyr Pro Pro Lys Leu Gln Asn Thr Leu Thr
            515                 520                 525 ttg tct ctt ttt gaa ggt gct gaa gta caa atg tat taa                1623
Leu Ser Leu Phe Glu Gly Ala Glu Val Gln Met Tyr
            530                 535                 540

<210> SEQ ID NO 32
<211> LENGTH: 540
<212> TYPE: PRT
<213> ORGANISM: Candida tropicalis

<400> SEQUENCE: 32

Met Ser Ser Ser Pro Ser Ile Ala Gln Glu Phe Leu Ala Thr Ile Thr
1               5                   10                  15

Pro Tyr Val Glu Tyr Cys Gln Glu Asn Tyr Thr Lys Trp Tyr Tyr Phe
                20                  25                  30

Ile Pro Leu Val Ile Leu Ser Leu Asn Leu Ile Ser Met Leu His Thr
            35                  40                  45

Lys Tyr Leu Glu Arg Lys Phe Lys Ala Lys Pro Leu Ala Val Tyr Val
        50                  55                  60

Gln Asp Tyr Thr Phe Gly Leu Ile Thr Pro Leu Val Leu Ile Tyr Tyr
65                  70                  75                  80

Lys Ser Lys Gly Thr Val Met Gln Phe Ala Cys Asp Leu Trp Asp Lys
                85                  90                  95

Lys Leu Ile Val Ser Asp Pro Lys Ala Lys Thr Ile Gly Leu Lys Ile
            100                 105                 110

Leu Gly Ile Pro Leu Ile Glu Thr Lys Asp Pro Glu Asn Val Lys Ala
        115                 120                 125

Ile Leu Ala Thr Gln Phe Asn Asp Phe Ser Leu Gly Thr Arg His Asp
130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Met Gln Val Leu Phe
            180                 185                 190

Lys His Ile Arg Lys His His Gly Gln Thr Phe Asp Ile Gln Glu Leu
        195                 200                 205

Phe Phe Arg Leu Thr Val Asp Ser Ala Thr Glu Phe Leu Phe Gly Glu
210                 215                 220

Ser Ala Glu Ser Leu Arg Asp Glu Ser Val Gly Leu Thr Pro Thr Thr
225                 230                 235                 240

Lys Asp Phe Asp Gly Arg Asn Glu Phe Ala Asp Ala Phe Asn Tyr Ser
                245                 250                 255

Gln Thr Tyr Gln Ala Tyr Arg Phe Leu Leu Gln Met Tyr Trp Ile
            260                 265                 270

Leu Asn Gly Ser Glu Phe Arg Lys Ser Ile Ala Ile Val His Lys Phe
        275                 280                 285

Ala Asp His Tyr Val Gln Lys Ala Leu Glu Leu Thr Asp Glu Asp Leu
```

```
                290                 295                 300
Glu Lys Lys Glu Gly Tyr Val Phe Leu Phe Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Leu Phe Phe Glu Leu
            340                 345                 350

Ser Arg Asn Pro Glu Ile Phe Ala Lys Leu Arg Glu Glu Ile Glu Asn
        355                 360                 365

Lys Phe Gly Leu Gly Gln Asp Ala Arg Val Glu Glu Ile Ser Phe Glu
    370                 375                 380

Thr Leu Lys Ser Cys Glu Tyr Leu Lys Ala Val Ile Asn Glu Thr Leu
385                 390                 395                 400

Arg Ile Tyr Pro Ser Val Pro His Asn Phe Arg Val Ala Thr Arg Asn
                405                 410                 415

Thr Thr Leu Pro Arg Gly Gly Gly Gly Leu Ser Pro Ile Ala
            420                 425                 430

Ile Lys Lys Gly Gln Val Val Met Tyr Thr Ile Leu Ala Thr His Arg
        435                 440                 445

Asp Lys Asp Ile Tyr Gly Glu Asp Ala Tyr Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Gly Asn Leu Lys
            500                 505                 510

Gln Asp Pro Asn Thr Glu Tyr Pro Pro Lys Leu Gln Asn Thr Leu Thr
        515                 520                 525

Leu Ser Leu Phe Glu Gly Ala Glu Val Gln Met Tyr
    530                 535                 540

<210> SEQ ID NO 33
<211> LENGTH: 1569
<212> TYPE: DNA
<213> ORGANISM: Candida tropicalis
<220> FEATURE:
<221> NAME/KEY: CDS
<222> LOCATION: (1)..(1566)

<400> SEQUENCE: 33 atg agt att caa gat att gtt gaa act tac agt acc aaa tgg tac gtt      48
Met Ser Ile Gln Asp Ile Val Glu Thr Tyr Ser Thr Lys Trp Tyr Val
1               5                  10                  15 gtt gta ctg gtt gct ttg att gta tac aag gtt ttt gat ttc ttt tat      96
Val Val Leu Val Ala Leu Ile Val Tyr Lys Val Phe Asp Phe Phe Tyr
                20                  25                  30 gct aga tat ttg atg tat aag ctt ggt gct aag cca ttc ctt caa agt     144
Ala Arg Tyr Leu Met Tyr Lys Leu Gly Ala Lys Pro Phe Leu Gln Ser
            35                  40                  45 caa acc gac ggt tat ctt ggt ttc aga gtt cca ttt gaa ttg atg gga     192
Gln Thr Asp Gly Tyr Leu Gly Phe Arg Val Pro Phe Glu Leu Met Gly
        50                  55                  60 aag aag agt gaa ggt aca ctt ata gac ttt aca tat caa cgt act ttg     240
Lys Lys Ser Glu Gly Thr Leu Ile Asp Phe Thr Tyr Gln Arg Thr Leu
65                  70                  75                  80 gag ctt gac aat ccc gat att cca aca ttt aca ttc cca ata ttt tct     288
```

-continued

```
                Glu Leu Asp Asn Pro Asp Ile Pro Thr Phe Thr Phe Pro Ile Phe Ser
                                 85                  90                  95 gtt ctg att atc tca act ctt gaa cca gac aac atc aaa gct att ttg          336
Val Leu Ile Ile Ser Thr Leu Glu Pro Asp Asn Ile Lys Ala Ile Leu
                100                 105                 110 gcc aca caa ttc aat gac ttt tca tta ggt aca aga cat tca cat ttt          384
Ala Thr Gln Phe Asn Asp Phe Ser Leu Gly Thr Arg His Ser His Phe
            115                 120                 125 gct cct tta tta ggt gac ggt att ttc act tta gat ggt gct ggt tgg          432
Ala Pro Leu Leu Gly Asp Gly Ile Phe Thr Leu Asp Gly Ala Gly Trp
        130                 135                 140 aaa cat agt aga tct atg ttg aga cca caa ttt gca aga gaa cag gtt          480
Lys His Ser Arg Ser Met Leu Arg Pro Gln Phe Ala Arg Glu Gln Val
145                 150                 155                 160 tct cac gtt aag ttg ttg gaa cca cat atg caa gtt ttt ttc aaa cat          528
Ser His Val Lys Leu Leu Glu Pro His Met Gln Val Phe Phe Lys His
                165                 170                 175 att aga aaa cat cat ggc caa acc ttt gat ata caa gaa ttg ttt ttc          576
Ile Arg Lys His His Gly Gln Thr Phe Asp Ile Gln Glu Leu Phe Phe
            180                 185                 190 aga tta act gtt gat tct gcc act gag ttt ttg ttt ggt gaa tct gtt          624
Arg Leu Thr Val Asp Ser Ala Thr Glu Phe Leu Phe Gly Glu Ser Val
        195                 200                 205 gag tct tta aga gac gag tcc atc ggt atg tta aac gat gct ctt gat          672
Glu Ser Leu Arg Asp Glu Ser Ile Gly Met Leu Asn Asp Ala Leu Asp
210                 215                 220 ttt gat ggt aag gct gga ttt gct gat gcc ttt aac tat tct caa aac          720
Phe Asp Gly Lys Ala Gly Phe Ala Asp Ala Phe Asn Tyr Ser Gln Asn
225                 230                 235                 240 tat ttg gct tct cga gct ctt atg caa caa atg tac tgg att ttg aac          768
Tyr Leu Ala Ser Arg Ala Leu Met Gln Gln Met Tyr Trp Ile Leu Asn
                245                 250                 255 gga aaa aag ttt aaa gaa tgt aat gcc aag gtt cac aag ttt gct gat          816
Gly Lys Lys Phe Lys Glu Cys Asn Ala Lys Val His Lys Phe Ala Asp
            260                 265                 270 tat tat gtt gaa aaa gca ttg gaa tta act ccg gac caa ttg gaa aaa          864
Tyr Tyr Val Glu Lys Ala Leu Glu Leu Thr Pro Asp Gln Leu Glu Lys
        275                 280                 285 caa gat ggg tat gtt ttc ttg tat gaa ttg gta aaa caa acc aga gac          912
Gln Asp Gly Tyr Val Phe Leu Tyr Glu Leu Val Lys Gln Thr Arg Asp
290                 295                 300 aga caa gtc ttg aga gat cag tta ttg aat ata tta gtt gct ggt aga          960
Arg Gln Val Leu Arg Asp Gln Leu Leu Asn Ile Leu Val Ala Gly Arg
305                 310                 315                 320 gat acc act gct ggt tta tta tca ttt gtg ttt ttt gaa ttg gca aga         1008
Asp Thr Thr Ala Gly Leu Leu Ser Phe Val Phe Phe Glu Leu Ala Arg
                325                 330                 335 act cca aga gta gca aat aaa tta aga gaa gaa atc gaa gac aaa ttt         1056
Thr Pro Arg Val Ala Asn Lys Leu Arg Glu Glu Ile Glu Asp Lys Phe
            340                 345                 350 ggc ctt gga caa gat gct cgt gtt gaa gaa att tcc ttt gaa tct tta         1104
Gly Leu Gly Gln Asp Ala Arg Val Glu Glu Ile Ser Phe Glu Ser Leu
        355                 360                 365 aaa tca tgt gaa tat ttg aag gca gtg ctt aat gaa tgt tta aga tta         1152
Lys Ser Cys Glu Tyr Leu Lys Ala Val Leu Asn Glu Cys Leu Arg Leu
370                 375                 380 tac cca tct gtt cca caa aac ttt aga gtt gct acc aga aat acc aca         1200
Tyr Pro Ser Val Pro Gln Asn Phe Arg Val Ala Thr Arg Asn Thr Thr
385                 390                 395                 400
```

```
tta cca aga ggt ggt ggc aag gat ggt tta tca cca gta tta gtt aga        1248
Leu Pro Arg Gly Gly Gly Lys Asp Gly Leu Ser Pro Val Leu Val Arg
            405                 410                 415 aag ggt caa act gtg atg tac agt gtg tat gct gcc cat aga aac aaa        1296
Lys Gly Gln Thr Val Met Tyr Ser Val Tyr Ala Ala His Arg Asn Lys
420                 425                 430 caa att tat ggt gaa gac gca ctt gaa ttc agg cca gaa aga tgg ttt        1344
Gln Ile Tyr Gly Glu Asp Ala Leu Glu Phe Arg Pro Glu Arg Trp Phe
    435                 440                 445 gaa cca gag aca aag aaa ttg ggc tgg gcc ttc tta cct ttt aat ggt        1392
Glu Pro Glu Thr Lys Lys Leu Gly Trp Ala Phe Leu Pro Phe Asn Gly
450                 455                 460 ggt cca aga att tgt ttg ggt caa caa ttt gct ttg act gaa gct tct        1440
Gly Pro Arg Ile Cys Leu Gly Gln Gln Phe Ala Leu Thr Glu Ala Ser
465                 470                 475                 480 tat gtt act gtt aga tta ctt caa gag ttt agc cac ttg aca atg gat        1488
Tyr Val Thr Val Arg Leu Leu Gln Glu Phe Ser His Leu Thr Met Asp
                485                 490                 495 cca aac act gaa tac ccg cca aag aaa atg tcc cat ttg aca atg tct        1536
Pro Asn Thr Glu Tyr Pro Pro Lys Lys Met Ser His Leu Thr Met Ser
            500                 505                 510 cta ttt gat ggt gcc aac att caa atg tat tag                            1569
Leu Phe Asp Gly Ala Asn Ile Gln Met Tyr
        515                 520
```

<210> SEQ ID NO 34
<211> LENGTH: 522
<212> TYPE: PRT
<213> ORGANISM: Candida tropicalis

<400> SEQUENCE: 34

```
Met Ser Ile Gln Asp Ile Val Glu Thr Tyr Ser Thr Lys Trp Tyr Val
1               5                   10                  15

Val Val Leu Val Ala Leu Ile Val Tyr Lys Val Phe Asp Phe Phe Tyr
            20                  25                  30

Ala Arg Tyr Leu Met Tyr Lys Leu Gly Ala Lys Pro Phe Leu Gln Ser
        35                  40                  45

Gln Thr Asp Gly Tyr Leu Gly Phe Arg Val Pro Phe Glu Leu Met Gly
    50                  55                  60

Lys Lys Ser Glu Gly Thr Leu Ile Asp Phe Thr Tyr Gln Arg Thr Leu
65                  70                  75                  80

Glu Leu Asp Asn Pro Asp Ile Pro Thr Phe Thr Phe Pro Ile Phe Ser
                85                  90                  95

Val Leu Ile Ile Ser Thr Leu Glu Pro Asp Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Val
145                 150                 155                 160

Ser His Val Lys Leu Leu Glu Pro His Met Gln Val Phe Phe Lys His
                165                 170                 175

Ile Arg Lys His His Gly Gln Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205
```

```
Glu Ser Leu Arg Asp Glu Ser Ile Gly Met Leu Asn Asp Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Leu Met Gln Gln Met Tyr Trp Ile Leu Asn
            245                 250                 255

Gly Lys Lys Phe Lys Glu Cys Asn Ala Lys Val His Lys Phe Ala Asp
                260                 265                 270

Tyr Tyr Val Glu Lys Ala Leu Glu Leu Thr Pro Asp Gln Leu Glu Lys
            275                 280                 285

Gln Asp Gly Tyr Val Phe Leu Tyr Glu Leu Val Lys Gln Thr Arg Asp
290                 295                 300

Arg Gln Val Leu Arg Asp Gln Leu Leu Asn Ile Leu Val Ala Gly Arg
305                 310                 315                 320

Asp Thr Thr Ala Gly Leu Leu Ser Phe Val Phe Glu Leu Ala Arg
                325                 330                 335

Thr Pro Arg Val Ala Asn Lys Leu Arg Glu Glu Ile Glu Asp Lys Phe
            340                 345                 350

Gly Leu Gly Gln Asp Ala Arg Val Glu Glu Ile Ser Phe Glu Ser Leu
                355                 360                 365

Lys Ser Cys Glu Tyr Leu Lys Ala Val Leu Asn Glu Cys Leu Arg Leu
    370                 375                 380

Tyr Pro Ser Val Pro Gln Asn Phe Arg Val Ala Thr Arg Asn Thr Thr
385                 390                 395                 400

Leu Pro Arg Gly Gly Gly Lys Asp Gly Leu Ser Pro Val Leu Val Arg
                405                 410                 415

Lys Gly Gln Thr Val Met Tyr Ser Val Tyr Ala Ala His Arg Asn Lys
            420                 425                 430

Gln Ile Tyr Gly Glu Asp Ala Leu Glu Phe Arg Pro Glu Arg Trp Phe
        435                 440                 445

Glu Pro Glu Thr Lys Lys Leu Gly Trp Ala Phe Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ser His Leu Thr Met Asp
                485                 490                 495

Pro Asn Thr Glu Tyr Pro Pro Lys Lys Met Ser His Leu Thr Met Ser
            500                 505                 510

Leu Phe Asp Gly Ala Asn Ile Gln Met Tyr
    515                 520
```

<210> SEQ ID NO 35
<211> LENGTH: 1572
<212> TYPE: DNA
<213> ORGANISM: Candida tropicalis
<220> FEATURE:
<221> NAME/KEY: CDS
<222> LOCATION: (1)..(1569)

<400> SEQUENCE: 35

```
atg gcc aca caa gaa att att gat tct gca ctt ccg tac ttg aca aag      48
Met Ala Thr Gln Glu Ile Ile Asp Ser Ala Leu Pro Tyr Leu Thr Lys
1               5                   10                  15 tgg tat act gtt atc act tta gca gct ttg gtt ttc tta att tca tct     96
Trp Tyr Thr Val Ile Thr Leu Ala Ala Leu Val Phe Leu Ile Ser Ser
            20                  25                  30
```

```
aat att aaa aat tac gtc aag gct aag aag ttg aaa tgc aga gat cct    144
Asn Ile Lys Asn Tyr Val Lys Ala Lys Lys Leu Lys Cys Arg Asp Pro
         35                  40                  45 cca tat ttc aaa gga gcc ggt tgg aca ggt att agt cca tta att gaa    192
Pro Tyr Phe Lys Gly Ala Gly Trp Thr Gly Ile Ser Pro Leu Ile Glu
 50                  55                  60 att att aaa gtt aaa ggt aat ggt aga ttg gca gat ttt gcc gat aaa    240
Ile Ile Lys Val Lys Gly Asn Gly Arg Leu Ala Asp Phe Ala Asp Lys
 65                  70                  75                  80 aca ttc gac gac tat cca aac cat act ttt tac atg tct att att ggt    288
Thr Phe Asp Asp Tyr Pro Asn His Thr Phe Tyr Met Ser Ile Ile Gly
                 85                  90                  95 gct ttg aaa atc gtc ttg act gtt gat cca gaa aat att aaa gct gtt    336
Ala Leu Lys Ile Val Leu Thr Val Asp Pro Glu Asn Ile Lys Ala Val
                100                 105                 110 ttg gct act caa ttt act gat ttc tcc tta ggt acc aga cat gct cat    384
Leu Ala Thr Gln Phe Thr Asp Phe Ser Leu Gly Thr Arg His Ala His
            115                 120                 125 ttc tat cca tta tta ggt gat ggt att ttt act ttg gat ggt gaa ggt    432
Phe Tyr Pro Leu Leu Gly Asp Gly Ile Phe Thr Leu Asp Gly Glu Gly
130                 135                 140 tgg aaa cat agt aga gct atg ttg aga cca caa ttt gct aga gat caa    480
Trp Lys His Ser Arg Ala Met Leu Arg Pro Gln Phe Ala Arg Asp Gln
145                 150                 155                 160 att ggt cat gtt aaa gct ttg gaa cca cat att caa atc ttg gcc aaa    528
Ile Gly His Val Lys Ala Leu Glu Pro His Ile Gln Ile Leu Ala Lys
                165                 170                 175 caa att aaa ttg aat aaa ggt aaa act ttt gat att caa gaa ttg ttt    576
Gln Ile Lys Leu Asn Lys Gly Lys Thr Phe Asp Ile Gln Glu Leu Phe
            180                 185                 190 ttc aga ttt act gtt gat act gct act gaa ttc ttg ttt ggt gaa tct    624
Phe Arg Phe Thr Val Asp Thr Ala Thr Glu Phe Leu Phe Gly Glu Ser
        195                 200                 205 gtt cac tct ttg tat gat gaa aaa tta ggt att cct act cca aat gaa    672
Val His Ser Leu Tyr Asp Glu Lys Leu Gly Ile Pro Thr Pro Asn Glu
210                 215                 220 att cca ggt aga gat aat ttt gca act gct ttt aac act tct caa cat    720
Ile Pro Gly Arg Asp Asn Phe Ala Thr Ala Phe Asn Thr Ser Gln His
225                 230                 235                 240 tat ttg gct acc aga aca tac tcc caa act ttc tac ttt tta act aac    768
Tyr Leu Ala Thr Arg Thr Tyr Ser Gln Thr Phe Tyr Phe Leu Thr Asn
            245                 250                 255 cct aag gaa ttt aga gac tgt aat gct aaa gtt cat tac ttg gct aaa    816
Pro Lys Glu Phe Arg Asp Cys Asn Ala Lys Val His Tyr Leu Ala Lys
        260                 265                 270 tat ttt gtc aat aaa gct ttg aat ttc act ccg gaa gaa att gaa gaa    864
Tyr Phe Val Asn Lys Ala Leu Asn Phe Thr Pro Glu Glu Ile Glu Glu
    275                 280                 285 aag tcc aaa tct ggt tat gtt ttc ttg tat gaa ttg gtt aaa caa acc    912
Lys Ser Lys Ser Gly Tyr Val Phe Leu Tyr Glu Leu Val Lys Gln Thr
290                 295                 300 aga gat cca aaa gtt tta caa gat caa tta ttg aac att atg gtt gcc    960
Arg Asp Pro Lys Val Leu Gln Asp Gln Leu Leu Asn Ile Met Val Ala
305                 310                 315                 320 ggt aga gat acc act gct ggt tta tta tca ttt gca atg ttt gaa tta   1008
Gly Arg Asp Thr Thr Ala Gly Leu Leu Ser Phe Ala Met Phe Glu Leu
                325                 330                 335 gct aga cat cca gaa att tgg tct aaa tta aga gaa gaa att gaa gtt   1056
Ala Arg His Pro Glu Ile Trp Ser Lys Leu Arg Glu Glu Ile Glu Val
            340                 345                 350
```

```
aac ttt ggt gtt ggt gaa gaa tct cgt gtt gaa gaa att act ttt gaa      1104
Asn Phe Gly Val Gly Glu Glu Ser Arg Val Glu Glu Ile Thr Phe Glu
        355                 360                 365 tct ttg aag aga tgt gaa tac ttg aaa gct att ctt aat gaa act ttg      1152
Ser Leu Lys Arg Cys Glu Tyr Leu Lys Ala Ile Leu Asn Glu Thr Leu
370                 375                 380 cgt atg tat cct tct gtt cca gtc aat tcc aga aca gcc act aga gat      1200
Arg Met Tyr Pro Ser Val Pro Val Asn Ser Arg Thr Ala Thr Arg Asp
385                 390                 395                 400 acc aca tta cca aga ggt ggt cca aat ggt act gat cca att ttt          1248
Thr Thr Leu Pro Arg Gly Gly Pro Asn Gly Thr Asp Pro Ile Phe
            405                 410                 415 att cca aag ggt tcc act gtt gct tat att gtt tac aaa act cat cgt      1296
Ile Pro Lys Gly Ser Thr Val Ala Tyr Ile Val Tyr Lys Thr His Arg
            420                 425                 430 tta gaa gaa tat tat ggt aaa gat gct gat gat ttc aga cca gaa aga      1344
Leu Glu Glu Tyr Tyr Gly Lys Asp Ala Asp Asp Phe Arg Pro Glu Arg
            435                 440                 445 tgg ttt gaa cca tca act aaa aag tta ggt tgg gct tat gtt cca ttt      1392
Trp Phe Glu Pro Ser Thr Lys Lys Leu Gly Trp Ala Tyr Val Pro Phe
    450                 455                 460 aat ggt ggt cca aga att tgt tta ggc caa caa ttt gct tta act gaa      1440
Asn Gly Gly Pro Arg Ile Cys Leu Gly Gln Gln Phe Ala Leu Thr Glu
465                 470                 475                 480 gct tct tat gtt att acc aga ttg gta caa atg ttt gaa act gtt tct      1488
Ala Ser Tyr Val Ile Thr Arg Leu Val Gln Met Phe Glu Thr Val Ser
                485                 490                 495 tct tcc cca gat gtt gaa tac cct cca cca aaa tgt att cat ttg act      1536
Ser Ser Pro Asp Val Glu Tyr Pro Pro Pro Lys Cys Ile His Leu Thr
            500                 505                 510 atg agt cat gat gat ggt gtt ttc gtt aaa atg taa                      1572
Met Ser His Asp Asp Gly Val Phe Val Lys Met
            515                 520

<210> SEQ ID NO 36
<211> LENGTH: 523
<212> TYPE: PRT
<213> ORGANISM: Candida tropicalis

<400> SEQUENCE: 36

Met Ala Thr Gln Glu Ile Ile Asp Ser Ala Leu Pro Tyr Leu Thr Lys
1               5                   10                  15

Trp Tyr Thr Val Ile Thr Leu Ala Ala Leu Val Phe Leu Ile Ser Ser
            20                  25                  30

Asn Ile Lys Asn Tyr Val Lys Ala Lys Lys Leu Lys Cys Arg Asp Pro
        35                  40                  45

Pro Tyr Phe Lys Gly Ala Gly Trp Thr Gly Ile Ser Pro Leu Ile Glu
    50                  55                  60

Ile Ile Lys Val Lys Gly Asn Gly Arg Leu Ala Asp Phe Ala Asp Lys
65                  70                  75                  80

Thr Phe Asp Asp Tyr Pro Asn His Thr Phe Tyr Met Ser Ile Ile Gly
                85                  90                  95

Ala Leu Lys Ile Val Leu Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125

Phe Tyr Pro Leu Leu Gly Asp Gly Ile Phe Thr Leu Asp Gly Glu Gly
    130                 135                 140
```

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Leu Ala Lys
            165                 170                 175

Gln Ile Lys Leu Asn Lys Gly Lys Thr Phe Asp Ile Gln Glu Leu Phe
        180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Asp Asn Phe Ala Thr Ala Phe Asn Thr Ser Gln His
225                 230                 235                 240

Tyr Leu Ala Thr Arg Thr Tyr Ser Gln Thr Phe Tyr Phe Leu Thr Asn
                245                 250                 255

Pro Lys Glu Phe Arg Asp Cys Asn Ala Lys Val His Tyr Leu Ala Lys
            260                 265                 270

Tyr Phe Val Asn Lys Ala Leu Asn Phe Thr Pro Glu Glu Ile Glu Glu
        275                 280                 285

Lys Ser Lys Ser Gly Tyr Val Phe Leu Tyr Glu Leu Val Lys Gln Thr
        290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Met Phe Glu Leu
                325                 330                 335

Ala Arg His Pro Glu Ile Trp Ser Lys Leu Arg Glu Glu Ile Glu Val
            340                 345                 350

Asn Phe Gly Val Gly Glu Glu Ser Arg Val Glu Glu Ile Thr Phe Glu
        355                 360                 365

Ser Leu Lys Arg Cys Glu Tyr Leu Lys Ala Ile Leu Asn Glu Thr Leu
        370                 375                 380

Arg Met Tyr Pro Ser Val Pro Val Asn Ser Arg Thr Ala Thr Arg Asp
385                 390                 395                 400

Thr Thr Leu Pro Arg Gly Gly Pro Asn Gly Thr Asp Pro Ile Phe
                405                 410                 415

Ile Pro Lys Gly Ser Thr Val Ala Tyr Ile Val Tyr Lys Thr His Arg
            420                 425                 430

Leu Glu Glu Tyr Tyr Gly Lys Asp Ala Asp Phe Arg Pro Glu Arg
        435                 440                 445

Trp Phe Glu Pro Ser Thr Lys Lys Leu Gly Trp Ala Tyr Val Pro Phe
        450                 455                 460

Asn Gly Gly Pro Arg Ile Cys Leu Gly Gln Gln Phe Ala Leu Thr Glu
465                 470                 475                 480

Ala Ser Tyr Val Ile Thr Arg Leu Val Gln Met Phe Glu Thr Val Ser
                485                 490                 495

Ser Ser Pro Asp Val Glu Tyr Pro Pro Lys Cys Ile His Leu Thr
            500                 505                 510

Met Ser His Asp Asp Gly Val Phe Val Lys Met
            515                 520

<210> SEQ ID NO 37
<211> LENGTH: 1512
<212> TYPE: DNA
<213> ORGANISM: Candida tropicalis
<220> FEATURE:

<221> NAME/KEY: CDS
<222> LOCATION: (1)..(1509)

<400> SEQUENCE: 37

```
atg tca tta aca gaa aca act gct acg ttt att tac aat tat tgg tac        48
Met Ser Leu Thr Glu Thr Thr Ala Thr Phe Ile Tyr Asn Tyr Trp Tyr
1               5                   10                  15 atc ata ttc att ata ttc tac aca acc agc aaa atc atc aag tat cat        96
Ile Ile Phe Ile Ile Phe Tyr Thr Thr Ser Lys Ile Ile Lys Tyr His
            20                  25                  30 cac acg aca tat ctt atg ata aag ttc aaa gct tct ccg cct ttg aat       144
His Thr Thr Tyr Leu Met Ile Lys Phe Lys Ala Ser Pro Pro Leu Asn
        35                  40                  45 tac ata aat aaa ggt ttt ttt gga att cag gcg acg ttc acg gaa ttg       192
Tyr Ile Asn Lys Gly Phe Phe Gly Ile Gln Ala Thr Phe Thr Glu Leu
    50                  55                  60 aaa cat ctt ata tgt cac aca tcg att gat tac gcc atc gat caa ttc       240
Lys His Leu Ile Cys His Thr Ser Ile Asp Tyr Ala Ile Asp Gln Phe
65                  70                  75                  80 aat aac gtc cca ttc cca cat gtt cat act ttt gta acc aaa gtt ctt       288
Asn Asn Val Pro Phe Pro His Val His Thr Phe Val Thr Lys Val Leu
                85                  90                  95 ggt aat gag tta atc atg aca aaa gat cct gaa aat att aaa gtt tta       336
Gly Asn Glu Leu Ile Met Thr Lys Asp Pro Glu Asn Ile Lys Val Leu
            100                 105                 110 ttg agt tcc agt ttt gat aag ttt gat tat gga aca cgt tca agt gcc       384
Leu Ser Ser Ser Phe Asp Lys Phe Asp Tyr Gly Thr Arg Ser Ser Ala
        115                 120                 125 gtg caa cca tct tta gga atg ggg ata ttc act ctt gaa gga gaa aat       432
Val Gln Pro Ser Leu Gly Met Gly Ile Phe Thr Leu Glu Gly Glu Asn
    130                 135                 140 tgg aaa gca aca aga agt gtt tta agg aac atg ttt gat aga aaa tca       480
Trp Lys Ala Thr Arg Ser Val Leu Arg Asn Met Phe Asp Arg Lys Ser
145                 150                 155                 160 att gac aag gta cat gat ttt gaa cca cat ttc aaa acc ctt cag aaa       528
Ile Asp Lys Val His Asp Phe Glu Pro His Phe Lys Thr Leu Gln Lys
                165                 170                 175 aga ata gat ggg aag gtt gga tat ttt gac atc caa cag gag ttt tta       576
Arg Ile Asp Gly Lys Val Gly Tyr Phe Asp Ile Gln Gln Glu Phe Leu
            180                 185                 190 aaa tta gga ttg gaa ttg agt att gag ttt att ttt ggt caa gtt gta       624
Lys Leu Gly Leu Glu Leu Ser Ile Glu Phe Ile Phe Gly Gln Val Val
        195                 200                 205 tcg gaa gat gtc cca cat tat gat gat ttt acc cag gct tgg gat aga       672
Ser Glu Asp Val Pro His Tyr Asp Asp Phe Thr Gln Ala Trp Asp Arg
    210                 215                 220 tgt caa gac tat atg atg cta aga tta ttg ttg ggg gat ttt tat tgg       720
Cys Gln Asp Tyr Met Met Leu Arg Leu Leu Leu Gly Asp Phe Tyr Trp
225                 230                 235                 240 ata gct aat gac tgg aga tat aaa cag tcc aat caa att gtg caa gct       768
Ile Ala Asn Asp Trp Arg Tyr Lys Gln Ser Asn Gln Ile Val Gln Ala
                245                 250                 255 ttt tgt gat tat ttg gtg caa aaa tca ctt gaa aat aca tgc aac gac       816
Phe Cys Asp Tyr Leu Val Gln Lys Ser Leu Glu Asn Thr Cys Asn Asp
            260                 265                 270 aaa ttt gtc ttt gta cag gaa ctt gca aaa cac acg acc aac aaa acg       864
Lys Phe Val Phe Val Gln Glu Leu Ala Lys His Thr Thr Asn Lys Thr
        275                 280                 285 ttc att aga gat caa gca tta agc ttg att atg gct tca aga gac aca       912
Phe Ile Arg Asp Gln Ala Leu Ser Leu Ile Met Ala Ser Arg Asp Thr
```

```
act gct gag ttg atg gca ttc acc ata cta gaa tta tcc aga aat ccc      960
Thr Ala Glu Leu Met Ala Phe Thr Ile Leu Glu Leu Ser Arg Asn Pro
305                 310                 315                 320 act atc tgg gaa aga tta aga gag gaa ata gat gcc aat ttt gga ttg     1008
Thr Ile Trp Glu Arg Leu Arg Glu Glu Ile Asp Ala Asn Phe Gly Leu
                325                 330                 335 gaa tca ccc gac ttg ctt aca ttt gat tca ctt cgc aag ttc aaa tat     1056
Glu Ser Pro Asp Leu Leu Thr Phe Asp Ser Leu Arg Lys Phe Lys Tyr
            340                 345                 350 gtt caa gct atc ttg aat gag act ctt agg atg tac cct gga gtt cca     1104
Val Gln Ala Ile Leu Asn Glu Thr Leu Arg Met Tyr Pro Gly Val Pro
        355                 360                 365 aga aat atg aaa act gct aaa tgt act act aca tta cca aaa gga gga     1152
Arg Asn Met Lys Thr Ala Lys Cys Thr Thr Thr Leu Pro Lys Gly Gly
370                 375                 380 ggg aaa gat ggt caa gat cca att cta gtt aaa aag ggt caa tct gtt     1200
Gly Lys Asp Gly Gln Asp Pro Ile Leu Val Lys Lys Gly Gln Ser Val
385                 390                 395                 400 ggg ttt att tcc ata gct act cat ttg gat ccg gtt tat ttt ggt agt     1248
Gly Phe Ile Ser Ile Ala Thr His Leu Asp Pro Val Tyr Phe Gly Ser
                405                 410                 415 gat gcc cat gtg ttt aga cca gac cgc tgg ttt gat tct agt atg aaa     1296
Asp Ala His Val Phe Arg Pro Asp Arg Trp Phe Asp Ser Ser Met Lys
            420                 425                 430 aat ttg ggg tgt aaa tac ttg ccc ttt aac gtc ggt cca aga acg tgt     1344
Asn Leu Gly Cys Lys Tyr Leu Pro Phe Asn Val Gly Pro Arg Thr Cys
        435                 440                 445 ttg gga caa cag tac act ttg att gag gca agc tac ttg tta gtt cgt     1392
Leu Gly Gln Gln Tyr Thr Leu Ile Glu Ala Ser Tyr Leu Leu Val Arg
    450                 455                 460 cta gcg caa aca tat gaa aca gtt gaa tca cat ccc gat tca gtt tat     1440
Leu Ala Gln Thr Tyr Glu Thr Val Glu Ser His Pro Asp Ser Val Tyr
465                 470                 475                 480 cca cca agg aag aaa gcg ttg atc aat atg tgt gct gca gac ggt gtt     1488
Pro Pro Arg Lys Lys Ala Leu Ile Asn Met Cys Ala Ala Asp Gly Val
                485                 490                 495 gat gtc aag ttc cat aga tta taa                                     1512
Asp Val Lys Phe His Arg Leu
                500

<210> SEQ ID NO 38
<211> LENGTH: 503
<212> TYPE: PRT
<213> ORGANISM: Candida tropicalis

<400> SEQUENCE: 38

Met Ser Leu Thr Glu Thr Thr Ala Thr Phe Ile Tyr Asn Tyr Trp Tyr
1               5                   10                  15

Ile Ile Phe Ile Ile Phe Tyr Thr Thr Ser Lys Ile Ile Lys Tyr His
                20                  25                  30

His Thr Thr Tyr Leu Met Ile Lys Phe Lys Ala Ser Pro Pro Leu Asn
            35                  40                  45

Tyr Ile Asn Lys Gly Phe Phe Gly Ile Gln Ala Thr Phe Thr Glu Leu
        50                  55                  60

Lys His Leu Ile Cys His Thr Ser Ile Asp Tyr Ala Ile Asp Gln Phe
65                  70                  75                  80

Asn Asn Val Pro Phe Pro His Val His Thr Phe Val Thr Lys Val Leu
                85                  90                  95
```

```
Gly Asn Glu Leu Ile Met Thr Lys Asp Pro Glu Asn Ile Lys Val Leu
            100                 105                 110

Leu Ser Ser Ser Phe Asp Lys Phe Asp Tyr Gly Thr Arg Ser Ser Ala
            115                 120                 125

Val Gln Pro Ser Leu Gly Met Gly Ile Phe Thr Leu Glu Gly Glu Asn
130                 135                 140

Trp Lys Ala Thr Arg Ser Val Leu Arg Asn Met Phe Asp Arg Lys Ser
145                 150                 155                 160

Ile Asp Lys Val His Asp Phe Glu Pro His Phe Lys Thr Leu Gln Lys
                165                 170                 175

Arg Ile Asp Gly Lys Val Gly Tyr Phe Asp Ile Gln Gln Glu Phe Leu
            180                 185                 190

Lys Leu Gly Leu Glu Leu Ser Ile Glu Phe Ile Phe Gly Gln Val Val
            195                 200                 205

Ser Glu Asp Val Pro His Tyr Asp Asp Phe Thr Gln Ala Trp Asp Arg
            210                 215                 220

Cys Gln Asp Tyr Met Met Leu Arg Leu Leu Leu Gly Asp Phe Tyr Trp
225                 230                 235                 240

Ile Ala Asn Asp Trp Arg Tyr Lys Gln Ser Asn Gln Ile Val Gln Ala
                245                 250                 255

Phe Cys Asp Tyr Leu Val Gln Lys Ser Leu Glu Asn Thr Cys Asn Asp
            260                 265                 270

Lys Phe Val Phe Val Gln Glu Leu Ala Lys His Thr Thr Asn Lys Thr
            275                 280                 285

Phe Ile Arg Asp Gln Ala Leu Ser Leu Ile Met Ala Ser Arg Asp Thr
            290                 295                 300

Thr Ala Glu Leu Met Ala Phe Thr Ile Leu Glu Leu Ser Arg Asn Pro
305                 310                 315                 320

Thr Ile Trp Glu Arg Leu Arg Glu Glu Ile Asp Ala Asn Phe Gly Leu
                325                 330                 335

Glu Ser Pro Asp Leu Leu Thr Phe Asp Ser Leu Arg Lys Phe Lys Tyr
            340                 345                 350

Val Gln Ala Ile Leu Asn Glu Thr Leu Arg Met Tyr Pro Gly Val Pro
            355                 360                 365

Arg Asn Met Lys Thr Ala Lys Cys Thr Thr Thr Leu Pro Lys Gly Gly
            370                 375                 380

Gly Lys Asp Gly Gln Asp Pro Ile Leu Val Lys Lys Gly Gln Ser Val
385                 390                 395                 400

Gly Phe Ile Ser Ile Ala Thr His Leu Asp Pro Val Tyr Phe Gly Ser
                405                 410                 415

Asp Ala His Val Phe Arg Pro Asp Arg Trp Phe Asp Ser Ser Met Lys
            420                 425                 430

Asn Leu Gly Cys Lys Tyr Leu Pro Phe Asn Val Gly Pro Arg Thr Cys
            435                 440                 445

Leu Gly Gln Gln Tyr Thr Leu Ile Glu Ala Ser Tyr Leu Leu Val Arg
            450                 455                 460

Leu Ala Gln Thr Tyr Glu Thr Val Glu Ser His Pro Asp Ser Val Tyr
465                 470                 475                 480

Pro Pro Arg Lys Lys Ala Leu Ile Asn Met Cys Ala Ala Asp Gly Val
            485                 490                 495

Asp Val Lys Phe His Arg Leu
            500
```

<210> SEQ ID NO 39
<211> LENGTH: 1554
<212> TYPE: DNA
<213> ORGANISM: Candida tropicalis
<220> FEATURE:
<221> NAME/KEY: CDS
<222> LOCATION: (1)..(1551)

<400> SEQUENCE: 39

```
atg atc gaa caa gtt gtt gaa tac tgg tac gtg gtc tta cca ttg gta     48
Met Ile Glu Gln Val Val Glu Tyr Trp Tyr Val Val Leu Pro Leu Val
1               5                   10                  15 ttt atc ctt cat aaa gta ttt gac atg tgg cac act cgt cgg ttg atg     96
Phe Ile Leu His Lys Val Phe Asp Met Trp His Thr Arg Arg Leu Met
                20                  25                  30 aag caa ttg ggc gct gct cct gtc aca aac caa tta cac gac aat ttt    144
Lys Gln Leu Gly Ala Ala Pro Val Thr Asn Gln Leu His Asp Asn Phe
            35                  40                  45 ttt ggt att atc aac gga tgg aaa gca ctt aag ttc aag aaa gaa ggt    192
Phe Gly Ile Ile Asn Gly Trp Lys Ala Leu Lys Phe Lys Lys Glu Gly
        50                  55                  60 aga gct caa gaa tat aat gat tat aaa ttt gcc aat tcg aaa att cca    240
Arg Ala Gln Glu Tyr Asn Asp Tyr Lys Phe Ala Asn Ser Lys Ile Pro
65                  70                  75                  80 agt gtg ggt act tat gtt agt acc atc ttt gga aca aag ctc ctc gtc    288
Ser Val Gly Thr Tyr Val Ser Thr Ile Phe Gly Thr Lys Leu Leu Val
                85                  90                  95 aca aaa gat ccg gag aat atc aaa gct tta tta gca acc caa ttc agt    336
Thr Lys Asp Pro Glu Asn Ile Lys Ala Leu Leu Ala Thr Gln Phe Ser
                100                 105                 110 gat ttt tcc ttg ggt aag agg cat aca ctt ttc aaa cca tta tta ggt    384
Asp Phe Ser Leu Gly Lys Arg His Thr Leu Phe Lys Pro Leu Leu Gly
            115                 120                 125 gac ggt att ttc act ttg gat gga gaa ggt tgg aaa cat agt cga gct    432
Asp Gly Ile Phe Thr Leu Asp Gly Glu Gly Trp Lys His Ser Arg Ala
        130                 135                 140 atg ttg aga cca cag ttt gca aga gaa caa gtt gcc cat gtc act tct    480
Met Leu Arg Pro Gln Phe Ala Arg Glu Gln Val Ala His Val Thr Ser
145                 150                 155                 160 tta gag cca cat ttc caa ttg ttg aaa aaa cat atc ctc aag aac aaa    528
Leu Glu Pro His Phe Gln Leu Leu Lys Lys His Ile Leu Lys Asn Lys
                165                 170                 175 gga ggt ttt ttt gat atc cag gaa ttg ttt tcc cga ttc act gtt gat    576
Gly Gly Phe Phe Asp Ile Gln Glu Leu Phe Phe Arg Phe Thr Val Asp
                180                 185                 190 tca gct act gag ttt ttg ttt ggt gaa tca gta cac tct ttg aag gat    624
Ser Ala Thr Glu Phe Leu Phe Gly Glu Ser Val His Ser Leu Lys Asp
            195                 200                 205 gaa aca att ggg tat aac caa gat gat atc gac ttt gtt ggt aga aag    672
Glu Thr Ile Gly Tyr Asn Gln Asp Asp Ile Asp Phe Val Gly Arg Lys
        210                 215                 220 gat ttt gcg gaa tcg ttc aac aag gca caa gag tat ctt gct att aga    720
Asp Phe Ala Glu Ser Phe Asn Lys Ala Gln Glu Tyr Leu Ala Ile Arg
225                 230                 235                 240 act ttg gtg caa gat ttt tat tat ctt gta aac aat cag gaa ttc aga    768
Thr Leu Val Gln Asp Phe Tyr Tyr Leu Val Asn Asn Gln Glu Phe Arg
                245                 250                 255 gat tgc aat aaa ctg gta cac aag ttt acc aac tac tat gtc caa aga    816
Asp Cys Asn Lys Leu Val His Lys Phe Thr Asn Tyr Tyr Val Gln Arg
                260                 265                 270
```

| | | | | | | | | | | | | | | |
|---|---|---|---|---|---|---|---|---|---|---|---|---|---|---|
| gca | ttg | gat | gcc | act | cct | gaa | gag | ctt | gaa | aag | caa | agt | gga | tat gtt | 864 |
| Ala | Leu | Asp | Ala | Thr | Pro | Glu | Glu | Leu | Glu | Lys | Gln | Ser | Gly | Tyr Val |
| | | | 275 | | | | 280 | | | | 285 | | | |

```
gca ttg gat gcc act cct gaa gag ctt gaa aag caa agt gga tat gtt    864
Ala Leu Asp Ala Thr Pro Glu Glu Leu Glu Lys Gln Ser Gly Tyr Val
            275                 280                 285 ttc ttg tat gaa ttg gtt aaa caa acc aga gac cct aat gta ttg aga    912
Phe Leu Tyr Glu Leu Val Lys Gln Thr Arg Asp Pro Asn Val Leu Arg
        290                 295                 300 gat caa tca ttg aac atc tta tta gct ggt aga gat acc act gct ggg    960
Asp Gln Ser Leu Asn Ile Leu Leu Ala Gly Arg Asp Thr Thr Ala Gly
305                 310                 315                 320 ttg ttg tca ttt gcg gta ttt gaa ctt gct agg aat cca cat att tgg   1008
Leu Leu Ser Phe Ala Val Phe Glu Leu Ala Arg Asn Pro His Ile Trp
                325                 330                 335 gcc aaa tta aga gaa gat gtt gaa tcc caa ttt ggt ctt ggt gaa gaa   1056
Ala Lys Leu Arg Glu Asp Val Glu Ser Gln Phe Gly Leu Gly Glu Glu
            340                 345                 350 tct cgc att gaa gag att acc ttt gaa agt tta aaa cga tgt gaa tac   1104
Ser Arg Ile Glu Glu Ile Thr Phe Glu Ser Leu Lys Arg Cys Glu Tyr
        355                 360                 365 ttg aaa gct ttc ctt aac gaa aca tta cgt gtt tat cca agt gtt cca   1152
Leu Lys Ala Phe Leu Asn Glu Thr Leu Arg Val Tyr Pro Ser Val Pro
370                 375                 380 aga aat ttc aga att gct acc aaa aac acc act tta cca aga ggt ggt   1200
Arg Asn Phe Arg Ile Ala Thr Lys Asn Thr Thr Leu Pro Arg Gly Gly
385                 390                 395                 400 ggt tca gac ggc aat tct cct gtt ttg gtc aaa aag ggc gag gct gtt   1248
Gly Ser Asp Gly Asn Ser Pro Val Leu Val Lys Lys Gly Glu Ala Val
                405                 410                 415 tca tat ggt ata aat tct act cac tta gat cct gtc tat tat ggt gac   1296
Ser Tyr Gly Ile Asn Ser Thr His Leu Asp Pro Val Tyr Tyr Gly Asp
            420                 425                 430 gat gct gca gaa ttt aga cca gaa aga tgg aac gag cca tca aca aga   1344
Asp Ala Ala Glu Phe Arg Pro Glu Arg Trp Asn Glu Pro Ser Thr Arg
        435                 440                 445 aaa ttg gga tgg gca tat tta ccg ttc aac gga ggc cca aga att tgt   1392
Lys Leu Gly Trp Ala Tyr Leu Pro Phe Asn Gly Gly Pro Arg Ile Cys
        450                 455                 460 tta ggt caa caa ttt gct tta acc gaa gcg ggt tat gta ttg gtt aga   1440
Leu Gly Gln Gln Phe Ala Leu Thr Glu Ala Gly Tyr Val Leu Val Arg
465                 470                 475                 480 ttg gcc caa agt ttt gac acc ttg gaa ttg aag cca cca gtt gtg tat   1488
Leu Ala Gln Ser Phe Asp Thr Leu Glu Leu Lys Pro Pro Val Val Tyr
                485                 490                 495 cca cca aag aga tta aca aac ttg act atg tct tta caa gac gga act   1536
Pro Pro Lys Arg Leu Thr Asn Leu Thr Met Ser Leu Gln Asp Gly Thr
            500                 505                 510 att gtc aag atc gat tag                                            1554
Ile Val Lys Ile Asp
        515
```

<210> SEQ ID NO 40
<211> LENGTH: 517
<212> TYPE: PRT
<213> ORGANISM: Candida tropicalis

<400> SEQUENCE: 40

Met Ile Glu Gln Val Val Glu Tyr Trp Tyr Val Leu Pro Leu Val
1               5                   10                  15

Phe Ile Leu His Lys Val Phe Asp Met Trp His Thr Arg Arg Leu Met
            20                  25                  30

Lys Gln Leu Gly Ala Ala Pro Val Thr Asn Gln Leu His Asp Asn Phe

```
                35                  40                  45
Phe Gly Ile Ile Asn Gly Trp Lys Ala Leu Lys Phe Lys Lys Glu Gly
 50                  55                  60
Arg Ala Gln Glu Tyr Asn Asp Tyr Lys Phe Ala Asn Ser Lys Ile Pro
 65                  70                  75                  80
Ser Val Gly Thr Tyr Val Ser Thr Ile Phe Gly Thr Lys Leu Leu Val
                 85                  90                  95
Thr Lys Asp Pro Glu Asn Ile Lys Ala Leu Leu Ala Thr Gln Phe Ser
                100                 105                 110
Asp Phe Ser Leu Gly Lys Arg His Thr Leu Phe Lys Pro Leu Leu Gly
            115                 120                 125
Asp Gly Ile Phe Thr Leu Asp Gly Glu Gly Trp Lys His Ser Arg Ala
130                 135                 140
Met Leu Arg Pro Gln Phe Ala Arg Glu Gln Val Ala His Val Thr Ser
145                 150                 155                 160
Leu Glu Pro His Phe Gln Leu Leu Lys Lys His Ile Leu Lys Asn Lys
                165                 170                 175
Gly Gly Phe Phe Asp Ile Gln Glu Leu Phe Phe Arg Phe Thr Val Asp
            180                 185                 190
Ser Ala Thr Glu Phe Leu Phe Gly Glu Ser Val His Ser Leu Lys Asp
            195                 200                 205
Glu Thr Ile Gly Tyr Asn Gln Asp Ile Asp Phe Val Gly Arg Lys
210                 215                 220
Asp Phe Ala Glu Ser Phe Asn Lys Ala Gln Glu Tyr Leu Ala Ile Arg
225                 230                 235                 240
Thr Leu Val Gln Asp Phe Tyr Tyr Leu Val Asn Asn Gln Glu Phe Arg
                245                 250                 255
Asp Cys Asn Lys Leu Val His Lys Phe Thr Asn Tyr Tyr Val Gln Arg
            260                 265                 270
Ala Leu Asp Ala Thr Pro Glu Glu Leu Glu Lys Gln Ser Gly Tyr Val
            275                 280                 285
Phe Leu Tyr Glu Leu Val Lys Gln Thr Arg Asp Pro Asn Val Leu Arg
290                 295                 300
Asp Gln Ser Leu Asn Ile Leu Leu Ala Gly Arg Asp Thr Thr Ala Gly
305                 310                 315                 320
Leu Leu Ser Phe Ala Val Phe Glu Leu Ala Arg Asn Pro His Ile Trp
                325                 330                 335
Ala Lys Leu Arg Glu Asp Val Glu Ser Gln Phe Gly Leu Gly Glu Glu
            340                 345                 350
Ser Arg Ile Glu Glu Ile Thr Phe Glu Ser Leu Lys Arg Cys Glu Tyr
            355                 360                 365
Leu Lys Ala Phe Leu Asn Glu Thr Leu Arg Val Tyr Pro Ser Val Pro
            370                 375                 380
Arg Asn Phe Arg Ile Ala Thr Lys Asn Thr Thr Leu Pro Arg Gly Gly
385                 390                 395                 400
Gly Ser Asp Gly Asn Ser Pro Val Leu Val Lys Lys Gly Glu Ala Val
                405                 410                 415
Ser Tyr Gly Ile Asn Ser Thr His Leu Asp Pro Val Tyr Gly Asp
            420                 425                 430
Asp Ala Ala Glu Phe Arg Pro Glu Arg Trp Asn Glu Pro Ser Thr Arg
            435                 440                 445
Lys Leu Gly Trp Ala Tyr Leu Pro Phe Asn Gly Gly Pro Arg Ile Cys
            450                 455                 460
```

```
Leu Gly Gln Gln Phe Ala Leu Thr Glu Ala Gly Tyr Val Leu Val Arg
465                 470                 475                 480

Leu Ala Gln Ser Phe Asp Thr Leu Glu Leu Lys Pro Pro Val Val Tyr
            485                 490                 495

Pro Pro Lys Arg Leu Thr Asn Leu Thr Met Ser Leu Gln Asp Gly Thr
        500                 505                 510

Ile Val Lys Ile Asp
        515

<210> SEQ ID NO 41
<211> LENGTH: 1539
<212> TYPE: DNA
<213> ORGANISM: Candida tropicalis
<220> FEATURE:
<221> NAME/KEY: CDS
<222> LOCATION: (1)..(1536)

<400> SEQUENCE: 41 atg att gaa cag gtt tta cat tat tgg tat att gtt tta cct gca ttt      48
Met Ile Glu Gln Val Leu His Tyr Trp Tyr Ile Val Leu Pro Ala Phe
1               5                   10                  15 ata att ttt cat tgg att gta tct gca att cat aca aat tcc ttg cgt      96
Ile Ile Phe His Trp Ile Val Ser Ala Ile His Thr Asn Ser Leu Arg
            20                  25                  30 aga aaa cta ggt gcc aaa cct ttc act cat aca caa ctt gat ggt ttt     144
Arg Lys Leu Gly Ala Lys Pro Phe Thr His Thr Gln Leu Asp Gly Phe
        35                  40                  45 tat gga ttt aaa ttt ggc cgt gat ttc ctt aaa gct aaa agg att ggt     192
Tyr Gly Phe Lys Phe Gly Arg Asp Phe Leu Lys Ala Lys Arg Ile Gly
    50                  55                  60 agg caa gtt gat tta atc aat tcc cgt ttc cca gac gat att gac aca     240
Arg Gln Val Asp Leu Ile Asn Ser Arg Phe Pro Asp Asp Ile Asp Thr
65                  70                  75                  80 ttt tca agt tat act ttc ggc aac cac gtg att ttt aca cgt gat cca     288
Phe Ser Ser Tyr Thr Phe Gly Asn His Val Ile Phe Thr Arg Asp Pro
                85                  90                  95 gaa aat atc aaa gct tta ttg gca aca caa ttt aat gat ttt tca tta     336
Glu Asn Ile Lys Ala Leu Leu Ala Thr Gln Phe Asn Asp Phe Ser Leu
            100                 105                 110 ggt ggt aga att aag ttt ttc aaa cca ttg ttg gga tat gga atc ttt     384
Gly Gly Arg Ile Lys Phe Phe Lys Pro Leu Leu Gly Tyr Gly Ile Phe
        115                 120                 125 act ttg gat gga gaa ggt tgg aaa cat agt cga gct atg ttg aga cca     432
Thr Leu Asp Gly Glu Gly Trp Lys His Ser Arg Ala Met Leu Arg Pro
    130                 135                 140 cag ttt gca aga gaa caa gtt gcc cat gtc act tct tta gaa cca cat     480
Gln Phe Ala Arg Glu Gln Val Ala His Val Thr Ser Leu Glu Pro His
145                 150                 155                 160 ttc caa ttg ttg aaa aag cat atc ctc aag aac aaa ggt ggg ttt ttt     528
Phe Gln Leu Leu Lys Lys His Ile Leu Lys Asn Lys Gly Gly Phe Phe
                165                 170                 175 gat atc cag gaa ttg ttt ttc cga ttc acc gtt gat tca gct act gag     576
Asp Ile Gln Glu Leu Phe Phe Arg Phe Thr Val Asp Ser Ala Thr Glu
            180                 185                 190 ttt ttg ttt ggt gaa tca gtg aac tct ttg aaa agt gca tca att ggt     624
Phe Leu Phe Gly Glu Ser Val Asn Ser Leu Lys Ser Ala Ser Ile Gly
        195                 200                 205 tgt gac gag gaa acc gag ctt gag gaa aga aag aaa ttt gcg gaa gca     672
Cys Asp Glu Glu Thr Glu Leu Glu Glu Arg Lys Lys Phe Ala Glu Ala
    210                 215                 220
```

```
ttc aat aaa gcg caa gag tat att tct act cga gtt gct ttg caa caa     720
Phe Asn Lys Ala Gln Glu Tyr Ile Ser Thr Arg Val Ala Leu Gln Gln
225                 230                 235                 240 tta tat tgg ttt gtt aat aat agc gaa ttc aag gaa tgt aac gaa att     768
Leu Tyr Trp Phe Val Asn Asn Ser Glu Phe Lys Glu Cys Asn Glu Ile
            245                 250                 255 gtt cat aag ttt acc aat tat tat gta caa aag gca ttg gat gct act     816
Val His Lys Phe Thr Asn Tyr Tyr Val Gln Lys Ala Leu Asp Ala Thr
        260                 265                 270 cct gaa gag ctt gaa aag caa agt gga tat gtt ttc ttg tat gaa ttg     864
Pro Glu Glu Leu Glu Lys Gln Ser Gly Tyr Val Phe Leu Tyr Glu Leu
    275                 280                 285 gtt aaa caa acc aga gac cct aat gta ttg aga gat caa tca ttg aat     912
Val Lys Gln Thr Arg Asp Pro Asn Val Leu Arg Asp Gln Ser Leu Asn
290                 295                 300 atc tta tta gct ggt aga gat acc act gct ggg ttg ttg tca ttt gcg     960
Ile Leu Leu Ala Gly Arg Asp Thr Thr Ala Gly Leu Leu Ser Phe Ala
305                 310                 315                 320 gta ttt gaa ctt gct agg aat cca cat att tgg gcc aaa tta aga gaa    1008
Val Phe Glu Leu Ala Arg Asn Pro His Ile Trp Ala Lys Leu Arg Glu
            325                 330                 335 gat gtc gaa tcc caa ttt ggt ctt ggt gaa gaa tct cgc att gaa gag    1056
Asp Val Glu Ser Gln Phe Gly Leu Gly Glu Glu Ser Arg Ile Glu Glu
        340                 345                 350 att acc ttt gaa agt tta aaa cga tgt gaa tat ttg aaa gcc gtg atg    1104
Ile Thr Phe Glu Ser Leu Lys Arg Cys Glu Tyr Leu Lys Ala Val Met
    355                 360                 365 aat gaa aca ttg aga ttg cat cca agt gtt cca aga aat gct aga ttt    1152
Asn Glu Thr Leu Arg Leu His Pro Ser Val Pro Arg Asn Ala Arg Phe
370                 375                 380 gca ctt aag gat aca act tta cct aga ggt gga ggt cca gat gga aaa    1200
Ala Leu Lys Asp Thr Thr Leu Pro Arg Gly Gly Gly Pro Asp Gly Lys
385                 390                 395                 400 gac ccg att tta gtt aga aaa aat gaa gtt gtt caa tat tcc att tct    1248
Asp Pro Ile Leu Val Arg Lys Asn Glu Val Val Gln Tyr Ser Ile Ser
            405                 410                 415 ggc aca caa att gat cca aaa cat tat ggc aaa gat gct aaa ttg ttt    1296
Gly Thr Gln Ile Asp Pro Lys His Tyr Gly Lys Asp Ala Lys Leu Phe
        420                 425                 430 aga cca gaa aga tgg ttt gaa tca agt aca aga aat tta ggt tgg gca    1344
Arg Pro Glu Arg Trp Phe Glu Ser Ser Thr Arg Asn Leu Gly Trp Ala
    435                 440                 445 tac tta cca ttc aac ggg ggt ccg aga att tgt tta ggt caa caa ttt    1392
Tyr Leu Pro Phe Asn Gly Gly Pro Arg Ile Cys Leu Gly Gln Gln Phe
450                 455                 460 gct tta acc gaa gca ggt tac ata ttg gtt aga ttg gct caa agt ttt    1440
Ala Leu Thr Glu Ala Gly Tyr Ile Leu Val Arg Leu Ala Gln Ser Phe
465                 470                 475                 480 gac acc ttg gaa ttg aaa cca gat aca gaa tac cct cca cca aga tta    1488
Asp Thr Leu Glu Leu Lys Pro Asp Thr Glu Tyr Pro Pro Pro Arg Leu
            485                 490                 495 gcc cat ttg act atg tgt ttg ttt gat ggt gcg ctt gtc aag atg gat    1536
Ala His Leu Thr Met Cys Leu Phe Asp Gly Ala Leu Val Lys Met Asp
        500                 505                 510 taa                                                                1539
```

<210> SEQ ID NO 42
<211> LENGTH: 512
<212> TYPE: PRT

<213> ORGANISM: Candida tropicalis

<400> SEQUENCE: 42

```
Met Ile Glu Gln Val Leu His Tyr Trp Tyr Ile Val Leu Pro Ala Phe
1               5                   10                  15

Ile Ile Phe His Trp Ile Val Ser Ala Ile His Thr Asn Ser Leu Arg
            20                  25                  30

Arg Lys Leu Gly Ala Lys Pro Phe Thr His Thr Gln Leu Asp Gly Phe
        35                  40                  45

Tyr Gly Phe Lys Phe Gly Arg Asp Phe Leu Lys Ala Lys Arg Ile Gly
    50                  55                  60

Arg Gln Val Asp Leu Ile Asn Ser Arg Phe Pro Asp Asp Ile Asp Thr
65                  70                  75                  80

Phe Ser Ser Tyr Thr Phe Gly Asn His Val Ile Phe Thr Arg Asp Pro
                85                  90                  95

Glu Asn Ile Lys Ala Leu Leu Ala Thr Gln Phe Asn Asp Phe Ser Leu
            100                 105                 110

Gly Gly Arg Ile Lys Phe Phe Lys Pro Leu Leu Gly Tyr Gly Ile Phe
        115                 120                 125

Thr Leu Asp Gly Glu Gly Trp Lys His Ser Arg Ala Met Leu Arg Pro
130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys Asn Lys Gly Gly Phe Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val Asn Ser Leu Lys Ser Ala Ser Ile Gly
        195                 200                 205

Cys Asp Glu Glu Thr Glu Leu Glu Gly Arg Lys Lys Phe Ala Glu Ala
    210                 215                 220

Phe Asn Lys Ala Gln Glu Tyr Ile Ser Thr Arg Val Ala Leu Gln Gln
225                 230                 235                 240

Leu Tyr Trp Phe Val Asn Asn Ser Glu Phe Lys Glu Cys Asn Glu Ile
                245                 250                 255

Val His Lys Phe Thr Asn Tyr Tyr Val Gln Lys Ala Leu Asp Ala Thr
            260                 265                 270

Pro Glu Glu Leu Glu Lys Gln Ser Gly Tyr Val Phe Leu Tyr Glu Leu
        275                 280                 285

Val Lys Gln Thr Arg Asp Pro Asn Val Leu Arg Asp Gln Ser Leu Asn
290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335

Asp Val Glu Ser Gln Phe Gly Leu Gly Glu Ser Arg Ile Glu Glu
            340                 345                 350

Ile Thr Phe Glu Ser Leu Lys Arg Cys Glu Tyr Leu Lys Ala Val Met
        355                 360                 365

Asn Glu Thr Leu Arg Leu His Pro Ser Val Pro Arg Asn Ala Arg Phe
    370                 375                 380

Ala Leu Lys Asp Thr Thr Leu Pro Arg Gly Gly Gly Pro Asp Gly Lys
385                 390                 395                 400
```

```
Asp Pro Ile Leu Val Arg Lys Asn Glu Val Val Gln Tyr Ser Ile Ser
                405                 410                 415

Gly Thr Gln Ile Asp Pro Lys His Tyr Gly Lys Asp Ala Lys Leu Phe
            420                 425                 430

Arg Pro Glu Arg Trp Phe Glu Ser Ser Thr Arg Asn Leu Gly Trp Ala
        435                 440                 445

Tyr Leu Pro Phe Asn Gly Gly Pro Arg Ile Cys Leu Gly Gln Gln Phe
    450                 455                 460

Ala Leu Thr Glu Ala Gly Tyr Ile Leu Val Arg Leu Ala Gln Ser Phe
465                 470                 475                 480

Asp Thr Leu Glu Leu Lys Pro Asp Thr Glu Tyr Pro Pro Arg Leu
                485                 490                 495

Ala His Leu Thr Met Cys Leu Phe Asp Gly Ala Leu Val Lys Met Asp
                500                 505                 510

<210> SEQ ID NO 43
<211> LENGTH: 1572
<212> TYPE: DNA
<213> ORGANISM: Candida tropicalis
<220> FEATURE:
<221> NAME/KEY: CDS
<222> LOCATION: (1)..(1569)

<400> SEQUENCE: 43 atg att aaa gaa ata gtg tat ttt gta tat tat gga att acc cac        48
Met Ile Lys Glu Ile Val Tyr Phe Val Tyr Tyr Tyr Gly Ile Thr His
1               5                   10                  15 tca gtt tca gtg cag gtc acc gct ctt gtc ctt atc gtg aca tac ttt    96
Ser Val Ser Val Gln Val Thr Ala Leu Val Leu Ile Val Thr Tyr Phe
            20                  25                  30 ttt gtt att cgt cca att aac tca cct tta tgg aga gtt ccc gga cca   144
Phe Val Ile Arg Pro Ile Asn Ser Pro Leu Trp Arg Val Pro Gly Pro
        35                  40                  45 tat tta cat cgg gta act tac ttt cca tgt tta aat gcc caa cga aag   192
Tyr Leu His Arg Val Thr Tyr Phe Pro Cys Leu Asn Ala Gln Arg Lys
    50                  55                  60 gga gaa tgg atc tcc aaa gtt tat gat ttg cac aag aaa tat ggt gat   240
Gly Glu Trp Ile Ser Lys Val Tyr Asp Leu His Lys Lys Tyr Gly Asp
65                  70                  75                  80 gta gtt tta ctt tct cca aat gaa atc agc gtc aat ggt gac cca aaa   288
Val Val Leu Leu Ser Pro Asn Glu Ile Ser Val Asn Gly Asp Pro Lys
                85                  90                  95 tat ttg act gat att tat gta aag aac ctc cca aag tca aag ttt tat   336
Tyr Leu Thr Asp Ile Tyr Val Lys Asn Leu Pro Lys Ser Lys Phe Tyr
            100                 105                 110 gaa aac ttt aga aat cat gga ttc cag gat aat att ttt gcc agt ttg   384
Glu Asn Phe Arg Asn His Gly Phe Gln Asp Asn Ile Phe Ala Ser Leu
        115                 120                 125 gaa aat gat aga cat atc aag tat aaa aga atg ata aat aac ttg tac   432
Glu Asn Asp Arg His Ile Lys Tyr Lys Arg Met Ile Asn Asn Leu Tyr
    130                 135                 140 agt aaa tct tcc atc ttc tcc aaa gaa aac cac aca aga tca gtt tta   480
Ser Lys Ser Ser Ile Phe Ser Lys Glu Asn His Thr Arg Ser Val Leu
145                 150                 155                 160 ttt gac acc aca aaa aca tta gtc gat gca gtt gct aga gaa tct ccg   528
Phe Asp Thr Thr Lys Thr Leu Val Asp Ala Val Ala Arg Glu Ser Pro
                165                 170                 175 tca att gat gtg ttt acg tta ttt ggt tcc ttg gcc atg gat gtg gtt   576
Ser Ile Asp Val Phe Thr Leu Phe Gly Ser Leu Ala Met Asp Val Val
            180                 185                 190
```

-continued

| | |
|---|---|
| tca agg ttt gaa ctt ggt aga gac aat gga acg gat tta ttg aat cat<br>Ser Arg Phe Glu Leu Gly Arg Asp Asn Gly Thr Asp Leu Leu Asn His<br>     195                    200                    205 | 624 |
| cca caa gaa agg cat att att gaa tct cat aga aag gtg tct tgt atg<br>Pro Gln Glu Arg His Ile Ile Glu Ser His Arg Lys Val Ser Cys Met<br>210                    215                    220 | 672 |
| ggg ttc tgg aca aca ttg atg cca agc ttc ttt tgg aat ttg gca gca<br>Gly Phe Trp Thr Thr Leu Met Pro Ser Phe Phe Trp Asn Leu Ala Ala<br>225                    230                    235                    240 | 720 |
| acc aag gcc acc ttg caa gct gtt gat gat att tgc aat ttc caa ttg<br>Thr Lys Ala Thr Leu Gln Ala Val Asp Asp Ile Cys Asn Phe Gln Leu<br>                    245                    250                    255 | 768 |
| ggt tta tat aaa att gca gaa tcc aat ctt gtg tcc aat ggt aaa aac<br>Gly Leu Tyr Lys Ile Ala Glu Ser Asn Leu Val Ser Asn Gly Lys Asn<br>                    260                    265                    270 | 816 |
| cta act acg ata caa aca ctc aag aag tac gga ttg gaa gga aat tct<br>Leu Thr Thr Ile Gln Thr Leu Lys Lys Tyr Gly Leu Glu Gly Asn Ser<br>     275                    280                    285 | 864 |
| gcg tat tct ttt ctc acg gat aat tta ttt gct gga cat gaa act aca<br>Ala Tyr Ser Phe Leu Thr Asp Asn Leu Phe Ala Gly His Glu Thr Thr<br>290                    295                    300 | 912 |
| gct gtt caa ttg aca tat ttg tgt tat gaa tta tca aga cca gct aat<br>Ala Val Gln Leu Thr Tyr Leu Cys Tyr Glu Leu Ser Arg Pro Ala Asn<br>305                    310                    315                    320 | 960 |
| tac aaa att cag aat aga tta aga tat gag ctt caa gaa gca ttt cca<br>Tyr Lys Ile Gln Asn Arg Leu Arg Tyr Glu Leu Gln Glu Ala Phe Pro<br>                    325                    330                    335 | 1008 |
| agt ggt caa att gaa gat ttg gaa gtg gtt gat aat ctt ccg tat ctt<br>Ser Gly Gln Ile Glu Asp Leu Glu Val Val Asp Asn Leu Pro Tyr Leu<br>                    340                    345                    350 | 1056 |
| aat gcg ttg ttg tcc gaa aat ggt cga att cac acc tca att cct gga<br>Asn Ala Leu Leu Ser Glu Asn Gly Arg Ile His Thr Ser Ile Pro Gly<br>     355                    360                    365 | 1104 |
| gct gag cca cgt gtg gtt gca aaa ccg tat act att ggc aaa ttg ctt<br>Ala Glu Pro Arg Val Val Ala Lys Pro Tyr Thr Ile Gly Lys Leu Leu<br>            370                    375                    380 | 1152 |
| att cca gtt ggt acg gtt atc tct tgt ctt cct tat gcg tat cat aga<br>Ile Pro Val Gly Thr Val Ile Ser Cys Leu Pro Tyr Ala Tyr His Arg<br>385                    390                    395                    400 | 1200 |
| aat ccg tcg gta ttt acc aat cct gat aaa ttt atc ccc gaa aga tgg<br>Asn Pro Ser Val Phe Thr Asn Pro Asp Lys Phe Ile Pro Glu Arg Trp<br>                    405                    410                    415 | 1248 |
| tta gtt gac aac gaa gaa gac aag aaa cga gtc aaa caa caa gcg aag<br>Leu Val Asp Asn Glu Glu Asp Lys Lys Arg Val Lys Gln Gln Ala Lys<br>            420                    425                    430 | 1296 |
| tat atg atg cca ttt ggt aaa ggt gta aga atg tgt ctt ggg atg aac<br>Tyr Met Met Pro Phe Gly Lys Gly Val Arg Met Cys Leu Gly Met Asn<br>                    435                    440                    445 | 1344 |
| ttg gca ctc att gaa atg aag ttg gcc att gca agt ttg tat tta aac<br>Leu Ala Leu Ile Glu Met Lys Leu Ala Ile Ala Ser Leu Tyr Leu Asn<br>450                    455                    460 | 1392 |
| ttt tct tct tcc att gac gaa gac tgg tgt ggc aaa gta tta gaa aat<br>Phe Ser Ser Ser Ile Asp Glu Asp Trp Cys Gly Lys Val Leu Glu Asn<br>465                    470                    475                    480 | 1440 |
| gat gac ccc ata ggt atc ggg aat tca tgc act cat gag act gat cag<br>Asp Asp Pro Ile Gly Ile Gly Asn Ser Cys Thr His Glu Thr Asp Gln<br>                    485                    490                    495 | 1488 |
| gat aaa atg aaa atg tac gat gct tat act acg aga cca atg cta gat<br>Asp Lys Met Lys Met Tyr Asp Ala Tyr Thr Thr Arg Pro Met Leu Asp | 1536 |

```
                   500              505              510
gaa tgt tac ttg aag tgg aca aga tta act cct tga                       1572
Glu Cys Tyr Leu Lys Trp Thr Arg Leu Thr Pro
        515                  520
```

<210> SEQ ID NO 44
<211> LENGTH: 523
<212> TYPE: PRT
<213> ORGANISM: Candida tropicalis

<400> SEQUENCE: 44

```
Met Ile Lys Glu Ile Val Tyr Phe Val Tyr Tyr Gly Ile Thr His
1               5                   10                  15

Ser Val Ser Val Gln Val Thr Ala Leu Val Leu Ile Val Thr Tyr Phe
            20                  25                  30

Phe Val Ile Arg Pro Ile Asn Ser Pro Leu Trp Arg Val Pro Gly Pro
        35                  40                  45

Tyr Leu His Arg Val Thr Tyr Phe Pro Cys Leu Asn Ala Gln Arg Lys
    50                  55                  60

Gly Glu Trp Ile Ser Lys Val Tyr Asp Leu His Lys Lys Tyr Gly Asp
65                  70                  75                  80

Val Val Leu Leu Ser Pro Asn Glu Ile Ser Val Asn Gly Asp Pro Lys
                85                  90                  95

Tyr Leu Thr Asp Ile Tyr Val Lys Asn Leu Pro Lys Ser Lys Phe Tyr
            100                 105                 110

Glu Asn Phe Arg Asn His Gly Phe Gln Asp Asn Ile Phe Ala Ser Leu
        115                 120                 125

Glu Asn Asp Arg His Ile Lys Tyr Lys Arg Met Ile Asn Asn Leu Tyr
    130                 135                 140

Ser Lys Ser Ser Ile Phe Ser Lys Glu Asn His Thr Arg Ser Val Leu
145                 150                 155                 160

Phe Asp Thr Thr Lys Thr Leu Val Asp Ala Val Ala Arg Glu Ser Pro
                165                 170                 175

Ser Ile Asp Val Phe Thr Leu Phe Gly Ser Leu Ala Met Asp Val Val
            180                 185                 190

Ser Arg Phe Glu Leu Gly Arg Asp Asn Gly Thr Asp Leu Leu Asn His
        195                 200                 205

Pro Gln Glu Arg His Ile Ile Glu Ser His Arg Lys Val Ser Cys Met
    210                 215                 220

Gly Phe Trp Thr Thr Leu Met Pro Ser Phe Phe Trp Asn Leu Ala Ala
225                 230                 235                 240

Thr Lys Ala Thr Leu Gln Ala Val Asp Asp Ile Cys Asn Phe Gln Leu
                245                 250                 255

Gly Leu Tyr Lys Ile Ala Glu Ser Leu Val Ser Asn Gly Lys Asn
            260                 265                 270

Leu Thr Thr Ile Gln Thr Leu Lys Lys Tyr Gly Leu Glu Gly Asn Ser
        275                 280                 285

Ala Tyr Ser Phe Leu Thr Asp Asn Leu Phe Ala Gly His Glu Thr Thr
    290                 295                 300

Ala Val Gln Leu Thr Tyr Leu Cys Tyr Glu Leu Ser Arg Pro Ala Asn
305                 310                 315                 320

Tyr Lys Ile Gln Asn Arg Leu Arg Tyr Glu Leu Gln Glu Ala Phe Pro
                325                 330                 335

Ser Gly Gln Ile Glu Asp Leu Glu Val Val Asp Asn Leu Pro Tyr Leu
            340                 345                 350
```

```
Asn Ala Leu Leu Ser Glu Asn Gly Arg Ile His Thr Ser Ile Pro Gly
            355                 360                 365

Ala Glu Pro Arg Val Val Ala Lys Pro Tyr Thr Ile Gly Lys Leu Leu
    370                 375                 380

Ile Pro Val Gly Thr Val Ile Ser Cys Leu Pro Tyr Ala Tyr His Arg
385                 390                 395                 400

Asn Pro Ser Val Phe Thr Asn Pro Asp Lys Phe Ile Pro Glu Arg Trp
                405                 410                 415

Leu Val Asp Asn Glu Glu Asp Lys Lys Arg Val Lys Gln Gln Ala Lys
            420                 425                 430

Tyr Met Met Pro Phe Gly Lys Gly Val Arg Met Cys Leu Gly Met Asn
            435                 440                 445

Leu Ala Leu Ile Glu Met Lys Leu Ala Ile Ala Ser Leu Tyr Leu Asn
            450                 455                 460

Phe Ser Ser Ser Ile Asp Glu Asp Trp Cys Gly Lys Val Leu Glu Asn
465                 470                 475                 480

Asp Asp Pro Ile Gly Ile Gly Asn Ser Cys Thr His Glu Thr Asp Gln
                485                 490                 495

Asp Lys Met Lys Met Tyr Asp Ala Tyr Thr Thr Arg Pro Met Leu Asp
            500                 505                 510

Glu Cys Tyr Leu Lys Trp Thr Arg Leu Thr Pro
            515                 520

<210> SEQ ID NO 45
<211> LENGTH: 1728
<212> TYPE: DNA
<213> ORGANISM: Candida tropicalis
<220> FEATURE:
<221> NAME/KEY: CDS
<222> LOCATION: (1)..(1725)

<400> SEQUENCE: 45 atg ctt ctg agc ata cca tgg gat caa tca ttg cta acg ttg cta aca      48
Met Leu Leu Ser Ile Pro Trp Asp Gln Ser Leu Leu Thr Leu Leu Thr
1               5                   10                  15 tat ctt gat acc cat cca ata gct acg ata ttc acc att att tta acc      96
Tyr Leu Asp Thr His Pro Ile Ala Thr Ile Phe Thr Ile Ile Leu Thr
                20                  25                  30 att tta aca att gga att tta ttt gat tat tgt cta tca cct aaa gag     144
Ile Leu Thr Ile Gly Ile Leu Phe Asp Tyr Cys Leu Ser Pro Lys Glu
            35                  40                  45 att gcc aat att ttc agt att cct gga gat ttg cca ttt att ggt cat     192
Ile Ala Asn Ile Phe Ser Ile Pro Gly Asp Leu Pro Phe Ile Gly His
        50                  55                  60 tta cat tta ata cta gat aat cca gca ttg att tat tta aca tgg tat     240
Leu His Leu Ile Leu Asp Asn Pro Ala Leu Ile Tyr Leu Thr Trp Tyr
65                  70                  75                  80 aaa tta tat aat aaa ctg gtt ttt caa att cgt att gga aat aaa cgt     288
Lys Leu Tyr Asn Lys Leu Val Phe Gln Ile Arg Ile Gly Asn Lys Arg
                85                  90                  95 gta gtt gtt gtt aat tca ttt gat gat gtt gtt gga tta tgg ata aat     336
Val Val Val Val Asn Ser Phe Asp Asp Val Val Gly Leu Trp Ile Asn
                100                 105                 110 cat agt tgt caa aat aat tca aga cct tta agt tat act ttt cat gga     384
His Ser Cys Gln Asn Asn Ser Arg Pro Leu Ser Tyr Thr Phe His Gly
            115                 120                 125 tta gtt tca gca tta caa ggt ttt aca gtt ggt tct act cct gca agt     432
Leu Val Ser Ala Leu Gln Gly Phe Thr Val Gly Ser Thr Pro Ala Ser
```

```
                130                 135                 140
tta aca ttt ctg aga aag aag aaa gtt att tca ctg tgt tta aga aag          480
Leu Thr Phe Leu Arg Lys Lys Lys Val Ile Ser Leu Cys Leu Arg Lys
145                 150                 155                 160 aaa gaa att gat gaa aaa gta tgt ctc ata gat aat gaa att tgt gtt          528
Lys Glu Ile Asp Glu Lys Val Cys Leu Ile Asp Asn Glu Ile Cys Val
                165                 170                 175 atg att aaa gaa ata att aaa aag aag gat ata tca act gat gta aat          576
Met Ile Lys Glu Ile Ile Lys Lys Lys Asp Ile Ser Thr Asp Val Asn
            180                 185                 190 atg tta cct tat tta caa aaa ttc ata tta aaa aca gct att ctt atg          624
Met Leu Pro Tyr Leu Gln Lys Phe Ile Leu Lys Thr Ala Ile Leu Met
        195                 200                 205 agt tat gga att gaa ttg gat tgt tat aat aaa gat gtt aaa tta tgt          672
Ser Tyr Gly Ile Glu Leu Asp Cys Tyr Asn Lys Asp Val Lys Leu Cys
    210                 215                 220 caa gag att atc acc gtg gag aat aat atc ata aga tta aga tca cca          720
Gln Glu Ile Ile Thr Val Glu Asn Asn Ile Ile Arg Leu Arg Ser Pro
225                 230                 235                 240 ata tct aat ctt caa gat tct gta cct ttc tta aga cta ata cca tgg          768
Ile Ser Asn Leu Gln Asp Ser Val Pro Phe Leu Arg Leu Ile Pro Trp
                245                 250                 255 ttt aat aat cga gaa ttt gcc ctt cgt tgt gga aat aga agg aat aaa          816
Phe Asn Asn Arg Glu Phe Ala Leu Arg Cys Gly Asn Arg Arg Asn Lys
            260                 265                 270 tat atg gat caa tta tat aat agg tta caa aat gga tta gct gaa aat          864
Tyr Met Asp Gln Leu Tyr Asn Arg Leu Gln Asn Gly Leu Ala Glu Asn
        275                 280                 285 gat cca aat ata gct aat agt att ctt gga caa tta att ctt aat aat          912
Asp Pro Asn Ile Ala Asn Ser Ile Leu Gly Gln Leu Ile Leu Asn Asn
    290                 295                 300 gat aat aat aat tct aac agc tta act agt caa gaa ata caa agt att          960
Asp Asn Asn Asn Ser Asn Ser Leu Thr Ser Gln Glu Ile Gln Ser Ile
305                 310                 315                 320 tgt tta aca tta gta agt gct gga tta gat aat acc cca ctt aat ttg         1008
Cys Leu Thr Leu Val Ser Ala Gly Leu Asp Asn Thr Pro Leu Asn Leu
                325                 330                 335 aat tat ctt att gga ata tta tca caa cca aga ata ggt aag ata ttt         1056
Asn Tyr Leu Ile Gly Ile Leu Ser Gln Pro Arg Ile Gly Lys Ile Phe
            340                 345                 350 caa gat aaa gct ata aaa gat att tta aat cat gca aat gga gat att         1104
Gln Asp Lys Ala Ile Lys Asp Ile Leu Asn His Ala Asn Gly Asp Ile
        355                 360                 365 att caa gca tgg aat caa ctg aat gaa gaa aat cga gat tgt aaa tat         1152
Ile Gln Ala Trp Asn Gln Leu Asn Glu Glu Asn Arg Asp Cys Lys Tyr
    370                 375                 380 att caa gct tta att ctt gaa act tta aga cat ttt aca gta tta cca         1200
Ile Gln Ala Leu Ile Leu Glu Thr Leu Arg His Phe Thr Val Leu Pro
385                 390                 395                 400 tta agt tta cct aga tta act aca aaa cca ata tat tat aaa aat ttt         1248
Leu Ser Leu Pro Arg Leu Thr Thr Lys Pro Ile Tyr Tyr Lys Asn Phe
                405                 410                 415 atg att cct aaa aat act cat atg ttt atg aat gca tat tct gca aat         1296
Met Ile Pro Lys Asn Thr His Met Phe Met Asn Ala Tyr Ser Ala Asn
            420                 425                 430 cat gat gaa tta ata ttc aaa aat cca ttt aaa ttt gat cca gaa aga         1344
His Asp Glu Leu Ile Phe Lys Asn Pro Phe Lys Phe Asp Pro Glu Arg
        435                 440                 445 tgg tta gat tca gaa act aat gaa att aaa tca aaa ata ctt gct act         1392
```

```
Trp Leu Asp Ser Glu Thr Asn Glu Ile Lys Ser Lys Ile Leu Ala Thr
    450                 455                 460 act tct tcg tct tct tct tcg aca cat cat ggt ggt gga aat gga ata      1440
Thr Ser Ser Ser Ser Ser Ser Thr His His Gly Gly Gly Asn Gly Ile
465                 470                 475                 480 aat gta cag aat ttt cat ttt gca ttt ggt gct gga tca aga atg tgt      1488
Asn Val Gln Asn Phe His Phe Ala Phe Gly Ala Gly Ser Arg Met Cys
                    485                 490                 495 tca ggt tat aat cta gtt atg aaa gaa atg tat atg atg ata att aaa      1536
Ser Gly Tyr Asn Leu Val Met Lys Glu Met Tyr Met Met Ile Ile Lys
                500                 505                 510 tta tta tta tta ttt gaa att aat cct cct gat aat aat aat aat aat      1584
Leu Leu Leu Leu Phe Glu Ile Asn Pro Pro Asp Asn Asn Asn Asn Asn
            515                 520                 525 ggg aaa tat tta atg gaa atg aat cct ttt gtt aat aat ctg aat cct      1632
Gly Lys Tyr Leu Met Glu Met Asn Pro Phe Val Asn Asn Leu Asn Pro
    530                 535                 540 aga ggt act tca ttt gaa cca cga ata cat aat att aaa tta caa tat      1680
Arg Gly Thr Ser Phe Glu Pro Arg Ile His Asn Ile Lys Leu Gln Tyr
545                 550                 555                 560 aga aaa cta cct aat tat gaa act cta cac gaa ata gtt ctc aaa tag      1728
Arg Lys Leu Pro Asn Tyr Glu Thr Leu His Glu Ile Val Leu Lys
                565                 570                 575

<210> SEQ ID NO 46
<211> LENGTH: 575
<212> TYPE: PRT
<213> ORGANISM: Candida tropicalis

<400> SEQUENCE: 46

Met Leu Leu Ser Ile Pro Trp Asp Gln Ser Leu Leu Thr Leu Leu Thr
1               5                   10                  15

Tyr Leu Asp Thr His Pro Ile Ala Thr Ile Phe Thr Ile Ile Leu Thr
            20                  25                  30

Ile Leu Thr Ile Gly Ile Leu Phe Asp Tyr Cys Leu Ser Pro Lys Glu
        35                  40                  45

Ile Ala Asn Ile Phe Ser Ile Pro Gly Asp Leu Pro Phe Ile Gly His
    50                  55                  60

Leu His Leu Ile Leu Asp Asn Pro Ala Leu Ile Tyr Leu Thr Trp Tyr
65                  70                  75                  80

Lys Leu Tyr Asn Lys Leu Val Phe Gln Ile Arg Ile Gly Asn Lys Arg
                85                  90                  95

Val Val Val Val Asn Ser Phe Asp Asp Val Val Gly Leu Trp Ile Asn
            100                 105                 110

His Ser Cys Gln Asn Asn Ser Arg Pro Leu Ser Tyr Thr Phe His Gly
        115                 120                 125

Leu Val Ser Ala Leu Gln Gly Phe Thr Val Gly Ser Thr Pro Ala Ser
    130                 135                 140

Leu Thr Phe Leu Arg Lys Lys Val Ile Ser Leu Cys Leu Arg Lys
145                 150                 155                 160

Lys Glu Ile Asp Glu Lys Val Cys Leu Ile Asp Asn Glu Ile Cys Val
                165                 170                 175

Met Ile Lys Glu Ile Lys Lys Asp Ile Ser Thr Asp Val Asn
            180                 185                 190

Met Leu Pro Tyr Leu Gln Lys Phe Ile Leu Lys Thr Ala Ile Leu Met
        195                 200                 205

Ser Tyr Gly Ile Glu Leu Asp Cys Tyr Asn Lys Asp Val Lys Leu Cys
```

```
                210                 215                 220
Gln Glu Ile Ile Thr Val Glu Asn Asn Ile Ile Arg Leu Arg Ser Pro
225                 230                 235                 240

Ile Ser Asn Leu Gln Asp Ser Val Pro Phe Leu Arg Leu Ile Pro Trp
                245                 250                 255

Phe Asn Asn Arg Glu Phe Ala Leu Arg Cys Gly Asn Arg Arg Asn Lys
            260                 265                 270

Tyr Met Asp Gln Leu Tyr Asn Arg Leu Gln Asn Gly Leu Ala Glu Asn
        275                 280                 285

Asp Pro Asn Ile Ala Asn Ser Ile Leu Gly Gln Leu Ile Leu Asn Asn
    290                 295                 300

Asp Asn Asn Ser Asn Ser Leu Thr Ser Gln Glu Ile Gln Ser Ile
305                 310                 315                 320

Cys Leu Thr Leu Val Ser Ala Gly Leu Asp Asn Thr Pro Leu Asn Leu
                325                 330                 335

Asn Tyr Leu Ile Gly Ile Leu Ser Gln Pro Arg Ile Gly Lys Ile Phe
            340                 345                 350

Gln Asp Lys Ala Ile Lys Asp Ile Leu Asn His Ala Asn Gly Asp Ile
        355                 360                 365

Ile Gln Ala Trp Asn Gln Leu Asn Glu Glu Asn Arg Asp Cys Lys Tyr
370                 375                 380

Ile Gln Ala Leu Ile Leu Glu Thr Leu Arg His Phe Thr Val Leu Pro
385                 390                 395                 400

Leu Ser Leu Pro Arg Leu Thr Thr Lys Pro Ile Tyr Tyr Lys Asn Phe
                405                 410                 415

Met Ile Pro Lys Asn Thr His Met Phe Met Asn Ala Tyr Ser Ala Asn
            420                 425                 430

His Asp Glu Leu Ile Phe Lys Asn Pro Phe Lys Phe Asp Pro Glu Arg
        435                 440                 445

Trp Leu Asp Ser Glu Thr Asn Glu Ile Lys Ser Lys Ile Leu Ala Thr
    450                 455                 460

Thr Ser Ser Ser Ser Ser Thr His His Gly Gly Asn Gly Ile
465                 470                 475                 480

Asn Val Gln Asn Phe His Phe Ala Phe Gly Ala Gly Ser Arg Met Cys
                485                 490                 495

Ser Gly Tyr Asn Leu Val Met Lys Glu Met Tyr Met Met Ile Ile Lys
            500                 505                 510

Leu Leu Leu Leu Phe Glu Ile Asn Pro Pro Asp Asn Asn Asn Asn
        515                 520                 525

Gly Lys Tyr Leu Met Glu Met Asn Pro Phe Val Asn Asn Leu Asn Pro
    530                 535                 540

Arg Gly Thr Ser Phe Glu Pro Arg Ile His Asn Ile Lys Leu Gln Tyr
545                 550                 555                 560

Arg Lys Leu Pro Asn Tyr Glu Thr Leu His Glu Ile Val Leu Lys
                565                 570                 575

<210> SEQ ID NO 47
<211> LENGTH: 1518
<212> TYPE: DNA
<213> ORGANISM: Candida tropicalis
<220> FEATURE:
<221> NAME/KEY: CDS
<222> LOCATION: (1)..(1515)

<400> SEQUENCE: 47
```

-continued

| | | |
|---|---|---|
| atg tat caa tta ttt tgt ttt ctt gct ggt ata att gtt gta tat aaa<br>Met Tyr Gln Leu Phe Cys Phe Leu Ala Gly Ile Ile Val Val Tyr Lys<br>1                    5                    10                 15 | | 48 |
| gca gca caa tac tac aag aga agg aca ctt gtg act aaa ttt cat tgc<br>Ala Ala Gln Tyr Tyr Lys Arg Arg Thr Leu Val Thr Lys Phe His Cys<br>                 20                    25                    30 | | 96 |
| aaa caa gca cgt att tcc cca aac aag tca tgg ttg gaa tat tta ggc<br>Lys Gln Ala Arg Ile Ser Pro Asn Lys Ser Trp Leu Glu Tyr Leu Gly<br>               35                    40                    45 | | 144 |
| att gcc tcc gtt gta cat gcc aat gaa atg att aga aaa gga gga ttg<br>Ile Ala Ser Val Val His Ala Asn Glu Met Ile Arg Lys Gly Gly Leu<br>    50                    55                    60 | | 192 |
| tat tca gaa att gat gga aga ttt aaa tcc ctt gat gtt tca aca ttc<br>Tyr Ser Glu Ile Asp Gly Arg Phe Lys Ser Leu Asp Val Ser Thr Phe<br>65                    70                    75                 80 | | 240 |
| aag tct ata act ttg gga aag aca acg tat gtt acc aaa gat att gaa<br>Lys Ser Ile Thr Leu Gly Lys Thr Thr Tyr Val Thr Lys Asp Ile Glu<br>                 85                    90                    95 | | 288 |
| aac atc cgt cat atc tta agt gca acg gaa atg aac tca tgg aat ctt<br>Asn Ile Arg His Ile Leu Ser Ala Thr Glu Met Asn Ser Trp Asn Leu<br>                100                    105                 110 | | 336 |
| ggt gcc cgt cca att gcg tta aga ccc ttg att ggt gat gga att ttt<br>Gly Ala Arg Pro Ile Ala Leu Arg Pro Leu Ile Gly Asp Gly Ile Phe<br>    115                    120                    125 | | 384 |
| gct agt gaa ggt caa tct tgg aaa cat agt cga atc atg ctt aga cca<br>Ala Ser Glu Gly Gln Ser Trp Lys His Ser Arg Ile Met Leu Arg Pro<br>130                    135                    140 | | 432 |
| gta ttt gca aaa gaa cac gtt aaa caa atc act tca atg gaa cca tat<br>Val Phe Ala Lys Glu His Val Lys Gln Ile Thr Ser Met Glu Pro Tyr<br>145                    150                    155                 160 | | 480 |
| gta caa ctg ttg atc aaa atc atc aag aac cat gaa ggg gaa cca tta<br>Val Gln Leu Leu Ile Lys Ile Ile Lys Asn His Glu Gly Glu Pro Leu<br>                165                    170                 175 | | 528 |
| gag ttt caa acc tta gcc cat ctt ttt aca ata gat tat tct act gat<br>Glu Phe Gln Thr Leu Ala His Leu Phe Thr Ile Asp Tyr Ser Thr Asp<br>                 180                    185                 190 | | 576 |
| ttc cta tta ggt gaa agt tgt gat agt ttg aag gat ttc cta gga gaa<br>Phe Leu Leu Gly Glu Ser Cys Asp Ser Leu Lys Asp Phe Leu Gly Glu<br>    195                    200                    205 | | 624 |
| gag tcc aat tcc aca tta gat aca tcg ttg aga ctg gca ttt gca tca<br>Glu Ser Asn Ser Thr Leu Asp Thr Ser Leu Arg Leu Ala Phe Ala Ser<br>210                    215                    220 | | 672 |
| cag ttt aat aaa acc cag cag caa atg aca att cga ttc atg ttg gga<br>Gln Phe Asn Lys Thr Gln Gln Gln Met Thr Ile Arg Phe Met Leu Gly<br>225                    230                    235                 240 | | 720 |
| aaa ttg gcc ttt ctc atg tat cca aag agt ttt caa aat agt att caa<br>Lys Leu Ala Phe Leu Met Tyr Pro Lys Ser Phe Gln Asn Ser Ile Gln<br>                245                    250                 255 | | 768 |
| atg caa aag gac ttt gtt gat gaa tat atc gac aga gta gta ggt atg<br>Met Gln Lys Asp Phe Val Asp Glu Tyr Ile Asp Arg Val Val Gly Met<br>                 260                    265                 270 | | 816 |
| tcc gaa gaa gaa ttg aac aat cat cca aag agc tat gtt ttg ttg tac<br>Ser Glu Glu Glu Leu Asn Asn His Pro Lys Ser Tyr Val Leu Leu Tyr<br>            275                    280                 285 | | 864 |
| caa tta gca aga caa act aag aat cgt gat ata tta caa gat gaa ttg<br>Gln Leu Ala Arg Gln Thr Lys Asn Arg Asp Ile Leu Gln Asp Glu Leu<br>290                    295                    300 | | 912 |
| atg tcc att tta ctt gca ggt aga gac acc act gcc agt ttg ttg act<br>Met Ser Ile Leu Leu Ala Gly Arg Asp Thr Thr Ala Ser Leu Leu Thr<br>305                    310                    315                 320 | | 960 |

```
ttt ttg ttt ttc gaa tta agt cac cat cca gaa gta ttt aac aaa tta      1008
Phe Leu Phe Phe Glu Leu Ser His His Pro Glu Val Phe Asn Lys Leu
                325                 330                 335 aaa gag gaa atc gaa aga cac ttt cct gat gtt gaa tcc gtt aca ttt      1056
Lys Glu Glu Ile Glu Arg His Phe Pro Asp Val Glu Ser Val Thr Phe
            340                 345                 350 gga act atc cag aga tgc gac tat ctt caa tgg tgt att aac gaa act      1104
Gly Thr Ile Gln Arg Cys Asp Tyr Leu Gln Trp Cys Ile Asn Glu Thr
        355                 360                 365 atg aga ctc cat cca tca gtt cct ttt aat ttc aga act gca gcc aat      1152
Met Arg Leu His Pro Ser Val Pro Phe Asn Phe Arg Thr Ala Ala Asn
    370                 375                 380 gac aca gta ata cca aga ggt gga ggt aaa tcc tgt aca gat cct att      1200
Asp Thr Val Ile Pro Arg Gly Gly Gly Lys Ser Cys Thr Asp Pro Ile
385                 390                 395                 400 ctt gtc cat aag ggt gaa caa gta tta ttc agt ttc tat tct gta aac      1248
Leu Val His Lys Gly Glu Gln Val Leu Phe Ser Phe Tyr Ser Val Asn
                405                 410                 415 aga gaa gaa aag tat ttt ggt aca aat acc gac aag ttt gct cca gaa      1296
Arg Glu Glu Lys Tyr Phe Gly Thr Asn Thr Asp Lys Phe Ala Pro Glu
            420                 425                 430 aga tgg agt gaa tca tta agg aga act gag ttc ata cca ttt tct gct      1344
Arg Trp Ser Glu Ser Leu Arg Arg Thr Glu Phe Ile Pro Phe Ser Ala
        435                 440                 445 gga cct cgt gcc tgt ttg ggt caa cag tta gct aga gtt gaa gct tca      1392
Gly Pro Arg Ala Cys Leu Gly Gln Gln Leu Ala Arg Val Glu Ala Ser
    450                 455                 460 tat gtt act att aga ttg ctt caa acc ttt cat ggg ttg cat aat gcc      1440
Tyr Val Thr Ile Arg Leu Leu Gln Thr Phe His Gly Leu His Asn Ala
465                 470                 475                 480 agt aaa caa tac cca cca aat aga gtg gtt gca gct aca atg aga ttg      1488
Ser Lys Gln Tyr Pro Pro Asn Arg Val Val Ala Ala Thr Met Arg Leu
                485                 490                 495 act gac ggt tgt aac gtt tgt ttt atc tag                              1518
Thr Asp Gly Cys Asn Val Cys Phe Ile
            500                 505

<210> SEQ ID NO 48
<211> LENGTH: 505
<212> TYPE: PRT
<213> ORGANISM: Candida tropicalis

<400> SEQUENCE: 48

Met Tyr Gln Leu Phe Cys Phe Leu Ala Gly Ile Ile Val Val Tyr Lys
1               5                   10                  15

Ala Ala Gln Tyr Tyr Lys Arg Arg Thr Leu Val Thr Lys Phe His Cys
                20                  25                  30

Lys Gln Ala Arg Ile Ser Pro Asn Lys Ser Trp Leu Glu Tyr Leu Gly
            35                  40                  45

Ile Ala Ser Val Val His Ala Asn Glu Met Ile Arg Lys Gly Gly Leu
        50                  55                  60

Tyr Ser Glu Ile Asp Gly Arg Phe Lys Ser Leu Asp Val Ser Thr Phe
65                  70                  75                  80

Lys Ser Ile Thr Leu Gly Lys Thr Thr Tyr Val Thr Lys Asp Ile Glu
                85                  90                  95

Asn Ile Arg His Ile Leu Ser Ala Thr Glu Met Asn Ser Trp Asn Leu
            100                 105                 110

Gly Ala Arg Pro Ile Ala Leu Arg Pro Leu Ile Gly Asp Gly Ile Phe
```

```
            115                 120                 125
Ala Ser Glu Gly Gln Ser Trp Lys His Ser Arg Ile Met Leu Arg Pro
130                 135                 140

Val Phe Ala Lys Glu His Val Lys Gln Ile Thr Ser Met Glu Pro Tyr
145                 150                 155                 160

Val Gln Leu Leu Ile Lys Ile Ile Lys Asn His Glu Gly Glu Pro Leu
                165                 170                 175

Glu Phe Gln Thr Leu Ala His Leu Phe Thr Ile Asp Tyr Ser Thr Asp
                180                 185                 190

Phe Leu Leu Gly Glu Ser Cys Asp Ser Leu Lys Asp Phe Leu Gly Glu
                195                 200                 205

Glu Ser Asn Ser Thr Leu Asp Thr Ser Leu Arg Leu Ala Phe Ala Ser
210                 215                 220

Gln Phe Asn Lys Thr Gln Gln Met Thr Ile Arg Phe Met Leu Gly
225                 230                 235                 240

Lys Leu Ala Phe Leu Met Tyr Pro Lys Ser Phe Gln Asn Ser Ile Gln
                245                 250                 255

Met Gln Lys Asp Phe Val Asp Glu Tyr Ile Asp Arg Val Val Gly Met
                260                 265                 270

Ser Glu Glu Glu Leu Asn Asn His Pro Lys Ser Tyr Val Leu Leu Tyr
        275                 280                 285

Gln Leu Ala Arg Gln Thr Lys Asn Arg Asp Ile Leu Gln Asp Glu Leu
290                 295                 300

Met Ser Ile Leu Leu Ala Gly Arg Asp Thr Thr Ala Ser Leu Leu Thr
305                 310                 315                 320

Phe Leu Phe Phe Glu Leu Ser His His Pro Glu Val Phe Asn Lys Leu
                325                 330                 335

Lys Glu Glu Ile Glu Arg His Phe Pro Asp Val Glu Ser Val Thr Phe
                340                 345                 350

Gly Thr Ile Gln Arg Cys Asp Tyr Leu Gln Trp Cys Ile Asn Glu Thr
                355                 360                 365

Met Arg Leu His Pro Ser Val Pro Phe Asn Phe Arg Thr Ala Ala Asn
370                 375                 380

Asp Thr Val Ile Pro Arg Gly Gly Lys Ser Cys Thr Asp Pro Ile
385                 390                 395                 400

Leu Val His Lys Gly Glu Gln Val Leu Phe Ser Phe Tyr Ser Val Asn
                405                 410                 415

Arg Glu Glu Lys Tyr Phe Gly Thr Asn Thr Asp Lys Phe Ala Pro Glu
                420                 425                 430

Arg Trp Ser Glu Ser Leu Arg Arg Thr Glu Phe Ile Pro Phe Ser Ala
        435                 440                 445

Gly Pro Arg Ala Cys Leu Gly Gln Gln Leu Ala Arg Val Glu Ala Ser
        450                 455                 460

Tyr Val Thr Ile Arg Leu Leu Gln Thr Phe His Gly Leu His Asn Ala
465                 470                 475                 480

Ser Lys Gln Tyr Pro Pro Asn Arg Val Val Ala Ala Thr Met Arg Leu
                485                 490                 495

Thr Asp Gly Cys Asn Val Cys Phe Ile
                500                 505

<210> SEQ ID NO 49
<211> LENGTH: 1584
<212> TYPE: DNA
<213> ORGANISM: Candida tropicalis
```

```
<220> FEATURE:
<221> NAME/KEY: CDS
<222> LOCATION: (1)..(1581)

<400> SEQUENCE: 49 atg agt gtc aat act act tct cca gtt gtg gat agt att agt gat aat    48
Met Ser Val Asn Thr Thr Ser Pro Val Val Asp Ser Ile Ser Asp Asn
1               5                   10                  15 gct act aca tat ttg agt aca aaa tat atc atc gat agt tta tat tca    96
Ala Thr Thr Tyr Leu Ser Thr Lys Tyr Ile Ile Asp Ser Leu Tyr Ser
            20                  25                  30 act tat caa caa gct tca tgg tta caa atc att tta acc tca atc att   144
Thr Tyr Gln Gln Ala Ser Trp Leu Gln Ile Ile Leu Thr Ser Ile Ile
        35                  40                  45 ctc att ttg act tat gat caa atc ctg tat caa atc aat aaa ggt tca   192
Leu Ile Leu Thr Tyr Asp Gln Ile Leu Tyr Gln Ile Asn Lys Gly Ser
    50                  55                  60 att gct ggt cca aaa ttc aaa ttt tgg cca att att ggt cca ttc ttg   240
Ile Ala Gly Pro Lys Phe Lys Phe Trp Pro Ile Ile Gly Pro Phe Leu
65                  70                  75                  80 gaa tct tta gat cca aaa ttc gaa gaa tat aaa gct aaa tgg gat tct   288
Glu Ser Leu Asp Pro Lys Phe Glu Glu Tyr Lys Ala Lys Trp Asp Ser
                85                  90                  95 ggt gaa ttg agt tgt gtt tcc att ttc cat aaa ttc gtt gtt att gct   336
Gly Glu Leu Ser Cys Val Ser Ile Phe His Lys Phe Val Val Ile Ala
            100                 105                 110 tct tct cgt gat tta gct aga aag att tta gca tct cca aaa tac gtt   384
Ser Ser Arg Asp Leu Ala Arg Lys Ile Leu Ala Ser Pro Lys Tyr Val
        115                 120                 125 aaa cct tgt gtt gtt gat gtt gct gtt aaa att tta aga cct tca aat   432
Lys Pro Cys Val Val Asp Val Ala Val Lys Ile Leu Arg Pro Ser Asn
    130                 135                 140 tgg gtt ttc tta gac ggt aaa gca cat act gat tac cgt cgt tct ttg   480
Trp Val Phe Leu Asp Gly Lys Ala His Thr Asp Tyr Arg Arg Ser Leu
145                 150                 155                 160 aat ggt tta ttc tcc caa aga gct ttg gaa att tac att cca gtt caa   528
Asn Gly Leu Phe Ser Gln Arg Ala Leu Glu Ile Tyr Ile Pro Val Gln
                165                 170                 175 gaa aaa tac atg gat att tat tta gat aga ttc tgt aag tac gac ggt   576
Glu Lys Tyr Met Asp Ile Tyr Leu Asp Arg Phe Cys Lys Tyr Asp Gly
            180                 185                 190 cca cgt gaa ttc ttc cca gaa ttt aga gaa ttg ttg tgt gct tta tct   624
Pro Arg Glu Phe Phe Pro Glu Phe Arg Glu Leu Leu Cys Ala Leu Ser
        195                 200                 205 ttg aga act ttc tgt ggg gat tac atc act gaa gat caa att gct tta   672
Leu Arg Thr Phe Cys Gly Asp Tyr Ile Thr Glu Asp Gln Ile Ala Leu
    210                 215                 220 gtt gct gat aac tat tac aga gtc act gct gct ttg gaa ttg gtc aat   720
Val Ala Asp Asn Tyr Tyr Arg Val Thr Ala Ala Leu Glu Leu Val Asn
225                 230                 235                 240 ttc cca atc att att cct tac act aaa act tgg tac ggt aag aag att   768
Phe Pro Ile Ile Ile Pro Tyr Thr Lys Thr Trp Tyr Gly Lys Lys Ile
                245                 250                 255 gct gat gat acc atg aag att ttt gaa aat tgt gct gct atg tcc aag   816
Ala Asp Asp Thr Met Lys Ile Phe Glu Asn Cys Ala Ala Met Ser Lys
            260                 265                 270 aaa cac att aat gaa aat aat ggt act cca ggt tgt gtt atg gat gaa   864
Lys His Ile Asn Glu Asn Asn Gly Thr Pro Gly Cys Val Met Asp Glu
        275                 280                 285 tgg att tac ttg atg aaa gaa gct aaa gaa aaa cac tct gat gat cca   912
```

```
Trp Ile Tyr Leu Met Lys Glu Ala Lys Glu Lys His Ser Asp Asp Pro
            290                 295                 300 gat tcc aaa tta ttg att aga gaa ttc tcc aac cgt gaa att tcc gaa         960
Asp Ser Lys Leu Leu Ile Arg Glu Phe Ser Asn Arg Glu Ile Ser Glu
305                 310                 315                 320 gcc att ttc act ttc ttg ttt gct tct caa gat gcc tct tct tct ttg        1008
Ala Ile Phe Thr Phe Leu Phe Ala Ser Gln Asp Ala Ser Ser Ser Leu
            325                 330                 335 gct tgt tgg tta ttc caa att gtc gcc gac aga cca gat gtt gtt gcc        1056
Ala Cys Trp Leu Phe Gln Ile Val Ala Asp Arg Pro Asp Val Val Ala
        340                 345                 350 aag att aga gaa gaa caa ttg aga gtt aga aac aat gac cca tct gtt        1104
Lys Ile Arg Glu Glu Gln Leu Arg Val Arg Asn Asn Asp Pro Ser Val
    355                 360                 365 aaa ttg tcc ttg gat ttg att aat gaa atg act tac acc aat gat gtt        1152
Lys Leu Ser Leu Asp Leu Ile Asn Glu Met Thr Tyr Thr Asn Asp Val
370                 375                 380 gtt aaa gaa tct ttg aga tac cgt cca cca gtc ttg atg gtt cca tat        1200
Val Lys Glu Ser Leu Arg Tyr Arg Pro Pro Val Leu Met Val Pro Tyr
385                 390                 395                 400 gtt gtt aag aaa gct ttc cca gtt act gaa aaa tac act gct cca aag        1248
Val Val Lys Lys Ala Phe Pro Val Thr Glu Lys Tyr Thr Ala Pro Lys
            405                 410                 415 ggt tct atg ctt atc cca act ttg tac cct gct tta cat gat cct gaa        1296
Gly Ser Met Leu Ile Pro Thr Leu Tyr Pro Ala Leu His Asp Pro Glu
        420                 425                 430 gtt tat gat gaa cca gat tct ttc att cca gaa aga tgg gcc act gct        1344
Val Tyr Asp Glu Pro Asp Ser Phe Ile Pro Glu Arg Trp Ala Thr Ala
    435                 440                 445 tct ggt gat atg tac aaa cgt aac tgg ttg gtc ttc ggt act ggt cca        1392
Ser Gly Asp Met Tyr Lys Arg Asn Trp Leu Val Phe Gly Thr Gly Pro
450                 455                 460 cac gtt tgt ttg ggt aag aac tat gtc atg atg ttg ttt act ggt atg        1440
His Val Cys Leu Gly Lys Asn Tyr Val Met Met Leu Phe Thr Gly Met
465                 470                 475                 480 ttg ggt aaa ttt gtc atg aac tct gat atc att cat cac aaa act gca        1488
Leu Gly Lys Phe Val Met Asn Ser Asp Ile Ile His His Lys Thr Ala
            485                 490                 495 tta tct gaa gaa atc aaa gtt ttc gct act att ttc cct aag gac gat        1536
Leu Ser Glu Glu Ile Lys Val Phe Ala Thr Ile Phe Pro Lys Asp Asp
        500                 505                 510 gtt att tta gaa tgg aaa aag aga gat ccg tta gct gct tct aat taa        1584
Val Ile Leu Glu Trp Lys Lys Arg Asp Pro Leu Ala Ala Ser Asn
    515                 520                 525

<210> SEQ ID NO 50
<211> LENGTH: 527
<212> TYPE: PRT
<213> ORGANISM: Candida tropicalis

<400> SEQUENCE: 50

Met Ser Val Asn Thr Thr Ser Pro Val Val Asp Ser Ile Ser Asp Asn
1               5                   10                  15

Ala Thr Thr Tyr Leu Ser Thr Lys Tyr Ile Ile Asp Ser Leu Tyr Ser
            20                  25                  30

Thr Tyr Gln Gln Ala Ser Trp Leu Gln Ile Ile Leu Thr Ser Ile Ile
        35                  40                  45

Leu Ile Leu Thr Tyr Asp Gln Ile Leu Tyr Gln Ile Asn Lys Gly Ser
    50                  55                  60
```

```
Ile Ala Gly Pro Lys Phe Lys Phe Trp Pro Ile Gly Pro Phe Leu
 65                  70                  75                  80

Glu Ser Leu Asp Pro Lys Phe Glu Glu Tyr Lys Ala Lys Trp Asp Ser
                 85                  90                  95

Gly Glu Leu Ser Cys Val Ser Ile Phe His Lys Phe Val Ile Ala
            100                 105                 110

Ser Ser Arg Asp Leu Ala Arg Lys Ile Leu Ala Ser Pro Lys Tyr Val
        115                 120                 125

Lys Pro Cys Val Val Asp Val Ala Val Lys Ile Leu Arg Pro Ser Asn
    130                 135                 140

Trp Val Phe Leu Asp Gly Lys Ala His Thr Asp Tyr Arg Arg Ser Leu
145                 150                 155                 160

Asn Gly Leu Phe Ser Gln Arg Ala Leu Glu Ile Tyr Ile Pro Val Gln
                165                 170                 175

Glu Lys Tyr Met Asp Ile Tyr Leu Asp Arg Phe Cys Lys Tyr Asp Gly
            180                 185                 190

Pro Arg Glu Phe Phe Pro Glu Phe Arg Glu Leu Leu Cys Ala Leu Ser
        195                 200                 205

Leu Arg Thr Phe Cys Gly Asp Tyr Ile Thr Glu Asp Gln Ile Ala Leu
    210                 215                 220

Val Ala Asp Asn Tyr Tyr Arg Val Thr Ala Ala Leu Glu Leu Val Asn
225                 230                 235                 240

Phe Pro Ile Ile Ile Pro Tyr Thr Lys Thr Trp Tyr Gly Lys Lys Ile
                245                 250                 255

Ala Asp Asp Thr Met Lys Ile Phe Glu Asn Cys Ala Ala Met Ser Lys
            260                 265                 270

Lys His Ile Asn Glu Asn Asn Gly Thr Pro Gly Cys Val Met Asp Glu
        275                 280                 285

Trp Ile Tyr Leu Met Lys Glu Ala Lys Glu Lys His Ser Asp Asp Pro
    290                 295                 300

Asp Ser Lys Leu Leu Ile Arg Glu Phe Ser Asn Arg Glu Ile Ser Glu
305                 310                 315                 320

Ala Ile Phe Thr Phe Leu Phe Ala Ser Gln Asp Ala Ser Ser Ser Leu
                325                 330                 335

Ala Cys Trp Leu Phe Gln Ile Val Ala Asp Arg Pro Asp Val Val Ala
            340                 345                 350

Lys Ile Arg Glu Glu Gln Leu Arg Val Arg Asn Asn Asp Pro Ser Val
        355                 360                 365

Lys Leu Ser Leu Asp Leu Ile Asn Glu Met Thr Tyr Thr Asn Asp Val
    370                 375                 380

Val Lys Glu Ser Leu Arg Tyr Arg Pro Pro Val Leu Met Val Pro Tyr
385                 390                 395                 400

Val Val Lys Lys Ala Phe Pro Val Thr Glu Lys Tyr Thr Ala Pro Lys
                405                 410                 415

Gly Ser Met Leu Ile Pro Thr Leu Tyr Pro Ala Leu His Asp Pro Glu
            420                 425                 430

Val Tyr Asp Glu Pro Asp Ser Phe Ile Pro Glu Arg Trp Ala Thr Ala
        435                 440                 445

Ser Gly Asp Met Tyr Lys Arg Asn Trp Leu Val Phe Gly Thr Gly Pro
    450                 455                 460

His Val Cys Leu Gly Lys Asn Tyr Val Met Met Leu Phe Thr Gly Met
465                 470                 475                 480

Leu Gly Lys Phe Val Met Asn Ser Asp Ile Ile His His Lys Thr Ala
```

```
                485                 490                 495
Leu Ser Glu Glu Ile Lys Val Phe Ala Thr Ile Phe Pro Lys Asp Asp
            500                 505                 510

Val Ile Leu Glu Trp Lys Lys Arg Asp Pro Leu Ala Ala Ser Asn
        515                 520                 525

<210> SEQ ID NO 51
<211> LENGTH: 1587
<212> TYPE: DNA
<213> ORGANISM: Candida tropicalis
<220> FEATURE:
<221> NAME/KEY: CDS
<222> LOCATION: (1)..(1584)

<400> SEQUENCE: 51 atg gct att gtt gat act gcc att gat ggc atc aat tat ttc tta tcc      48
Met Ala Ile Val Asp Thr Ala Ile Asp Gly Ile Asn Tyr Phe Leu Ser
1               5                   10                  15 tta tca tta act caa caa atc acc atc ttg gtt gtt ttc cca ttc atc      96
Leu Ser Leu Thr Gln Gln Ile Thr Ile Leu Val Val Phe Pro Phe Ile
                20                  25                  30 tac aac ata gca tgg caa tta ctt tac tcc tta aga aaa gat aga gtt     144
Tyr Asn Ile Ala Trp Gln Leu Leu Tyr Ser Leu Arg Lys Asp Arg Val
            35                  40                  45 cca atg gtt ttc tac tgg atc cca tgg ttt ggt tct gct gct agt tat     192
Pro Met Val Phe Tyr Trp Ile Pro Trp Phe Gly Ser Ala Ala Ser Tyr
        50                  55                  60 ggt atg caa cca tac gaa ttc ttt gaa aag tgc aga ttg aaa tat ggt     240
Gly Met Gln Pro Tyr Glu Phe Phe Glu Lys Cys Arg Leu Lys Tyr Gly
65                  70                  75                  80 gat gtt ttt tca ttt atg tta tta ggt aaa gtt atg act gtt tat ttg     288
Asp Val Phe Ser Phe Met Leu Leu Gly Lys Val Met Thr Val Tyr Leu
                85                  90                  95 ggt cca aaa ggt cac gaa ttc att tac aat gct aaa tta tcc gat gtt     336
Gly Pro Lys Gly His Glu Phe Ile Tyr Asn Ala Lys Leu Ser Asp Val
            100                 105                 110 tct gct gaa gaa gct tat acc cat ttg act act cct gtt ttt ggt aaa     384
Ser Ala Glu Glu Ala Tyr Thr His Leu Thr Thr Pro Val Phe Gly Lys
        115                 120                 125 ggt gtt att tat gat tgt cca aac tct aga tta atg gaa caa aag aag     432
Gly Val Ile Tyr Asp Cys Pro Asn Ser Arg Leu Met Glu Gln Lys Lys
    130                 135                 140 ttt gct aaa ttt gct ttg act act gat tct ttc aaa acc tat gtt cca     480
Phe Ala Lys Phe Ala Leu Thr Thr Asp Ser Phe Lys Thr Tyr Val Pro
145                 150                 155                 160 aag atc aga gaa gaa gtt ttg aat tat ttt gtt aac gat gtt agt ttc     528
Lys Ile Arg Glu Glu Val Leu Asn Tyr Phe Val Asn Asp Val Ser Phe
                165                 170                 175 aaa acc aag gaa aga gac cat ggt gtt gct agt gtt atg aaa act caa     576
Lys Thr Lys Glu Arg Asp His Gly Val Ala Ser Val Met Lys Thr Gln
            180                 185                 190 cca gaa atc act att ttc act gct tct cgt tgt tta ttt ggt gat gaa     624
Pro Glu Ile Thr Ile Phe Thr Ala Ser Arg Cys Leu Phe Gly Asp Glu
        195                 200                 205 atg aga aag agt ttc gac aga tca ttt gct caa ttg tat gct gac ttg     672
Met Arg Lys Ser Phe Asp Arg Ser Phe Ala Gln Leu Tyr Ala Asp Leu
    210                 215                 220 gat aaa ggt ttc acc cca atc aac ttt gtt ttc cca aac ttg cca tta     720
Asp Lys Gly Phe Thr Pro Ile Asn Phe Val Phe Pro Asn Leu Pro Leu
225                 230                 235                 240
```

| | | |
|---|---|---|
| cct cat tac tgg aga cgt gac gct gct caa aga aag ata tct gct cat<br>Pro His Tyr Trp Arg Arg Asp Ala Ala Gln Arg Lys Ile Ser Ala His<br>245 250 255 | | 768 |
| tac atg aag gaa att aag aga aga aga gaa agc ggt gat att gat cca<br>Tyr Met Lys Glu Ile Lys Arg Arg Arg Glu Ser Gly Asp Ile Asp Pro<br>260 265 270 | | 816 |
| aag aga gat ttg att gat tcc ttg ttg gtt aac tct act tat aaa gat<br>Lys Arg Asp Leu Ile Asp Ser Leu Leu Val Asn Ser Thr Tyr Lys Asp<br>275 280 285 | | 864 |
| ggt gtt aaa atg act gat caa gaa att gct aac ctt tta att ggt gtt<br>Gly Val Lys Met Thr Asp Gln Glu Ile Ala Asn Leu Leu Ile Gly Val<br>290 295 300 | | 912 |
| ttg atg ggt ggt caa cat act tct gct tcc act tct gcc tgg ttc ttg<br>Leu Met Gly Gly Gln His Thr Ser Ala Ser Thr Ser Ala Trp Phe Leu<br>305 310 315 320 | | 960 |
| ttg cat ttg gct gaa caa cca caa tta caa gat gat ctt tac gaa gaa<br>Leu His Leu Ala Glu Gln Pro Gln Leu Gln Asp Asp Leu Tyr Glu Glu<br>325 330 335 | | 1008 |
| ttg acc aac ttg ttg aaa gaa aag ggt ggt gac ttg aac gat ttg act<br>Leu Thr Asn Leu Leu Lys Glu Lys Gly Gly Asp Leu Asn Asp Leu Thr<br>340 345 350 | | 1056 |
| tac gaa gac ttg caa aaa tta cca ttg gtt aac aac act att aaa gaa<br>Tyr Glu Asp Leu Gln Lys Leu Pro Leu Val Asn Asn Thr Ile Lys Glu<br>355 360 365 | | 1104 |
| act ttg aga atg cac atg cca ttg cat tct att ttc aga aaa gtt atg<br>Thr Leu Arg Met His Met Pro Leu His Ser Ile Phe Arg Lys Val Met<br>370 375 380 | | 1152 |
| aac cca ttg aga gtc cca aat acc aaa tat gtt att cca aaa ggt cac<br>Asn Pro Leu Arg Val Pro Asn Thr Lys Tyr Val Ile Pro Lys Gly His<br>385 390 395 400 | | 1200 |
| tat gtc tta gtt tct gcc ggt tat gct cat acc agt gat aga tgg ttt<br>Tyr Val Leu Val Ser Ala Gly Tyr Ala His Thr Ser Asp Arg Trp Phe<br>405 410 415 | | 1248 |
| gaa cac cca gaa cat ttc aac cca aga aga tgg gaa tct gat gat acc<br>Glu His Pro Glu His Phe Asn Pro Arg Arg Trp Glu Ser Asp Asp Thr<br>420 425 430 | | 1296 |
| aag gct agt gct gtt tct ttc aat tct gaa gat act gtt gat tat ggt<br>Lys Ala Ser Ala Val Ser Phe Asn Ser Glu Asp Thr Val Asp Tyr Gly<br>435 440 445 | | 1344 |
| ttc ggt aaa att tcc aaa ggt gtc tcc tct cca tac ttg cca ttc ggt<br>Phe Gly Lys Ile Ser Lys Gly Val Ser Ser Pro Tyr Leu Pro Phe Gly<br>450 455 460 | | 1392 |
| ggt gga aga cac aga tgt att ggt gaa caa ttt gct tat gtt caa ttg<br>Gly Gly Arg His Arg Cys Ile Gly Glu Gln Phe Ala Tyr Val Gln Leu<br>465 470 475 480 | | 1440 |
| gga act att ttg acc act tat atc tac aac ttc aaa tgg aga tta aac<br>Gly Thr Ile Leu Thr Thr Tyr Ile Tyr Asn Phe Lys Trp Arg Leu Asn<br>485 490 495 | | 1488 |
| ggt gat aag gtt cca gat gtt gat tac caa tcc atg gtt acc tta cca<br>Gly Asp Lys Val Pro Asp Val Asp Tyr Gln Ser Met Val Thr Leu Pro<br>500 505 510 | | 1536 |
| tta gaa cct gct gaa atc gtt tgg gaa aag aga gat act tgt atg gtt<br>Leu Glu Pro Ala Glu Ile Val Trp Glu Lys Arg Asp Thr Cys Met Val<br>515 520 525 | | 1584 |
| tag | | 1587 |

<210> SEQ ID NO 52
<211> LENGTH: 528
<212> TYPE: PRT
<213> ORGANISM: Candida tropicalis -continued

```
<400> SEQUENCE: 52

Met Ala Ile Val Asp Thr Ala Ile Asp Gly Ile Asn Tyr Phe Leu Ser
1               5                   10                  15

Leu Ser Leu Thr Gln Gln Ile Thr Ile Leu Val Val Phe Pro Phe Ile
            20                  25                  30

Tyr Asn Ile Ala Trp Gln Leu Leu Tyr Ser Leu Arg Lys Asp Arg Val
                35                  40                  45

Pro Met Val Phe Tyr Trp Ile Pro Trp Phe Gly Ser Ala Ala Ser Tyr
    50                  55                  60

Gly Met Gln Pro Tyr Glu Phe Phe Glu Lys Cys Arg Leu Lys Tyr Gly
65                  70                  75                  80

Asp Val Phe Ser Phe Met Leu Leu Gly Lys Val Met Thr Val Tyr Leu
                85                  90                  95

Gly Pro Lys Gly His Glu Phe Ile Tyr Asn Ala Lys Leu Ser Asp Val
            100                 105                 110

Ser Ala Glu Glu Ala Tyr Thr His Leu Thr Thr Pro Val Phe Gly Lys
        115                 120                 125

Gly Val Ile Tyr Asp Cys Pro Asn Ser Arg Leu Met Glu Gln Lys Lys
130                 135                 140

Phe Ala Lys Phe Ala Leu Thr Thr Asp Ser Phe Lys Thr Tyr Val Pro
145                 150                 155                 160

Lys Ile Arg Glu Glu Val Leu Asn Tyr Phe Val Asn Asp Val Ser Phe
                165                 170                 175

Lys Thr Lys Glu Arg Asp His Gly Val Ala Ser Val Met Lys Thr Gln
            180                 185                 190

Pro Glu Ile Thr Ile Phe Thr Ala Ser Arg Cys Leu Phe Gly Asp Glu
        195                 200                 205

Met Arg Lys Ser Phe Asp Arg Ser Phe Ala Gln Leu Tyr Ala Asp Leu
    210                 215                 220

Asp Lys Gly Phe Thr Pro Ile Asn Phe Val Phe Pro Asn Leu Pro Leu
225                 230                 235                 240

Pro His Tyr Trp Arg Arg Asp Ala Ala Gln Arg Lys Ile Ser Ala His
                245                 250                 255

Tyr Met Lys Glu Ile Lys Arg Arg Glu Ser Gly Asp Ile Asp Pro
            260                 265                 270

Lys Arg Asp Leu Ile Asp Ser Leu Leu Val Asn Ser Thr Tyr Lys Asp
        275                 280                 285

Gly Val Lys Met Thr Asp Gln Glu Ile Ala Asn Leu Leu Ile Gly Val
290                 295                 300

Leu Met Gly Gly Gln His Thr Ser Ala Ser Thr Ser Ala Trp Phe Leu
305                 310                 315                 320

Leu His Leu Ala Glu Gln Pro Gln Leu Gln Asp Asp Leu Tyr Glu Glu
                325                 330                 335

Leu Thr Asn Leu Leu Lys Glu Lys Gly Gly Asp Leu Asn Asp Leu Thr
            340                 345                 350

Tyr Glu Asp Leu Gln Lys Leu Pro Leu Val Asn Asn Thr Ile Lys Glu
        355                 360                 365

Thr Leu Arg Met His Met Pro Leu His Ser Ile Phe Arg Lys Val Met
    370                 375                 380

Asn Pro Leu Arg Val Pro Asn Thr Lys Tyr Val Ile Pro Lys Gly His
385                 390                 395                 400

Tyr Val Leu Val Ser Ala Gly Tyr Ala His Thr Ser Asp Arg Trp Phe
```

```
                          405                 410                 415
Glu His Pro Glu His Phe Asn Pro Arg Arg Trp Glu Ser Asp Asp Thr
                420                 425                 430

Lys Ala Ser Ala Val Ser Phe Asn Ser Glu Asp Thr Val Asp Tyr Gly
            435                 440                 445

Phe Gly Lys Ile Ser Lys Gly Val Ser Ser Pro Tyr Leu Pro Phe Gly
        450                 455                 460

Gly Gly Arg His Arg Cys Ile Gly Glu Gln Phe Ala Tyr Val Gln Leu
465                 470                 475                 480

Gly Thr Ile Leu Thr Thr Tyr Ile Tyr Asn Phe Lys Trp Arg Leu Asn
                485                 490                 495

Gly Asp Lys Val Pro Asp Val Asp Tyr Gln Ser Met Val Thr Leu Pro
            500                 505                 510

Leu Glu Pro Ala Glu Ile Val Trp Glu Lys Arg Asp Thr Cys Met Val
        515                 520                 525

<210> SEQ ID NO 53
<211> LENGTH: 2097
<212> TYPE: DNA
<213> ORGANISM: Candida cloacae
<220> FEATURE:
<221> NAME/KEY: CDS
<222> LOCATION: (1)..(2094)

<400> SEQUENCE: 53 atg tcc cat caa gtt gaa gac cac gac tta gac gtg ttc tgt tta ttg      48
Met Ser His Gln Val Glu Asp His Asp Leu Asp Val Phe Cys Leu Leu
1               5                   10                  15 gcc gat gcc gtg ctc cat gaa att cct ccc agc gaa atc gtg gag tac      96
Ala Asp Ala Val Leu His Glu Ile Pro Pro Ser Glu Ile Val Glu Tyr
            20                  25                  30 ctt cat cct gac ttc ccc aaa gat aag atc gaa gag tat ttg aca ggc     144
Leu His Pro Asp Phe Pro Lys Asp Lys Ile Glu Glu Tyr Leu Thr Gly
        35                  40                  45 ttt tcc cgt ccg tct gct gtt cct cag ttt aga caa tgt gcc aag aag     192
Phe Ser Arg Pro Ser Ala Val Pro Gln Phe Arg Gln Cys Ala Lys Lys
    50                  55                  60 ctt atc aac aga ggc tcc gag ctg tcg atc aag ttg ttt ttg tac ttg     240
Leu Ile Asn Arg Gly Ser Glu Leu Ser Ile Lys Leu Phe Leu Tyr Leu
65                  70                  75                  80 acc act gcg ttg gac tca aga atc ctt gca cct gcc ttg acc aat tcg     288
Thr Thr Ala Leu Asp Ser Arg Ile Leu Ala Pro Ala Leu Thr Asn Ser
                85                  90                  95 ttg act ttg atc agg gat atg gat ctt tcc caa aga gag gag ttg ttg     336
Leu Thr Leu Ile Arg Asp Met Asp Leu Ser Gln Arg Glu Glu Leu Leu
            100                 105                 110 aga tca tgg aga gac tct cct tta act gca aaa aga aga tta ttt aga     384
Arg Ser Trp Arg Asp Ser Pro Leu Thr Ala Lys Arg Arg Leu Phe Arg
        115                 120                 125 gtg tat gcc tct ttt acc ttg tct act ttt aac aag ttg gga aca gac     432
Val Tyr Ala Ser Phe Thr Leu Ser Thr Phe Asn Lys Leu Gly Thr Asp
    130                 135                 140 ttg cac ttt aag gcg ttg ggc tac cca ggt aga gag ctc aga acg caa     480
Leu His Phe Lys Ala Leu Gly Tyr Pro Gly Arg Glu Leu Arg Thr Gln
145                 150                 155                 160 att caa gac tac gaa gtc gac cct ttt aga tat tcg ttt atg gag aaa     528
Ile Gln Asp Tyr Glu Val Asp Pro Phe Arg Tyr Ser Phe Met Glu Lys
                165                 170                 175 ctt aaa cac gag ggc cac gaa ttg ttc ctt cct gat att gac gtt tta     576
Leu Lys His Glu Gly His Glu Leu Phe Leu Pro Asp Ile Asp Val Leu
```

```
                Leu Lys His Glu Gly His Glu Leu Phe Leu Pro Asp Ile Asp Val Leu
                                180                 185                 190 atc atc ggg tcg gga tca gga gca ggt gtg gtt gca caa act ctt act          624
Ile Ile Gly Ser Gly Ser Gly Ala Gly Val Val Ala Gln Thr Leu Thr
            195                 200                 205 gaa agt ggc ctc aaa tca ttg gtt ttg gaa aag ggc aaa tac ttt gcc          672
Glu Ser Gly Leu Lys Ser Leu Val Leu Glu Lys Gly Lys Tyr Phe Ala
210                 215                 220 agt gaa gaa ttg tgc atg acg gac ttg gac ggt aac gag gca tta ttc          720
Ser Glu Glu Leu Cys Met Thr Asp Leu Asp Gly Asn Glu Ala Leu Phe
225                 230                 235                 240 gaa agt gga gga aca att cct tcc acc aac caa caa ttg ttc atg att          768
Glu Ser Gly Gly Thr Ile Pro Ser Thr Asn Gln Gln Leu Phe Met Ile
                245                 250                 255 gca ggt tcg act ttt ggt ggt ggt tct aca gtt aat tgg tct gcc tgt          816
Ala Gly Ser Thr Phe Gly Gly Gly Ser Thr Val Asn Trp Ser Ala Cys
            260                 265                 270 ttg aag acc cca ttc aaa gta aga aag gaa tgg tat gac gat ttc gga          864
Leu Lys Thr Pro Phe Lys Val Arg Lys Glu Trp Tyr Asp Asp Phe Gly
        275                 280                 285 ctt gat ttt gtc gct act caa caa tac gac gat tgt atg gat tac gtg          912
Leu Asp Phe Val Ala Thr Gln Gln Tyr Asp Asp Cys Met Asp Tyr Val
    290                 295                 300 tgg aag aaa atg ggt gct tcg acc gaa cat atc gaa cat tct gct gca          960
Trp Lys Lys Met Gly Ala Ser Thr Glu His Ile Glu His Ser Ala Ala
305                 310                 315                 320 aat gcc gtc atc atg gac ggg gca gca aaa ctt ggc tac gca cac aga         1008
Asn Ala Val Ile Met Asp Gly Ala Ala Lys Leu Gly Tyr Ala His Arg
                325                 330                 335 gca ctt gag cag aat acc ggg ggc cat gtt cac gac tgt ggg atg tgc         1056
Ala Leu Glu Gln Asn Thr Gly Gly His Val His Asp Cys Gly Met Cys
            340                 345                 350 cac ttg gga tgt aga ttc ggt atc aaa caa ggt ggt gta aat tgc tgg         1104
His Leu Gly Cys Arg Phe Gly Ile Lys Gln Gly Gly Val Asn Cys Trp
        355                 360                 365 ttc cgt gaa cct agt gaa aag ggt tct aag ttc atg gaa caa gtt gtt         1152
Phe Arg Glu Pro Ser Glu Lys Gly Ser Lys Phe Met Glu Gln Val Val
    370                 375                 380 gtt gaa aag att ttg cag cac aag ggt aaa gct act ggg att ttg tgt         1200
Val Glu Lys Ile Leu Gln His Lys Gly Lys Ala Thr Gly Ile Leu Cys
385                 390                 395                 400 aga gat act gaa agt ggg att aaa ttc aaa atc act gga cca aag aaa         1248
Arg Asp Thr Glu Ser Gly Ile Lys Phe Lys Ile Thr Gly Pro Lys Lys
                405                 410                 415 tac gtt gtt tcc ggt ggt tct ttg caa acc cca gtt ttg tta caa aaa         1296
Tyr Val Val Ser Gly Gly Ser Leu Gln Thr Pro Val Leu Leu Gln Lys
            420                 425                 430 tct ggt ttc aag aat aaa cat att gga gct aac tta aaa ctt cac cca         1344
Ser Gly Phe Lys Asn Lys His Ile Gly Ala Asn Leu Lys Leu His Pro
        435                 440                 445 gtc tcg gtt gcc ctt ggg gac ttt ggt aat gaa gtg gac ttt gaa gcc         1392
Val Ser Val Ala Leu Gly Asp Phe Gly Asn Glu Val Asp Phe Glu Ala
    450                 455                 460 tac aag aga cca ctt atg acc gcc gtt tgt aat gcc gtc gat gat tta         1440
Tyr Lys Arg Pro Leu Met Thr Ala Val Cys Asn Ala Val Asp Asp Leu
465                 470                 475                 480 gat ggc aag gcc cat gga aca aga att gaa gcc att ttg cat gct cca         1488
Asp Gly Lys Ala His Gly Thr Arg Ile Glu Ala Ile Leu His Ala Pro
                485                 490                 495
```

| | | |
|---|---|---|
| tac gtc act gcc cca ttt tac cca tgg caa tca ggt gct caa gca aga<br>Tyr Val Thr Ala Pro Phe Tyr Pro Trp Gln Ser Gly Ala Gln Ala Arg<br>500                         505                           510 | | 1536 |
| aag aac ctc ttg aaa tat aaa caa act gtg ccg tta tta ctt ctt tct<br>Lys Asn Leu Leu Lys Tyr Lys Gln Thr Val Pro Leu Leu Leu Leu Ser<br>            515                      520                      525 | | 1584 |
| aga gat aca tca tca ggt acc gtt aca tat gat aaa caa aag cct gac<br>Arg Asp Thr Ser Ser Gly Thr Val Thr Tyr Asp Lys Gln Lys Pro Asp<br>530                         535                         540 | | 1632 |
| gta ttg gta gtt gac tac act gtt aac aag ttt gac aga aat tcg att<br>Val Leu Val Val Asp Tyr Thr Val Asn Lys Phe Asp Arg Asn Ser Ile<br>545                         550                      555                      560 | | 1680 |
| tta caa ggg ttt ttg gtt gct tcc gac atc ttg tat att gaa ggt gct<br>Leu Gln Gly Phe Leu Val Ala Ser Asp Ile Leu Tyr Ile Glu Gly Ala<br>                  565                      570                      575 | | 1728 |
| aaa gag att ttg tca cca caa gct tgg gta cca acc ttc aag agc aac<br>Lys Glu Ile Leu Ser Pro Gln Ala Trp Val Pro Thr Phe Lys Ser Asn<br>                 580                      585                      590 | | 1776 |
| aaa cca aaa cat gct aga tcg atc aaa gac gaa gat tac gtc aaa tgg<br>Lys Pro Lys His Ala Arg Ser Ile Lys Asp Glu Asp Tyr Val Lys Trp<br>595                         600                         605 | | 1824 |
| aga gaa acc gtg gcc aag atc cca ttt gac tcc tac ggt tcg cca tac<br>Arg Glu Thr Val Ala Lys Ile Pro Phe Asp Ser Tyr Gly Ser Pro Tyr<br>610                         615                         620 | | 1872 |
| ggt tct gct cat caa atg agt tcg tgt aga atg tct ggt aag gga cca<br>Gly Ser Ala His Gln Met Ser Ser Cys Arg Met Ser Gly Lys Gly Pro<br>625                         630                      635                      640 | | 1920 |
| gga tac ggt gct tgt gac act aaa gga aga tta ttt gaa tgt aac aac<br>Gly Tyr Gly Ala Cys Asp Thr Lys Gly Arg Leu Phe Glu Cys Asn Asn<br>                 645                      650                      655 | | 1968 |
| gtt tac gtt gct gat gct tcg gtt atg cct act gca tcg gga gtc aat<br>Val Tyr Val Ala Asp Ala Ser Val Met Pro Thr Ala Ser Gly Val Asn<br>                 660                      665                      670 | | 2016 |
| cct atg atc act aca atg gct ttt gca aga cat gtg gcc tta tgt ctt<br>Pro Met Ile Thr Thr Met Ala Phe Ala Arg His Val Ala Leu Cys Leu<br>675                         680                         685 | | 2064 |
| gct aaa gac ttg caa cca caa act aaa ctt tag<br>Ala Lys Asp Leu Gln Pro Gln Thr Lys Leu<br>690                         695 | | 2097 |

```
<210> SEQ ID NO 54
<211> LENGTH: 698
<212> TYPE: PRT
<213> ORGANISM: Candida cloacae

<400> SEQUENCE: 54
```

Met Ser His Gln Val Glu Asp His Asp Leu Asp Val Phe Cys Leu Leu
1               5                   10                  15

Ala Asp Ala Val Leu His Glu Ile Pro Pro Ser Glu Ile Val Glu Tyr
            20                  25                  30

Leu His Pro Asp Phe Pro Lys Asp Lys Ile Glu Glu Tyr Leu Thr Gly
        35                  40                  45

Phe Ser Arg Pro Ser Ala Val Pro Gln Phe Arg Gln Cys Ala Lys Lys
    50                  55                  60

Leu Ile Asn Arg Gly Ser Glu Leu Ser Ile Lys Leu Phe Leu Tyr Leu
65                  70                  75                  80

Thr Thr Ala Leu Asp Ser Arg Ile Leu Ala Pro Ala Leu Thr Asn Ser
            85                  90                  95

Leu Thr Leu Ile Arg Asp Met Asp Leu Ser Gln Arg Glu Glu Leu Leu

```
                100                 105                 110
Arg Ser Trp Arg Asp Ser Pro Leu Thr Ala Lys Arg Arg Leu Phe Arg
        115                 120                 125

Val Tyr Ala Ser Phe Thr Leu Ser Thr Phe Asn Lys Leu Gly Thr Asp
        130                 135                 140

Leu His Phe Lys Ala Leu Gly Tyr Pro Gly Arg Glu Leu Arg Thr Gln
145                 150                 155                 160

Ile Gln Asp Tyr Glu Val Asp Pro Phe Arg Tyr Ser Phe Met Glu Lys
                165                 170                 175

Leu Lys His Glu Gly His Glu Leu Phe Leu Pro Asp Ile Asp Val Leu
            180                 185                 190

Ile Ile Gly Ser Gly Ser Gly Ala Gly Val Val Ala Gln Thr Leu Thr
            195                 200                 205

Glu Ser Gly Leu Lys Ser Leu Val Leu Glu Lys Gly Lys Tyr Phe Ala
            210                 215                 220

Ser Glu Glu Leu Cys Met Thr Asp Leu Asp Gly Asn Glu Ala Leu Phe
225                 230                 235                 240

Glu Ser Gly Gly Thr Ile Pro Ser Thr Asn Gln Gln Leu Phe Met Ile
                245                 250                 255

Ala Gly Ser Thr Phe Gly Gly Gly Ser Thr Val Asn Trp Ser Ala Cys
            260                 265                 270

Leu Lys Thr Pro Phe Lys Val Arg Lys Glu Trp Tyr Asp Asp Phe Gly
            275                 280                 285

Leu Asp Phe Val Ala Thr Gln Gln Tyr Asp Asp Cys Met Asp Tyr Val
            290                 295                 300

Trp Lys Lys Met Gly Ala Ser Thr Glu His Ile Glu His Ser Ala Ala
305                 310                 315                 320

Asn Ala Val Ile Met Asp Gly Ala Ala Lys Leu Gly Tyr Ala His Arg
                325                 330                 335

Ala Leu Glu Gln Asn Thr Gly Gly His Val His Asp Cys Gly Met Cys
            340                 345                 350

His Leu Gly Cys Arg Phe Gly Ile Lys Gln Gly Gly Val Asn Cys Trp
            355                 360                 365

Phe Arg Glu Pro Ser Glu Lys Gly Ser Lys Phe Met Glu Gln Val Val
            370                 375                 380

Val Glu Lys Ile Leu Gln His Lys Gly Lys Ala Thr Gly Ile Leu Cys
385                 390                 395                 400

Arg Asp Thr Glu Ser Gly Ile Lys Phe Lys Ile Thr Gly Pro Lys Lys
                405                 410                 415

Tyr Val Val Ser Gly Gly Ser Leu Gln Thr Pro Val Leu Leu Gln Lys
            420                 425                 430

Ser Gly Phe Lys Asn Lys His Ile Gly Ala Asn Leu Lys Leu His Pro
            435                 440                 445

Val Ser Val Ala Leu Gly Asp Phe Gly Asn Glu Val Asp Phe Glu Ala
            450                 455                 460

Tyr Lys Arg Pro Leu Met Thr Ala Val Cys Asn Ala Val Asp Asp Leu
465                 470                 475                 480

Asp Gly Lys Ala His Gly Thr Arg Ile Glu Ala Ile Leu His Ala Pro
                485                 490                 495

Tyr Val Thr Ala Pro Phe Tyr Pro Trp Gln Ser Gly Ala Gln Ala Arg
            500                 505                 510

Lys Asn Leu Leu Lys Tyr Lys Gln Thr Val Pro Leu Leu Leu Leu Ser
            515                 520                 525
```

```
Arg Asp Thr Ser Ser Gly Thr Val Thr Tyr Asp Lys Gln Lys Pro Asp
            530                 535                 540

Val Leu Val Val Asp Tyr Thr Val Asn Lys Phe Asp Arg Asn Ser Ile
545                 550                 555                 560

Leu Gln Gly Phe Leu Val Ala Ser Asp Ile Leu Tyr Ile Glu Gly Ala
                565                 570                 575

Lys Glu Ile Leu Ser Pro Gln Ala Trp Val Pro Thr Phe Lys Ser Asn
            580                 585                 590

Lys Pro Lys His Ala Arg Ser Ile Lys Asp Glu Asp Tyr Val Lys Trp
        595                 600                 605

Arg Glu Thr Val Ala Lys Ile Pro Phe Asp Ser Tyr Gly Ser Pro Tyr
    610                 615                 620

Gly Ser Ala His Gln Met Ser Ser Cys Arg Met Ser Gly Lys Gly Pro
625                 630                 635                 640

Gly Tyr Gly Ala Cys Asp Thr Lys Gly Arg Leu Phe Glu Cys Asn Asn
                645                 650                 655

Val Tyr Val Ala Asp Ala Ser Val Met Pro Thr Ala Ser Gly Val Asn
            660                 665                 670

Pro Met Ile Thr Thr Met Ala Phe Ala Arg His Val Ala Leu Cys Leu
        675                 680                 685

Ala Lys Asp Leu Gln Pro Gln Thr Lys Leu
    690                 695

<210> SEQ ID NO 55
<211> LENGTH: 2097
<212> TYPE: DNA
<213> ORGANISM: Candida cloacae
<220> FEATURE:
<221> NAME/KEY: CDS
<222> LOCATION: (1)..(2094)

<400> SEQUENCE: 55 atg aat ccc gtt gtt gaa gac agc cat tta gat gtg ttc tgc ttg tta    48
Met Asn Pro Val Val Glu Asp Ser His Leu Asp Val Phe Cys Leu Leu
1               5                   10                  15 gcc gat gct gtg gtc cat gag ata cct cct agt gag atc gta gag tac    96
Ala Asp Ala Val Val His Glu Ile Pro Pro Ser Glu Ile Val Glu Tyr
            20                  25                  30 tta cat cct gat ttc cca aag gac aag gtt gaa gag tat ttg gct gag   144
Leu His Pro Asp Phe Pro Lys Asp Lys Val Glu Glu Tyr Leu Ala Glu
        35                  40                  45 ttt tct cat cct tca gca att ccc gaa ttt aga gaa gtt gca aaa aga   192
Phe Ser His Pro Ser Ala Ile Pro Glu Phe Arg Glu Val Ala Lys Arg
    50                  55                  60 att att aac aaa ggg act gtg ctg tca ata aag ttg ttt ttg ctc ttg   240
Ile Ile Asn Lys Gly Thr Val Leu Ser Ile Lys Leu Phe Leu Leu Leu
65                  70                  75                  80 gca act gct cta gac tcg aga atc ctt gct cct gcg ttg acc aac tcg   288
Ala Thr Ala Leu Asp Ser Arg Ile Leu Ala Pro Ala Leu Thr Asn Ser
                85                  90                  95 acg acg tta atc aga gat atg gat ctt tct caa aga gaa gaa tta ttg   336
Thr Thr Leu Ile Arg Asp Met Asp Leu Ser Gln Arg Glu Glu Leu Leu
            100                 105                 110 aga tca tgg aga gac tct cca ttc act aca aaa agg aaa ttg ttc agg   384
Arg Ser Trp Arg Asp Ser Pro Phe Thr Thr Lys Arg Lys Leu Phe Arg
        115                 120                 125 gtg tat aat tca ttc acc ttg aac gcg ttt agt aag acc gca aca gat   432
Val Tyr Asn Ser Phe Thr Leu Asn Ala Phe Ser Lys Thr Ala Thr Asp
```

```
              130                 135                 140
ttg cac ttc aaa gcg ttg gga tat cct ggt aga gag ctc agg act caa      480
Leu His Phe Lys Ala Leu Gly Tyr Pro Gly Arg Glu Leu Arg Thr Gln
145                 150                 155                 160 att cag gac tat gag gtc gat cct ttc aga tat acg ttc ttg gaa aaa      528
Ile Gln Asp Tyr Glu Val Asp Pro Phe Arg Tyr Thr Phe Leu Glu Lys
                165                 170                 175 ccc caa caa gac ggc cag gag tta cat ttt ccc gac att gat gtc ttg      576
Pro Gln Gln Asp Gly Gln Glu Leu His Phe Pro Asp Ile Asp Val Leu
            180                 185                 190 att atc ggg tct ggt tcg gga gca gga gtg gtt gct caa act ctt tcg      624
Ile Ile Gly Ser Gly Ser Gly Ala Gly Val Val Ala Gln Thr Leu Ser
        195                 200                 205 gaa aac gga ctt aaa tca ttg gtg ttg gaa aaa ggt aaa tac ttt tcc      672
Glu Asn Gly Leu Lys Ser Leu Val Leu Glu Lys Gly Lys Tyr Phe Ser
    210                 215                 220 aat gat gag ttg acc atg aat gat ttg gaa ggt agt gag gca tta ttc      720
Asn Asp Glu Leu Thr Met Asn Asp Leu Glu Gly Ser Glu Ala Leu Phe
225                 230                 235                 240 gaa aat gga ggt gcc ctc agt agt acc aac caa cag ata ttt ata att      768
Glu Asn Gly Gly Ala Leu Ser Ser Thr Asn Gln Gln Ile Phe Ile Ile
                245                 250                 255 gca ggt tcg act ttt ggg ggt ggt tct aca gtt aat tgg tct gcc tgt      816
Ala Gly Ser Thr Phe Gly Gly Gly Ser Thr Val Asn Trp Ser Ala Cys
            260                 265                 270 tta aaa act ccg ttc aaa gta aga aaa gag tgg tat gac aac ttc gga      864
Leu Lys Thr Pro Phe Lys Val Arg Lys Glu Trp Tyr Asp Asn Phe Gly
        275                 280                 285 ctt gat ttc gtc gca acc caa tac tac gaa gat tgt atg gat tat gtt      912
Leu Asp Phe Val Ala Thr Gln Tyr Tyr Glu Asp Cys Met Asp Tyr Val
    290                 295                 300 tgg aag aaa atg ggt gct tcg aac gaa aat atc gac cat tct ggt gct      960
Trp Lys Lys Met Gly Ala Ser Asn Glu Asn Ile Asp His Ser Gly Ala
305                 310                 315                 320 aat agt gtt ata ttg gaa ggg tcc aaa aaa ctt ggc tac cct cac agg     1008
Asn Ser Val Ile Leu Glu Gly Ser Lys Lys Leu Gly Tyr Pro His Arg
                325                 330                 335 gcc gtt gaa caa aat aat ggg ggc aaa att cat gac tgt ggt atg tgt     1056
Ala Val Glu Gln Asn Asn Gly Gly Lys Ile His Asp Cys Gly Met Cys
            340                 345                 350 cac ttg ggt tgt aga ttt ggt att aaa cag gga agt gta aat tgc tgg     1104
His Leu Gly Cys Arg Phe Gly Ile Lys Gln Gly Ser Val Asn Cys Trp
        355                 360                 365 ttc cgt ggt cca agt gaa aac gga tcc aag ttt atg caa caa gtt ctc     1152
Phe Arg Gly Pro Ser Glu Asn Gly Ser Lys Phe Met Gln Gln Val Leu
    370                 375                 380 gtg gat aag ata ttg caa cgt gac ggt aaa gca gtc ggt gtt ttg tgt     1200
Val Asp Lys Ile Leu Gln Arg Asp Gly Lys Ala Val Gly Val Leu Cys
385                 390                 395                 400 aga gat gtt gta acc ggt gtt aag ttc aag atc act gga cca aag aaa     1248
Arg Asp Val Val Thr Gly Val Lys Phe Lys Ile Thr Gly Pro Lys Lys
                405                 410                 415 att gtt gtt ttc tgg tgg ttc ttt gca aac tcc ggt ttt gtt aca aaa     1296
Ile Val Val Phe Trp Trp Phe Phe Ala Asn Ser Gly Phe Val Thr Lys
            420                 425                 430 tca ggt ttc aag aat aaa cac att ggt gct aac ttg aag ctc cat cca     1344
Ser Gly Phe Lys Asn Lys His Ile Gly Ala Asn Leu Lys Leu His Pro
        435                 440                 445 gtt tca ctt acg ctt gga gac ttc ggt aac aac gtg gat ttc gaa gct     1392
```

-continued

```
Val Ser Leu Thr Leu Gly Asp Phe Gly Asn Asn Val Asp Phe Glu Ala
    450                 455                 460 tac agg aaa cca att atg aca tca att tgt aat aaa gtc gaa gat tta      1440
Tyr Arg Lys Pro Ile Met Thr Ser Ile Cys Asn Lys Val Glu Asp Leu
465                 470                 475                 480 gat gga aag gcc cat ggt aca aga att gaa gct atg ttg aat gct cca      1488
Asp Gly Lys Ala His Gly Thr Arg Ile Glu Ala Met Leu Asn Ala Pro
                485                 490                 495 tat ggt gtt gca cca ttt ttc ccc tgg aaa tca ggc gct gaa tca aga      1536
Tyr Gly Val Ala Pro Phe Phe Pro Trp Lys Ser Gly Ala Glu Ser Arg
            500                 505                 510 aag gat ctc ttg aga tac aaa caa act gtg cct ata tta ctt ctt tcc      1584
Lys Asp Leu Leu Arg Tyr Lys Gln Thr Val Pro Ile Leu Leu Leu Ser
        515                 520                 525 aga gat act act tca ggg tct gtc aca tat gat aaa caa aaa cca gat      1632
Arg Asp Thr Thr Ser Gly Ser Val Thr Tyr Asp Lys Gln Lys Pro Asp
    530                 535                 540 gca ttg gtg att gat tac ctg tta aac aag ttt gac aga aac tca att      1680
Ala Leu Val Ile Asp Tyr Leu Leu Asn Lys Phe Asp Arg Asn Ser Ile
545                 550                 555                 560 tta caa ggg ttt ttg ata gct tca gac ctt tta tat att gaa ggt gcc      1728
Leu Gln Gly Phe Leu Ile Ala Ser Asp Leu Leu Tyr Ile Glu Gly Ala
                565                 570                 575 agt aga gat cat gtc acc tac aag ctt ggg tac caa tgg ttc aag agt      1776
Ser Arg Asp His Val Thr Tyr Lys Leu Gly Tyr Gln Trp Phe Lys Ser
            580                 585                 590 tct aaa cct aaa cat gcc aga tcg att gaa gat gaa gac tac gta aac      1824
Ser Lys Pro Lys His Ala Arg Ser Ile Glu Asp Glu Asp Tyr Val Asn
        595                 600                 605 tgg aga gct aaa gtt gca aag att cca ttt gat tcc tac gga tca cca      1872
Trp Arg Ala Lys Val Ala Lys Ile Pro Phe Asp Ser Tyr Gly Ser Pro
    610                 615                 620 tac ggt tca gct cac caa atg agt aca tgc aga atg tca ggt aag gga      1920
Tyr Gly Ser Ala His Gln Met Ser Thr Cys Arg Met Ser Gly Lys Gly
625                 630                 635                 640 cca gga tat gga gct tgt gat acc aaa gga aaa tta ttt gaa tgt agc      1968
Pro Gly Tyr Gly Ala Cys Asp Thr Lys Gly Lys Leu Phe Glu Cys Ser
                645                 650                 655 aat gtt tat gtt gca gat gct tcc act ttg cct act gca tca ggg gct      2016
Asn Val Tyr Val Ala Asp Ala Ser Thr Leu Pro Thr Ala Ser Gly Ala
            660                 665                 670 aat cca atg gtt agt acc atg tca ttt gca agg cac gtg tcc tta gga      2064
Asn Pro Met Val Ser Thr Met Ser Phe Ala Arg His Val Ser Leu Gly
        675                 680                 685 att gtt aaa gaa ttg caa caa agt aaa ctt tag                          2097
Ile Val Lys Glu Leu Gln Gln Ser Lys Leu
    690                 695
```

<210> SEQ ID NO 56
<211> LENGTH: 698
<212> TYPE: PRT
<213> ORGANISM: Candida cloacae

<400> SEQUENCE: 56

```
Met Asn Pro Val Val Glu Asp Ser His Leu Asp Val Phe Cys Leu Leu
1               5                   10                  15

Ala Asp Ala Val Val His Glu Ile Pro Pro Ser Glu Ile Val Glu Tyr
            20                  25                  30

Leu His Pro Asp Phe Pro Lys Asp Lys Val Glu Glu Tyr Leu Ala Glu
        35                  40                  45
```

```
Phe Ser His Pro Ser Ala Ile Pro Glu Phe Arg Glu Val Ala Lys Arg
     50                  55                  60

Ile Ile Asn Lys Gly Thr Val Leu Ser Ile Lys Leu Phe Leu Leu Leu
 65                  70                  75                  80

Ala Thr Ala Leu Asp Ser Arg Ile Leu Ala Pro Ala Leu Thr Asn Ser
                     85                  90                  95

Thr Thr Leu Ile Arg Asp Met Asp Leu Ser Gln Arg Glu Glu Leu Leu
            100                 105                 110

Arg Ser Trp Arg Asp Ser Pro Phe Thr Thr Lys Arg Lys Leu Phe Arg
        115                 120                 125

Val Tyr Asn Ser Phe Thr Leu Asn Ala Phe Ser Lys Thr Ala Thr Asp
    130                 135                 140

Leu His Phe Lys Ala Leu Gly Tyr Pro Gly Arg Glu Leu Arg Thr Gln
145                 150                 155                 160

Ile Gln Asp Tyr Glu Val Asp Pro Phe Arg Tyr Thr Phe Leu Glu Lys
                165                 170                 175

Pro Gln Gln Asp Gly Gln Glu Leu His Phe Pro Asp Ile Asp Val Leu
            180                 185                 190

Ile Ile Gly Ser Gly Ser Gly Ala Gly Val Val Ala Gln Thr Leu Ser
        195                 200                 205

Glu Asn Gly Leu Lys Ser Leu Val Leu Glu Lys Gly Lys Tyr Phe Ser
    210                 215                 220

Asn Asp Glu Leu Thr Met Asn Asp Leu Glu Gly Ser Glu Ala Leu Phe
225                 230                 235                 240

Glu Asn Gly Gly Ala Leu Ser Ser Thr Asn Gln Gln Ile Phe Ile Ile
                245                 250                 255

Ala Gly Ser Thr Phe Gly Gly Ser Thr Val Asn Trp Ser Ala Cys
            260                 265                 270

Leu Lys Thr Pro Phe Lys Val Arg Lys Glu Trp Tyr Asp Asn Phe Gly
        275                 280                 285

Leu Asp Phe Val Ala Thr Gln Tyr Tyr Glu Asp Cys Met Asp Tyr Val
    290                 295                 300

Trp Lys Lys Met Gly Ala Ser Asn Glu Asn Ile Asp His Ser Gly Ala
305                 310                 315                 320

Asn Ser Val Ile Leu Glu Gly Ser Lys Lys Leu Gly Tyr Pro His Arg
                325                 330                 335

Ala Val Glu Gln Asn Asn Gly Lys Ile His Asp Cys Gly Met Cys
            340                 345                 350

His Leu Gly Cys Arg Phe Gly Ile Lys Gln Gly Ser Val Asn Cys Trp
        355                 360                 365

Phe Arg Gly Pro Ser Glu Asn Gly Ser Lys Phe Met Gln Gln Val Leu
    370                 375                 380

Val Asp Lys Ile Leu Gln Arg Asp Gly Lys Ala Val Gly Val Leu Cys
385                 390                 395                 400

Arg Asp Val Val Thr Gly Val Lys Phe Lys Ile Thr Gly Pro Lys Lys
                405                 410                 415

Ile Val Val Phe Trp Trp Phe Ala Asn Ser Gly Phe Val Thr Lys
            420                 425                 430

Ser Gly Phe Lys Asn Lys His Ile Gly Ala Asn Leu Lys Leu His Pro
        435                 440                 445

Val Ser Leu Thr Leu Gly Asp Phe Gly Asn Asn Val Asp Phe Glu Ala
    450                 455                 460
```

```
Tyr Arg Lys Pro Ile Met Thr Ser Ile Cys Asn Lys Val Glu Asp Leu
465                 470                 475                 480

Asp Gly Lys Ala His Gly Thr Arg Ile Glu Ala Met Leu Asn Ala Pro
            485                 490                 495

Tyr Gly Val Ala Pro Phe Phe Pro Trp Lys Ser Gly Ala Glu Ser Arg
        500                 505                 510

Lys Asp Leu Leu Arg Tyr Lys Gln Thr Val Pro Ile Leu Leu Leu Ser
    515                 520                 525

Arg Asp Thr Thr Ser Gly Ser Val Thr Tyr Asp Lys Gln Lys Pro Asp
530                 535                 540

Ala Leu Val Ile Asp Tyr Leu Leu Asn Lys Phe Asp Arg Asn Ser Ile
545                 550                 555                 560

Leu Gln Gly Phe Leu Ile Ala Ser Asp Leu Leu Tyr Ile Glu Gly Ala
                565                 570                 575

Ser Arg Asp His Val Thr Tyr Lys Leu Gly Tyr Gln Trp Phe Lys Ser
            580                 585                 590

Ser Lys Pro Lys His Ala Arg Ser Ile Glu Asp Glu Asp Tyr Val Asn
        595                 600                 605

Trp Arg Ala Lys Val Ala Lys Ile Pro Phe Asp Ser Tyr Gly Ser Pro
    610                 615                 620

Tyr Gly Ser Ala His Gln Met Ser Thr Cys Arg Met Ser Gly Lys Gly
625                 630                 635                 640

Pro Gly Tyr Gly Ala Cys Asp Thr Lys Gly Lys Leu Phe Glu Cys Ser
                645                 650                 655

Asn Val Tyr Val Ala Asp Ala Ser Thr Leu Pro Thr Ala Ser Gly Ala
            660                 665                 670

Asn Pro Met Val Ser Thr Met Ser Phe Ala Arg His Val Ser Leu Gly
        675                 680                 685

Ile Val Lys Glu Leu Gln Gln Ser Lys Leu
    690                 695

<210> SEQ ID NO 57
<211> LENGTH: 948
<212> TYPE: DNA
<213> ORGANISM: Candida tropicalis
<220> FEATURE:
<221> NAME/KEY: CDS
<222> LOCATION: (1)..(948)

<400> SEQUENCE: 57 cca ttg caa tac acc gat atc cca gtt cca gtc cct aag cca aac gaa    48
Pro Leu Gln Tyr Thr Asp Ile Pro Val Pro Val Pro Lys Pro Asn Glu
1               5                   10                  15 ttg ctc gtc cac gtc aaa tac tcc ggt gtt tgt cac tca gat ata cac    96
Leu Leu Val His Val Lys Tyr Ser Gly Val Cys His Ser Asp Ile His
            20                  25                  30 gtc tgg aag ggt gac tgg ttc cca gca tcg aaa ttg ccc gtt gtt ggt   144
Val Trp Lys Gly Asp Trp Phe Pro Ala Ser Lys Leu Pro Val Val Gly
        35                  40                  45 ggt cac gaa ggt gcc ggt gtt gtc gtt gcc att ggt gaa aac gtc caa   192
Gly His Glu Gly Ala Gly Val Val Val Ala Ile Gly Glu Asn Val Gln
    50                  55                  60 ggc tgg aaa gta ggt gac ttg gca ggt ata aag atg ttg aat ggt tcc   240
Gly Trp Lys Val Gly Asp Leu Ala Gly Ile Lys Met Leu Asn Gly Ser
65                  70                  75                  80 tgt atg aac tgt gaa tac tgt caa caa ggt gct gaa cca aac tgt ccc   288
Cys Met Asn Cys Glu Tyr Cys Gln Gln Gly Ala Glu Pro Asn Cys Pro
                85                  90                  95
```

```
cac gct gat gtc tcg ggt tac tcc cac gac ggt act ttc caa cag tac    336
His Ala Asp Val Ser Gly Tyr Ser His Asp Gly Thr Phe Gln Gln Tyr
            100                 105                 110 gct acc gcc gat gct gtt caa gct gct aaa ttc cca gct ggt tct gat    384
Ala Thr Ala Asp Ala Val Gln Ala Ala Lys Phe Pro Ala Gly Ser Asp
        115                 120                 125 tta gct agc atc gca cct ata tcc tgc gcc ggt gtt act gtt tac aaa    432
Leu Ala Ser Ile Ala Pro Ile Ser Cys Ala Gly Val Thr Val Tyr Lys
130                 135                 140 gca ttg aaa act gca ggc ttg cag cca ggt caa tgg gtt gcc atc tct    480
Ala Leu Lys Thr Ala Gly Leu Gln Pro Gly Gln Trp Val Ala Ile Ser
145                 150                 155                 160 ggt gca gct ggt ggt ttg ggt tct ttg gct gtg caa tac gcc aag gcc    528
Gly Ala Ala Gly Gly Leu Gly Ser Leu Ala Val Gln Tyr Ala Lys Ala
                165                 170                 175 atg ggt ttg aga gtc gtg gcc att gac ggt ggt gac gaa aga gga gtg    576
Met Gly Leu Arg Val Val Ala Ile Asp Gly Gly Asp Glu Arg Gly Val
            180                 185                 190 ttt gtc aaa tcg ttg ggt gct gaa gtt ttc gtt gat ttc acc aaa gag    624
Phe Val Lys Ser Leu Gly Ala Glu Val Phe Val Asp Phe Thr Lys Glu
        195                 200                 205 gcc aat gtc tct gag gct atc atc aag gct acc gac ggt ggt gcc cat    672
Ala Asn Val Ser Glu Ala Ile Ile Lys Ala Thr Asp Gly Gly Ala His
210                 215                 220 ggc gtc atc aac gtt tcc att tct gaa aaa gcc atc aac cag tct gtt    720
Gly Val Ile Asn Val Ser Ile Ser Glu Lys Ala Ile Asn Gln Ser Val
225                 230                 235                 240 gaa tat gtt aga act ttg gga act gtt gtc ttg gtt ggt ttg cca gct    768
Glu Tyr Val Arg Thr Leu Gly Thr Val Val Leu Val Gly Leu Pro Ala
                245                 250                 255 ggt gca aag ctc gaa gct cct atc ttc aat gcc gtt gcc aaa tcc atc    816
Gly Ala Lys Leu Glu Ala Pro Ile Phe Asn Ala Val Ala Lys Ser Ile
            260                 265                 270 caa atc aaa ggt tct tac gtg gga aac aga aga gac act gct gag gct    864
Gln Ile Lys Gly Ser Tyr Val Gly Asn Arg Arg Asp Thr Ala Glu Ala
        275                 280                 285 gtt gat ttc ttc gct aga ggt ttg gtc aaa tgt cca att aag gtt gtt    912
Val Asp Phe Phe Ala Arg Gly Leu Val Lys Cys Pro Ile Lys Val Val
290                 295                 300 ggg ttg agt gaa ttg cca gag att ttc aaa ttg ttg                    948
Gly Leu Ser Glu Leu Pro Glu Ile Phe Lys Leu Leu
305                 310                 315

<210> SEQ ID NO 58
<211> LENGTH: 316
<212> TYPE: PRT
<213> ORGANISM: Candida tropicalis

<400> SEQUENCE: 58

Pro Leu Gln Tyr Thr Asp Ile Pro Val Pro Val Pro Lys Pro Asn Glu
1               5                   10                  15

Leu Leu Val His Val Lys Tyr Ser Gly Val Cys His Ser Asp Ile His
                20                  25                  30

Val Trp Lys Gly Asp Trp Phe Pro Ala Ser Lys Leu Pro Val Val Gly
            35                  40                  45

Gly His Glu Gly Ala Gly Val Val Val Ala Ile Gly Glu Asn Val Gln
        50                  55                  60

Gly Trp Lys Val Gly Asp Leu Ala Gly Ile Lys Met Leu Asn Gly Ser
65                  70                  75                  80
```

```
Cys Met Asn Cys Glu Tyr Cys Gln Gln Gly Ala Glu Pro Asn Cys Pro
             85                  90                  95

His Ala Asp Val Ser Gly Tyr Ser His Asp Gly Thr Phe Gln Gln Tyr
            100                 105                 110

Ala Thr Ala Asp Ala Val Gln Ala Lys Phe Pro Ala Gly Ser Asp
        115                 120                 125

Leu Ala Ser Ile Ala Pro Ile Ser Cys Ala Gly Val Thr Val Tyr Lys
        130                 135                 140

Ala Leu Lys Thr Ala Gly Leu Gln Pro Gly Gln Trp Val Ala Ile Ser
145                 150                 155                 160

Gly Ala Ala Gly Gly Leu Gly Ser Leu Ala Val Gln Tyr Ala Lys Ala
                165                 170                 175

Met Gly Leu Arg Val Val Ala Ile Asp Gly Gly Asp Glu Arg Gly Val
                180                 185                 190

Phe Val Lys Ser Leu Gly Ala Glu Val Phe Val Asp Phe Thr Lys Glu
            195                 200                 205

Ala Asn Val Ser Glu Ala Ile Ile Lys Ala Thr Asp Gly Gly Ala His
        210                 215                 220

Gly Val Ile Asn Val Ser Ile Ser Glu Lys Ala Ile Asn Gln Ser Val
225                 230                 235                 240

Glu Tyr Val Arg Thr Leu Gly Thr Val Leu Val Gly Leu Pro Ala
                245                 250                 255

Gly Ala Lys Leu Glu Ala Pro Ile Phe Asn Ala Val Ala Lys Ser Ile
                260                 265                 270

Gln Ile Lys Gly Ser Tyr Val Gly Asn Arg Arg Asp Thr Ala Glu Ala
            275                 280                 285

Val Asp Phe Phe Ala Arg Gly Leu Val Lys Cys Pro Ile Lys Val Val
        290                 295                 300

Gly Leu Ser Glu Leu Pro Glu Ile Phe Lys Leu Leu
305                 310                 315

<210> SEQ ID NO 59
<211> LENGTH: 948
<212> TYPE: DNA
<213> ORGANISM: Candida tropicalis
<220> FEATURE:
<221> NAME/KEY: CDS
<222> LOCATION: (1)..(948)

<400> SEQUENCE: 59 aaa tta gaa tac aag gac atc cca gtt cca aag cca aag cca aac gaa      48
Lys Leu Glu Tyr Lys Asp Ile Pro Val Pro Lys Pro Lys Pro Asn Glu
1                5                  10                  15 ttg ctc atc aac gtc aag tac tcc ggt gtc tgc cac act gat tta cac      96
Leu Leu Ile Asn Val Lys Tyr Ser Gly Val Cys His Thr Asp Leu His
                20                  25                  30 gcc tgg aag ggt gac tgg cca ttg gac acc aag ttg cca ttg gtg ggt     144
Ala Trp Lys Gly Asp Trp Pro Leu Asp Thr Lys Leu Pro Leu Val Gly
            35                  40                  45 ggt cac gaa ggt gct ggt gtt gtt gtt gcc att ggt gac aat gtc aag     192
Gly His Glu Gly Ala Gly Val Val Val Ala Ile Gly Asp Asn Val Lys
        50                  55                  60 gga tgg aag gtc ggt gat ttg gcc ggt gtc aag tgg ttg aac ggt tcc     240
Gly Trp Lys Val Gly Asp Leu Ala Gly Val Lys Trp Leu Asn Gly Ser
65                  70                  75                  80 tgt atg aac tgt gag tac tgt caa cag ggt gcc gaa cca aac tgt cca     288
Cys Met Asn Cys Glu Tyr Cys Gln Gln Gly Ala Glu Pro Asn Cys Pro
```

```
            85                  90                  95
cag gct gac ttg tct ggt tac acc cac gac ggt tct ttc cag caa tac    336
Gln Ala Asp Leu Ser Gly Tyr Thr His Asp Gly Ser Phe Gln Gln Tyr
            100                 105                 110 gcc act gca gat gcc gtg caa gcc gct aga att cca gct ggt act gat    384
Ala Thr Ala Asp Ala Val Gln Ala Ala Arg Ile Pro Ala Gly Thr Asp
        115                 120                 125 tta gcc aac gtt gcc ccc atc ttg tgt gct ggt gtc act gtt tac aag    432
Leu Ala Asn Val Ala Pro Ile Leu Cys Ala Gly Val Thr Val Tyr Lys
130                 135                 140 gcc ttg aag acc gcc gac ttg cag cca ggt caa tgg gtc gcc att tcc    480
Ala Leu Lys Thr Ala Asp Leu Gln Pro Gly Gln Trp Val Ala Ile Ser
145                 150                 155                 160 ggt gcc gct ggt ggt ttg ggt tct ttg gcc gtt caa tac gcc aag gcc    528
Gly Ala Ala Gly Gly Leu Gly Ser Leu Ala Val Gln Tyr Ala Lys Ala
                165                 170                 175 atg ggc tac aga gtt gtc gcc atc gat ggt ggt gcc gac aag ggt gag    576
Met Gly Tyr Arg Val Val Ala Ile Asp Gly Gly Ala Asp Lys Gly Glu
                180                 185                 190 ttc gtc aag tct ttg ggc gct gag gtc ttt gtt gat ttc ctc aag gaa    624
Phe Val Lys Ser Leu Gly Ala Glu Val Phe Val Asp Phe Leu Lys Glu
            195                 200                 205 aag gac att gtt ggt gct gtc aag aag gca acc gat ggt ggc cca cac    672
Lys Asp Ile Val Gly Ala Val Lys Lys Ala Thr Asp Gly Gly Pro His
        210                 215                 220 ggt gcc gtt aac gtt tcc atc tcc gaa aag gcc atc aac caa tct gtc    720
Gly Ala Val Asn Val Ser Ile Ser Glu Lys Ala Ile Asn Gln Ser Val
225                 230                 235                 240 gac tac gtt aga acc ttg ggt aag gtt gtc ttg gtc ggt ttg cca gct    768
Asp Tyr Val Arg Thr Leu Gly Lys Val Val Leu Val Gly Leu Pro Ala
                245                 250                 255 ggc tcc aag gtt tct gct cca gtc ttt gac tcc gtc gtc aag tcc atc    816
Gly Ser Lys Val Ser Ala Pro Val Phe Asp Ser Val Val Lys Ser Ile
                260                 265                 270 caa atc aag ggt tcc tat gtc ggt aac aga aag gac act gcc gaa gct    864
Gln Ile Lys Gly Ser Tyr Val Gly Asn Arg Lys Asp Thr Ala Glu Ala
            275                 280                 285 gtt gac ttt ttc tcc aga ggc ttg atc aag tgt cca atc aag gtt gtc    912
Val Asp Phe Phe Ser Arg Gly Leu Ile Lys Cys Pro Ile Lys Val Val
        290                 295                 300 ggt ttg agt gaa ttg cca gaa gtc tac aag ttg atg                    948
Gly Leu Ser Glu Leu Pro Glu Val Tyr Lys Leu Met
305                 310                 315

<210> SEQ ID NO 60
<211> LENGTH: 316
<212> TYPE: PRT
<213> ORGANISM: Candida tropicalis

<400> SEQUENCE: 60

Lys Leu Glu Tyr Lys Asp Ile Pro Val Pro Lys Pro Lys Pro Asn Glu
1               5                   10                  15

Leu Leu Ile Asn Val Lys Tyr Ser Gly Val Cys His Thr Asp Leu His
            20                  25                  30

Ala Trp Lys Gly Asp Trp Pro Leu Asp Thr Lys Leu Pro Leu Val Gly
        35                  40                  45

Gly His Glu Gly Ala Gly Val Val Val Ala Ile Gly Asp Asn Val Lys
    50                  55                  60

Gly Trp Lys Val Gly Asp Leu Ala Gly Val Lys Trp Leu Asn Gly Ser
```

```
                65                  70                  75                  80
Cys Met Asn Cys Glu Tyr Cys Gln Gln Gly Ala Glu Pro Asn Cys Pro
                    85                  90                  95

Gln Ala Asp Leu Ser Gly Tyr Thr His Asp Gly Ser Phe Gln Gln Tyr
                100                 105                 110

Ala Thr Ala Asp Ala Val Gln Ala Ala Arg Ile Pro Ala Gly Thr Asp
                115                 120                 125

Leu Ala Asn Val Ala Pro Ile Leu Cys Ala Gly Val Thr Val Tyr Lys
            130                 135                 140

Ala Leu Lys Thr Ala Asp Leu Gln Pro Gly Gln Trp Val Ala Ile Ser
145                 150                 155                 160

Gly Ala Ala Gly Gly Leu Gly Ser Leu Ala Val Gln Tyr Ala Lys Ala
                    165                 170                 175

Met Gly Tyr Arg Val Val Ala Ile Asp Gly Gly Ala Asp Lys Gly Glu
                180                 185                 190

Phe Val Lys Ser Leu Gly Ala Glu Val Phe Asp Phe Leu Lys Glu
                195                 200                 205

Lys Asp Ile Val Gly Ala Val Lys Ala Thr Asp Gly Gly Pro His
            210                 215                 220

Gly Ala Val Asn Val Ser Ile Ser Glu Lys Ala Ile Asn Gln Ser Val
225                 230                 235                 240

Asp Tyr Val Arg Thr Leu Gly Lys Val Val Leu Val Gly Leu Pro Ala
                    245                 250                 255

Gly Ser Lys Val Ser Ala Pro Val Phe Asp Ser Val Lys Ser Ile
                260                 265                 270

Gln Ile Lys Gly Ser Tyr Val Gly Asn Arg Lys Asp Thr Ala Glu Ala
            275                 280                 285

Val Asp Phe Phe Ser Arg Gly Leu Ile Lys Cys Pro Ile Lys Val Val
                290                 295                 300

Gly Leu Ser Glu Leu Pro Glu Val Tyr Lys Leu Met
305                 310                 315

<210> SEQ ID NO 61
<211> LENGTH: 456
<212> TYPE: DNA
<213> ORGANISM: Candida tropicalis
<220> FEATURE:
<221> NAME/KEY: CDS
<222> LOCATION: (1)..(456)

<400> SEQUENCE: 61 aac tgt gag ttt tgc caa cag ggc gct gaa cct aat tgt cca aga gcc        48
Asn Cys Glu Phe Cys Gln Gln Gly Ala Glu Pro Asn Cys Pro Arg Ala
1               5                   10                  15 gac atg tct gga tat acc cac gat ggg act ttc caa caa tat gct acc        96
Asp Met Ser Gly Tyr Thr His Asp Gly Thr Phe Gln Gln Tyr Ala Thr
                20                  25                  30 gcc gat gcc gtc caa gct gcc aag atc cca gaa ggc gca gac atg gct       144
Ala Asp Ala Val Gln Ala Ala Lys Ile Pro Glu Gly Ala Asp Met Ala
            35                  40                  45 agt atc gcc ccg atc ttg tgt gct ggt gtg acc gtg tac aag gct ttg       192
Ser Ile Ala Pro Ile Leu Cys Ala Gly Val Thr Val Tyr Lys Ala Leu
        50                  55                  60 aag aac gcc gac ttg ttg gct ggc caa tgg gtg gct atc tct ggt gct       240
Lys Asn Ala Asp Leu Leu Ala Gly Gln Trp Val Ala Ile Ser Gly Ala
65                  70                  75                  80 ggt ggt ggt ttg ggc tcc ttg ggt gtg cag tac gct aaa gcc atg ggt       288
```

```
        Gly Gly Gly Leu Gly Ser Leu Gly Val Gln Tyr Ala Lys Ala Met Gly
                        85                  90                  95 tac aga gtg tta gcc atc gat ggt ggt gat gag aga gga gag ttt gtc      336
Tyr Arg Val Leu Ala Ile Asp Gly Gly Asp Glu Arg Gly Glu Phe Val
            100                 105                 110 aag tca ttg ggc gcc gaa gtg tac att gac ttc ctt aag gaa cag gac      384
Lys Ser Leu Gly Ala Glu Val Tyr Ile Asp Phe Leu Lys Glu Gln Asp
        115                 120                 125 att gtt agt gcc att aga aag gca act ggt ggt ggc cca cac ggt gtt      432
Ile Val Ser Ala Ile Arg Lys Ala Thr Gly Gly Gly Pro His Gly Val
    130                 135                 140 att aac gtc tcg gtg tcc gaa aag                                      456
Ile Asn Val Ser Val Ser Glu Lys
145                 150

<210> SEQ ID NO 62
<211> LENGTH: 152
<212> TYPE: PRT
<213> ORGANISM: Candida tropicalis

<400> SEQUENCE: 62

Asn Cys Glu Phe Cys Gln Gln Gly Ala Glu Pro Asn Cys Pro Arg Ala
1               5                   10                  15

Asp Met Ser Gly Tyr Thr His Asp Gly Thr Phe Gln Gln Tyr Ala Thr
            20                  25                  30

Ala Asp Ala Val Gln Ala Ala Lys Ile Pro Glu Gly Ala Asp Met Ala
        35                  40                  45

Ser Ile Ala Pro Ile Leu Cys Ala Gly Val Thr Val Tyr Lys Ala Leu
    50                  55                  60

Lys Asn Ala Asp Leu Leu Ala Gly Gln Trp Val Ala Ile Ser Gly Ala
65                  70                  75                  80

Gly Gly Gly Leu Gly Ser Leu Gly Val Gln Tyr Ala Lys Ala Met Gly
                85                  90                  95

Tyr Arg Val Leu Ala Ile Asp Gly Gly Asp Glu Arg Gly Glu Phe Val
            100                 105                 110

Lys Ser Leu Gly Ala Glu Val Tyr Ile Asp Phe Leu Lys Glu Gln Asp
        115                 120                 125

Ile Val Ser Ala Ile Arg Lys Ala Thr Gly Gly Gly Pro His Gly Val
    130                 135                 140

Ile Asn Val Ser Val Ser Glu Lys
145                 150

<210> SEQ ID NO 63
<211> LENGTH: 948
<212> TYPE: DNA
<213> ORGANISM: Candida tropicalis
<220> FEATURE:
<221> NAME/KEY: CDS
<222> LOCATION: (1)..(948)

<400> SEQUENCE: 63 aag tta gaa tac aaa gac gtg ccg gtc cct gtc cct aaa ccc aac gaa      48
Lys Leu Glu Tyr Lys Asp Val Pro Val Pro Val Pro Lys Pro Asn Glu
1               5                   10                  15 ttg ctt gtc aac gtc aag tac tcg ggt gtg tgt cat tct gac ttg cat      96
Leu Leu Val Asn Val Lys Tyr Ser Gly Val Cys His Ser Asp Leu His
            20                  25                  30 gtc tgg aaa ggc gac tgg ccc att cct gcc aag ttg ccc ttg gtg gga     144
Val Trp Lys Gly Asp Trp Pro Ile Pro Ala Lys Leu Pro Leu Val Gly
        35                  40                  45
```

```
ggt cac gaa ggt gct ggt gtc gtt gtc ggc atg ggt gac aac gtc aag      192
Gly His Glu Gly Ala Gly Val Val Val Gly Met Gly Asp Asn Val Lys
 50                  55                  60 ggc tgg aag gtg ggg gac ttg gct ggt atc aag tgg ttg aat ggt tcg      240
Gly Trp Lys Val Gly Asp Leu Ala Gly Ile Lys Trp Leu Asn Gly Ser
 65                  70                  75                  80 tgt atg aac tgt gag ttt tgc caa cag ggc gca gaa cct aac tgt tca      288
Cys Met Asn Cys Glu Phe Cys Gln Gln Gly Ala Glu Pro Asn Cys Ser
                 85                  90                  95 aga gcc gac atg tct ggg tat acc cac gat gga act ttc caa caa tac      336
Arg Ala Asp Met Ser Gly Tyr Thr His Asp Gly Thr Phe Gln Gln Tyr
            100                 105                 110 gcc act gct gat gct gtc caa gct gcc aag atc cca gaa ggc gcc gac      384
Ala Thr Ala Asp Ala Val Gln Ala Ala Lys Ile Pro Glu Gly Ala Asp
        115                 120                 125 atg gct agt atc gcc ccg atc ttg tgc gct ggt gtg acc gtg tac aag      432
Met Ala Ser Ile Ala Pro Ile Leu Cys Ala Gly Val Thr Val Tyr Lys
130                 135                 140 gct ttg aag aac gcc gac ttg ttg gct ggc caa tgg gtg gct atc tct      480
Ala Leu Lys Asn Ala Asp Leu Leu Ala Gly Gln Trp Val Ala Ile Ser
145                 150                 155                 160 ggt gct ggt ggt ggt ttg ggc tcc ttg ggt gtg cag tac gct aaa gcc      528
Gly Ala Gly Gly Gly Leu Gly Ser Leu Gly Val Gln Tyr Ala Lys Ala
                165                 170                 175 atg ggt tac aga gtg ttg gct atc gac ggt ggt gac gag aga gga gag      576
Met Gly Tyr Arg Val Leu Ala Ile Asp Gly Gly Asp Glu Arg Gly Glu
            180                 185                 190 ttt gtc aag tcc ttg ggc gcc gaa gtg tac att gac ttc ctt aag gaa      624
Phe Val Lys Ser Leu Gly Ala Glu Val Tyr Ile Asp Phe Leu Lys Glu
        195                 200                 205 cag gac atc gtt agt gct atc aga aag gca act ggt ggt gga cca cac      672
Gln Asp Ile Val Ser Ala Ile Arg Lys Ala Thr Gly Gly Gly Pro His
    210                 215                 220 ggt gtt att aac gtg tca gtg tcc gaa aag gca atc aac cag tcg gtg      720
Gly Val Ile Asn Val Ser Val Ser Glu Lys Ala Ile Asn Gln Ser Val
225                 230                 235                 240 gag tac gtc aga act ttg ggg aaa gtg gtt tta gtt agc ttg ccg gca      768
Glu Tyr Val Arg Thr Leu Gly Lys Val Val Leu Val Ser Leu Pro Ala
                245                 250                 255 ggt ggt aaa ctc act gct cct ctt ttc gag tct gtt gct aga tca atc      816
Gly Gly Lys Leu Thr Ala Pro Leu Phe Glu Ser Val Ala Arg Ser Ile
            260                 265                 270 cag att aga act acg tgt gtt ggc aac aga aag gat act act gaa gct      864
Gln Ile Arg Thr Thr Cys Val Gly Asn Arg Lys Asp Thr Thr Glu Ala
        275                 280                 285 att gat ttc ttt gtt aga ggg ttg atc gat tgc cca att aaa gtc gct      912
Ile Asp Phe Phe Val Arg Gly Leu Ile Asp Cys Pro Ile Lys Val Ala
    290                 295                 300 ggt tta agt gaa gtg cca gag att ttt gac ttg atg                      948
Gly Leu Ser Glu Val Pro Glu Ile Phe Asp Leu Met
305                 310                 315

<210> SEQ ID NO 64
<211> LENGTH: 316
<212> TYPE: PRT
<213> ORGANISM: Candida tropicalis

<400> SEQUENCE: 64

Lys Leu Glu Tyr Lys Asp Val Pro Val Pro Lys Pro Asn Glu
 1               5                   10                  15
```

```
Leu Leu Val Asn Val Lys Tyr Ser Gly Val Cys His Ser Asp Leu His
             20                  25                  30

Val Trp Lys Gly Asp Trp Pro Ile Pro Ala Lys Leu Pro Leu Val Gly
         35                  40                  45

Gly His Glu Gly Ala Gly Val Val Val Gly Met Gly Asp Asn Val Lys
     50                  55                  60

Gly Trp Lys Val Gly Asp Leu Ala Gly Ile Lys Trp Leu Asn Gly Ser
 65                  70                  75                  80

Cys Met Asn Cys Glu Phe Cys Gln Gln Gly Ala Glu Pro Asn Cys Ser
                 85                  90                  95

Arg Ala Asp Met Ser Gly Tyr Thr His Asp Gly Thr Phe Gln Gln Tyr
            100                 105                 110

Ala Thr Ala Asp Ala Val Gln Ala Ala Lys Ile Pro Glu Gly Ala Asp
        115                 120                 125

Met Ala Ser Ile Ala Pro Ile Leu Cys Ala Gly Val Thr Val Tyr Lys
    130                 135                 140

Ala Leu Lys Asn Ala Asp Leu Leu Ala Gly Gln Trp Val Ala Ile Ser
145                 150                 155                 160

Gly Ala Gly Gly Gly Leu Gly Ser Leu Gly Val Gln Tyr Ala Lys Ala
                165                 170                 175

Met Gly Tyr Arg Val Leu Ala Ile Asp Gly Gly Asp Glu Arg Gly Glu
            180                 185                 190

Phe Val Lys Ser Leu Gly Ala Glu Val Tyr Ile Asp Phe Leu Lys Glu
        195                 200                 205

Gln Asp Ile Val Ser Ala Ile Arg Lys Ala Thr Gly Gly Gly Pro His
    210                 215                 220

Gly Val Ile Asn Val Ser Val Ser Glu Lys Ala Ile Asn Gln Ser Val
225                 230                 235                 240

Glu Tyr Val Arg Thr Leu Gly Lys Val Val Val Ser Leu Pro Ala
                245                 250                 255

Gly Gly Lys Leu Thr Ala Pro Leu Phe Glu Ser Val Ala Arg Ser Ile
            260                 265                 270

Gln Ile Arg Thr Thr Cys Val Gly Asn Arg Lys Asp Thr Thr Glu Ala
        275                 280                 285

Ile Asp Phe Phe Val Arg Gly Leu Ile Asp Cys Pro Ile Lys Val Ala
    290                 295                 300

Gly Leu Ser Glu Val Pro Glu Ile Phe Asp Leu Met
305                 310                 315

<210> SEQ ID NO 65
<211> LENGTH: 948
<212> TYPE: DNA
<213> ORGANISM: Candida tropicalis
<220> FEATURE:
<221> NAME/KEY: CDS
<222> LOCATION: (1)..(948)

<400> SEQUENCE: 65 gaa tta gaa tac aaa gat atc cca gtg cca acc cca aag gcc aac gaa      48
Glu Leu Glu Tyr Lys Asp Ile Pro Val Pro Thr Pro Lys Ala Asn Glu
 1               5                  10                  15 ttg ctc atc aac gtc aaa tac tcg ggt gtc tgc cac act gat ttg cac      96
Leu Leu Ile Asn Val Lys Tyr Ser Gly Val Cys His Thr Asp Leu His
             20                  25                  30 gcc tgg aag ggt gac tgg cca ttg gcc acc aag ttg cca ttg gtt ggt     144
Ala Trp Lys Gly Asp Trp Pro Leu Ala Thr Lys Leu Pro Leu Val Gly
         35                  40                  45
```

| | | | | | | | | | | | | | | | |
|---|---|---|---|---|---|---|---|---|---|---|---|---|---|---|---|
| | | 35 | | | | 40 | | | | | 45 | | | | |
| ggt | cac | gaa | ggt | gct | ggt | gtc | gtt | gtc | ggc | atg | ggt | gaa | aac | gtc | aag | 192
| Gly | His | Glu | Gly | Ala | Gly | Val | Val | Val | Gly | Met | Gly | Glu | Asn | Val | Lys |
| | 50 | | | | 55 | | | | | 60 | | | | | | ggt cac gaa ggt gct ggt gtc gtt gtc ggc atg ggt gaa aac gtc aag    192
Gly His Glu Gly Ala Gly Val Val Val Gly Met Gly Glu Asn Val Lys
     50                  55                  60 ggc tgg aag att ggt gac ttc gcc ggt atc aaa tgg ttg aac ggt tcc    240
Gly Trp Lys Ile Gly Asp Phe Ala Gly Ile Lys Trp Leu Asn Gly Ser
 65                  70                  75                  80 tgt atg tcc tgt gag ttc tgt caa caa ggt gct gaa cca aac tgt ggt    288
Cys Met Ser Cys Glu Phe Cys Gln Gln Gly Ala Glu Pro Asn Cys Gly
                 85                  90                  95 gag gcc gac ttg tct ggt tac acc cac gat ggt tct ttc gaa caa tac    336
Glu Ala Asp Leu Ser Gly Tyr Thr His Asp Gly Ser Phe Glu Gln Tyr
            100                 105                 110 gcc act gct gat gct gtt caa gcc gcc aga atc cca gct ggt act gat    384
Ala Thr Ala Asp Ala Val Gln Ala Ala Arg Ile Pro Ala Gly Thr Asp
        115                 120                 125 ttg gcc gaa gtt gcc cca atc ttg tgt gcg ggt gtc acc gtc tac aaa    432
Leu Ala Glu Val Ala Pro Ile Leu Cys Ala Gly Val Thr Val Tyr Lys
    130                 135                 140 gcc ttg aag act gcc gac ttg gcc gct ggt caa tgg gtc gct atc tcc    480
Ala Leu Lys Thr Ala Asp Leu Ala Ala Gly Gln Trp Val Ala Ile Ser
145                 150                 155                 160 ggt gct ggt ggt ggt ttg ggt tcc ttg gct gtc caa tac gcc gtc gcc    528
Gly Ala Gly Gly Gly Leu Gly Ser Leu Ala Val Gln Tyr Ala Val Ala
                165                 170                 175 atg ggc ttg aga gtc gtt gcc att gac ggt ggt gac gaa aag ggt gcc    576
Met Gly Leu Arg Val Val Ala Ile Asp Gly Gly Asp Glu Lys Gly Ala
            180                 185                 190 ttt gtc aag tcc ttg ggt gct gaa gcc tac att gat ttc ctc aag gaa    624
Phe Val Lys Ser Leu Gly Ala Glu Ala Tyr Ile Asp Phe Leu Lys Glu
        195                 200                 205 aag gac att gtc tct gct gtc aag aag gcc acc gat gga ggt cca cac    672
Lys Asp Ile Val Ser Ala Val Lys Lys Ala Thr Asp Gly Gly Pro His
    210                 215                 220 ggt gct atc aat gtt tcc gtt tcc gaa aaa gcc att gac caa tcc gtc    720
Gly Ala Ile Asn Val Ser Val Ser Glu Lys Ala Ile Asp Gln Ser Val
225                 230                 235                 240 gag tac gtt aga cca ttg ggt aag gtt gtt ttg gtt ggt ttg cca gct    768
Glu Tyr Val Arg Pro Leu Gly Lys Val Val Leu Val Gly Leu Pro Ala
                245                 250                 255 ggc tcc aag gtc act gct ggt gtt ttc gaa gcc gtt gtc aag tcc att    816
Gly Ser Lys Val Thr Ala Gly Val Phe Glu Ala Val Val Lys Ser Ile
            260                 265                 270 gaa atc aag ggt tcc tat gtc ggt aac aga aag gat acc gcc gaa gcc    864
Glu Ile Lys Gly Ser Tyr Val Gly Asn Arg Lys Asp Thr Ala Glu Ala
        275                 280                 285 gtt gac ttt ttc tcc aga ggt ttg atc aag tgt cca atc aag att gtt    912
Val Asp Phe Phe Ser Arg Gly Leu Ile Lys Cys Pro Ile Lys Ile Val
    290                 295                 300 ggc ttg agt gaa ttg cca cag gtc ttc aag ttg atg                    948
Gly Leu Ser Glu Leu Pro Gln Val Phe Lys Leu Met
305                 310                 315

<210> SEQ ID NO 66
<211> LENGTH: 316
<212> TYPE: PRT
<213> ORGANISM: Candida tropicalis

<400> SEQUENCE: 66

Glu Leu Glu Tyr Lys Asp Ile Pro Val Pro Thr Pro Lys Ala Asn Glu

```
  1               5                  10                 15
Leu Leu Ile Asn Val Lys Tyr Ser Gly Val Cys His Thr Asp Leu His
                20                 25                 30
Ala Trp Lys Gly Asp Trp Pro Leu Ala Thr Lys Leu Pro Leu Val Gly
                35                 40                 45
Gly His Glu Gly Ala Gly Val Val Gly Met Gly Glu Asn Val Lys
         50                 55                 60
Gly Trp Lys Ile Gly Asp Phe Ala Gly Ile Lys Trp Leu Asn Gly Ser
 65                 70                 75                 80
Cys Met Ser Cys Glu Phe Cys Gln Gln Gly Ala Glu Pro Asn Cys Gly
                85                 90                 95
Glu Ala Asp Leu Ser Gly Tyr Thr His Asp Gly Ser Phe Glu Gln Tyr
                100                105                110
Ala Thr Ala Asp Ala Val Gln Ala Ala Arg Ile Pro Ala Gly Thr Asp
                115                120                125
Leu Ala Glu Val Ala Pro Ile Leu Cys Ala Gly Val Thr Val Tyr Lys
                130                135                140
Ala Leu Lys Thr Ala Asp Leu Ala Ala Gly Gln Trp Val Ala Ile Ser
145                150                155                160
Gly Ala Gly Gly Gly Leu Gly Ser Leu Ala Val Gln Tyr Ala Val Ala
                165                170                175
Met Gly Leu Arg Val Val Ala Ile Asp Gly Gly Asp Glu Lys Gly Ala
                180                185                190
Phe Val Lys Ser Leu Gly Ala Glu Ala Tyr Ile Asp Phe Leu Lys Glu
                195                200                205
Lys Asp Ile Val Ser Ala Val Lys Lys Ala Thr Asp Gly Gly Pro His
                210                215                220
Gly Ala Ile Asn Val Ser Val Ser Glu Lys Ala Ile Asp Gln Ser Val
225                230                235                240
Glu Tyr Val Arg Pro Leu Gly Lys Val Val Leu Val Gly Leu Pro Ala
                245                250                255
Gly Ser Lys Val Thr Ala Gly Val Phe Glu Ala Val Val Lys Ser Ile
                260                265                270
Glu Ile Lys Gly Ser Tyr Val Gly Asn Arg Lys Asp Thr Ala Glu Ala
                275                280                285
Val Asp Phe Phe Ser Arg Gly Leu Ile Lys Cys Pro Ile Lys Ile Val
                290                295                300
Gly Leu Ser Glu Leu Pro Gln Val Phe Lys Leu Met
305                310                315

<210> SEQ ID NO 67
<211> LENGTH: 1992
<212> TYPE: DNA
<213> ORGANISM: Candida tropicalis
<220> FEATURE:
<221> NAME/KEY: CDS
<222> LOCATION: (1)..(1992)

<400> SEQUENCE: 67 ctt atg tta tta tgt gac ggg atc atc cac gaa acc acc gtc gac caa      48
Leu Met Leu Leu Cys Asp Gly Ile Ile His Glu Thr Thr Val Asp Gln
 1               5                  10                 15 atc aaa gac gtt att gct cct gac ttc cct gct gac aag tac gaa gag      96
Ile Lys Asp Val Ile Ala Pro Asp Phe Pro Ala Asp Lys Tyr Glu Glu
                20                 25                 30 tac gtc agg aca ttc acc aaa ccc tcc gaa acc cca ggg ttc agg gaa     144
```

-continued

```
                Tyr Val Arg Thr Phe Thr Lys Pro Ser Glu Thr Pro Gly Phe Arg Glu
                             35                  40                  45 acc gtc tac aac aca gtc aac gca aac acc acg gac gca atc cac cag      192
Thr Val Tyr Asn Thr Val Asn Ala Asn Thr Thr Asp Ala Ile His Gln
         50                  55                  60 ttc att atc ttg acc aat gtt ttg gca tcc agg gtc ttg gct cca gct      240
Phe Ile Ile Leu Thr Asn Val Leu Ala Ser Arg Val Leu Ala Pro Ala
 65              70                  75                  80 ttg acc aac tcg ttg acg cct atc aag gac atg agc ttg gaa gac cgt      288
Leu Thr Asn Ser Leu Thr Pro Ile Lys Asp Met Ser Leu Glu Asp Arg
                 85                  90                  95 gaa aaa ttg ttg gcc tcg tgg cgc gac tcc cca atc gct gcc aaa agg      336
Glu Lys Leu Leu Ala Ser Trp Arg Asp Ser Pro Ile Ala Ala Lys Arg
             100                 105                 110 aaa ttg ttc agg ttg gtt tcc acg ctt acc ttg gtt act ttc acg aga      384
Lys Leu Phe Arg Leu Val Ser Thr Leu Thr Leu Val Thr Phe Thr Arg
                 115                 120                 125 ttg gcc aat gag ttg cat ttg aaa gcc att cac tat cca gga aga gaa      432
Leu Ala Asn Glu Leu His Leu Lys Ala Ile His Tyr Pro Gly Arg Glu
             130                 135                 140 gac cgt gaa aag gct tat gaa acc cag gag att gac cct ttc aag tac      480
Asp Arg Glu Lys Ala Tyr Glu Thr Gln Glu Ile Asp Pro Phe Lys Tyr
145                 150                 155                 160 cag ttt atg gaa aag cca aag ttt gac ggc gct gag ttg tac ttg cca      528
Gln Phe Met Glu Lys Pro Lys Phe Asp Gly Ala Glu Leu Tyr Leu Pro
                 165                 170                 175 gat att gat gtt atc att att gga tct ggt gcc ggt gct ggt gtt gtg      576
Asp Ile Asp Val Ile Ile Ile Gly Ser Gly Ala Gly Ala Gly Val Val
             180                 185                 190 gcc cac act ttg gcc aac gat ggc ttc aag agt ttg gtt ttg gaa aag      624
Ala His Thr Leu Ala Asn Asp Gly Phe Lys Ser Leu Val Leu Glu Lys
             195                 200                 205 ggc aaa tac ttt agc aac tcc gag ttg aac ttt gat gac aag gac ggc      672
Gly Lys Tyr Phe Ser Asn Ser Glu Leu Asn Phe Asp Asp Lys Asp Gly
         210                 215                 220 gtt caa gaa tta tac caa agt gga ggt act ttg act aca gtc aac caa      720
Val Gln Glu Leu Tyr Gln Ser Gly Gly Thr Leu Thr Thr Val Asn Gln
225                 230                 235                 240 cag ttg ttt gtt ctt gct ggt tcc act ttt ggt ggc ggt acc act gtc      768
Gln Leu Phe Val Leu Ala Gly Ser Thr Phe Gly Gly Gly Thr Thr Val
                 245                 250                 255 aat tgg tca gcc tgt ctt aag acg cca ttc aag gtg cgt aag gaa tgg      816
Asn Trp Ser Ala Cys Leu Lys Thr Pro Phe Lys Val Arg Lys Glu Trp
             260                 265                 270 tat gat gag ttt ggt gtt gac ttt gct gct gat gaa gca tac gat aaa      864
Tyr Asp Glu Phe Gly Val Asp Phe Ala Ala Asp Glu Ala Tyr Asp Lys
         275                 280                 285 gcg cag gat tat gtt tgg cag caa atg gga gct tct acc gaa ggc atc      912
Ala Gln Asp Tyr Val Trp Gln Gln Met Gly Ala Ser Thr Glu Gly Ile
     290                 295                 300 acc cac tct ttg gct aac gag att att att gaa ggt ggt aag aaa tta      960
Thr His Ser Leu Ala Asn Glu Ile Ile Ile Glu Gly Gly Lys Lys Leu
305                 310                 315                 320 ggt tac aag gcc aag gta tta gac caa aac agc ggt ggt cat cct cag     1008
Gly Tyr Lys Ala Lys Val Leu Asp Gln Asn Ser Gly Gly His Pro Gln
                 325                 330                 335 cac aga tgc ggt ttc tgt tat ttg ggc tgt aag cac ggt atc aag cag     1056
His Arg Cys Gly Phe Cys Tyr Leu Gly Cys Lys His Gly Ile Lys Gln
             340                 345                 350
```

-continued

```
ggt tct gtt aat aac tgg ttt aga gac gca gct gcc cac ggt tcc cag      1104
Gly Ser Val Asn Asn Trp Phe Arg Asp Ala Ala Ala His Gly Ser Gln
        355                 360                 365 ttc atg caa cag gtt aga gtt ttg caa ata ctt aac aag aag ggg atc      1152
Phe Met Gln Gln Val Arg Val Leu Gln Ile Leu Asn Lys Lys Gly Ile
370                 375                 380 gct tac ggt atc ttg tgt gag gat gtt gta acc ggc gcc aag ttc acc      1200
Ala Tyr Gly Ile Leu Cys Glu Asp Val Val Thr Gly Ala Lys Phe Thr
385                 390                 395                 400 att act ggc ccc aaa aag ttt gtt gtt gct gcc ggt gct ttg aac act      1248
Ile Thr Gly Pro Lys Lys Phe Val Val Ala Ala Gly Ala Leu Asn Thr
                405                 410                 415 cca tct gtg ttg gtc aac tcc ggc ttc aag aac aag aac atc ggt aag      1296
Pro Ser Val Leu Val Asn Ser Gly Phe Lys Asn Lys Asn Ile Gly Lys
            420                 425                 430 aac tta act ttg cac cca gtt tct gtc gtg ttt ggt gat ttt ggc aaa      1344
Asn Leu Thr Leu His Pro Val Ser Val Val Phe Gly Asp Phe Gly Lys
        435                 440                 445 gac gtt caa gca gac cac ttc cac aac tcc atc atg act gcc ctt tgt      1392
Asp Val Gln Ala Asp His Phe His Asn Ser Ile Met Thr Ala Leu Cys
450                 455                 460 tca gaa gcc gct gat tta gac ggc aag ggc cat gga tgc aga att gaa      1440
Ser Glu Ala Ala Asp Leu Asp Gly Lys Gly His Gly Cys Arg Ile Glu
465                 470                 475                 480 acc atc ttg aac gct cca ttc atc cag gct tca ttc tta cca tgg aga      1488
Thr Ile Leu Asn Ala Pro Phe Ile Gln Ala Ser Phe Leu Pro Trp Arg
                485                 490                 495 ggt agt aac gag gct aga cga gac ttg ttg cgt tac aac aac atg gtg      1536
Gly Ser Asn Glu Ala Arg Arg Asp Leu Leu Arg Tyr Asn Asn Met Val
            500                 505                 510 gcg atg ttg ctc ctt agt cgt gac acc acc agt ggt tcc gtt tct gct      1584
Ala Met Leu Leu Leu Ser Arg Asp Thr Thr Ser Gly Ser Val Ser Ala
        515                 520                 525 cat cca acc aaa cct gaa gct ttg gtt gtc gag tac gac gtg aac aag      1632
His Pro Thr Lys Pro Glu Ala Leu Val Val Glu Tyr Asp Val Asn Lys
530                 535                 540 ttt gac aga aac tcg atc ttg cag gca ttg ttg gtc act gct gac ttg      1680
Phe Asp Arg Asn Ser Ile Leu Gln Ala Leu Leu Val Thr Ala Asp Leu
545                 550                 555                 560 ttg tat atc caa ggt gcc aag aga atc ctt agt cca cag gca tgg gtg      1728
Leu Tyr Ile Gln Gly Ala Lys Arg Ile Leu Ser Pro Gln Ala Trp Val
                565                 570                 575 cca att ttt gaa tcc gac aag cca aag gat aag aga tca atc aag gac      1776
Pro Ile Phe Glu Ser Asp Lys Pro Lys Asp Lys Arg Ser Ile Lys Asp
            580                 585                 590 gag gac tat gtc gaa tgg aga gcc aag gtt gcc aag att cct ttc gac      1824
Glu Asp Tyr Val Glu Trp Arg Ala Lys Val Ala Lys Ile Pro Phe Asp
        595                 600                 605 acc tac ggc tca cct tat ggt tcg gca cat caa atg tct tct tgc cgt      1872
Thr Tyr Gly Ser Pro Tyr Gly Ser Ala His Gln Met Ser Ser Cys Arg
610                 615                 620 atg tca ggt aag ggt cct aaa tac ggt gct gtt gac acc gat ggt aga      1920
Met Ser Gly Lys Gly Pro Lys Tyr Gly Ala Val Asp Thr Asp Gly Arg
625                 630                 635                 640 ttg ttt gaa tgt tcg aat gtt tat gtt gcc gat gca agt ctt ttg cca      1968
Leu Phe Glu Cys Ser Asn Val Tyr Val Ala Asp Ala Ser Leu Leu Pro
                645                 650                 655 act gca agc ggt gct aat cct atg                                      1992
Thr Ala Ser Gly Ala Asn Pro Met
            660
```

<210> SEQ ID NO 68
<211> LENGTH: 664
<212> TYPE: PRT
<213> ORGANISM: Candida tropicalis

<400> SEQUENCE: 68

```
Leu Met Leu Leu Cys Asp Gly Ile Ile His Glu Thr Thr Val Asp Gln
1               5                   10                  15

Ile Lys Asp Val Ile Ala Pro Asp Phe Pro Ala Asp Lys Tyr Glu Glu
            20                  25                  30

Tyr Val Arg Thr Phe Thr Lys Pro Ser Glu Thr Pro Gly Phe Arg Glu
        35                  40                  45

Thr Val Tyr Asn Thr Val Asn Ala Asn Thr Thr Asp Ala Ile His Gln
    50                  55                  60

Phe Ile Ile Leu Thr Asn Val Leu Ala Ser Arg Val Leu Ala Pro Ala
65                  70                  75                  80

Leu Thr Asn Ser Leu Thr Pro Ile Lys Asp Met Ser Leu Glu Asp Arg
                85                  90                  95

Glu Lys Leu Leu Ala Ser Trp Arg Asp Ser Pro Ile Ala Ala Lys Arg
            100                 105                 110

Lys Leu Phe Arg Leu Val Ser Thr Leu Thr Leu Val Thr Phe Thr Arg
        115                 120                 125

Leu Ala Asn Glu Leu His Leu Lys Ala Ile His Tyr Pro Gly Arg Glu
    130                 135                 140

Asp Arg Glu Lys Ala Tyr Glu Thr Gln Glu Ile Asp Pro Phe Lys Tyr
145                 150                 155                 160

Gln Phe Met Glu Lys Pro Lys Phe Asp Gly Ala Glu Leu Tyr Leu Pro
                165                 170                 175

Asp Ile Asp Val Ile Ile Ile Gly Ser Gly Ala Gly Ala Gly Val Val
            180                 185                 190

Ala His Thr Leu Ala Asn Asp Gly Phe Lys Ser Leu Val Leu Glu Lys
        195                 200                 205

Gly Lys Tyr Phe Ser Asn Ser Glu Leu Asn Phe Asp Asp Lys Asp Gly
    210                 215                 220

Val Gln Glu Leu Tyr Gln Ser Gly Gly Thr Leu Thr Thr Val Asn Gln
225                 230                 235                 240

Gln Leu Phe Val Leu Ala Gly Ser Thr Phe Gly Gly Gly Thr Thr Val
                245                 250                 255

Asn Trp Ser Ala Cys Leu Lys Thr Pro Phe Lys Val Arg Lys Glu Trp
            260                 265                 270

Tyr Asp Glu Phe Gly Val Asp Phe Ala Ala Asp Glu Ala Tyr Asp Lys
        275                 280                 285

Ala Gln Asp Tyr Val Trp Gln Gln Met Gly Ala Ser Thr Glu Gly Ile
    290                 295                 300

Thr His Ser Leu Ala Asn Glu Ile Ile Glu Gly Gly Lys Lys Leu
305                 310                 315                 320

Gly Tyr Lys Ala Lys Val Leu Asp Gln Asn Ser Gly Gly His Pro Gln
                325                 330                 335

His Arg Cys Gly Phe Cys Tyr Leu Gly Cys Lys His Gly Ile Lys Gln
            340                 345                 350

Gly Ser Val Asn Asn Trp Phe Arg Asp Ala Ala His Gly Ser Gln
        355                 360                 365

Phe Met Gln Gln Val Arg Val Leu Gln Ile Leu Asn Lys Lys Gly Ile
```

-continued

```
                370                 375                 380
Ala Tyr Gly Ile Leu Cys Glu Asp Val Val Thr Gly Ala Lys Phe Thr
385                 390                 395                 400

Ile Thr Gly Pro Lys Lys Phe Val Val Ala Ala Gly Ala Leu Asn Thr
                405                 410                 415

Pro Ser Val Leu Val Asn Ser Gly Phe Lys Asn Lys Asn Ile Gly Lys
                420                 425                 430

Asn Leu Thr Leu His Pro Val Ser Val Val Phe Gly Asp Phe Gly Lys
            435                 440                 445

Asp Val Gln Ala Asp His Phe His Asn Ser Ile Met Thr Ala Leu Cys
        450                 455                 460

Ser Glu Ala Ala Asp Leu Asp Gly Lys Gly His Gly Cys Arg Ile Glu
465                 470                 475                 480

Thr Ile Leu Asn Ala Pro Phe Ile Gln Ala Ser Phe Leu Pro Trp Arg
                485                 490                 495

Gly Ser Asn Glu Ala Arg Arg Asp Leu Leu Arg Tyr Asn Asn Met Val
                500                 505                 510

Ala Met Leu Leu Leu Ser Arg Asp Thr Thr Ser Gly Ser Val Ser Ala
            515                 520                 525

His Pro Thr Lys Pro Glu Ala Leu Val Val Glu Tyr Asp Val Asn Lys
        530                 535                 540

Phe Asp Arg Asn Ser Ile Leu Gln Ala Leu Leu Val Thr Ala Asp Leu
545                 550                 555                 560

Leu Tyr Ile Gln Gly Ala Lys Arg Ile Leu Ser Pro Gln Ala Trp Val
                565                 570                 575

Pro Ile Phe Glu Ser Asp Lys Pro Lys Asp Lys Arg Ser Ile Lys Asp
                580                 585                 590

Glu Asp Tyr Val Glu Trp Arg Ala Lys Val Ala Lys Ile Pro Phe Asp
            595                 600                 605

Thr Tyr Gly Ser Pro Tyr Gly Ser Ala His Gln Met Ser Ser Cys Arg
        610                 615                 620

Met Ser Gly Lys Gly Pro Lys Tyr Gly Ala Val Asp Thr Asp Gly Arg
625                 630                 635                 640

Leu Phe Glu Cys Ser Asn Val Tyr Val Ala Asp Ala Ser Leu Leu Pro
                645                 650                 655

Thr Ala Ser Gly Ala Asn Pro Met
                660
```

CANDIDA TROPICALIS CELLS AND USE THEREOF

This application is a divisional of U.S. Ser. No. 13/764,996 filed Feb. 12, 2013, now U.S. Pat. No. 8,999,684, which is a divisional of U.S. application Ser. No. 12/943,145 filed Nov. 10, 2010, abandoned, and claims the benefit of DE 102009046626.6 filed Nov. 11, 2009.

FIELD OF THE INVENTION

The invention relates to genetically engineered *Candida tropicalis* cells, use thereof and a method of production of ω-hydroxycarboxylic acids and ω-hydroxycarboxylic acid esters.

BACKGROUND OF THE INVENTION

Owing to its ability to form dicarboxylic acids from alkanes, *Candida tropicalis* is a well-characterized ascomycete.

WO91/006660 describes *Candida tropicalis* cells that are completely inhibited in β-oxidation through interruption of the POX4 and/or POX5 genes, and achieve increased yields of α,ω-dicarboxylic acids.

WO00/020566 describes cytochrome P450 monooxygenases and NADPH cytochrome P450 oxidoreductases from *Candida tropicalis* and use thereof for influencing ω-hydroxylation, the first step in ω-oxidation.

WO03/089610 describes enzymes from *Candida tropicalis* which catalyse the second step of ω-oxidation, the conversion of a fatty alcohol to an aldehyde, and use thereof for improved production of dicarboxylic acids.

The cells and methods described so far are not suitable for the production of ω-hydroxycarboxylic acids or their esters, as the ω-hydroxycarboxylic acids are always only present as a short-lived intermediate and are immediately metabolized further.

ω-Hydroxycarboxylic acids and their esters are economically important compounds as precursors of polymers, and this forms the basis of the commercial usability of the present invention.

The task of the invention was to find a way of preparing ω-hydroxycarboxylic acids or ω-hydroxycarboxylic acid esters by fermentation in sufficient amounts, in particular in the medium surrounding the cells.

DESCRIPTION OF THE INVENTION

It was found, surprisingly, that the cells described hereunder make a contribution to solution of this task.

The object of the present invention is therefore a cell as described in claim 1.

Another object of the invention is the use of the cell according to the invention and a method of production of ω-hydroxycarboxylic acids and ω-hydroxycarboxylic acid esters using the cells according to the invention.

Advantages of the invention are the gentle conversion of the educt used to the ω-hydroxycarboxylic acids and corresponding esters and a high specificity of the method and an associated high yield based on the educt used.

One object of the present invention is a *Candida tropicalis* cell, in particular one from the strain ATCC 20336, which is characterized in that the cell has, compared with its wild type, a reduced activity of at least one of the enzymes that are encoded by the intron-free nucleic acid sequences selected from the two group comprising A) Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25, Seq ID No. 27, Seq ID No. 29, Seq ID No. 31, Seq ID No. 33, Seq ID No. 35, Seq ID No. 37, Seq ID No. 39, Seq ID No. 41, Seq ID No. 43, Seq ID No. 45, Seq ID No. 47, Seq ID No. 49, Seq ID No. 51, Seq ID No. 53, Seq ID No. 55, Seq ID No. 57, Seq ID No. 59, Seq ID No. 61, Seq ID No. 63, Seq ID No. 65 and Seq ID No. 67; in particular Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25, Seq ID No. 27, Seq ID No. 29, Seq ID No. 31, Seq ID No. 33, Seq ID No. 35, Seq ID No. 37, Seq ID No. 39, Seq ID No. 41, Seq ID No. 43, Seq ID No. 45, Seq ID No. 47, Seq ID No. 49 and Seq ID No. 51; quite especially Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25 and Seq ID No. 27, B) a sequence that is identical to at least 80%, especially preferably to at least 90%, even more preferably to at least 95% and most preferably to at least 99% to one of the sequences Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25, Seq ID No. 27, Seq ID No. 29, Seq ID No. 31, Seq ID No. 33, Seq ID No. 35, Seq ID No. 37, Seq ID No. 39, Seq ID No. 41, Seq ID No. 43, Seq ID No. 45, Seq ID No. 47, Seq ID No. 49, Seq ID No. 51, Seq ID No. 53, Seq ID No. 55, Seq ID No. 57, Seq ID No. 59, Seq ID No. 61, Seq ID No. 63, Seq ID No. 65 and Seq ID No. 67; in particular to Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25, Seq ID No. 27, Seq ID No. 29, Seq ID No. 31, Seq ID No. 33, Seq ID No. 35, Seq ID No. 37, Seq ID No. 39, Seq ID No. 41, Seq ID No. 43, Seq ID No. 45, Seq ID No. 47, Seq ID No. 49 and Seq ID No. 51; quite especially to Seq ID No. 1, Seq ID No. 3, Seq ID No. 5, Seq ID No. 7, Seq ID No. 9, Seq ID No. 11, Seq ID No. 13, Seq ID No. 15, Seq ID No. 17, Seq ID No. 19, Seq ID No. 21, Seq ID No. 23, Seq ID No. 25 and Seq ID No. 27.

In this connection, the nucleic acid sequence group that is preferred according to the invention is group A).

A "wild type" of a cell preferably means, in connection with the present invention, the starting strain from which the cell according to the invention was derived by manipulation of the elements (for example the genes comprising the aforesaid nucleic acid sequences coding for a corresponding enzyme or the promoters contained in the corresponding gene, which are linked functionally with the aforesaid nucleic acid sequences), which influence the activities of the enzymes encoded by the stated nucleic acid Seq ID No. If for example the activity of the enzyme encoded by Seq ID No. 1 in the strain ATCC 20336 is reduced by interruption of the corresponding gene, then the strain ATCC 20336 that is unchanged and was used for the corresponding manipulation is to be regarded as the "wild type".

The term "gene" means, in connection with the present invention, not only the encoding DNA region or that transcribed to mRNA, the "structural gene", but in addition promoter, possible intron, enhancer and other regulatory sequence, and terminator, regions.

The term "activity of an enzyme" always means, in connection with the invention, the enzymatic activity that catalyses the reactions of 12-hydroxydodecanoic acid to 1,12-dodecane diacid by the entire cell. This activity is preferably determined by the following method:

Starting from a single colony, a 100-ml Erlenmeyer flask with 10 ml of YM medium (0.3% yeast extract, 0.3% malt extract, 0.5% peptone and 1.0% (w/w) glucose) is cultivated at 30° C. and 90 rpm for 24 h. Then, starting from this culture, 10 ml is inoculated into a 1-liter Erlenmeyer flask with 100 ml of production medium (for 1 liter: 25 g glucose, 7.6 g $NH_4Cl$, 1.5 g $Na_2SO_4$, 300 ml of a 1 mM potassium phosphate buffer (pH 7.0), 20 mg $ZnSO_4 \times 7\ H_2O$, 20 mg $MnSO_4 \times 4\ H_2O$, 20 mg nicotinic acid, 20 mg pyridoxine, 8 mg thiamine and 6 mg pantothenate). It is cultivated for 24 h at 30° C.

After 24 h, 12-hydroxydodecanoic acid is added to the cell suspension, so that the concentration is not greater than 0.5 g/l. Glucose or glycerol is also added as co-substrate, so that the concentration of the co-substrate does not drop below 0.2 g/l. After 0 h, 0.5 h, 1 h, and then hourly up to a cultivation time of 24 h, samples (1 ml) are taken for measurement of 12-hydroxydodecanoic acid, 12-oxo-dodecanoic acid and 1,12-dodecane diacid and the corresponding methyl esters, and for checking the cell count. After each measurement, the pH is kept between 5.0 and 6.5 with 6N NaOH or 4N $H_2SO_4$. During cultivation, cell growth is verified by checking the "colony forming units" (CFU). The decrease of 12-hydroxy-dodecanoic acid and the production of 1,12-dodecane diacid or the corresponding methyl esters are verified by LC-MS. For this, 500 µl of culture broth is adjusted to pH 1 and then extracted with the same volume of diethyl ether or ethyl acetate and analysed by LC-MS.

The measuring system consists of an HP1100 HPLC (Agilent Technologies, Waldbronn, Germany) with degasser, autosampler and column furnace, coupled to a mass-selective quadrupole detector MSD (Agilent Technologies, Waldbronn, Germany). Chromatographic separation is achieved on a reversed phase e.g. 125×2 mm Luna C18(2) column (Phenomenex, Aschaffenburg, Germany) at 40° C. Gradient elution is performed at a flow of 0.3 ml/min (A: 0.02% formic acid in water and B: 0.02% formic acid in acetonitrile). Alternatively, the organic extracts are analysed by GC-FID (Perkin Elmer, Rodgau-Jügesheim, Germany). Chromatographic separation is performed on a methylpolysiloxane (5% phenyl) phase e.g. Elite 5, 30 m, 0.25 mm ID, 0.25 µm FD (Perkin Elmer, Rodgau-Jügesheim, Germany). Before measurement, a methylation reagent e.g. trimethylsulphonium hydroxide "TMSH" (Macherey-Nagel GmbH & Co. KG, Düren, Germany) is added to free acids and on injection they are converted to the corresponding methyl esters.

By calculating the measured concentration of 1,12-dodecane diacid and the cell number at the time of sampling, it is possible to determine the specific production rate of 1,12-dodecane diacid from 12-hydroxydodecanoic acid and therefore the "activity of an enzyme" in a cell as defined above. The formulation "reduced activity compared with its wild type" means an activity relative to the wild-type activity preferably reduced by at least 50%, especially preferably by at least 90%, more preferably by at least 99.9%, even more preferably by at least 99.99% and most preferably by at least 99.999%.

The decrease in activity of the cell according to the invention compared with its wild type is determined by the method described above for determining activity using cell numbers/concentrations as identical as possible, the cells having been grown under the same conditions, for example medium, gassing, agitation.

"Nucleotide identity" relative to the stated sequences can be determined using known methods. Generally, special computer programs are used with algorithms taking special requirements into account. Preferred methods for determining identity first produce the greatest agreement between the sequences to be compared. Computer programs for determining identity comprise, but are not restricted to, the GCG software package, including GAP (Deveroy, J. et al., Nucleic Acid Research 12 (1984), page 387, Genetics Computer Group University of Wisconsin, Medicine (Wi), and BLASTP, BLASTN and FASTA (Altschul, S. et al., Journal of Molecular Biology 215 (1990), pages 403-410.

The BLAST program can be obtained from the National Center for Biotechnology Information (NCBI) and from other sources (BLAST Manual, Altschul S. et al., NCBI NLM NIH Bethesda N.D. 22894; Altschul S. et al., above).

The known Smith-Waterman algorithm can also be used for determining nucleotide identity.

Preferred parameters for the determination of "nucleotide identity" are, when using the BLASTN program (Altschul, S. et al., Journal of Molecular Biology 215 (1990), pages 403-410):

Expect Threshold: 10
Word size: 28
Match score: 1
Mismatch score: −2
Gap costs: linear The above parameters are the default parameters in nucleotide sequence comparison.

The GAP program is also suitable for use with the above parameters.

An identity of 80% according to the above algorithm means, in connection with the present invention, 80% identity. The same applies to higher identities.

The term "that are encoded by the intron-free nucleic acid sequences" makes clear that in a sequence comparison with the sequences given here, the nucleic acid sequences to be compared must be purified of any introns beforehand.

All stated percentages (%) are percentages by weight unless stated otherwise.

Methods of lowering enzymatic activities in microorganisms are known by a person skilled in the art.

In particular, techniques in molecular biology can be used for this. A person skilled in the art can find instructions on modification and decrease of protein expression and the associated decrease in enzyme activity especially for *Candida tropicalis*, in particular for interrupting specified genes, in WO91/006660; WO03/100013; Picataggio et al. Mol Cell Biol. 1991 September; 11 (9):4333-9; Rohrer et al. Appl Microbiol Biotechnol. 1992 February; 36 (5):650-4; Picataggio et al. Biotechnology (NY). 1992 August; 10 (8):894-8; Ueda et al. Biochim Biophys Acta. 2003 Mar. 17; 1631(2): 160-8; Ko et al. Appl Environ Microbiol. 2006 June; 72 (6):4207-13; Hara et al. Arch Microbiol. 2001 November; 176 (5):364-9; Kanayama et al. J Bacteriol. 1998 February; 180 (3): 690-8.

Cells preferred according to the invention are characterized in that the decrease in enzymatic activity is achieved by modification of at least one gene comprising one of the sequences selected from the previously stated nucleic acid sequence groups A) and B), the modification being selected from the group comprising, preferably consisting of, insertion of foreign DNA into the gene, deletion at least of parts of the gene, point mutations in the gene sequence and subjecting the gene to the influence of RNA interference or exchange of parts of the gene with foreign DNA, in particular of the promoter region.

Foreign DNA means, in this context, any DNA sequence that is "foreign" to the gene (and not to the organism), i.e.

even *Candida tropicalis* endogenous DNA sequences can, in this context, function as "foreign DNA".

In this context, it is in particular preferable for the gene to be interrupted by insertion of a selection marker gene, therefore the foreign DNA is a selection marker gene, the insertion preferably having been effected by homologous recombination into the gene locus.

In this context, it may be advantageous if the selection marker gene is expanded with further functionalities, which in their turn make subsequent removal from the gene possible, this can be achieved for example with a Cre/loxP system, with *Flippase Recognition Targets* (FRT) or by homologous recombination.

Cells preferred according to the invention are characterized in that they are blocked in their β-oxidation at least partially, preferably completely, as this prevents outflow of substrate and therefore higher titres become possible.

Examples of *Candida tropicalis* cells partially blocked in their β-oxidation are described in EP0499622 as strains H41, H41B, H51, H45, H43, H53, H534, H534B and H435, from which a *Candida tropicalis* cell preferred according to the invention is derived.

Other *Candida tropicalis* cells blocked for β-oxidation are described for example in WO03/100013.

In this context, cells are preferred for which the β-oxidation is caused by an induced malfunction of at least one of the genes POX2, POX4 or POX5.

Therefore, in this context, cells are preferred that are characterized in that a *Candida tropicalis* cell preferred according to the invention is derived from strains selected from the group comprising ATCC 20962 and the *Candida tropicalis* HDC100 described in US2004/0014198.

The use of the cells according to the invention for the production of ω-hydroxycarboxylic acids or ω-hydroxycarboxylic acid esters also contributes to solution of the task facing the invention.

In particular, the use of the cells according to the invention for the production of ω-hydroxycarboxylic acids or ω-hydroxycarboxylic acid esters with a chain length of the carboxylic acid from 6 to 24, preferably 8 to 18 and especially preferably 10 to 16 carbon atoms, which are preferably linear, saturated and unsubstituted, and a chain length of the alcohol component of the ester from 1 to 4, in particular 1 or 2 carbon atoms, is advantageous. In this context, it is preferable for the ω-hydroxycarboxylic acids to be 12-hydroxydodecanoic acid and for the ω-hydroxycarboxylic acid ester to be 12-hydroxydodecanoic acid methyl ester.

A preferred use is characterized according to the invention in that preferred cells according to the invention as described above are used.

Another contribution to solving the task facing the invention is made by a method of production of the *C. tropicalis* cell according to the invention described above comprising the steps:

I) Preparation of a *C. tropicalis* cell, preferably a cell that is blocked in its β-oxidation at least partially, preferably completely II) Modification of at least one gene comprising one of the intron-free nucleic acid sequences selected from the previously stated nucleic acid sequence groups A) and B) by insertion of foreign DNA, in particular of DNA coding for a selection marker gene, into the gene, deletion of at least parts of the gene, point mutations in the gene sequence and subjecting the gene to the influence of RNA interference or exchange of parts of the gene with foreign DNA, in particular of the promoter region.

Another contribution to solving the task facing the invention is made by a method of production of ω-hydroxycarboxylic acids or ω-hydroxycarboxylic acid esters, in particular of ω-hydroxycarboxylic acids or ω-hydroxycarboxylic acid esters with a chain length of the carboxylic acid from 6 to 24, preferably 8 to 18 and especially preferably 10 to 16 carbon atoms, which are preferably linear, saturated and unsubstituted, and a chain length of the alcohol component of the ester from 1 to 4, in particular of 1 or 2 carbon atoms, in particular of 12-hydroxydodecanoic acid or 12-hydroxydodecanoic acid methyl ester comprising the steps A) contacting a previously described cell according to the invention with a medium comprising a carboxylic acid or a carboxylic acid ester, in particular a carboxylic acid or a carboxylic acid ester with a chain length of the carboxylic acid from 6 to 24, preferably 8 to 18 and especially preferably 10 to 16 carbon atoms, which are preferably linear, saturated and unsubstituted, and a chain length of the alcohol component of the ester from 1 to 4 carbon atoms, in particular dodecanoic acid or dodecanoic acid methyl ester, B) cultivating the cell under conditions that enable the cell to form the corresponding ω-hydroxycarboxylic acid or ω-hydroxycarboxylic acid esters from the carboxylic acid or the carboxylic acid ester and C) optionally isolating the ω-hydroxycarboxylic acid or ω-hydroxycarboxylic acid esters that formed.

Preferred methods according to the invention use cells stated above as being preferred according to the invention.

Therefore, for example a method of production of 12-hydroxydodecanoic acid or 12-hydroxydodecanoic acid methyl ester comprising the steps a) contacting a *Candida tropicalis* cell of the strain ATTC 20336 at least partially blocked in its β-oxidation, which has, compared with its wild type, a reduced activity of at least one of the enzymes, which are encoded by the intron-free nucleic acid sequences selected from the previously stated nucleic acid sequence groups A) and B), the decrease in enzymatic activity being achieved by modification of a gene comprising one of the nucleic acid sequences selected from the previously stated nucleic acid sequence groups A) and B), wherein the modification consists of insertion of a selection marker gene into the gene, with a medium comprising dodecanoic acid or dodecanoic acid methyl ester, b) cultivating the cell under conditions that enable the cell to form the corresponding ω-hydroxycarboxylic acid or ω-hydroxycarboxylic acid esters from the carboxylic acid or the carboxylic acid ester and c) optionally isolating the ω-hydroxycarboxylic acid or ω-hydroxycarboxylic acid esters that formed is quite especially preferred.

Suitable cultivation conditions for *Candida tropicalis* are known by a person skilled in the art. In particular, suitable conditions for step b) are those that are known by a person skilled in the art from bioconversion methods of production of dicarboxylic acids with *Candida tropicalis*.

These cultivation conditions are described for example in WO00/017380 and WO00/015828.

Methods for isolating the ω-hydroxycarboxylic acid or ω-hydroxycarboxylic acid esters that formed are known by a person skilled in the art. These are standard methods for isolating long-chain carboxylic acids from aqueous solution, for example distillation or extraction, and can for example also be found in WO2009/077461.

It is advantageous to use the ω-hydroxycarboxylic acids or ω-hydroxycarboxylic acid esters obtained by the method according to the invention for the production of polymers, in particular polyesters. Moreover, lactones can also be produced from the ω-hydroxy carboxylic acids, and can then for example be used in their turn for the production of polyesters.

Another advantageous use is to convert the ω-hydroxycarboxylic acids or ω-hydroxycarboxylic acid esters to ω-aminocarboxylic acids or ω-aminocarboxylic acid esters, in order to obtain polyamides as polymers. The ω-aminocarboxylic acids or ω-aminocarboxylic acid esters can also be converted first to the corresponding lactams, which can then in their turn be converted using anionic, or also acid catalysis to a polyamide.

It is quite especially advantageous, in a first reaction step, to convert the ω-hydroxycarboxylic acids or corresponding esters into the ω-oxo-carboxylic acids or the corresponding esters and then to carry out amination of the oxo-group, e.g. in the course of reductive amination.

In this context, the use of 12-hydroxy dodecanoic acid or 12-hydroxydodecanoic acid methyl ester for the production of polymers, in particular of polyamide 12, is especially preferred.

The invention claimed is:

1. A method for production of ω-aminocarboxylic acids or ω-aminocarboxylic acid esters, comprising
   a) contacting a *Candida tropicalis* cell with a medium comprising a carboxylic acid or a carboxylic acid ester,
   b) cultivating the *Candida tropicalis* cell under conditions that enable the *Candida tropicalis* cell to form corresponding ω-hydroxycarboxylic acid or ω-hydroxycarboxylic acid esters from the carboxylic acid or the carboxylic acid ester,
   c) optionally isolating the ω-hydroxycarboxylic acid or ω-hydroxycarboxylic acid esters that formed, converting the ω-hydroxycarboxylic acids or corresponding esters into the ω-oxo-carboxylic acids or the corresponding esters and then aminating the oxo-group, wherein the *Candida tropicalis* cell has, compared with its wild type, a reduced activity of at least one of enzyme encoded by an intron-free nucleic acid sequences selected from the group consisting of SEQ ID NO: 61, SEQ ID NO:63, a sequence that is 95% identical to SEQ ID NO: 61, and a sequence that is 95% identical to SEQ ID NO:63.

2. The method according to claim 1, wherein the reduced enzymatic activity comprises insertion of a foreign DNA into SEQ ID NO: 61, or SEQ ID NO:63 contained in a chromosome of the *Candida tropicalis* cell, deletion of at least a part of SEQ ID NO: 61, or SEQ ID NO:63 in a chromosome of the *Candida tropicalis* cell, a point mutation in SEQ ID NO: 61, or SEQ ID NO:63 in a chromosome of the *Candida tropicalis* cell, providing an interfering RNA molecule targeting expression of SEQ ID NO: 61, or SEQ ID NO:63, and exchanging a part of SEQ ID NO: 61, or SEQ ID NO:63 in a chromosome of the *Candida tropicalis* cell with foreign DNA, and exchanging a part of a transcription promoter controlling expression of SEQ ID NO: 61, or SEQ ID NO:63 in the *Candida tropicalis* cell with foreign DNA.

3. The method according to claim 2, wherein the foreign DNA is a selection marker gene.

4. The method according to claim 1, wherein the *Candida tropicalis* cell is blocked at least partially in its β-oxidation.

5. The method according to claim 1, wherein the *Candida tropicalis* cell is obtained from a strain selected from the group consisting of *Candida tropicalis* H41, *Candida tropicalis* H41B, *Candida tropicalis* H51, *Candida tropicalis* H45, *Candida tropicalis* H43, *Candida tropicalis* H53, *Candida tropicalis* H534, *Candida tropicalis* 534B, *Candida tropicalis* H435, *Candida tropicalis* ATCC20962 and *Candida tropicalis* HDC100.

6. The method according to claim 1, wherein the *Candida tropicalis* cell is obtained from a strain selected from the group consisting of *Candida tropicalis* ATCC20962 and *Candida tropicalis* HDC100.

7. The method according to claim 1, wherein the ω-hydroxycarboxylic acid has a carboxylic acid chain length of from 6 to 24 or the ω-hydroxycarboxylic acid ester has a carboxylic acid chain length of from 6 to 24 and an alcohol chain length from 1 to 4.

8. The method according to claim 1, wherein the ω-hydroxycarboxylic acid or ω-hydroxycarboxylic acid ester is 12-hydroxydodecanoic acid or 12-hydroxydodecanoic acid methyl ester.

9. The method according to claim 1, wherein the enzyme is encoded by SEQ ID NO: 61, or SEQ ID NO:63.

10. The method according to claim 1, wherein the enzyme is encoded by a sequence that is 95% identical to SEQ ID NO: 61, or SEQ ID NO:63.

* * * * *